US012653380B2

(12) United States Patent
Gono et al.

(10) Patent No.: US 12,653,380 B2
(45) Date of Patent: Jun. 16, 2026

(54) INFORMATION PROCESSING SYSTEM, MEDICAL SYSTEM AND CANNULATION METHOD

(71) Applicant: OLYMPUS CORPORATION, Tokyo (JP)

(72) Inventors: Kazuhiro Gono, Sagamihara (JP); Shotaro Takemoto, Tokyo (JP); Shintaro Inoue, Cambridge, MA (US); Hiroyuki Mino, Westborough, MA (US); Mark Lavender, Plymouth, MN (US)

(73) Assignee: OLYMPUS CORPORATION, Tokyo (JP)

( * ) Notice: Subject to any disclaimer, the term of this patent is extended or adjusted under 35 U.S.C. 154(b) by 547 days.

(21) Appl. No.: 17/989,108

(22) Filed: Nov. 17, 2022

(65) Prior Publication Data

US 2023/0148847 A1 May 18, 2023

Related U.S. Application Data

(60) Provisional application No. 63/294,451, filed on Dec. 29, 2021, provisional application No. 63/294,444, (Continued)

(51) Int. Cl.
*A61B 1/00* (2006.01)

(52) U.S. Cl.
CPC .... *A61B 1/00131* (2013.01); *A61B 1/000094* (2022.02); *A61B 1/000095* (2022.02)

(58) Field of Classification Search
CPC .......... A61B 1/00009; A61B 1/000094; A61B 1/000095; A61B 1/00131
See application file for complete search history.

(56) References Cited

U.S. PATENT DOCUMENTS 7,953,612 B1    5/2011  Palmese et al.
11,801,114 B2  10/2023  Lang
(Continued)

FOREIGN PATENT DOCUMENTS

JP        H11-019027 A       1/1999
JP        2003-038419 A      2/2003
(Continued)

OTHER PUBLICATIONS

US Office Action dated Apr. 8, 2025 received in U.S. Appl. No. 17/989,126.
(Continued)

*Primary Examiner* — Aaron B Fairchild
(74) *Attorney, Agent, or Firm* — Scully, Scott, Murphy & Presser, P.C.

(57) ABSTRACT

An information processing system, including a processor comprising hardware. The processor being configured to: acquire an endoscope image from an endoscope, the endoscope image showing a papillary portion, determine route information of a lumen based on the endoscope image, the lumen being at least one of a biliary duct or a pancreatic duct, generate a display image based on a result of the determination of the route information of the lumen, the display image having a route guide image to provide guidance of a route of the lumen leading to the papillary portion superimposed on the endoscope image, and display the display image on a display.

17 Claims, 69 Drawing Sheets

Related U.S. Application Data filed on Dec. 29, 2021, provisional application No. 63/294,466, filed on Dec. 29, 2021, provisional application No. 63/280,716, filed on Nov. 18, 2021.

(56) References Cited

U.S. PATENT DOCUMENTS

| | | | |
|---|---|---|---|
| 12,048,413 | B2 | 7/2024 | Tada et al. |
| 12,290,414 | B2 | 5/2025 | Lang |
| 12,478,433 | B2 | 11/2025 | Mino et al. |
| 2003/0078473 | A1 | 4/2003 | Richardson |
| 2004/0015329 | A1 | 1/2004 | Shayegan et al. |
| 2007/0038080 | A1* | 2/2007 | Salisbury, Jr. ......... A61B 34/35 |
| | | | 600/427 |
| 2007/0185377 | A1 | 8/2007 | Murakami et al. |
| 2008/0058425 | A1 | 3/2008 | Hurley et al. |
| 2008/0214890 | A1 | 9/2008 | Motai et al. |
| 2008/0249356 | A1 | 10/2008 | Motai et al. |
| 2008/0249358 | A1 | 10/2008 | Motai et al. |
| 2010/0041949 | A1 | 2/2010 | Tolkowsky |
| 2010/0056910 | A1 | 3/2010 | Yanuma |
| 2010/0134605 | A1 | 6/2010 | Demos et al. |
| 2014/0212849 | A1 | 7/2014 | Naiwala et al. |
| 2014/0303435 | A1 | 10/2014 | Taniguchi |
| 2015/0164608 | A1 | 6/2015 | Bartenstein |
| 2015/0265807 | A1 | 9/2015 | Park et al. |
| 2016/0206227 | A1 | 7/2016 | Marashdeh et al. |
| 2016/0206228 | A1 | 7/2016 | Angulo et al. |
| 2016/0338716 | A1 | 11/2016 | Aslinia et al. |
| 2016/0353970 | A1 | 12/2016 | Inoue |
| 2017/0086929 | A1 | 3/2017 | Moll et al. |
| 2018/0040126 | A1 | 2/2018 | Bayer |
| 2018/0296281 | A1 | 10/2018 | Yeung et al. |
| 2019/0029757 | A1 | 1/2019 | Roh et al. |
| 2019/0208990 | A1 | 7/2019 | Chelala et al. |
| 2019/0340956 | A1 | 11/2019 | Lindkvist et al. |
| 2020/0030575 | A1 | 1/2020 | Bogusky et al. |
| 2020/0178773 | A1 | 6/2020 | Miller |
| 2020/0281449 | A1 | 9/2020 | Yoshimura |
| 2021/0137634 | A1 | 5/2021 | Lang |
| 2021/0153808 | A1 | 5/2021 | Tada et al. |
| 2021/0196398 | A1 | 7/2021 | Ye et al. |
| 2022/0192466 | A1 | 6/2022 | Nishimura |
| 2023/0123739 | A1 | 4/2023 | Mino et al. |
| 2023/0148848 | A1 | 5/2023 | Gono et al. |
| 2023/0148849 | A1 | 5/2023 | Inoue et al. |
| 2023/0149043 | A1 | 5/2023 | Gono et al. |
| 2023/0153288 | A1 | 5/2023 | Gono |
| 2023/0157768 | A1 | 5/2023 | Meguro |
| 2023/0200682 | A1 | 6/2023 | Yoshioka et al. |
| 2024/0016551 | A1 | 1/2024 | Duval et al. |
| 2024/0197163 | A1 | 6/2024 | Inoue et al. |
| 2024/0252775 | A1 | 8/2024 | Gage et al. |
| 2025/0017689 | A1 | 1/2025 | Lang |
| 2025/0064296 | A1 | 2/2025 | Sokolov et al. |

FOREIGN PATENT DOCUMENTS

| | | |
|---|---|---|
| JP | 2005-334474 A | 12/2005 |
| JP | 2008-253780 A | 10/2008 |
| JP | 2011-240152 A | 12/2011 |
| JP | 2012-213436 A | 11/2012 |
| JP | 2013-069251 A | 4/2013 |
| JP | 2019-197436 A | 11/2019 |
| WO | 2006042186 A2 | 4/2006 |
| WO | 2021/049475 A1 | 3/2021 |

OTHER PUBLICATIONS

Japanese Office Action dated Mar. 5, 2024 received in 2022-171250.
Japanese Office Action dated Oct. 3, 2023 received in 2022-171250.
Yi et al., "Quantitative Analysis of Colonoscopy Skills Using the KAIST-Ewha Colonoscopy Simulator II", Frontier in the Convergence of Bioscience and Information Technologies 2007, Year: 2007.
US Office Action dated Dec. 18, 2023 received in U.S. Appl. No. 17/989,160.
US Office Action dated Apr. 18, 2025 received in U.S. Appl. No. 17/989,146.
US Office Action dated Jul. 7, 2025 received in U.S. Appl. No. 17/989,186.
Extended European Search Report dated Apr. 5, 2023 received in 22207769.5.
US Final Office Action dated Oct. 15, 2025 received in U.S. Appl. No. 17/989,146.
US Office Action dated Feb. 25, 2026 received in U.S. Appl. No. 18/612,092.
US Office Action dated Mar. 26, 2026 received in U.S. Appl. No. 17/989,146.
US Office Action dated Apr. 8, 2026 received in U.S. Appl. No. 17/989,126.

* cited by examiner

ESOPHAGUS

LIVER

GALLBLADDER

INSERTION SECTION
OF ENDOSCOPE

BILIARY DUCT

DUODENUM

PANCREAS

DISTAL END OF
ENDOSCOPE

PAPILLARY PORTION

PANCREATIC DUCT

FIG.3

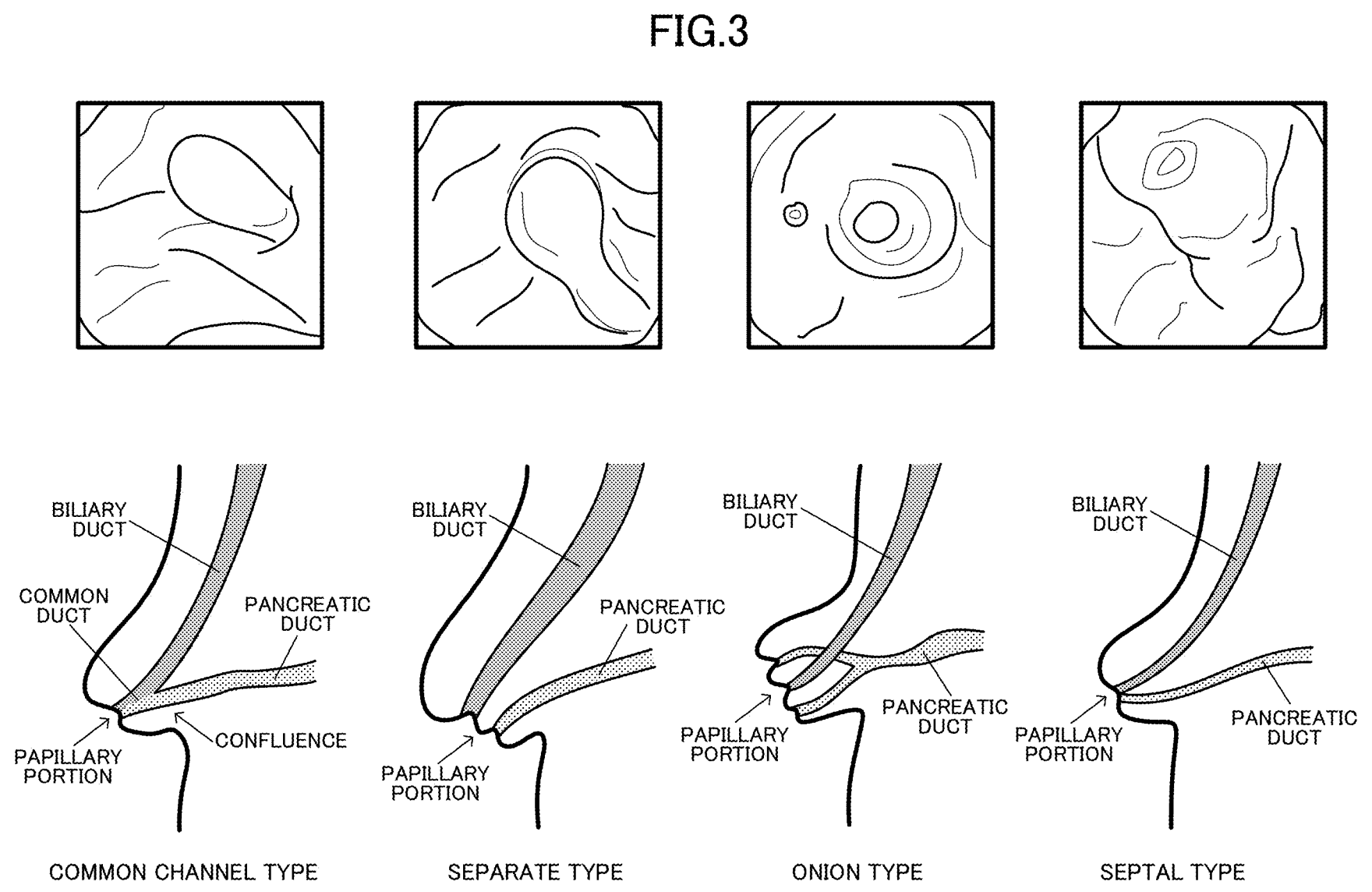

BILIARY DUCT

PANCREATIC DUCT

PAPILLARY PORTION

SEPTAL TYPE

BILIARY DUCT

PANCREATIC DUCT

PAPILLARY PORTION

ONION TYPE

BILIARY DUCT

PANCREATIC DUCT

PAPILLARY PORTION

SEPARATE TYPE

BILIARY DUCT

PANCREATIC DUCT

CONFLUENCE

COMMON DUCT

PAPILLARY PORTION

COMMON CHANNEL TYPE

ROUTE GUIDE IMAGE

FIG.15

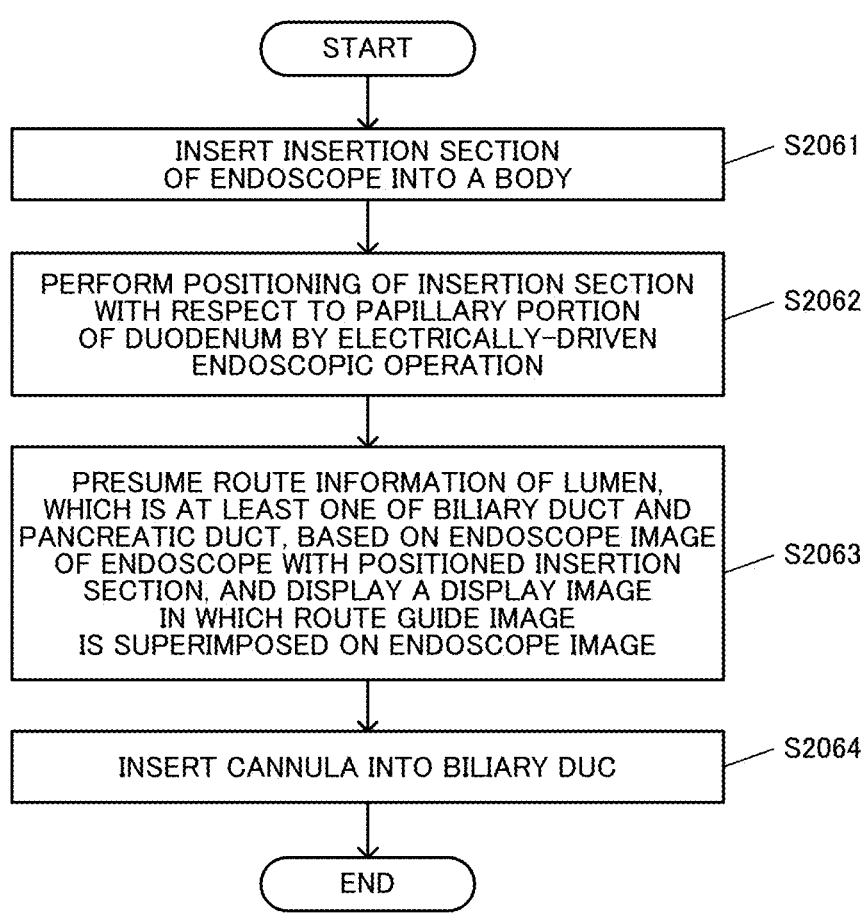

START

INSERT INSERTION SECTION
OF ENDOSCOPE INTO A BODY — S2061

PERFORM POSITIONING OF INSERTION SECTION
WITH RESPECT TO PAPILLARY PORTION
OF DUODENUM BY ELECTRICALLY-DRIVEN
ENDOSCOPIC OPERATION — S2062

PRESUME ROUTE INFORMATION OF LUMEN,
WHICH IS AT LEAST ONE OF BILIARY DUCT AND
PANCREATIC DUCT, BASED ON ENDOSCOPE IMAGE
OF ENDOSCOPE WITH POSITIONED INSERTION
SECTION, AND DISPLAY A DISPLAY IMAGE
IN WHICH ROUTE GUIDE IMAGE
IS SUPERIMPOSED ON ENDOSCOPE IMAGE — S2063

INSERT CANNULA INTO BILIARY DUC — S2064

END

CT IMAGE

FIG.17
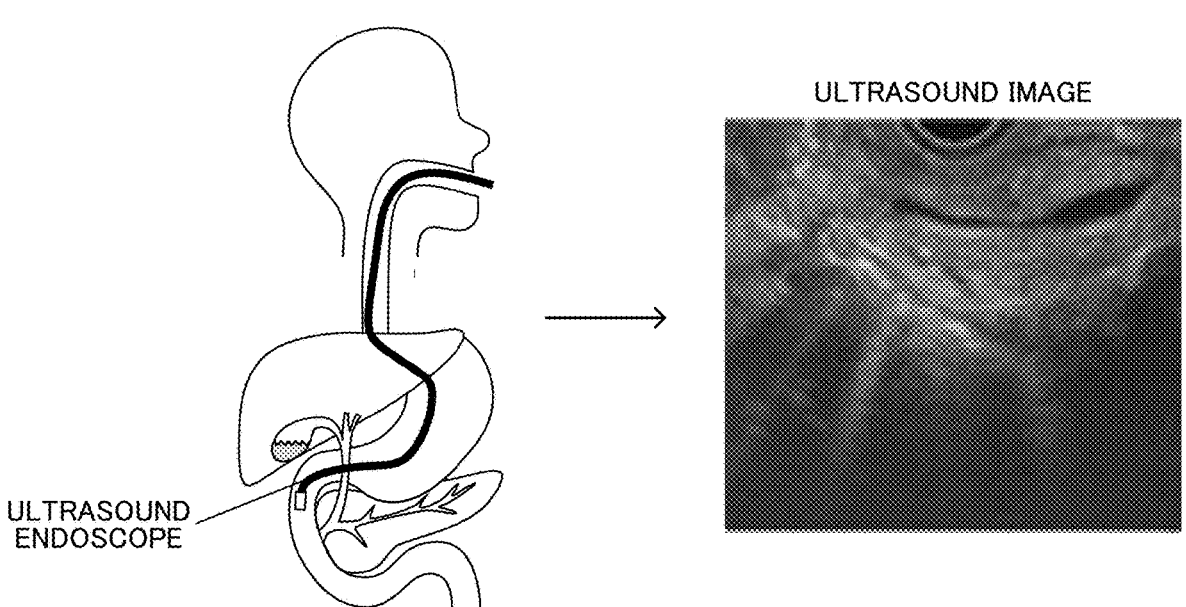
ULTRASOUND
ENDOSCOPE
ULTRASOUND IMAGE
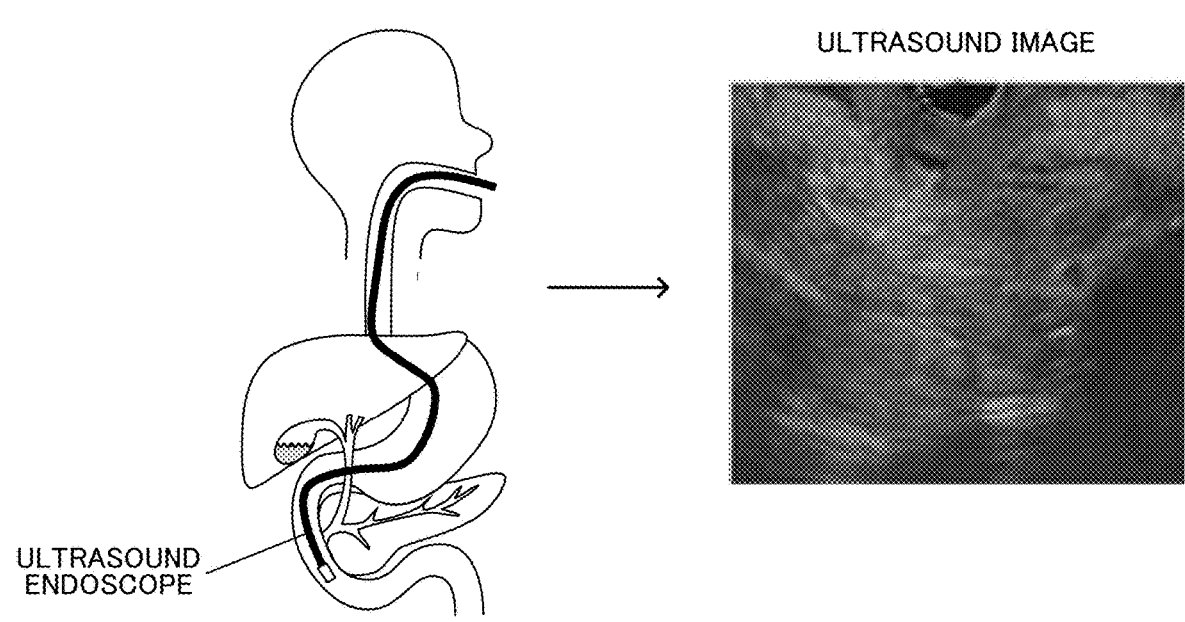
ULTRASOUND
ENDOSCOPE
ULTRASOUND IMAGE

FIG.18

ENDOSCOPE IMAGE

2072

TRAINED MODEL

ROUTE GUIDE IMAGE

RT

ULTRASOUND IMAGE

2074

ESOPHAGUS

LIVER

GALLBLADDER

INSERTION SECTION
OF ENDOSCOPE

BILIARY DUCT

DUODENUM

PANCREAS

DISTAL END OF
ENDOSCOPE

PAPILLARY PORTION          PANCREATIC DUCT

FIG.44

INFORMATION PROCESSING SYSTEM, MEDICAL SYSTEM AND CANNULATION METHOD

CROSS-REFERENCE TO RELATED APPLICATIONS

This application claims the benefit of priority to U.S. Provisional Application No. 63/280,716 filed Nov. 18, 2021; 63/294,466 filed Dec. 29, 2021; 63/294,451 filed Dec. 29, 2021, and 63/294,444 filed Dec. 29, 2021, the entire contents of each of which is incorporated herein by reference.

BACKGROUND

A technique called endoscopic retrograde cholangiopancreatography (ERCP) has been known that captures an X-ray image or a CT image of biliary duct by inserting a cannula into a biliary duct from a treatment tool channel of an endoscope, injecting a contrast agent from the cannula, and performing X-ray imaging or CT imaging. A method for inserting an endoscope into an organ with a bifurcation, in which insertion of an endoscope into an organ with a bifurcation, such as a biliary duct, is facilitated by virtually superimposing the center line of lumen on an image is also known.

In this regard, such method discloses facilitating insertion into an organ with a bifurcation, such as a biliary duct, by virtually superimposing the center line of lumen on an image. However, such method fails to disclose the individual differences in the shape of the papillary portion or the difficulties in predicting the routes of the biliary duct and the pancreatic duct due to individual differences. Such method is also silent about the need of the prediction of the insertion direction before the insertion into the papillary portion or the solutions to these problems.

Methods are also known that scan the inner wall of the colon using an endoscope and generate an alert when the scanning speed is high. Specifically, such known methods include acquiring an image of the colon using an imaging device positioned on the sidewall of the colonoscope, calculating the scanning speed of the imaging device, and generating an alert indicating whether the scanning speed exceeds the scanning speed threshold. A technique called endoscopic retrograde cholangiopancreatography (ERCP) has been known that captures an X-ray image or a CT image of biliary duct by inserting a cannula into a biliary duct from a treatment tool channel of an endoscope, injecting a contrast agent from the cannula, and performing X-ray imaging or CT imaging. It is known that ERCP can be applied to a robotic catheter system for performing procedures by remotely operating a catheter system.

SUMMARY

Accordingly, there is provided an information processing system, comprising: a processor comprising hardware, the processor being configured to: acquire an endoscope image from an endoscope, the endoscope image showing a papillary portion, determine route information of a lumen based on the endoscope image, the lumen being at least one of a biliary duct or a pancreatic duct, generate a display image based on a result of the determination of the route information of the lumen, the display image having a route guide image to provide guidance of a route of the lumen leading to the papillary portion superimposed on the endoscope image, and display the display image on a display.

The route guide image can comprise a lumen route image indicating a route of the biliary duct and a route of the pancreatic duct.

The route guide image can comprise at least one of an image indicating a distance between a distal end of a treatment tool of the endoscope and the papillary portion or an image indicating an insertion direction of the treatment tool.

The information processing system can further comprise a storage for storing a trained model trained to output the route information of the lumen based on the endoscope image, wherein the processor can determine the route information from the endoscope image by a processing based on the trained model. The trained model can be trained using training data based on a classification pattern of the papillary portion. The trained model can be trained using training data based on an MRCP image. The trained model can be trained using training data based on an ultrasound endoscope image.

The processor can acquire an MRCP image showing a part of the lumen, and determine a route of the lumen between the papillary portion and the part of the lumen shown in the MRCP image based on the endoscope image and the MRCP image. The information processing system can further comprise a storage for storing a trained model trained to output the route information of the lumen based on the endoscope image and the MRCP image, wherein the processor can determine the route of the lumen between the papillary portion and the part of the lumen shown in the MRCP image from the endoscope image and the MRCP image by a processing based on the trained model.

The endoscope can be an endoscope that electrically drives an endoscopic operation, the endoscopic operation can be at least one of forward and backward movement of an insertion section, a bending angle of a bending section of the insertion section, or rolling rotation of the insertion section; the processor can control positioning of a distal end section of the endoscope with respect to the papillary portion by the electrically-driven endoscopic operation; and subsequent to the positioning, acquire the endoscope image.

The endoscope can be an endoscope that electrically drives an endoscopic operation, the endoscopic operation can be at least one of forward and backward movement of an insertion section, a bending angle of a bending section of the insertion section, or rolling rotation of the insertion section; and the processor can control the electrically-driven endoscopic operation based on the result of the determination of the route information of the lumen.

Also provided is a medical system comprising: the information processing system and the endoscope.

Still further provided is a cannulation method using an endoscope that electrically drives an endoscopic operation, the endoscopic operation being at least one of forward and backward movement of an insertion section, a bending angle of a bending section of the insertion section, or rolling rotation of the insertion section, and captures an endoscope image. The method comprising, inserting the insertion section of the endoscope into a body; positioning the insertion section with respect to a papillary portion of duodenum by the electrically-driven endoscopic operation; subsequent to the positioning, determining route information of a lumen based on the endoscope image, is the lumen being at least one of a biliary duct or a pancreatic duct, generating a display image based on the determined route information of the lumen, the display image having a route guide image to provide guidance of a route of the lumen superimposed on the endoscope image; displaying the display image on a display; and subsequent to the displaying, inserting a cannula into the biliary duct.

BRIEF DESCRIPTION OF THE DRAWINGS

FIG. 3 shows endoscope images of papillary portion, and the corresponding classification types for the biliary duct and the pancreatic duct.

FIG. 15 is a flowchart for explaining a cannulation method of the present embodiment.

FIG. 17 is an explanatory view of the processing of the present embodiment when an ultrasound image is used.

FIG. 18 is an explanatory view of the processing of the present embodiment when an ultrasound image and a trained model are used.

FIG. 44 is a schematic view of an endoscope including a bending section and a driving mechanism thereof.

Figure 1:
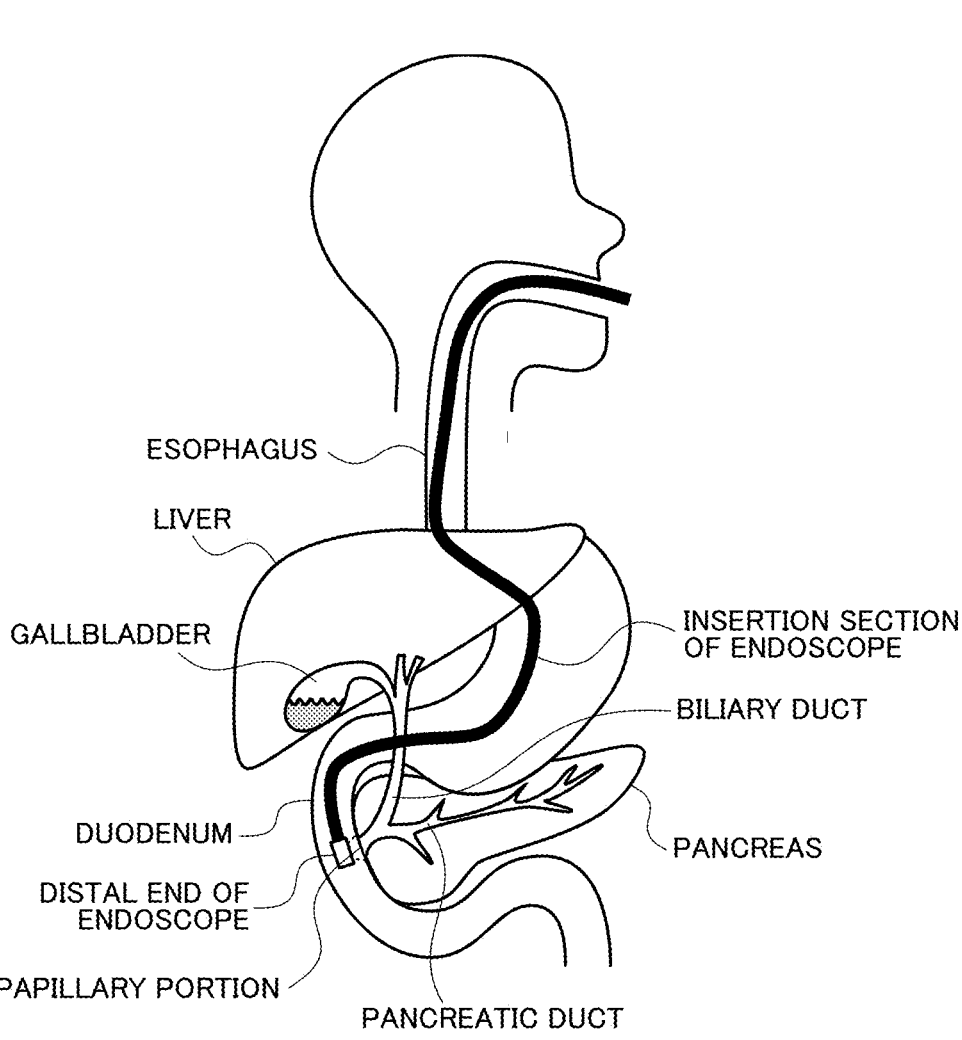
FIG. 1 shows organs and tissues involved in the ERCP procedure.

DESCRIPTION OF EXEMPLARY
EMBODIMENTS

The following disclosure provides many different embodiments, or examples, for implementing different features of the provided subject matter. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Explanation of ERCP

The present embodiment relates to a route guide for the biliary duct and the pancreatic duct when conducting ERCP, or the like. ERCP stands for Endoscopic Retrograde Cholangiopancreatography. First, before describing the present embodiment, the details of procedure of ERCP is described below.

FIG. 1 shows organs and tissues involved in the ERCP procedure. The organs include multiple types of tissues, forming a unique structure with a specific function. In FIG. 1, the liver, gallbladder, pancreas, esophagus, stomach, and duodenum are shown as organs. Tissues are formed by related cells combined, and examples include blood vessels, muscles, skin, and the like. In FIG. 1, a biliary duct and a pancreatic duct are shown as tissues.

The biliary duct is the target of the ERCP procedure. The biliary duct is a pipeline for allowing the bile produced in the liver to flow into the duodenum. When approaching the biliary duct using an endoscope, a treatment tool inserted into the channel of the endoscope is inserted to the biliary duct from the papillary portion of the duodenum while holding the endoscope at the position of the duodenum. Hereinafter, the papillary portion of the duodenum is simply referred to as a papillary portion. The papillary portion is a region including an opening of the luminal tissue with respect to the duodenum. Not only the opening but also the structure around the opening is referred to as a papillary portion. The opening of the luminal tissue is the opening of a common duct with respect to the duodenum. The common duct is formed as the confluence of the biliary duct and pancreatic duct. However, as described later, the papillary portion largely varies between individuals. For example, in some cases, the biliary duct opens directly to the duodenum without being merged with the pancreatic duct. In this case, the opening of the luminal tissue is the opening of the biliary duct.

Figure 2:
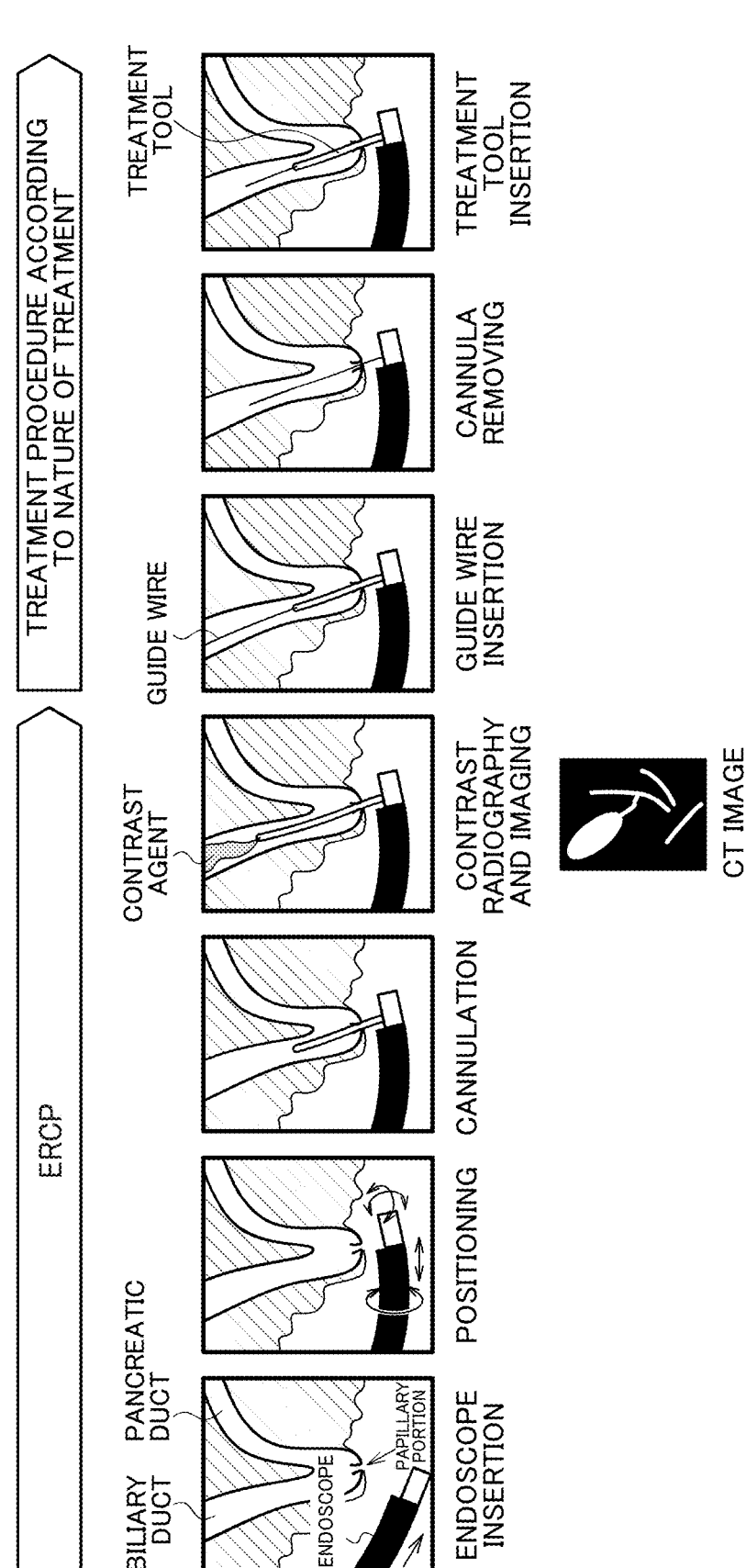
FIG. 2 shows a flow of the ERCP procedure.

FIG. 2 shows a flow of the ERCP procedure. In ERCP, a side-viewing type endoscope in which a camera, an illumination lens, and an opening of a treatment tool channel are provided on a side surface of a distal end section of the endoscope is used. The camera is also referred to as an imaging device.

In the endoscope insertion step, the insertion section of the endoscope is inserted from the mouth to the duodenum through the esophagus and stomach. At this time, the insertion section is inserted until the papillary portion becomes roughly visible in the field of view of the endoscope. Next, in the positioning step, the position of the endoscope is adjusted relative to the papillary portion. Specifically, the position of the distal end section of the endoscope is adjusted so that the papillary portion is within the imaging range of the camera of the endoscope. Alternatively, the position of the distal end section of the endoscope is adjusted so that the camera of the endoscope is facing directly front of the papillary portion and the papillary portion appears in the center of the field of view.

Then, in the cannulation step, a cannula is inserted from the papillary portion into the biliary duct. Specifically, the cannula is inserted into the treatment tool channel of the endoscope so that the cannula protrudes from the channel opening of the distal end section of the endoscope. The distal end of the cannula is inserted into the common duct from the opening of the common duct, and the cannula is further inserted through the confluence of the biliary duct and the pancreatic duct toward the direction of the biliary duct. Cannulation refers to insertion of a cannula into a body. A cannula is a medical tube that is inserted into a body for medical purposes.

Next, in the contrast radiography and imaging step, a contrast agent is injected into the cannula and poured into the biliary duct through the distal end of the cannula. By performing X-ray or CT imaging in this state, an X-ray image or a CT (Computed Tomography) image showing the biliary duct, gallbladder, and pancreatic duct can be obtained. The procedure of ERCP has been described. After the procedure, various treatments are performed according to the results of diagnosis based on the X-ray image or CT image. An example of the treatment is described below.

In a guide wire insertion step, a guide wire is inserted into a cannula so that the guide wire is protruded from the distal end of the cannula, and the guide wire is inserted into the biliary duct. In a cannula removing step, the cannula is removed while leaving the guide wire inside the biliary duct. As a result, only the guide wire protrudes from the distal end section of the endoscope, indwelling in the biliary duct. Next, in a treatment tool insertion step, the treatment tool is inserted into the biliary duct along the guide wire. An example of a treatment tool is a basket or stent. The basket is used with a catheter. While allowing the guide wire to pass through the catheter, the catheter is inserted into the biliary duct along the guide wire. A basket made of a plurality of metal wires is inserted into the biliary duct from the distal end of the catheter. An object to be removed, such as a gallstone, is placed in the basket and held, and the object to be removed is taken out from the biliary duct by removing the basket and catheter in this state from the biliary duct. A stent is also used in a similar manner with a catheter and inserted into the biliary duct from the distal end of the catheter. The narrow portion of the biliary duct can be widened by inserting a stent; further, by keeping the stent therein, the narrow portion is held in a widened state by the indwelling stent.

The procedure of ERCP is performed in the manner described above. However, in the cannulation step, in terms of the operator's field of view, the operator can only observe an endoscope image showing the papillary portion viewed from the outside. Therefore, it is difficult for the operator to predict the direction of the biliary duct or the pancreatic duct from this endoscope image. For example, the route of the biliary duct and of the pancreatic duct has individual differences, and it is difficult to predict the route. That is, it is difficult to specify the direction of cannulation or the insertion angle of the cannula by the endoscope image alone. Therefore, the operator has been required to perform cannulation while predicting the direction of the biliary duct relying on the feel in the hand based on his/her experience; that is, the procedure has been dependent on the operator's experience.

Display of Lumen Route Guide Image

In view of such circumstances, the present embodiment presumes (determines) route information of a lumen, which is at least one of the biliary duct or the pancreatic duct, based on an endoscope image. The present embodiment generates a display image, in which a route guide image to provide guidance of a route of a lumen leading to the papillary portion is superimposed on an endoscope image, based on the result of presumption of the route information of the lumen. In the following, at least one of the biliary duct and the pancreatic duct is referred to as a lumen, as necessary. The lumen may also be referred to as a luminal tissue or a luminal organ.

For example, FIG. 3 shows examples of classification patterns of the papillary portion and the endoscope images observed in the classification patterns. The classification patterns of the routes of the biliary duct and the pancreatic duct include, for example, the common channel type, the separate type, the onion type, and the septal type, as shown in FIG. 3. In the common channel type, the biliary duct and the pancreatic duct merge into a common duct at the confluence thereof, and the common duct opens to the papillary portion. In the separate type, the biliary duct and the pancreatic duct are separately open to the papillary portion and there is no confluence or common duct. In the onion type, the pancreatic duct is branched into two parts, and the biliary duct opens in the center of the opening of the two branched pancreatic ducts. In the septal type, the biliary duct and the pancreatic duct open to the papillary portion at their confluence, and there is no common duct. The common channel type is most common among the classification patterns of the papillary portion in patients; however, there are also patients having the separate type, the onion type, and the septal type. The classification patterns in the present embodiment are not limited to those in FIG. 3, and various types of classification patterns to classify the opening form of the papillary portion can be used, for example, those classified into individual type, gyrate type, annular type, villous type, unstructured type, and longitudinal type.

Figure 4:
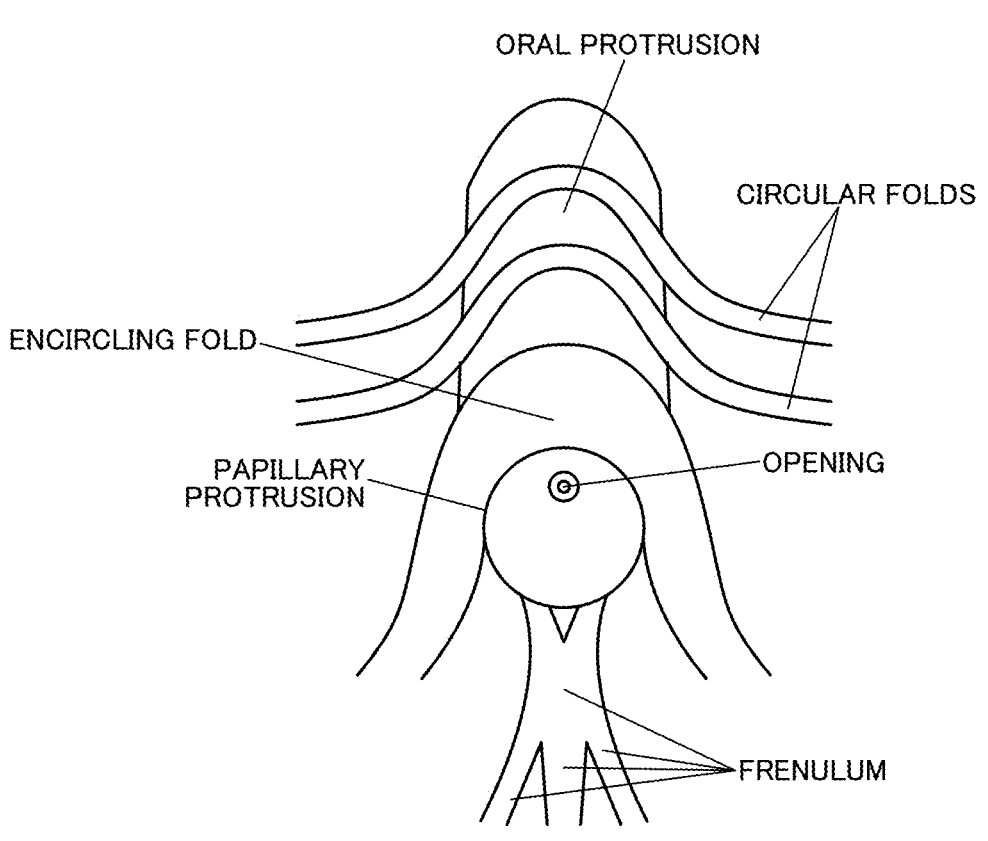
FIG. 4 is a schematic diagram of the form of papillary portion viewed directly from the front.
Figure 5:
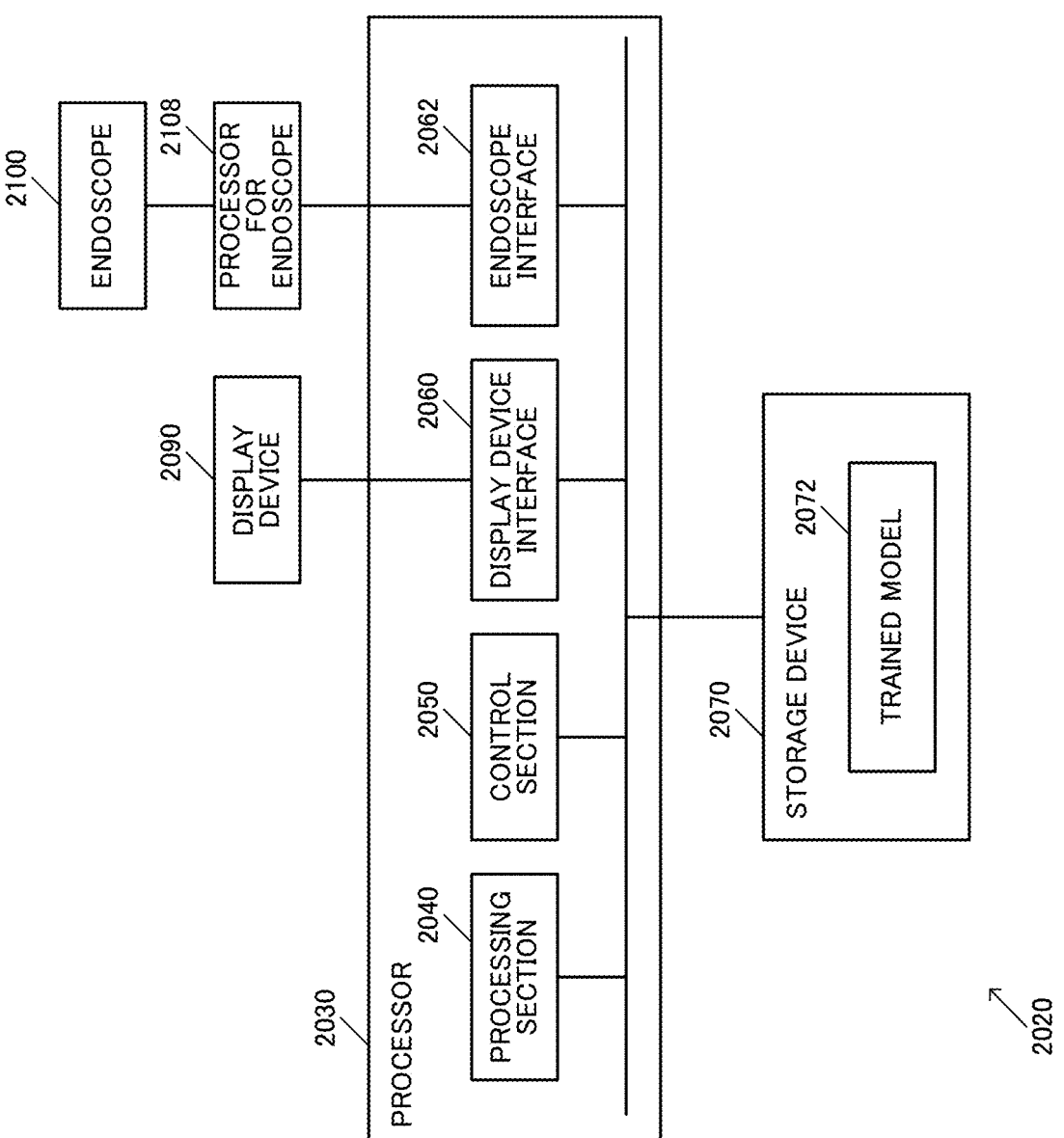
FIG. 5 shows a configuration example of an information processing system of the present embodiment.

FIG. 4 is a schematic diagram of the form of papillary portion viewed directly from the front. As shown in FIG. 4, structures peculiar to the papillary portion are present around the opening of the papillary portion. Specifically, structures called frenulum, papillary protrusion, encircling fold, circular fold, and oral protrusion are present around the opening, which is the main papilla. For example, in the case of the separate type in FIG. 3, the difficulty is low because intubation can be done by observing the papillary portion carefully and selecting the biliary duct. The difficulty is also relatively low for the onion type because the intubation into the biliary duct can be done by intubation into the opening in the middle of the papillary portion. However, the intubation for the common channel type and the septal type is more difficult than that for the separate type and the onion type. As shown in FIG. 3, there is a certain correlation between the endoscope image and the routes of the biliary duct and the pancreatic duct. Therefore, the present embodiment employs a method of presuming the route information of the biliary duct or the pancreatic duct based on an endoscope image obtained by an endoscope, and displaying a route guide image for providing guidance of the route presumed by the route information. FIG. 5 shows a configuration example of an information processing system 2020 for implementing the method of the present embodiment.

As shown in FIG. 5, the information processing system 2020 includes a processor 2030. The information processing system 2020 may also include a storage device 2070. The information processing system 2020 can be implemented, for example, by the control device 600 of the medical system 2010 described later with reference to FIG. 20. In this case, the medical system 2010 is implemented by the endoscope 100 and the information processing system 2020. In this case, for example, part or all of the information processing system 2020 may be implemented by the drive control device 2200 or the video control device 2500 in the control device 2600, or by an information processing device such as a personal computer (PC) provided in the control device 2600 separately from the drive control device 2200 and the video control device 2500. Alternatively, part or all of the information processing system 2020 may be implemented by for example, a server in a cloud system.

The processor 2030 includes hardware. The hardware of the processor 2030 may be implemented by a digital circuit that processes digital signals, or by a digital circuit and an analog circuit that processes analog signals. Further, the processor 2030 may be implemented by one or a plurality of circuit devices (IC) or one or a plurality of circuit elements mounted on a circuit board. Specifically, the processor 2030 may be implemented, for example, by a Central Processing Unit (CPU). However, the processor 2030 is not limited to CPU, and various processors such as a graphics processing unit (GPU) or a digital signal processor (DSP) may be used for the processor 2030. The processor 2030 may also be implemented by a hardware circuit such as an ASIC.

The storage device 2070 is a device for storing information, such as a memory. The storage device 2070 serving as a storage section may be implemented by a semiconductor memory such as SRAM or DRAM. The storage device 2070 may also be implemented by a magnetic storage device, such as a Hard Disk Drive (HDD), or by an optical storage device. The storage device 2070 serves, for example, as a work area for the processing executed by the processor 2030. For example, the storage device 2070 stores therein a computer-readable command, and the processes of the sections of the information processing system 2020 are implemented with the processor 2030 executing the command. The command herein may be a set of commands constituting a program, or may be a command for instructing an operation to a hardware circuit of the processor 2030.

The processor 2030 includes a processing section 2040. The processor 2030 may also include a control section 2050, a display device interface 2060, and an endoscope interface 2062. The processing section 2040 performs a process of presuming route information of a lumen, a process of generating a display image, and the like. The control section 2050 performs a control process of the electrically-driven endoscopic operation. The details of the processing section 2040 and the control section 2050 are described later.

The display device interface 2060 is a section for outputting the display image and performs an interface process with respect to the display device 2090. For example, the display image data generated by the processor 2030 is output to the display device 2090 via the display device interface 2060, and the display image is displayed on the display device 2090. The endoscope interface 2062 serves as an image acquisition section and performs an interface process with respect to the endoscope 2100. Specifically, the endoscope interface 2062 performs an interface process with an endoscope processor 2108, which performs various processes with respect to the endoscope 2100. For example, the processor 2030 acquires an endoscope image captured by the endoscope 2100 via the endoscope interface 2062. In this case, the endoscope processor 2108 performs various processes, such as image processing, with respect to the endoscope image. The endoscope processor 2108 is implemented, for example, by the video control device 2500 described later with reference to FIG. 20. The display device 2090 may be implemented by, for example, a liquid crystal display (LDC), an organic EL display, a CRT or the like. The details of the endoscope 2100 are described later.

Figure 6:
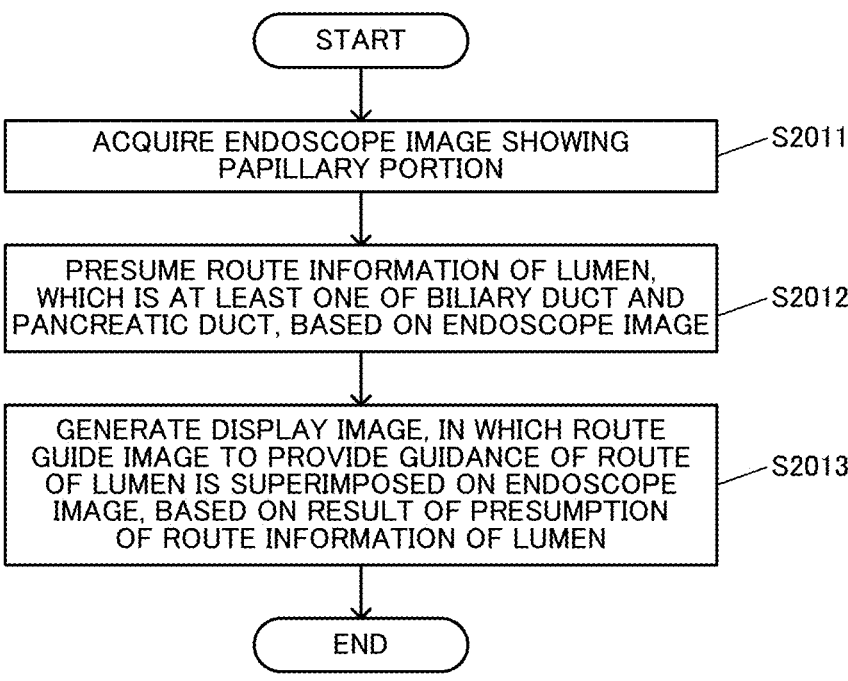
FIG. 6 is a flowchart for explaining the processing of the present embodiment.
Figure 7:
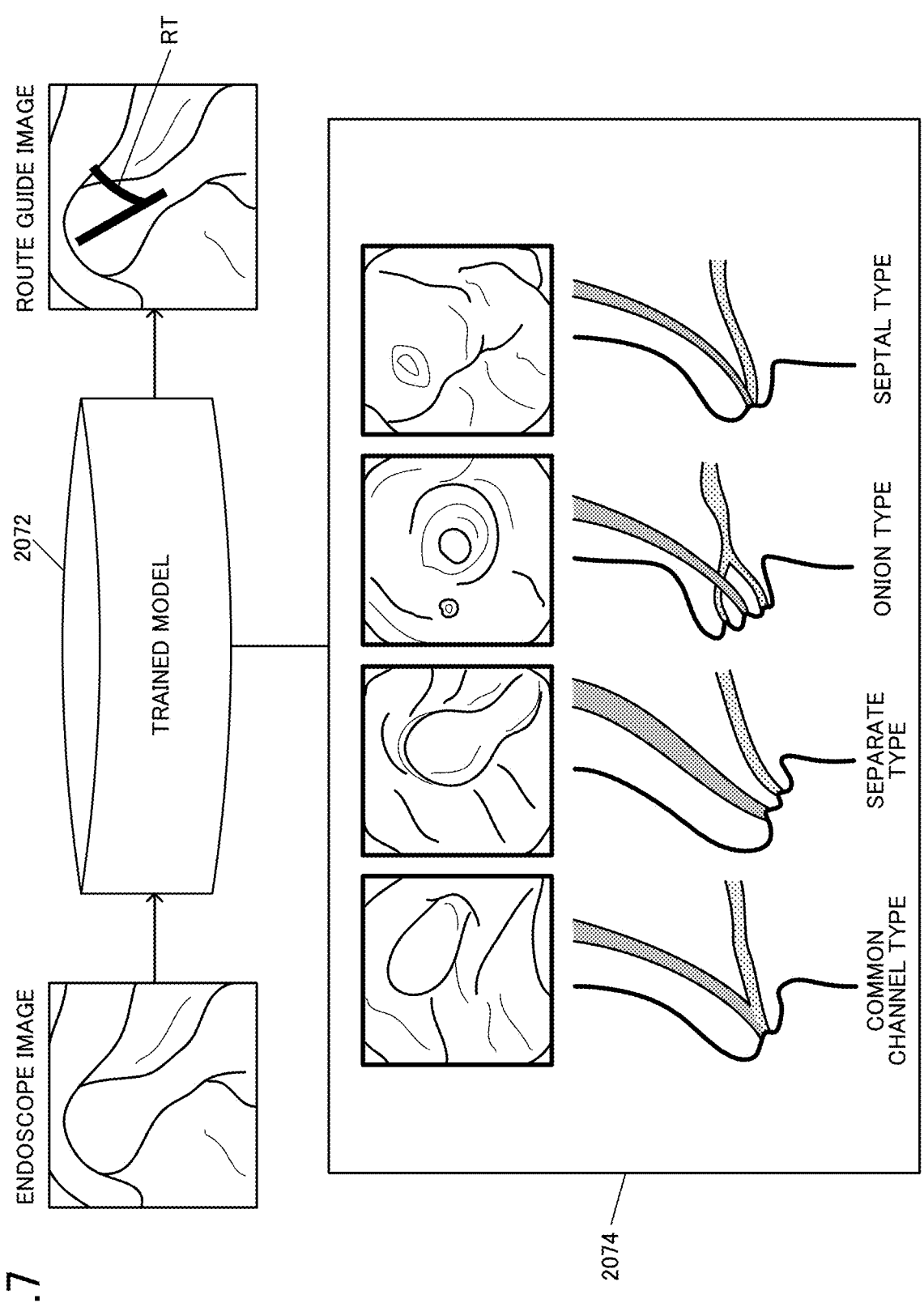
FIG. 7 is an explanatory view of the processing using a trained model.
Figure 8:
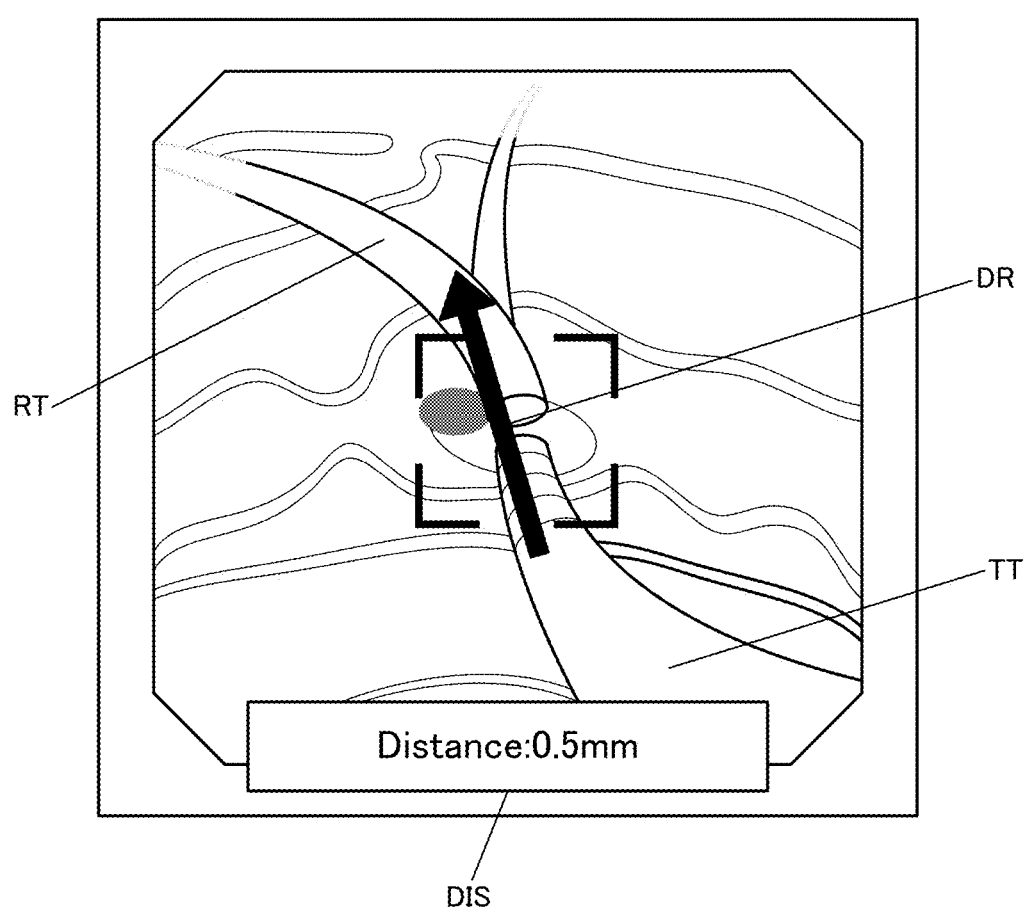
FIG. 8 is another example of a route guide image.

FIG. 6 is a flowchart for explaining the processing of the present embodiment. As shown in FIG. 6, the processor 2030 (the processing section 2040, the same hereafter) including hardware acquires an endoscope image showing the papillary portion from the endoscope 2100 (step S2011). For example, the processor 2030 acquires an endoscope image (endoscope video) captured by the endoscope 2100 via the endoscope interface 2062. The processor 2030 then performs processing of generating a display image to be displayed on the display device 2090, based on the acquired endoscope image. The generated display image is output to the display device 2090 by the display device interface 2060 and is displayed on the display device 2090. More specifically, the processor 2030 presumes route information of a lumen, which is at least one of the biliary duct and the pancreatic duct, based on the endoscope image (step S2012). The route information of a lumen is information to identify the route of the biliary duct or the pancreatic duct. The route information may be, for example, information to identify one of the route classification patterns shown in FIG. 3, or direction information, position information, shape information or the like of the lumen to identify the route of the lumen. The processor 2030 then generates a display image in which the route guide image is superimposed on the endoscope image based on the result of the presumption of the route information of the lumen (step S2013). The process of presuming the route information and the process of generating the display image are performed by the processing section 2040. The route guide image is an image to provide guidance of the route of the lumen (the biliary duct, the pancreatic duct) leading to the papillary portion. For example, as shown in FIG. 7 and FIG. 8 below, the route guide image is an image by which the operator visually recognizes the route of the lumen, or an image that displays various types of guide information necessary for the insertion of the treatment tool, such as the cannula, into the lumen. The display image in which the route guide image is superimposed on the endoscope image is a display image in which the route guide image visually overlaps with the endoscope image, which is a living body image.

For example, in the present embodiment, if the classification pattern presumed from the endoscope image is the common channel type shown in FIG. 3, a route guide image to guide the operator to perform the intubation up toward the 2011 to 12 o'clock direction is displayed. If the classification pattern is the separate type, a route guide image to guide the operator to perform the intubation by selecting, among the opening of the biliary duct and the opening of the pancreatic duct, the opening of the biliary duct is displayed. If the classification pattern is the onion type, a route guide image to guide the operator to perform the intubation substantially perpendicularly to the opening in the center of the concentric structure is displayed. If the classification pattern is the septal type, for example, a route guide image to guide the operator to perform the intubation by flipping up the 11:30 to 12 o'clock direction of the upper edge of the opening of the papillary portion is displayed.

Thus, in the present embodiment, the route information of the lumen, which is at least one of the biliary duct and the pancreatic duct, is presumed from the endoscope image showing the papillary portion, and the route guide image of the lumen is superimposed on the endoscope image. Therefore, the operator will be able to properly insert the treatment tool, such as the cannula, based on the route guide image superimposed on the endoscope image. In this way, it is possible to properly assist inexperienced operators and the like in the procedure of ERCP.

Further, as shown in FIG. 5, the storage device 2070 stores a trained model 2072. More specifically, the storage device 2070 stores the trained model 2072 trained to output the route information of a lumen, which is at least one of the biliary duct and the pancreatic duct, with respect to the endoscope image. The processor 2030 (processing section 2040) then presumes the route information from the endoscope image by the processing based on the trained model 2072. For example, the processor 2030 presumes the route information of a lumen based on the output information of the trained model 2072 in which the endoscope image has been entered.

In this way, by using the trained model 2072, it is possible to more accurately presume the route information of a lumen, thereby displaying a route guide image that allows for more appropriate guidance of the route of the lumen on the display device 2090.

The trained model 2072 used herein has been trained by machine learning using training data, and is implemented by, for example, a neural network or the like. For example, the trained model 2072 has been trained using the training data, which is a data set in which input data and correct answer data are associated with each other. For example, the storage device 2070 stores a program that describes an inference algorithm and parameters used for the inference algorithm, as the information of the trained model 2072. Then, the processor 2030 performs the processing based on the information of the trained model 2072. That is, the processor 2030 executes the process of presuming the route information of a lumen based on the endoscope image by executing the program using the parameters stored in the storage device 2070. For example, a neural network may be used as the inference algorithm. The weight coefficients of the inter-node connections in the neural network correspond to the parameters. The neural network includes an input layer to which input data is entered, an intermediate layer for performing a calculation process with respect to the data entered via the input layer, and an output layer for outputting a recognition result based on the calculation result output from the intermediate layer. The inference algorithm is not limited to a neural network, and various types of machine learning process for use in recognition process may be used. The trained model 2072 is generated by a learning device. The learning device generates the trained model 2072 by inputting the training data, which is also referred to as teacher data, into the trained model, and providing feedback to the trained model based on the inference result. The training data contains multiple sets of data, each set containing input data and correct answer data. The correct answer data is the inference result that is supposed to be provided in response to the input data. The correct answer data is prepared in advance, for example, by a medical service worker.

For example, the input data of the trained model 2072 in the present embodiment is the endoscope image from the endoscope 2100. As described later, the input data of the trained model 2072 may also be a MRCP image, an ultrasound image, a CT image, or the like. The correct answer data of the trained model 2072 is also the data for the presumption of the route information of a lumen. For example, the correct answer data is the information of classification pattern of the lumen route or the classification pattern of the papillary portion described in FIG. 3. The correct answer data may also be the direction information, position information, shape information or the like of the lumen identified by the MRCP image, the ultrasound image, or the CT image. Alternatively, the trained model 2072 may be trained to output the route guide image directly from the endoscope image, which is the input data. In this case, the trained model 2072 may be implemented by a Convolutional Neural Network (CNN) or the like.

FIG. 7 is an explanatory view of an example of the processing using the trained model 2072. In FIG. 7, the trained model 2072 has been trained by training data 2074 in which endoscope images (for learning) and classification patterns of the lumen route are associated with each other. For example, the trained model 2072 has been trained by the training data 2074 for which endoscope images are used as input data and the classification patterns, i.e., the common channel type, the separate type, the onion type, and the septal type, are used as the correct answer data. Therefore, upon the inference, if an endoscope image with the characteristics of the common channel type is input to the trained model 2072, information indicating that the classification pattern of lumen route is the common channel type is output from the trained model 2072. Similarly, when an endoscope image with the characteristics of the separate type, the onion type, or the septal type is input to the trained model 2072, information indicating that the classification pattern is the separate type, the onion type, or the septal type, respectively, is output from the trained model 2072. Then, a route guide image corresponding to each classification pattern is generated, and is superimposed on the endoscope image. For example, in FIG. 7, the lumen route image RT as the route guide image showing the routes of the biliary duct and the pancreatic duct are superimposed on the endoscope image. For example, in the case of the common channel type, the route guide image with the biliary duct, the pancreatic duct, and the common duct is generated as shown in FIG. 7. In the case of the separate type, a route guide image in which the biliary duct and the pancreatic duct are separated is generated. In the case of the onion type, a route guide image with one biliary duct and two pancreatic ducts is generated. In the case of the septal type, a route guide image with the biliary duct and the pancreatic duct without the common duct is generated.

Thus, in FIG. 7, the processor 2030 (processing section 2040) superimposes the lumen route image RT as the route guide image showing the routes of the biliary duct and the pancreatic duct on the endoscope image. The lumen route image RT is an image by which the operator can visually recognize what kind of route the biliary duct and the pancreatic duct have. In FIG. 7, the lumen route image RT is a marker image showing the routes of the biliary duct and the pancreatic duct. In this way, by viewing the lumen route image RT, the operator can visually identify what kind of route the biliary duct and the pancreatic duct have. This allows the operator to confirm the route of the biliary duct or the pancreatic duct in the back of the opening using the lumen route image RT in the endoscope image showing the papillary portion such as that shown in FIG. 4, thereby enabling intubation of the treatment tool, such as the cannula, from the opening. This allows even inexperienced operators and the like to easily perform the procedure of ERCP using the lumen route image RT as a guide.

FIG. 8 shows another example of a route guide image. In FIG. 8, the processor 2030 superimposes, as the route guide images, an image DIS showing the distance between the papillary portion and the distal end of the treatment tool TT of the endoscope, and an image DR showing the insertion direction of the treatment tool TT, on the endoscope image. In FIG. 8, the lumen route image RT is also displayed by being superimposed. The distance between the papillary portion and the distal end of the treatment tool TT may be acquired, for example, based on the parallax information of the endoscope images of a binocular endoscope, or by measuring the distance with a distance measuring sensor provided at the distal end section of the endoscope. The insertion direction of the treatment tool TT may be acquired by extracting it from the image of the treatment tool TT shown in the endoscope image, or by detecting the distal end position or the direction of the treatment tool TT by a sensor (not shown). In FIG. 8, both the image DIS showing the distance and the image DR showing the insertion direction are shown; however, it may be arranged such that only one of the images DIS and DR is shown.

Figure 9:
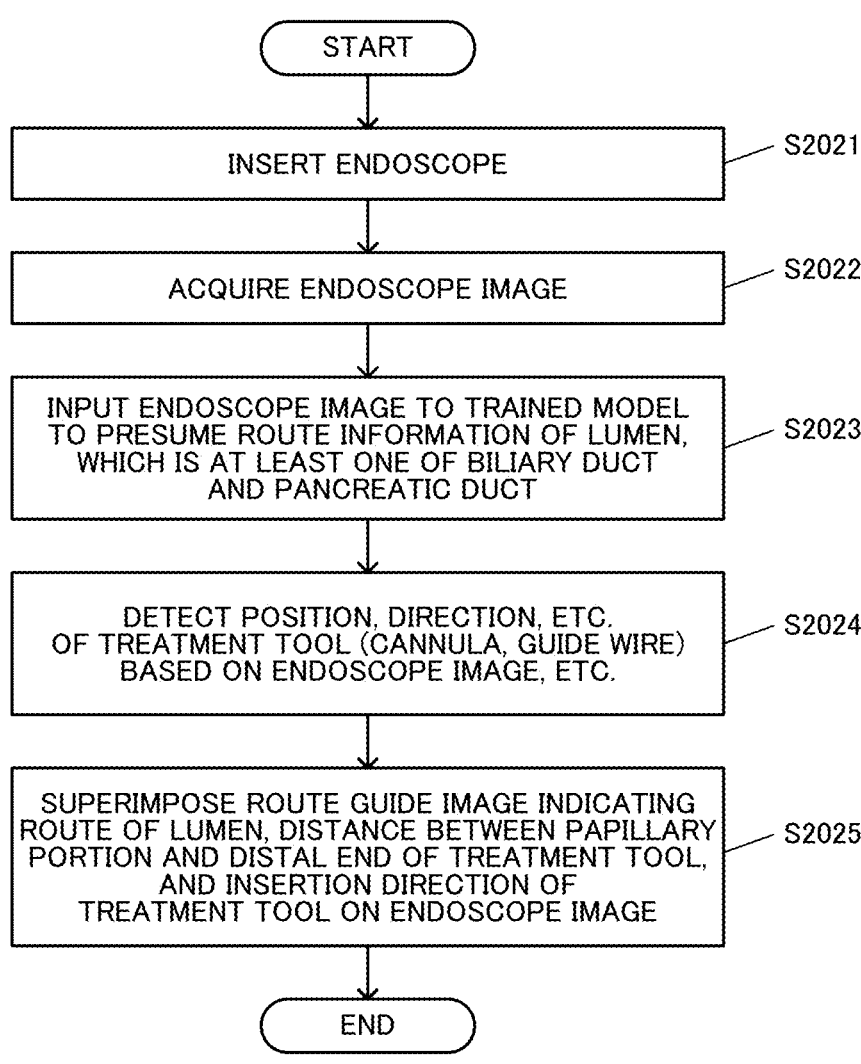
FIG. 9 is a flowchart for explaining the processing of the present embodiment when a trained model is used.

FIG. 9 is a flowchart for explaining the processing of the present embodiment when a route guide image in FIG. 8 is generated using the trained model 2072. First, an endoscope is inserted (step S2021), and the processor 2030 (processing section 2040) acquires an endoscope image (step S2022). Then, the processor 2030 inputs the endoscope image into the trained model 2072, followed by presumption of the route information of a lumen, which is at least one of the biliary duct and the pancreatic duct (step S2023). For example, it is possible to presume the route information of a lumen based on the information indicating the classification pattern of the route output from the trained model 2072. Further, the processor 2030 detects the position, direction, and the like of the treatment tool (cannula, guide wire) based on the endoscope image or the like (step S2024). Then, the route guide image indicating the route of the lumen, the distance between the papillary portion and the distal end of the treatment tool, and the insertion direction of the treatment tool is superimposed on the endoscope image (step S2025). As a result, the display image in which the route guide image is superimposed on the endoscope image, such as that shown in FIG. 8, is displayed on the display device 2090.

As shown above, in FIG. 8 and FIG. 9, the processor 2030 (processing section 2040) superimposes, as the route guide images, at least one of the image DIS showing the distance between the papillary portion and the distal end of the treatment tool TT of the endoscope, and the image DR showing the insertion direction of the treatment tool, on the endoscope image. For example, in FIG. 8, the text indicating the distance is displayed as the image DIS, and an arrow indicating the insertion direction (insertion angle) is displayed as the image DR. In this way, the operator can confirm the distance between the papillary portion and the distal end of the treatment tool TT of the endoscope by viewing the image DIS. This allows the operator to easy grasp how much the treatment tool TT should be moved to make the treatment tool TT reach the papillary portion. Further, by viewing the image DR, the operator easily grasps the direction to which the treatment tool TT is inserted. This allows the operator to easy grasp the direction in which the treatment tool TT should be inserted for proper intubation.

Further, the processor 2030 (processing section 2040) presumes the route information from the endoscope image by the processing based on the trained model 2072, and the trained model 2072 has been trained by the training data 2074 based on the classification pattern of the papillary portion. By using such a trained model 2072 trained by the training data 2074, it is possible to perform appropriate presumption of the lumen route according to the classification pattern of the papillary portion, thereby generating a route guide image reflecting the classification pattern. Therefore, for example, by superimposing an appropriate route guide image according to the classification pattern, which is widely used in the medical field, on the endoscope image, it is possible to assist the operator in the procedure of ERCP. The training data 2074 based on the classification pattern used herein is a data set of input data and correct answer data prepared using, for example, the classification data, to be used for the learning. For example, the training data 2074 in FIG. 7 is a data set in which the endoscope image is the input data and the classification pattern of the route of the papillary portion is the correct answer data, and the trained model 2072 has been trained by this data set. The papillary portion classification data may be the classification patterns of the route of the papillary portion, such as the common channel type, the separate type, the onion type, and the septal type, or the classification patterns of the opening in the papillary portion, such as the individual type, the gyrate type, the annular type, the villous type, the unstructured type, and the longitudinal type. Further, for example, the trained model 2072 implemented by CNN may be trained by training data in which the correct answer data is not the classification pattern itself but the route guide image based on the classification pattern.

As shown in FIG. 7, in the present embodiment, it is desirable to perform, but not limited to, presumption of the route information of a lumen using the trained model 2072. For example, it is possible to prepare a reference image for each classification pattern and determine the similarity between the reference image and the endoscope image, thereby presuming the route information of a lumen. For example, a first reference image for the common channel type, a second reference image for the separate type, a third reference image for the onion type, and a fourth reference image for the septal type are prepared. Then, the similarity between the endoscope image captured by the endoscope 2100 and the first to fourth reference images (the first to Nth reference images) is determined. For example, the similarity is determined by judging, for example, the degree of matching between the feature point of the endoscope image and the feature point of each of the first to fourth reference images. Then, based on the result of this similarity determination, the route information of a lumen is presumed. For example, the route information of a lumen is presumed by determining the similarity between the endoscope image and the first to fourth reference images and determining that the classification pattern of the route of the lumen in the endoscope image is the classification pattern corresponding to the reference image with the highest similarity.

It is also possible to use the first display device and the second display device as the display device 2090. It is also possible to set the first display region and the second display region in the display screen of the display device 2090 so that both the endoscope image, on which the route guide image of a lumen is superimposed, and the endoscope image, on which the route guide image of a lumen is not superimposed, are displayed. For example, the endoscope image on which the route guide image is superimposed is displayed on the first display device or the first display region, and the endoscope image on which the route guide image is not superimposed is displayed on the second display device or the second display region. This allows the operator to perform the procedure of ERCP while viewing both the endoscope image on which the route guide image is superimposed and the endoscope image on which the route guide image is not superimposed; therefore, the operator can proceed with each step of the procedure more appropriately and smoothly.

Use of MRCP Image

Figure 10:
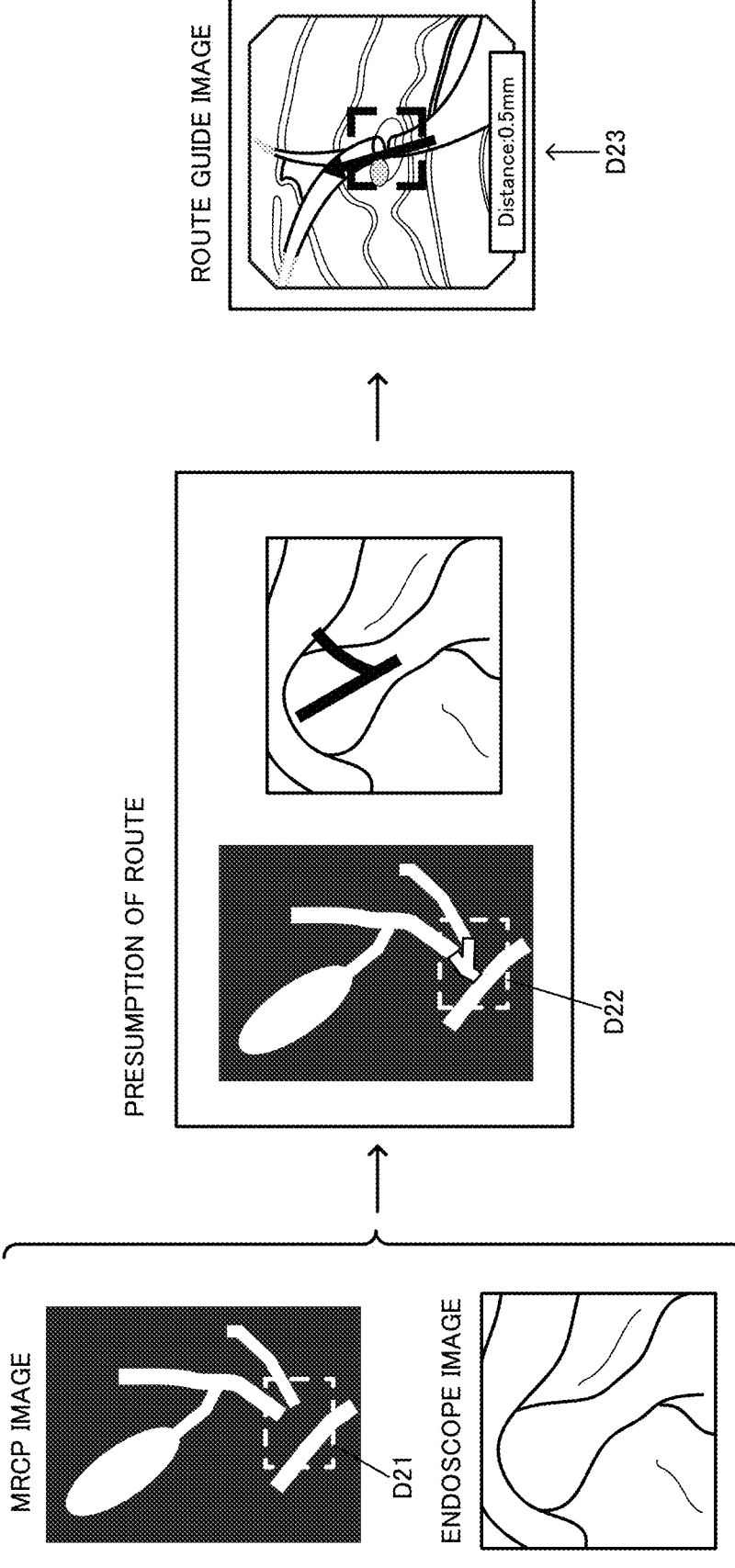
FIG. 10 is an explanatory view of the processing of the present embodiment when an MRCP image is used.
Figure 11:
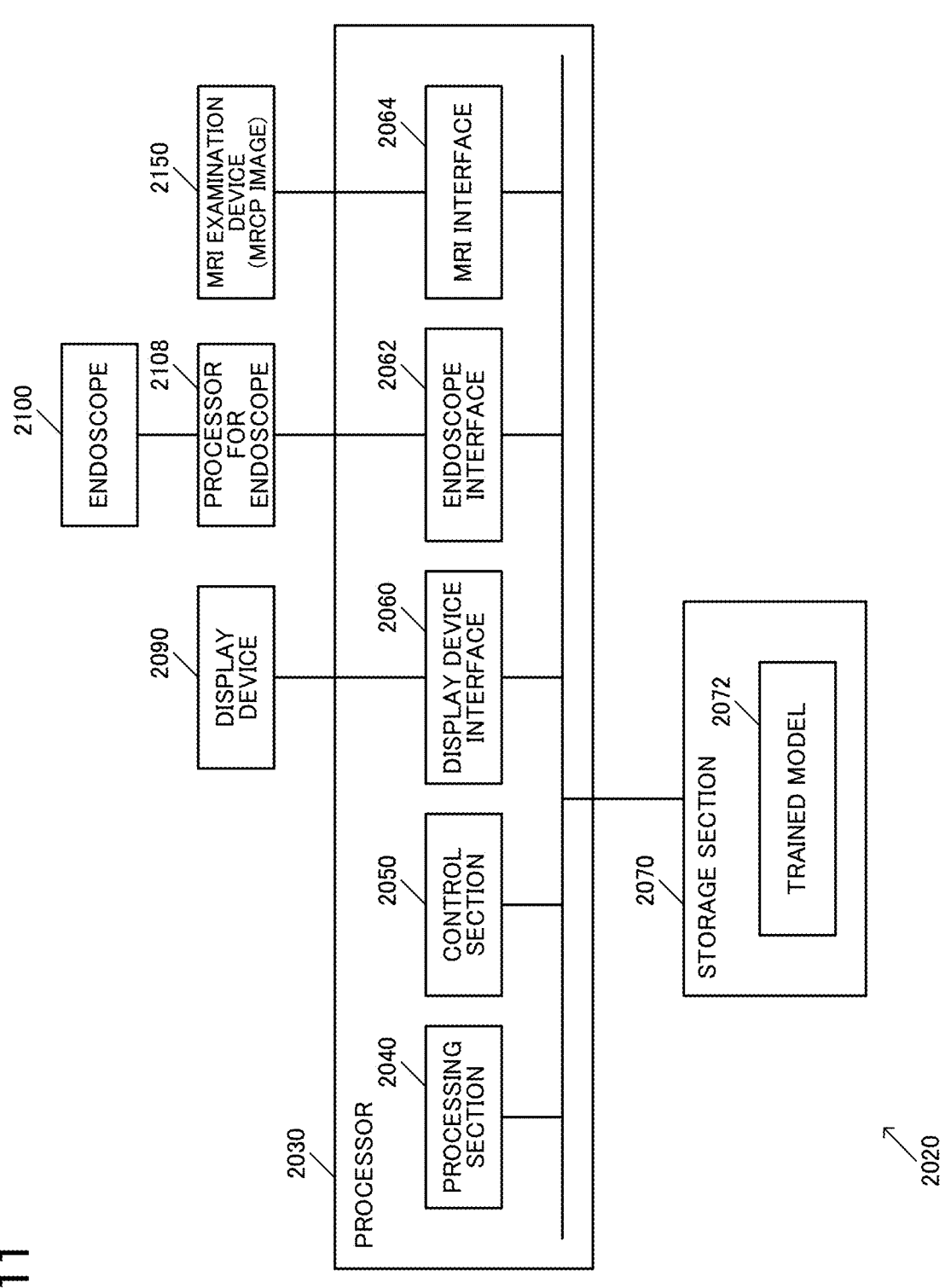
FIG. 11 is a configuration example of an information processing system of the present embodiment when an MRCP image is used.

Although the case where the route information of a lumen is presumed using the endoscope image captured by the endoscope 2100 was described above, the present embodiment is not limited to this case. As shown in FIG. 10, a route guide image may be generated by presuming the route information of a lumen using a MRCP image (MRCP: Magnetic Resonance Cholangio Pancreatgraphy), in addition to the endoscope image. FIG. 11 shows a configuration example of the information processing system 2020 of the present embodiment in this case. In FIG. 11, the processor 2030 includes an MRI interface 2064 for performing an interface process with respect to an MRI examination device 2150 (MRI: Magnetic Resonance Imaging), in addition to the components of FIG. 5. An MRCP image is an image acquired by the MRI examination device 2150. The processor 2030 acquires an MRCP image from the MRI examination device 2150 by the MRI interface 2064 serving as an image acquisition section. MRCP is an examination in which the gallbladder, the biliary duct, and the pancreatic duct are simultaneously extracted by the MRI examination device 2150.

As shown in FIG. 10, the presumption accuracy can be improved by presuming the route of the lumen using a combination of the MRCP image and the endoscope image. The MRCP image is, for example, an MRI image acquired before the surgery. By using the MRCP image, it is possible to acquire the route to the gallbladder. On the other hand, as shown in D21 in FIG. 10, the MRCP image has a drawback in that a lumen near the papilla cannot be clearly imaged. Therefore, in the MRCP image, the unclear region of D21, which is a region in which the image of the lumen cannot be captured is specified, and the route of the lumen in the unclear region is presumed based on the endoscope image. By thus using the endoscope image and the MRCP image in combination, it is possible to generate the route guide image such as that shown in D23 by complementing the route of the lumen in the unclear region of the MRCP image, as shown in D22 in FIG. 10. This improves the accuracy in the presumption of the route of a lumen. For example, in the regions other than the unclear region, more accurate route information of a lumen can be acquired by using an MRCP image.

Figure 12:
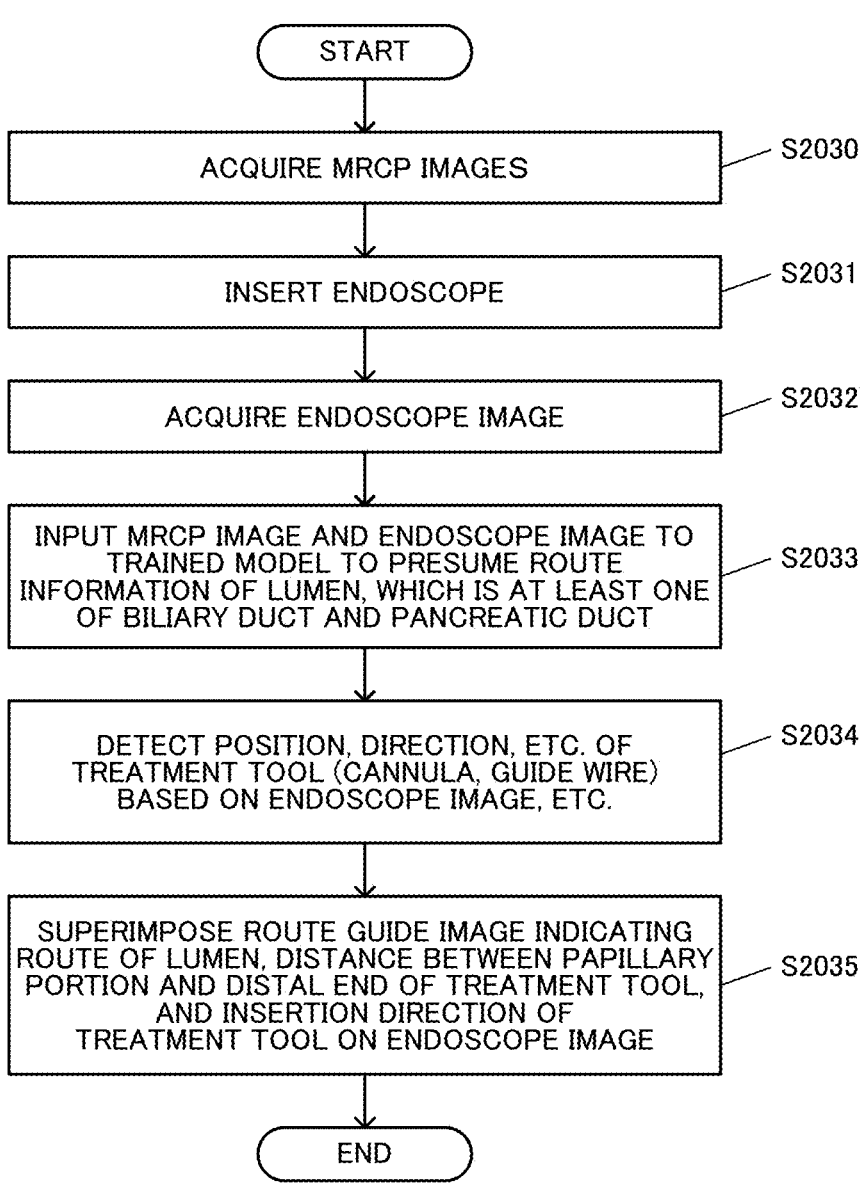
FIG. 12 is a flowchart for explaining the processing of the present embodiment when an MRCP image is used.

FIG. 12 is a flowchart for explaining the processing of the present embodiment when an MRCP image is used. First, the processor 2030 (processing section 2040) acquires an MRCP image, for example, before the surgery (step S2030). For example, the processor 2030 acquires an MRCP image of the patient from the MRI examination device 2150 via the MRI interface 2064. The endoscope 2100 is then inserted (step S2031) and the processor 2030 acquires an endoscope image (step S2032). Then, the processor 2030 inputs the endoscope image into the trained model 2072, followed by presumption of the route information of a lumen, which is at least one of the biliary duct and the pancreatic duct (step S2033). Further, the processor 2030 detects the position, direction, and the like of the treatment tool based on the endoscope image or the like (step S2034). Then, the route guide image indicating the route of the lumen, the distance between the papillary portion and the distal end of the treatment tool, and the insertion direction of the treatment tool is superimposed on the endoscope image (step S2035).

As described above, in the present embodiment, the trained model 2072 may be trained by the training data based on the MRCP image. By thus using the trained model 2072 having been trained by the training data based on the MRCP image, it is possible to perform inference using not only the endoscope image but also the MRCP image, thus improving the accuracy of presumption of the route of the lumen. The training data based on the MRCP image used herein is a data set of input data and correct answer data prepared using, for example, the MRCP image. For example, upon the training, the endoscope image and the MRCP image for the training are input into a model to be trained and feedback is given to the model based on the inference result, thereby generating the trained model 2072. Then, also upon the inference, the endoscope image and the MRCP image are input to the trained model 2072 to presume the route of the lumen, thus generating the route guide image. The MRCP image may also be used as the correct answer data for the training data at the time of training. For example, the endoscope image is input to the model to be trained, and it is determined whether or not the inference of the route of the lumen by the model is correct using the correct answer data based on the MRCP image. In this way, it is possible to generate the trained model 2072 capable of the inference of route of a lumen more accurately.

Further, in the present embodiment, the processor 2030 also acquires a MRCP image in which a part of a lumen is captured, as shown in D21 in FIG. 10. That is, in D21, not the whole lumen but only a part of the lumen is shown in the MRCP image; thus, the confluence tube near the papilla is not shown in the image. In this case, the processor 2030 presumes the route of the lumen between the part of the lumen and the papillary portion shown in the MRCP image based on the endoscope image and the MRCP image. Specifically, the processor 2030 presumes the route the lumen in the portion D22 between the part of the lumen and the papillary portion shown in the MRCP image. In this way, even if the image of the part of the lumen near the papilla is not clearly captured in the MRCP image, it is possible to complement this part of the image, thereby generating the route guide image such as that shown in D23, as well as the MRCP image in which the part is complemented. This makes it possible to provide an information processing system 2020 capable of generating a route guide image by performing more appropriate inference of the route of a lumen in the case where both the endoscope image and the MRCP image are used.

Specifically, the information processing system 2020 of the present embodiment further includes the storage device 2070 that stores the trained model 2072 trained to output the route information of a lumen with respect to the endoscope image and the MRCP image. The processor 2030 then presumes the route of the lumen between the part of the lumen and the papillary portion shown in the MRCP image using the endoscope image and the MRCP image by the process based on the trained model 2072. In this way, even if the image of the part of the lumen near the papilla is not clearly captured in the MRCP image, it is possible to complement this part of the image using the trained model 2072 in which the endoscope image and the MRCP image are input, thereby generating the route guide image such as that shown in D23, as well as the MRCP image in which the part is complemented. Also, by presuming the route of the lumen using the trained model 2072, it is possible to perform more accurate presumption of the route of the lumen.

When the MRCP image is used, the endoscope image on which the route guide image is superimposed may be displayed on the first display device or the first display region, and the MRCP image may be displayed on the second display device or the second display region. This allows the operator to use the route guide image as a guide for the procedure of ERCP, while confirming the route of the lumen with the MRCP image. In this case, in the MRCP image displayed on the second display device or the second display region, the route of the lumen in the unclear region may be complemented when displayed, as shown in D22 in FIG. 10. This allows the operator to more accurately identify the route of the lumen in the MRCP image.

Electrical Control of Endoscopic Operation

Figure 13:
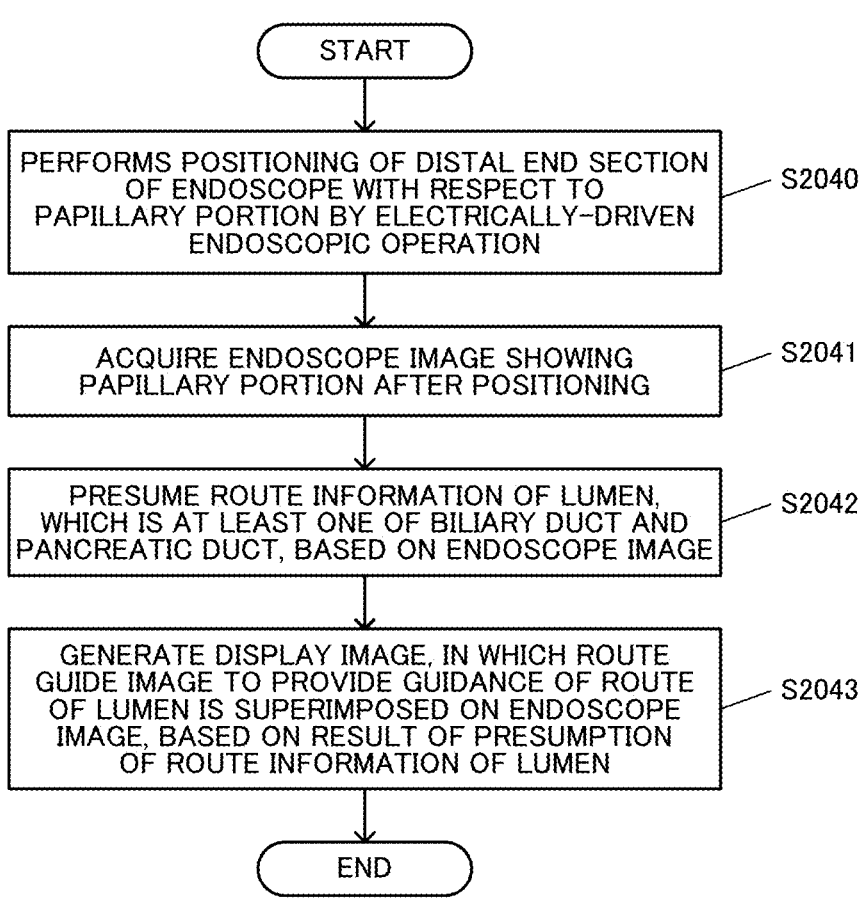
FIG. 13 is a flowchart for explaining the processing of the present embodiment when an electrically-driven endoscopic operation is performed.

As described later with reference to FIG. 20, in the present embodiment, an endoscope in which the endoscopic operation, which is at least one of forward and backward movement of an insertion section, a bending angle of a bending section of the insertion section, and rolling rotation of the insertion section, is electrically driven is used as the endoscope 2100. Then the processor 2030 performs positioning of the distal end section of the endoscope 2100 with respect to the papillary portion by, for example, the electrically-driven endoscopic operation, and generates a display image in which a route guide image is superimposed on an endoscope image based on the endoscope image acquired after the positioning. In this case, the positioning of the distal end section of the endoscope 2100 by the electrically-driven endoscopic operation is performed by the control section 2050, and the generation of the display image is performed by the processing section 2040. FIG. 13 is a flowchart for explaining the processing of the present embodiment when such an electrically-driven endoscopic operation is performed.

First, the processor 2030 (control section 2050; the same hereafter) performs the positioning of the distal end section of the endoscope 2100 with respect to the papillary portion by the electrically-driven endoscopic operation (step S2040). For example, as shown in FIG. 4, the positioning of the distal end section of the endoscope 2100 is performed so that the endoscope image is captured at a predetermined angle of view or in a predetermined imaging direction. For example, it may be possible to prepare a reference image for the positioning, determine the similarity between the endoscope image and the reference image, and perform positioning of the distal end section of the endoscope 2100 so that the endoscope image matches with the reference image as much as possible. The details of the positioning are described later. Then, the processor 2030 (processing section 2040) acquires an endoscope image in which the papillary portion is shown after the positioning of the distal end section of the endoscope 2100 (step S2041). That is, the processor 2030 acquires the endoscope image via the endoscope interface 2062. Then, the processor 2030 presumes the route information of a lumen, which is at least one of the biliary duct and the pancreatic duct, based on the endoscope image (step S2042). For example, as mentioned above, the processor 2030 presumes the route information using the trained model 2072. The processor 2030 then generates a display image in which the route guide image is superimposed on the endoscope image, which is used as a guide of the lumen route, based on the result of presumption of the route information of the lumen (step S2043).

As described above, in FIG. 13, the route guide image is generated by presuming the route information of a lumen based on the endoscope image acquired after the positioning of the distal end section of the endoscope 2100 by the electrically-driven endoscopic operation. By thus using the endoscope image acquired after the positioning by the electrically-driven operation, for example, the presumption of the route information of a lumen based on the endoscope image can be facilitated and the accuracy of the presumption can be improved. For example, if endoscope images at various angles of view or captured in various imaging direction are input to the trained model 2072 upon the inference of the route, it causes a problem of decrease in the inference accuracy. A problem may occur also upon the training such that an enormous number of endoscope images for training needs to be prepared to enable the presumption of the route information of a lumen for the endoscope images with various angles of view and the endoscope images captured in various imaging directions. In this regard, in FIG. 13, the presumption of the route of a lumen is performed based on the endoscope image acquired after the positioning by the electrically-driven endoscopic operation; therefore, the above problem can be prevented.

Figure 14:
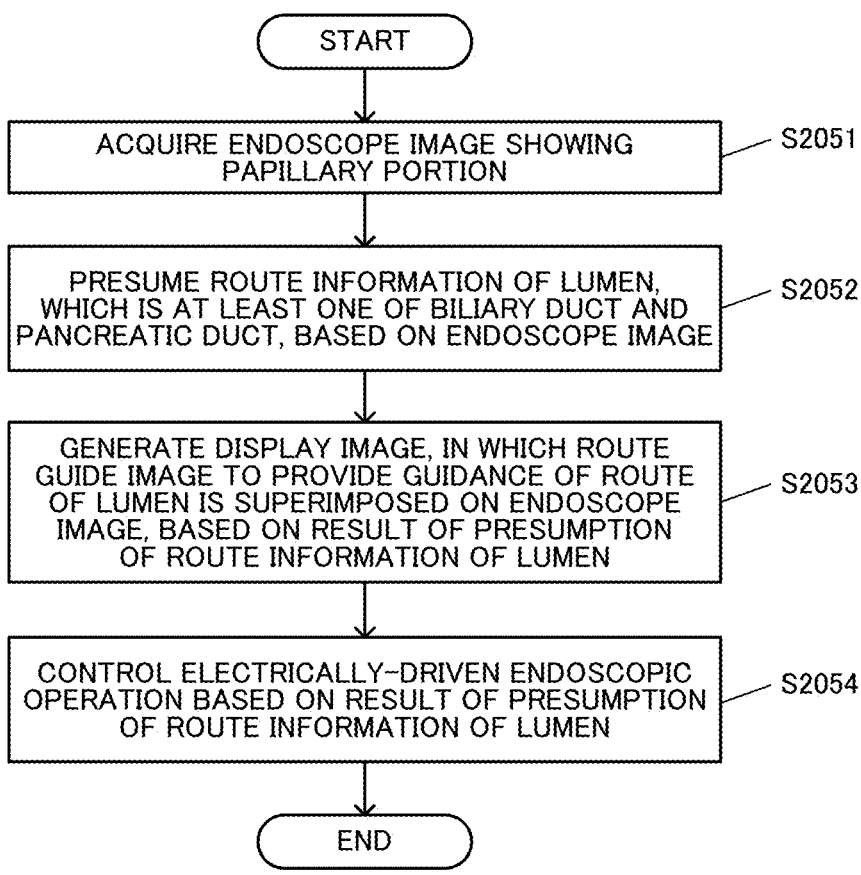
FIG. 14 is a flowchart for explaining the processing of the present embodiment when an electrically-driven endoscopic operation is performed.

Further, in the present embodiment, when an endoscope in which the endoscopic operation (which is at least one of forward and backward movement of an insertion section, a bending angle of a bending section of the insertion section, and rolling rotation of the insertion section) is electrically driven is used as the endoscope 2100, the processor 2030 (control section 2050) controls the electrically-driven endoscopic operation based on the result of presumption of the route information of a lumen. For example, the processor 2030 performs the step of inserting the treatment tool of the cannula etc. into the lumen of the biliary duct or the like by controlling the electrically-driven endoscopic operation based on the result of presumption of the route information of the lumen. In this case, the control of the electrically-driven endoscopic operation based on the result of presumption of the route information of a lumen is performed by the control section 2050. FIG. 14 is a flowchart for explaining the processing of the present embodiment when such an electrically-driven endoscopic operation is performed.

Since steps S2051, S2052, and S2053 in FIG. 14 are similar to steps S2041, S2042, and S2043 in FIG. 12, the detailed explanations of these steps are omitted. Before step S2051 in FIG. 14, the positioning of the distal end section of the endoscope may be performed by the electrically-driven endoscopic operation as in step S2040 in FIG. 13, and after the positioning, the endoscope image in which the papillary portion is shown may be acquired. Further, in FIG. 14, after step S2053, the processor 2030 (control section 2050) controls the electrically-driven endoscopic operation based on the result of presumption of the route information of the lumen (step S2054). That is, the endoscopic operation, which is at least one of the forward and backward movement of an insertion section of the endoscope 2100, a bending angle of a bending section of the insertion section, and rolling rotation of the insertion section, is electrically driven. For example, the electrically-driven endoscopic operation is controlled so that the treatment tool, such as the cannula, is inserted along the lumen such as the biliary duct.

In this way, it is possible to control the electrically-driven endoscopic operation by effectively utilizing the result of presumption of the route information of a lumen used for the generation of the route guide image. For example, as shown in FIG. 4, in the endoscope image showing the direct front of the papillary portion, the shape of the route of the lumen in the back of the opening is not visible to the operator. Therefore, intubation of the treatment tool, such as the cannula, into the opening and insertion of the treatment tool along, for example, the biliary duct requires a high skill of the operator. In this regard, by effectively utilizing the presumption result of the route information of a lumen used for the generation of the route guide image, it is possible to properly perform intubation of the treatment tool, such as the cannula, inserted into the opening along the shape of the lumen by the electrically-driven endoscopic operation based on the result of presumption of the route information of the lumen. For example, the insertion direction of the treatment tool, etc., can be controlled by the electrically-driven endoscopic operation, thus enabling more accurate intubation of the treatment tool. This makes it possible to appropriately assist inexperienced operators and the like, for example, in the intubation of the treatment tool during the procedure of ERCP.

Cannulation Method

Next, a cannulation method of the present embodiment is described below. FIG. 15 is a flowchart for explaining a cannulation method of the present embodiment. The cannulation method of the present embodiment is a cannulation method using an endoscope that electrically drives an endoscopic operation, which is at least one of the forward and backward movement of an insertion section, a bending angle of a bending section of the insertion section, and rolling rotation of the insertion section, and captures an endoscope image. As shown in FIG. 15, the cannulation method includes step S2061 of inserting the insertion section of the endoscope 2100 into a body. This step of inserting the insertion section may be performed by the electrically-driven endoscopic operation, or by manually and non-electrically inserting the insertion section into a body by the operator. The cannulation method also includes step S2062 of positioning the insertion section with respect to the papillary portion of the duodenum by the electrically-driven endoscopic operation. For example, by electrically controlling the forward and backward movement of the insertion section of the endoscope 2100, the bending angle of the bending section of the insertion section, or the rolling rotation of the insertion section, the positioning of the insertion section is performed so that the papillary portion of the duodenum is viewed in the direct front. The cannulation method also includes a step S2063 of presuming the route information of a lumen (which is at least one of a biliary duct and a pancreatic duct) based on the endoscope image of the endoscope 2100 with the positioned insertion section. Step 2063 also includes displaying a display image, in which a route guide image to provide guidance of the route of the lumen is superimposed on the endoscope image, based on the presumed route information of the lumen. That is, according to the method described in FIG. 3 to FIG. 14, etc., the route information of a lumen is presumed, and the display image in which the route guide image is superimposed on the endoscope image is displayed on the display device 2090. The cannulation method further includes step S2064 of inserting a cannula into the biliary duct. This step of inserting the cannula into the biliary duct may be performed by the electrically-driven endoscopic operation, or by manually and non-electrically inserting the cannula into the biliary duct by the operator.

According to the cannulation method of the present embodiment described above, the positioning of the insertion section with respect to the papillary portion of the duodenum is performed by the electrically-driven endoscopic operation. Then, the route information of a lumen is presumed based on the endoscope image acquired after the positioning, and the display image in which the route guide image is superimposed on the endoscope image is displayed, allowing insertion of the cannula into the biliary duct. As is clear from the above, since the route information of a lumen can be presumed based on the endoscope image that is captured at more appropriate angle of view or in more appropriate imaging direction, etc., the presumption accuracy can be improved. Further, since the display image in which the route guide image is superimposed on the endoscope image is displayed, it is possible to facilitate the insertion of the cannula into the biliary duct. This makes it possible to appropriately assist inexperienced operators and the like, for example, in the intubation of cannula during the procedure of ERCP.

As described later with reference to FIG. 20, the medical system 2010 of the present embodiment includes the information processing system 2020 and the endoscope 2100. The present embodiment may also be embodied as a method of operating the medical system 2010. The method of operating the medical system 2010 is a method for operating the medical system 2010 including the endoscope 2100 that electrically drives an endoscopic operation, which is at least one of the forward and backward movement of an insertion section, a bending angle of a bending section of the insertion section, and rolling rotation of the insertion section, and captures an endoscope image. The operating method includes a step of performing positioning of the insertion section with respect to the papillary portion of the duodenum by the electrically-driven endoscopic operation, a step of presuming the route information of a lumen, which is at least one of a biliary duct and a pancreatic duct, based on the endoscope image of the endoscope 2100 with the insertion section having been positioned, and a step of displaying a display image in which the route guide image to provide guidance of the route of the lumen is superimposed on the endoscope image based on the presumed route information of the lumen.

Modifications

Figure 16:
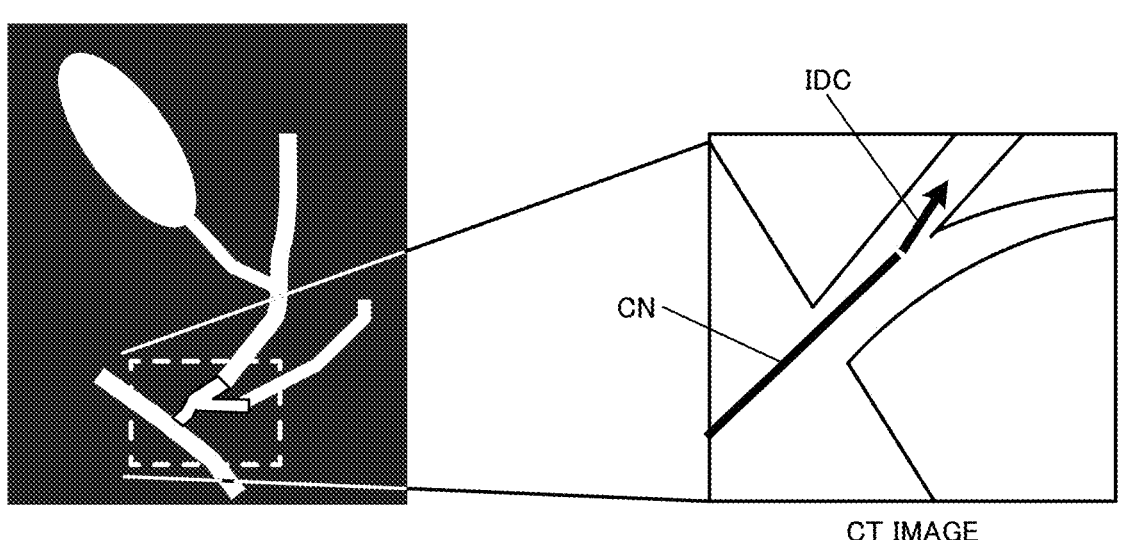
FIG. 16 is an explanatory view of the processing of the present embodiment when a CT image is used.

Various modifications of the present embodiment are described below. For example, in the present embodiment, CT images (CT: Computed Tomography) may be used, in addition to endoscope images and MRCP images. For example, as shown in FIG. 16, an indicator IDC, such as an arrow indicating the direction of the biliary duct, may be displayed on a CT image obtained before the surgery. In this case, if the position of the cannula CN can be detected in real time, the position and the direction of the indicator IDC may be updated in real time according to the position of the cannula CN. It is also possible to display an alert when the cannula CN moves not in the direction of the biliary duct but in the direction of the pancreatic duct. Examples include various types of alert, such as display on the screen, sound, vibration, and a combination of these. Further, the presumption of the route information of a lumen may be performed using the direction information, position information, shape information or the like of the lumen detected from the CT images. For example, the presumption of the route information of a lumen may be performed using the trained model 2072 trained by the training data based on the CT images.

It is also possible to use ultrasound images obtained by an ultrasound endoscope, as shown in FIG. 17. For example, an ultrasound endoscope is inserted into the body to obtain ultrasound images at multiple positions around the papillary portion of the duodenum. Then, using these ultrasound images, the route information of a lumen is presumed. By thus using the ultrasound images, it is possible to presume the route information of a lumen with high accuracy in generating the route guide image.

Figure 18:
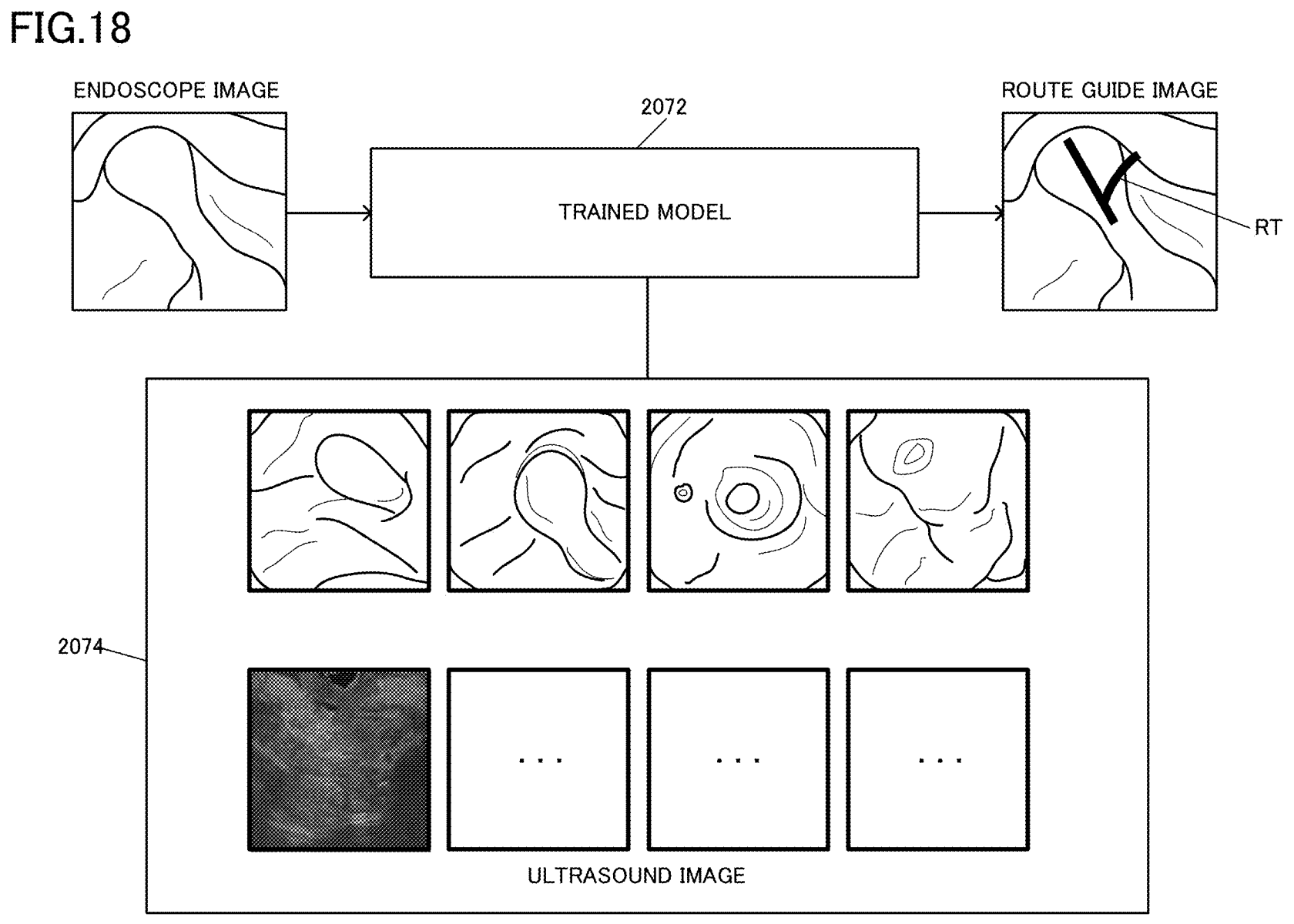

Specifically, as shown in FIG. 18, the trained model 2072 trained by the training data 2074 based on the ultrasound image is used. Then, the route information of a lumen is presumed by using the trained model 2072 thus trained, thereby generating the route guide image. By thus using the trained model 2072 trained by the training data 2074 based on the ultrasound image, it is possible to perform inference using not only the endoscope image but also the ultrasound image, thus improving the accuracy in the presumption of the route of a lumen. The training data 2074 based on ultrasound image herein is a data set of input data and correct answer data prepared for the training using, for example, ultrasound images. For example, upon the training, the endoscope image and the ultrasound image for the training are input into a model to be trained and feedback is given to the model based on the inference result, thereby generating the trained model 2072. Then, also upon the inference, the endoscope image and the ultrasound image are input to the trained model 2072 to presume the route of the lumen, thus generating the route guide image. The ultrasound image may also be used as the correct answer data for the training data 2074 at the time of training. For example, the endoscope image is input to the model to be trained, and it is determined whether or not the inference of the route of the lumen by the model is correct based on the shape of the lumen or the like shown in the ultrasound image, which is the correct answer data. In this way, it is possible to generate the trained model 2072 capable of the inference of route of a lumen more accurately.

In this case, the endoscopic operation by the ultrasound endoscope may be controlled by electrical driving. For example, by performing the positioning of the ultrasound endoscope and the positioning of the normal endoscope by electrical driving, it is possible to set the ultrasound endoscope and the endoscope so that they have a similar positional relationship with respect to the papillary portion, thereby enabling the ultrasound image and the endoscope image of the papillary portion to be captured at a similar angle of view or in a similar imaging direction. It also becomes easy to associate the endoscope image with the direction information, position information, or shape information of the lumen obtained from the ultrasound image.

Figure 19:
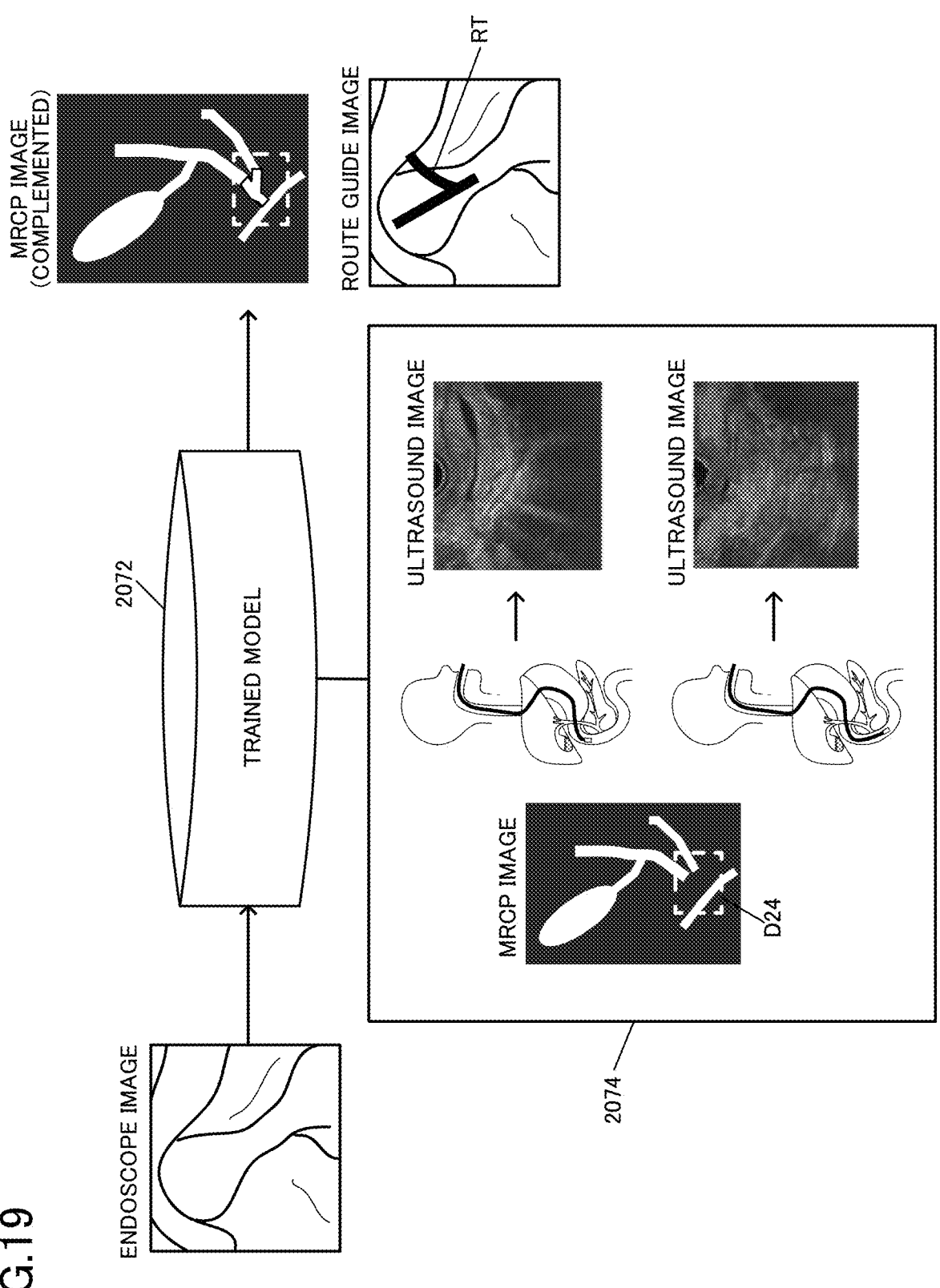
FIG. 19 is an explanatory view of the processing of the present embodiment when an MRCP image and an ultrasound image are used.

Further, in FIG. 19, the training of the trained model 2072 is performed by the training data 2074 based on the MRCP image, which is obtained by the MRI examination device 2150, and the ultrasound image, which is obtained by the ultrasound endoscope. For example, the route information of a lumen in the unclear region shown in D24 of the MRCP image is complemented based on the direction information, position information, shape information or the like of the lumen obtained from the ultrasound image. For example, the endoscope image, the MRCP image, and the ultrasound image are input to the trained model 2072 to presume the route information of a lumen, thus generating a display image in which the route guide image of a lumen is superimposed on the endoscope image. In this case, for example, the display image in which the route guide image is superimposed on the endoscope image may be displayed on the first display device or in the first display region and the MRCP image may be displayed on the second display device or in the second display region. The ultrasound image may also be displayed on the third display device or in the third display region. The second display device or the second display region shows, for example, the MRCP image in which the route of the lumen in the unclear region shown in D24 in FIG. 19 is complemented. This allows the operator to perform the procedure of ERCP while viewing the endoscope image on which the route guide image is superimposed, the MRCP image in which the route is complemented, and the ultrasound image; therefore, the operator can proceed with each step of the procedure more appropriately and smoothly.

Medical System

The medical system of the present embodiment is described below. When cannulation into the biliary duct is performed, it is performed by referring to an endoscope image showing the papillary portion. As described with reference to FIGS. 3 and 4, there are various forms of papillary portion and luminal tissue, and it is difficult to specify the insertion position and insertion direction of the cannula from the endoscope image.

On the other hand, the operator estimates the position of the opening and the traveling direction of the biliary duct based on past cases, experiences, and the like while viewing the endoscope image, and tries to insert the cannula from the opening into the biliary duct according to the estimation. At this time, in order to more accurately estimate the position of the opening and the traveling direction of the biliary duct, it is desirable that the position of the papillary portion in the image and the angle of view of the image are easy to compare with those in the past cases or are familiar to the operator.

As shown in FIG. 1, such positioning of the endoscope is performed by operating the distal end of the endoscope insertion section reaching the duodenum from outside the body. However, since the insertion section and the organ through which the insertion section passes are flexible, the operation performed at the base end of the insertion section is not easily transmitted to the distal end section. In addition, since the distal end section of the endoscope is not fixed to the duodenum and floats in the air, the distal end section of the endoscope is not stable with respect to the papillary portion, and the positional relationship between the distal end section and the papillary portion is not easily determined. For these reasons, it is difficult to adjust the position of the distal end section of the endoscope so that the field of view of the endoscope is facing directly front of the papillary portion or so that the papillary portion appears in the center of the field of view.

Therefore, in the present embodiment, the above-described positioning is automated by an electric medical system to assist the ERCP procedure. Further, by adding a configuration in which the insertion section of the endoscope is held in the duodenum, the electrically-driven force can be easily transmitted to the distal end section of the endoscope and the position of the distal end section can be desirably controlled. The details of this structure are described below.

Figure 20:
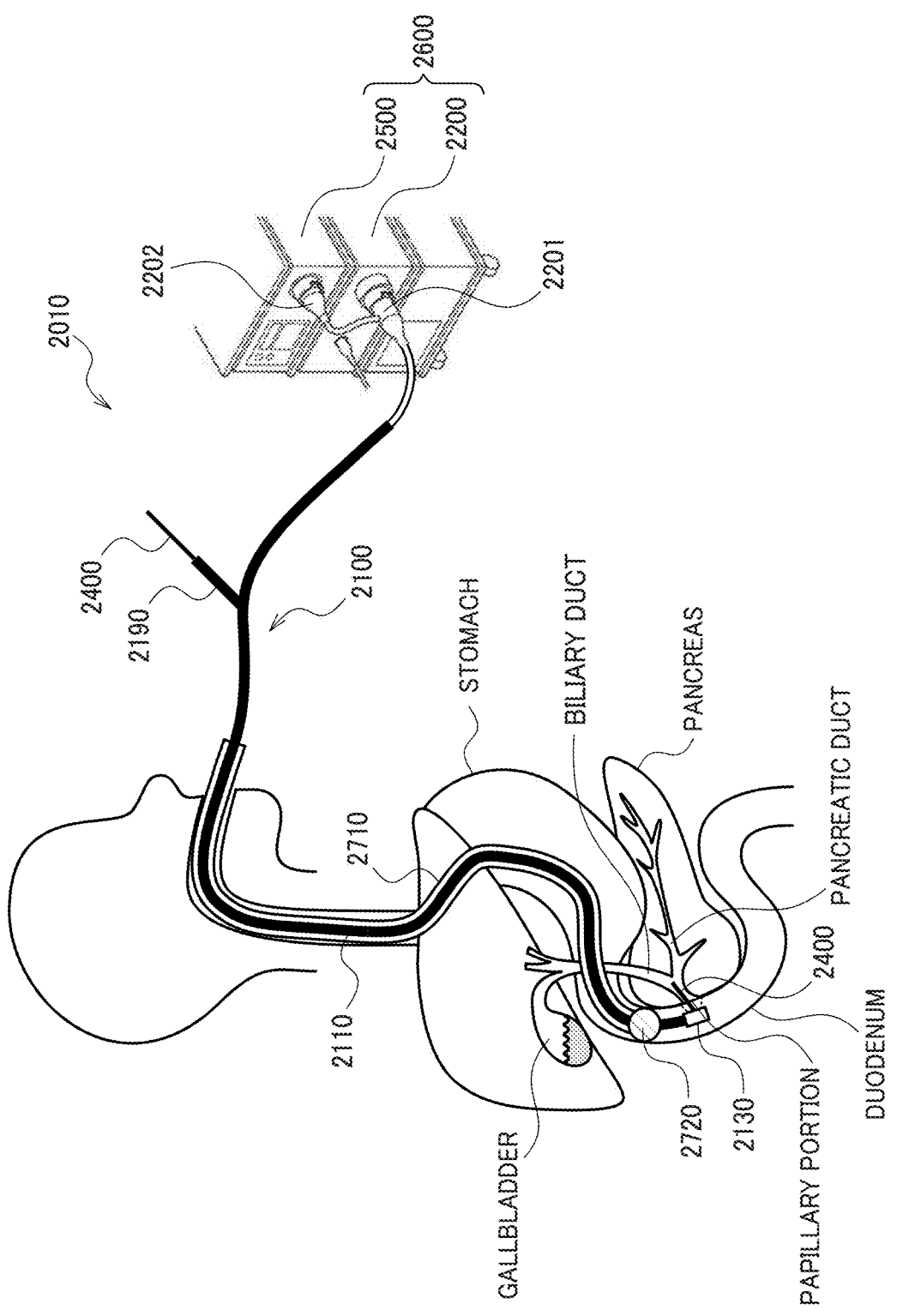
FIG. 20 shows a configuration example of a medical system of the present embodiment.

FIG. 20 shows a configuration example of a medical system 2010 according to the present embodiment. The medical system 2010 includes an endoscope 2100 and a control device 2600. Further, the medical system 2010 may include an overtube 2710, a balloon 2720, and a treatment tool 2400. The medical system 2010 is also referred to as an endoscope system or an electric endoscope system. The information processing system 2020 described in FIG. 5 and FIG. 11 may be implemented, for example, by the hardware of the control device 2600 in FIG. 20. As described above, the medical system 2010 of the present embodiment includes the information processing system 2020 implemented by the control device 2600, and the endoscope 2100.

The overtube 2710 is a tube with a variable hardness that covers the insertion section 2110 of the endoscope 2100. The balloon 2720 is provided near the distal end on the outer side of the overtube 2710. When the endoscope 2100 and the overtube 2710 are inserted into the body, at least the bending section of the insertion section 2110 is exposed from the distal end of the overtube 2710. The bending section refers to a section structured to be bent at an angle corresponding to the bending operation in the vicinity of the distal end of the insertion section 2110. The base end of the overtube 2710 is present outside the body. The base end side of the insertion section 2110 is exposed from the base end of the overtube 2710.

An insertion opening 2190 of the treatment tool is provided at the base end side of the insertion section 2110, and a treatment tool channel for allowing the treatment tool 2400 to pass through from the insertion opening 2190 to the opening of the distal end section 2130 is provided inside the insertion section 2110. The insertion opening 2190 of the treatment tool is also called a forceps opening; however, the treatment tool to be used is not limited to forceps.

The endoscope 2100 is detachably connected to a control device 2600 using connectors 2201 and 2202. The control device 2600 includes a drive control device 2200 to which the connector 2201 is connected, and a video control device 2500 to which the connector 2202 is connected. The drive control device 2200 controls the electrical driving of the endoscope 2100 via the connector 2201. Although not shown in FIG. 20, an operation device for manually operating the electrical driving may be connected to the drive control device 2200. The video control device 2500 receives an image signal from a camera provided at the distal end section 2130 of the endoscope 2100 via the connector 2202, generates a display image from the image signal, and displays it on a display device (not shown). In FIG. 20, the drive control device 2200 and the video control device 2500 are shown as separate devices, but they may be structured as a single device. In this case, the connectors 2201 and 2202 may be integrated into a single connector.

Figure 21:
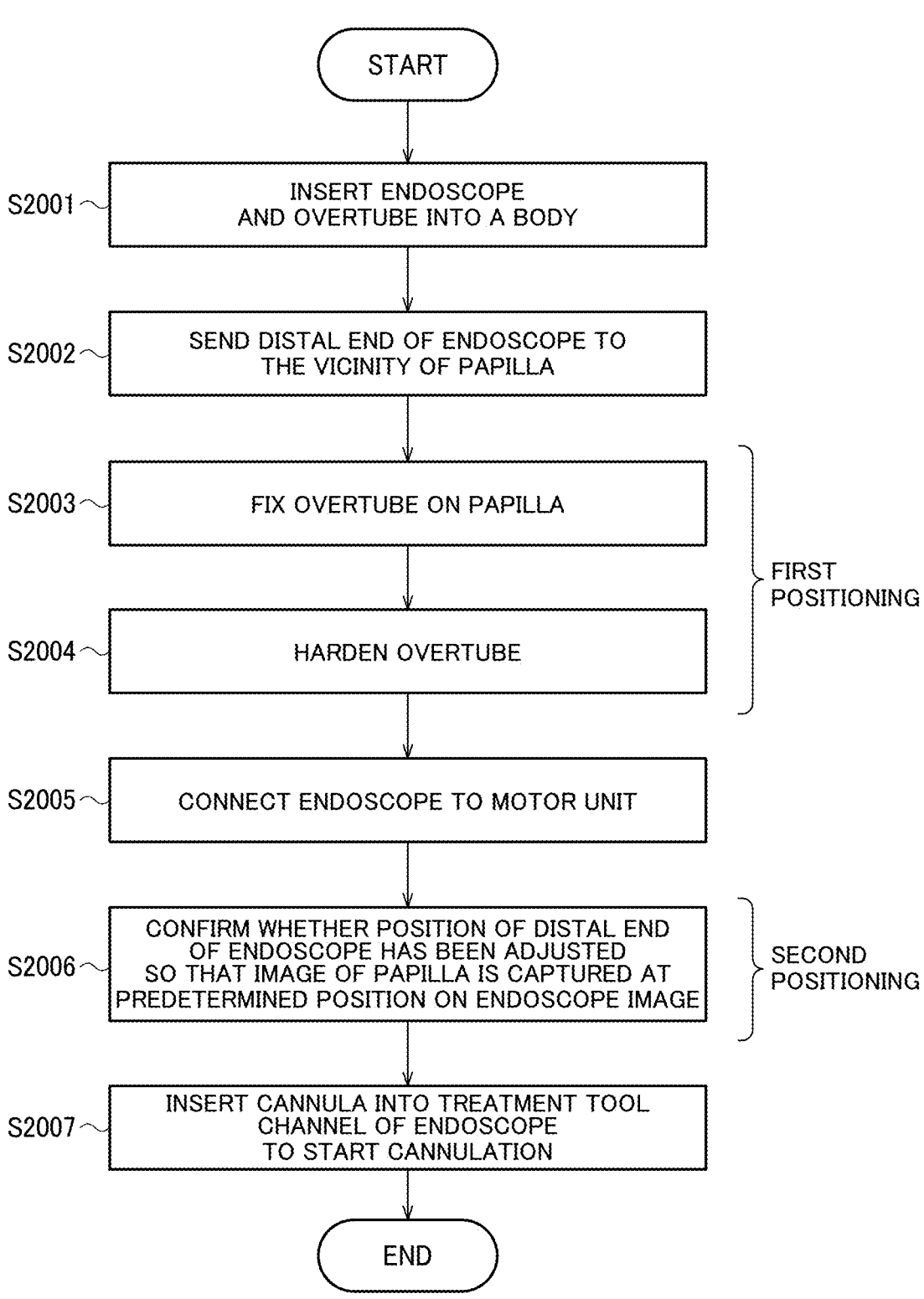
FIG. 21 is a flowchart of the procedure according to the present embodiment.

FIG. 21 shows a flowchart of the procedure in the present embodiment. Here, an electric endoscope is assumed in which the forward and backward movement of the insertion section 2110 of the endoscope 2100, the bending of the bending section of the insertion section 2110, and the rolling rotation of the insertion section 2110 are electrically driven. However, it is sufficient that at least one of these functions is electrically driven. The term "electrical driving" means that the endoscope is driven by a motor or the like based on an electrical signal for controlling the endoscopic operation. For example, when the electrical driving is manually operated, an operation input to the operation device is converted into an electrical signal, and the endoscope is driven based on the electrical signal. In the following, the forward and backward movement may be simply referred to as "forward/backward movement".

In step S2001, the operator inserts the insertion section 2110 of the endoscope 2100 and the overtube 2710 into the duodenum. More specifically, in a state where the insertion section 2110 is inserted into the overtube 2710, the insertion section 2110 and the overtube 2710 are inserted into the duodenum together. The overtube 2710, which is changeable in hardness, is soft in step S2001. For example, the operator can move the insertion section 2110 and the overtube 2710 forward by a non-electrically-driven manual operation so that they are inserted into the body. The non-electrical driving means that the endoscope 2100 is not electrically driven by a motor or the like, instead, the force applied to the operation section is directly transmitted to the endoscope by a wire or the like, thereby operating the endoscope. For example, in the present embodiment, steps S2001 to S2004 are not electrically driven. In this case, it is sufficient that at least the forward/backward movement is not electrically driven, and the bending, the rolling rotation, or both may be manually operated by electrical driving.

In step S2002, the operator inserts the insertion section 2110 until the distal end section 2130 reaches the vicinity of the papillary portion. For example, when the operator manually inserts the insertion section 2110 by non-electrical driving, the operator inserts the insertion section 2110 until the papillary portion becomes visible in the endoscope image. At this point, the distal end of the endoscope 2100 does not need to accurately reach the papillary portion; the distal end of the endoscope 2100 may reach a position before the papillary portion or past the papillary portion.

In step S2003, the operator fixes the distal end of the overtube 2710 to the duodenum. As an example, the operator performs an operation to inflate the balloon 2720 provided near the distal end of the overtube 2710, and fixes the distal end of the overtube 2710 to the duodenum by the balloon 2720. In step S2004, the operator performs an operation to harden the overtube 2710. At this time, the overtube 2710 is hardened while maintaining its shape in a state immediately before hardening, that is, the shape when it is inserted from the mouth to the duodenum. As a result, the insertion section 2110 is held by the hardened overtube 2710 and the balloon 2720, thereby fixing the insertion route of the insertion section 2110. These steps S2003 and S2004 are referred to as first positioning.

In step S2005, the endoscope 2100 is connected to the motor unit, and the non-electrical driving is switched to the electrical driving. The method of switching between the non-electrical driving and the electrical driving varies depending on the configuration of the drive mechanism. For example, in steps S2001 to S2004, the forward/backward movement may be non-electrically driven and the bending and the rolling rotation may be electrically driven. In this case, the forward/backward movement may be switched from the non-electrical driving to the electrical driving by connecting the endoscope 2100 to the forward/backward drive device (not shown). Further, when the bending operation by non-electrical driving is enabled by providing a bending operation dial or the like capable of non-electrically performing the bending operation, the bending movement may be switched from the non-electrical driving to the electrical driving, for example, by connecting the connector 2201 to the drive control device 2200. Alternatively, even if the motor unit is kept connected, the motor may be structured to be detachable by a clutch mechanism or the like, and the non-electrical driving may be switched to the electrical driving by the clutch mechanism. Step S2005 may be performed before step S2001. For example, when the forward/backward movement is manually operated by electrical driving, the endoscope 2100 may be connected to the motor unit before step S2001.

In step S2006, the drive control device 2200 automatically positions the distal end section 2130 at the papillary portion, and the operator confirms that the position of the distal end section 2130 has been adjusted so that the papillary portion is captured at a predetermined position on the endoscope image. The drive control device 2200 acquires an endoscope image from the video control device 2500 and performs positioning of the distal end section 2130 of the endoscope 2100 based on the endoscope image. More specifically, the drive control device 2200 controls the forward/backward movement, bending, or rolling rotation by electrical driving so that the papillary portion is captured at a position registered in advance on the endoscope image. The position registered in advance is, for example, the center of the image. The positioning may be performed so that the opening of the luminal tissue is captured at a position registered in advance. Further, the drive control device 2200 may perform electrical driving control based on the endoscope image so that the camera faces directly the front of the papillary portion or so that the papillary portion is captured at an appropriate angle of view. The drive control device 2200 may also adjust the angle of view in imaging the papillary portion by controlling the diameter of the balloon 2720 by electrical driving based on the endoscope image so that the distance between the camera and the papillary portion can be changed without changing the line-of-sight direction of the camera. This step S2006 is referred to as second positioning.

In step S2007, the operator inserts a cannula into the treatment tool channel through the insertion opening 2190 to start cannulation into the biliary duct.

In FIG. 21, although the operation of the balloon in step S2003 and the hardening of the overtube in step S2004 are performed by non-electrical driving, they may be performed by electrical driving. In this case, the operator inputs an instruction from the operation device, and the drive control device 2200 may inflate the balloon or harden the overtube by electrical driving using the instruction as a trigger. Alternatively, the drive control device 2200 may perform an image recognition process for detecting the papillary portion from the endoscope image, and may automatically inflate the balloon or harden the overtube using the detection of the papillary portion from the endoscope image as a trigger.

According to the procedure flow described above, by inflating the balloon 2720 before hardening the overtube 2710 in step S2003, the position of the distal end of the overtube 2710 does not shift when the overtube 2710 is hardened. Specifically, the distal end of the overtube 2710 can be accurately positioned. In addition, by the first positioning in steps S2003 and S2004, the insertion route of the insertion section 2110 is held by the balloon 2720 and the overtube 2710. As a result, in the second positioning in step S2006, the forward/backward movement, bending, or rolling rotation of the endoscope 2100 due to the electrical driving is easily transmitted from the base end side to the distal end of the insertion section 2110.

Figure 22:
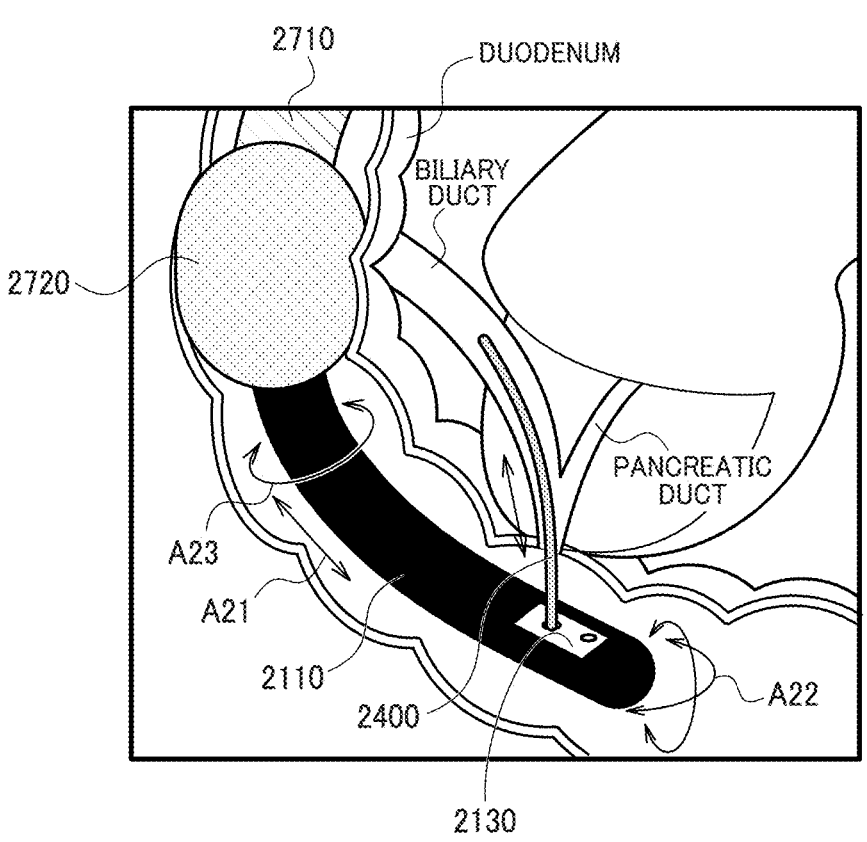
FIG. 22 shows the vicinity of the distal end of an endoscope positioned by an overtube and a balloon.

FIG. 22 shows the vicinity of the distal end of an endoscope positioned by the overtube 2710 and the balloon 2720. As shown in FIG. 22, the balloon 2720 is fixed at a position slightly apart from the papillary portion to the pyloric side of the stomach. More specifically, the balloon 2720 is positioned closer to the base end of the insertion section 2110 than the base end of the bending section of the insertion section 2110. By combining such a balloon 2720 with the overtube 2710 having a variable hardness, the bending section exposed to the papillary portion side from the balloon 2720 and the distal end section 2130 can be freely operated without being fixed, and the electrical driving from the base end side can be efficiently transmitted to the distal end section 2130 of the endoscope.

The endoscopic operation by the electrical driving is the forward and backward movement shown in A21, a bending movement shown in A22, or a rolling rotation shown in A23. The forward movement is a shift toward the distal end side along the axial direction of the insertion section 2110, and the backward movement is a shift toward the base end side along the axial direction of the insertion section 2110. The bending movement is a movement by which the angle of the distal end section 2130 is changed due to the bending of the bending section. The bending movement includes bending movements in two orthogonal directions, which can be controlled independently. One of the two orthogonal directions is referred to as the vertical direction and the other is referred to as the horizontal direction. The rolling rotation is a rotation about an axis of the insertion section 2110.

FIG. 22 shows an example in which the balloon 2720 is attached to the distal end of the overtube 2710 and the endoscope protrudes from the distal end of the overtube 2710. However, it is sufficient that the overtube 2710 and the balloon 2720 are configured so that a portion of the bending section beyond the base end can freely move. For example, it may also be arranged such that a soft tube with a constant hardness extends beyond the overtube with a variable hardness, and the balloon 2720 is attached to the boundary thereof. In this case, although a part of the base end side of the bending section is covered with the soft tube, its movement is not hindered.

Figure 23:
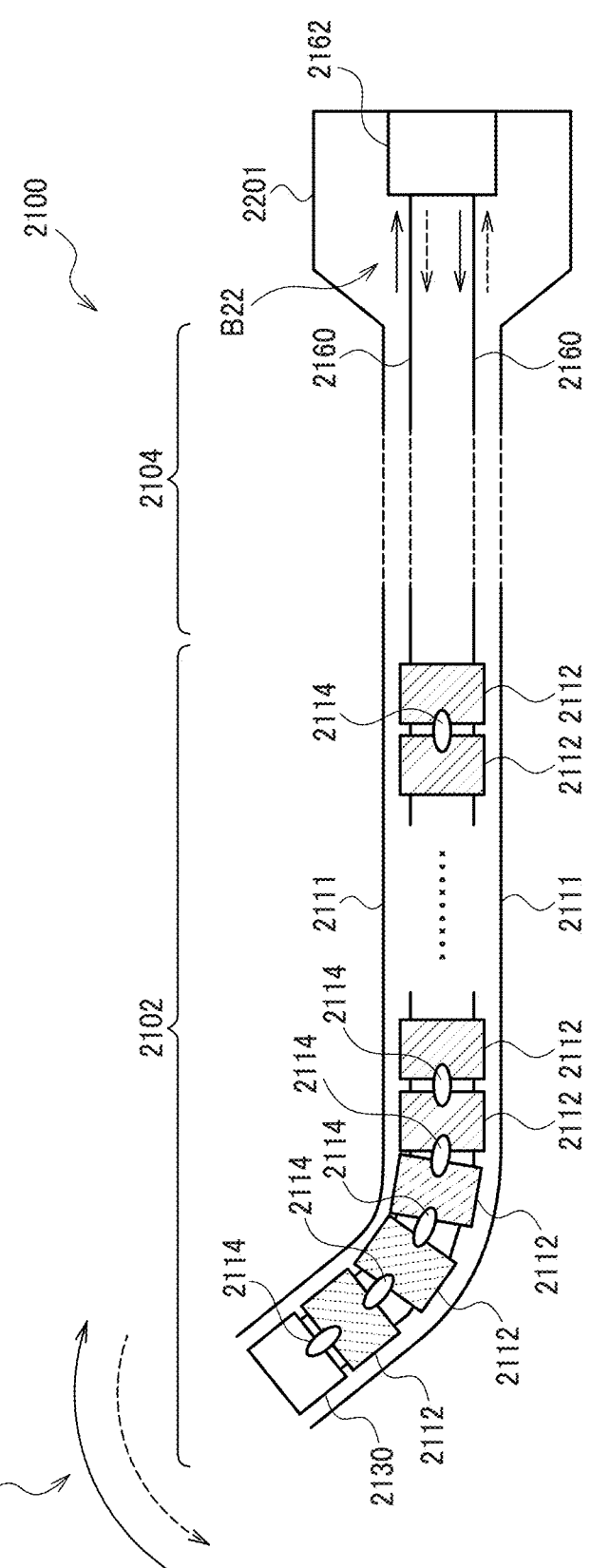
FIG. 23 is a schematic view of an endoscope including a bending section and a driving mechanism thereof.

FIG. 23 is a schematic view of an endoscope 2100 including a bending section 2102 and a driving mechanism thereof. An endoscope 2100 includes a bending section 2102, a soft section 2104, and a connector 2201.

The bending section 2102 and the soft section 2104 are covered with an outer sheath 2111. The bending section 2102 includes a plurality of bending pieces 2112 and a distal end section 2130 connected to the distal end of the bending pieces 2112. Each of the plurality of bending pieces 2112 and the distal end section 2130 is connected in series from the base end side to the distal end side by a rotatable connecting section 2114, thereby forming a multi-joint structure. The connector 2201 is provided with a coupling mechanism 2162 on the endoscope side connected to a coupling mechanism on the drive control device 2200 side. By attaching the connector 2201 to the drive control device 2200, it is possible to electrically drive the bending movement. A bending wire 2160 is provided in the outer sheath 2111. One end of the bending wire 2160 is connected to the distal end section 2130. The bending wire 2160 passes through the soft section 2104 by penetrating through a plurality of bending pieces 2112, turns back in a coupling mechanism 2162, passes through the soft section 2104 again, penetrates through the plurality of bending pieces 2112. The other end of the bending wire 2160 is connected to the distal end section 2130. The driving force from the wire drive section of the drive control device 2200 is transmitted to the bending wire 2160 via the coupling mechanism 2162 as the pulling force of the bending wire 2160.

As shown by the solid line arrow B22 in FIG. 23, when the upper wire in the figure is pulled, the lower wire is pushed, whereby the multiple joints of the bending pieces 2112 are bent upward in the figure. As a result, as indicated by the solid line arrow A22, the bending section 2102 is bent upward in the figure. When the lower wire in the figure is pulled as indicated by the dotted arrow B22, similarly, the bending section 2102 is bent downward in the figure as indicated by the dotted arrow A22. As described with reference to FIG. 22, the bending section 2102 can be bent independently in two orthogonal directions. Although FIG. 23 shows a bending mechanism for one direction, two sets of bending wires are actually provided, and each bending wire can be bent independently in two directions by being pulled independently by the coupling mechanism 2162.

Note that the mechanism for the electrically-driven bending is not limited to that described above. For example, a motor unit may be provided instead of the coupling mechanism 2162. Specifically, it may be arranged such that the drive control device 2200 transmits a control signal to the motor unit via the connector 2201, and the motor unit drives the bending movement by pulling or relaxing the bending wire 2160 based on the control signal.

Figure 24:
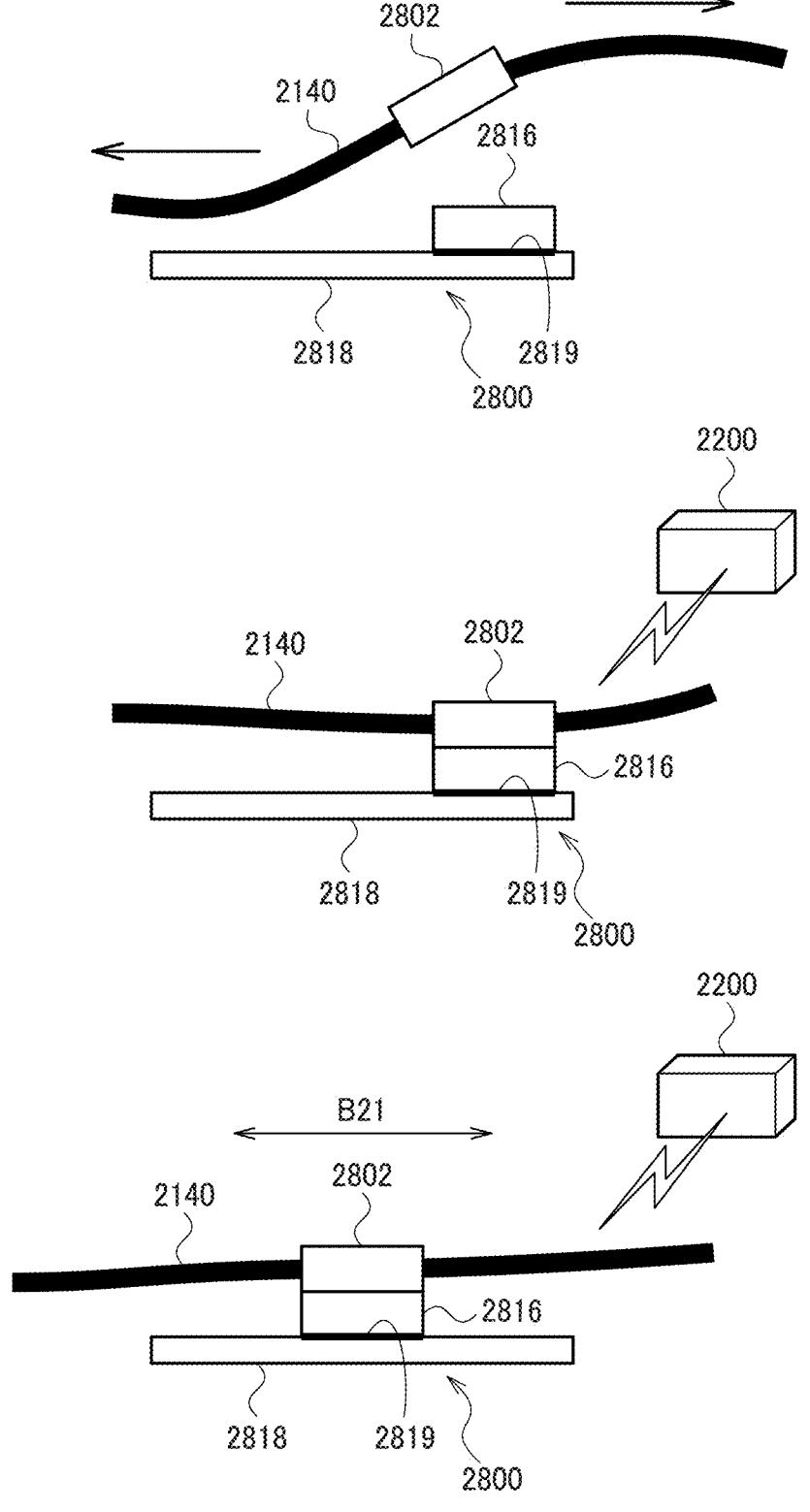
FIG. 24 shows a detailed configuration example of a forward/backward drive device.

FIG. 24 shows a detailed configuration example of a forward/backward drive device 2800. The forward/backward drive device 2800 includes a motor unit 2816, a base 2818, and a slider 2819.

As shown in the upper and middle figures, the extracorporeal soft section 2140 of the endoscope 2100 is provided with an attachment 2802 detachable from the motor unit 2816. As shown in the middle figure, the attachment of the attachment 2802 to the motor unit 2816 enables electrical driving of forward/backward movement. As shown in the lower figure, the slider 2819 supports the motor unit 2816 while enabling the motor unit 2816 to move linearly with respect to the base 2818. The slider 2819 is fixed to an operating table. As shown in B21, the drive control device 2200 transmits a forward or backward control signal to the motor unit 2816 by wireless communication, and the motor unit 2816 and the attachment 2802 move linearly on the slider 2819 based on the control signal. As a result, the forward and backward movement of the endoscope 2100 shown in A21 in FIG. 22 is achieved. Note that the drive control device 2200 and the motor unit 2816 may be connected by wired connection.

Figure 25:
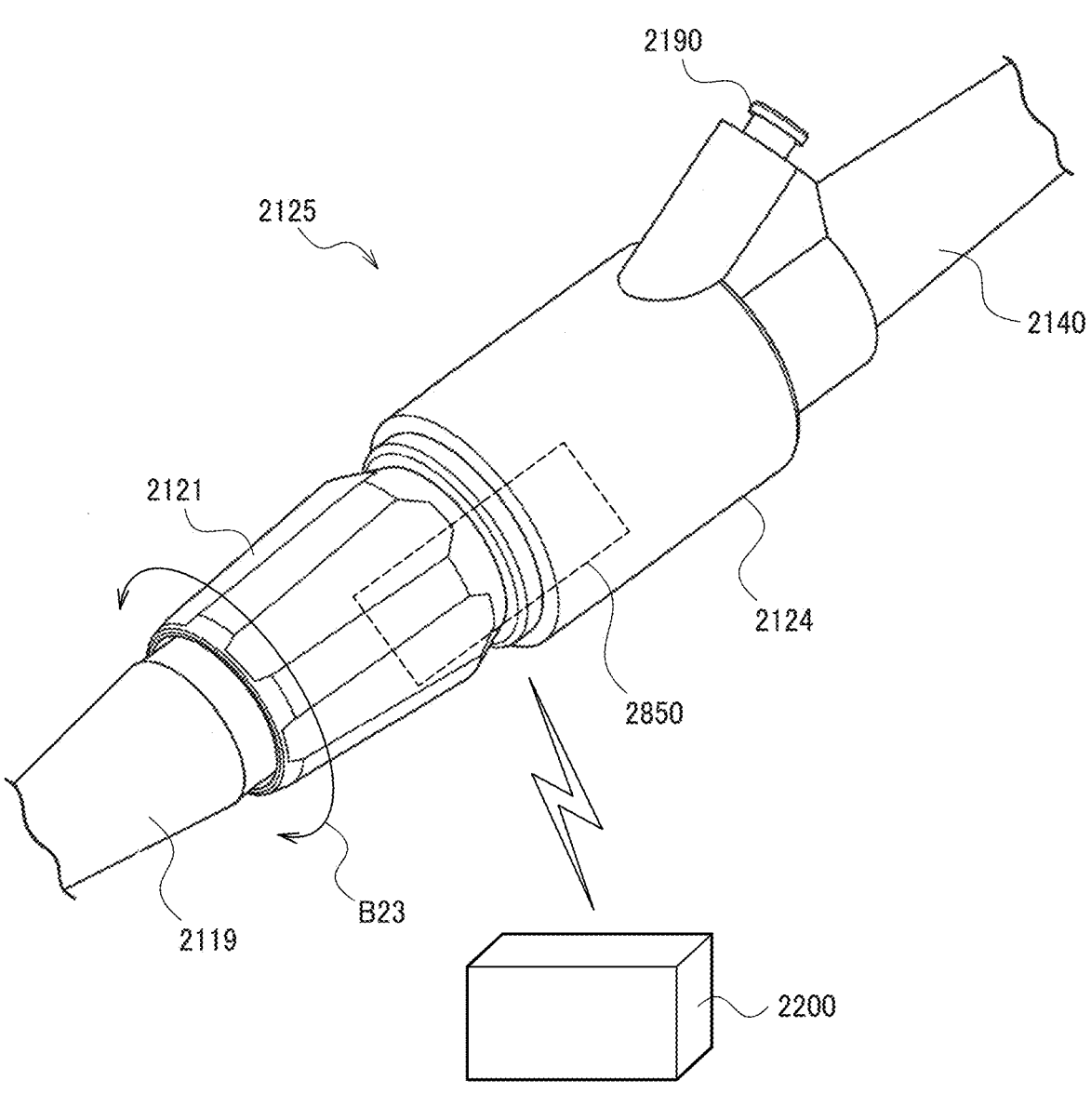
FIG. 25 is a perspective view of a connecting section including a rolling drive device.

FIG. 25 is a perspective view of the connecting section 2125 including a rolling drive device 2850. The connecting section 2125 includes a connecting section main body 2124 and a rolling drive device 2850.

The insertion opening 2190 of the treatment tool is provided in the connecting section main body 2124 and is connected to the treatment tool channel inside the connecting section main body 2124. The connecting section main body 2124 has a cylindrical shape, and a cylindrical member coaxial with the cylinder is rotatably provided inside the connecting section main body 2124. The base end section of the intracorporeal soft section 2119 is fixed to the outside of the cylindrical member, and the base end section serves as a rolling operation section 2121. As a result, the intracorporeal soft section 2119 and the cylindrical member can rotate with respect to the connecting section main body 2124 about the axial direction of the intracorporeal soft section 2119. The rolling drive device 2850 is a motor unit provided inside the connecting section main body 2124. As shown in B23, the drive control device 2200 transmits a rolling rotation control signal to the rolling drive device 2850 by wireless communication, and the rolling drive device 2850 rotates the base end section of the intracorporeal soft section 2119 with respect to the connecting section main body 2124 based on the control signal, thereby causing rolling rotation of the intracorporeal soft section 2119. As a result, the rolling rotation of the endoscope 2100 shown in A23 in FIG. 22 is achieved. The rolling drive device 2850 may include a clutch mechanism, and the rolling rotation may be switched between non-electrical driving and electrical driving by the clutch mechanism. The drive control device 2200 and the rolling drive device 2850 may be connected by wired connection via a signal line passing through the internal route 2101.

Figure 26:
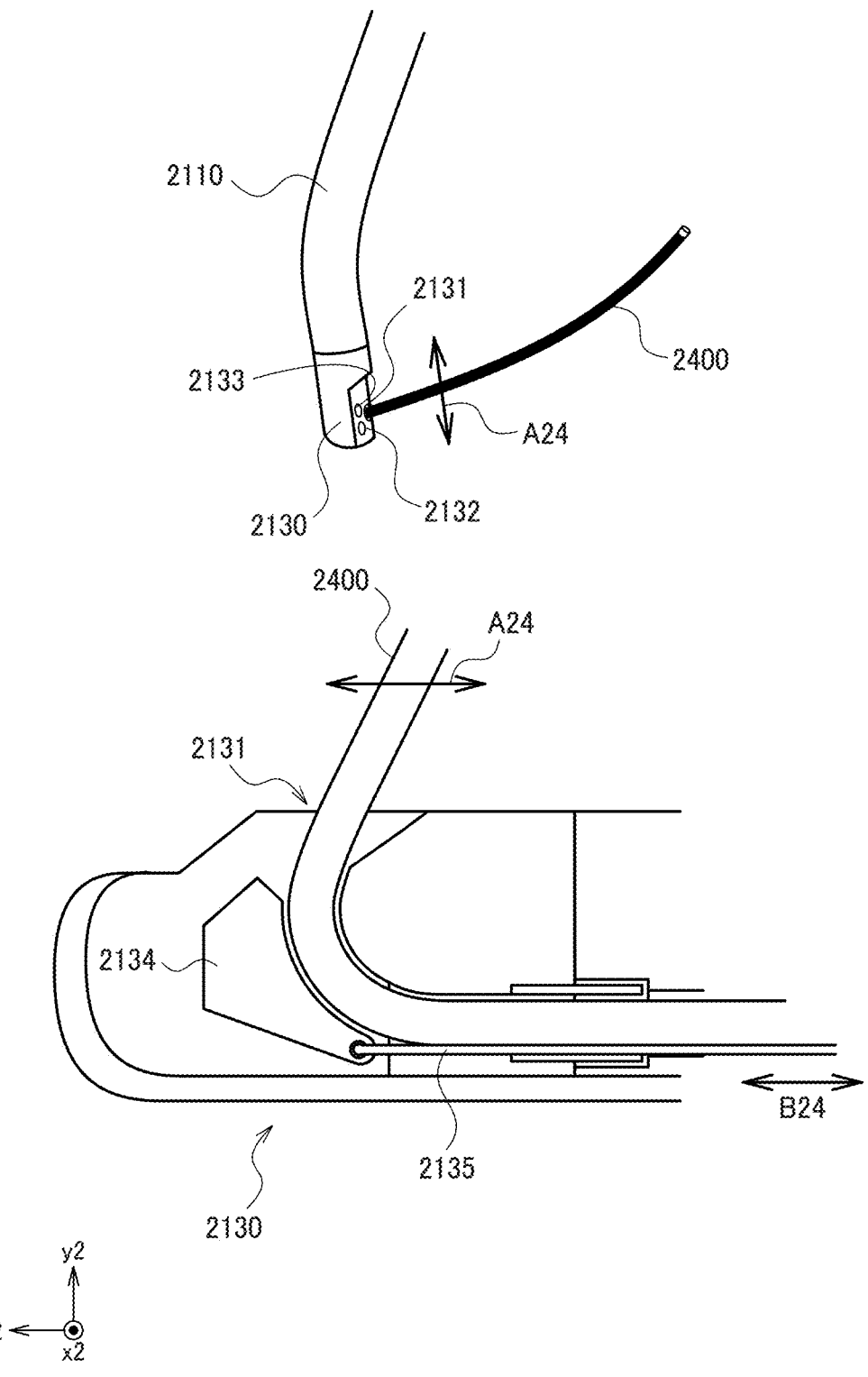
FIG. 26 shows a detailed configuration example of a distal end section of an endoscope including a raising base of a treatment tool.

FIG. 26 shows a detailed configuration example of a distal end section 2130 of an endoscope including a raising base of a treatment tool. The upper figure shows an external view of the distal end section 2130. An opening 2131 of a treatment tool channel, a camera 2132, and an illumination lens 2133 are provided on the side surface of the distal end section 2130. As shown in the lower figure, the direction parallel to the axial direction of the distal end section 2130 is defined as z2 direction, the direction parallel to the line-of-sight direction of the camera 2132 is defined as y2 direction, and the direction orthogonal to the z2 direction and the y2 direction is defined as x2 direction. The lower figure shows a cross-sectional view of the distal end section 2130 in a plane that is parallel to the y2z2 plane of the treatment tool channel and that passes through the opening 2131 of the treatment tool channel.

The distal end section 2130 includes a raising base 2134 and a raising base wire 2135. The raising base 2134 is swingable about an axis parallel to the x2 direction. One end of the raising base wire 2135 is connected to the raising base 2134, while the other end is connected to the drive control device 2200 via the connector 2201. As shown in B24, the wire drive section of the drive control device 2200 pushes and pulls the raising base wire 2135 to swing the raising base 2134, thereby, as shown in A24, changing the raising angle of the treatment tool 2400. The raising angle is an angle of the treatment tool 2400 protruding from the opening 2131. The raising angle can be defined, for example, by an angle formed by the treatment tool 2400 protruding from the opening 2131 and the z2 direction.

In accordance with one of some aspect, there is provided a medical system including:

an endoscope configured to electrically drive an endoscopic operation, which is at least one of forward and backward movement of an insertion section, a bending angle of a bending section of the insertion section, rolling rotation of the insertion section, and air supply suction, and capture an endoscope image; and a controller comprising hardware, the controller being configured to control the electrically-driven endoscopic operation, the controller performing a return processing of controlling the electrically-driven endoscopic operation so as to return the endoscope image to a reference endoscope image of a papillary portion of a duodenum.

In accordance with another aspect, there is provided a method for operating a medical system, including causing an endoscope that electrically drives an endoscopic operation, which is at least one of forward and backward movement of an insertion section, a bending angle of a bending section of the insertion section, rolling rotation of the insertion section, and air supply suction, to capture an endoscope image; and performing a return processing of controlling the electrically-driven endoscopic operation so as to return the endoscope image to a reference endoscope image of a papillary portion of a duodenum.

Explanation of ERCP

The present embodiment relates to automatic control when performing ERCP using an electric medical system. ERCP stands for Endoscopic Retrograde Cholangiopancreatography. First, before describing the present embodiment, the details of procedure of ERCP is described below.

Figure 27:
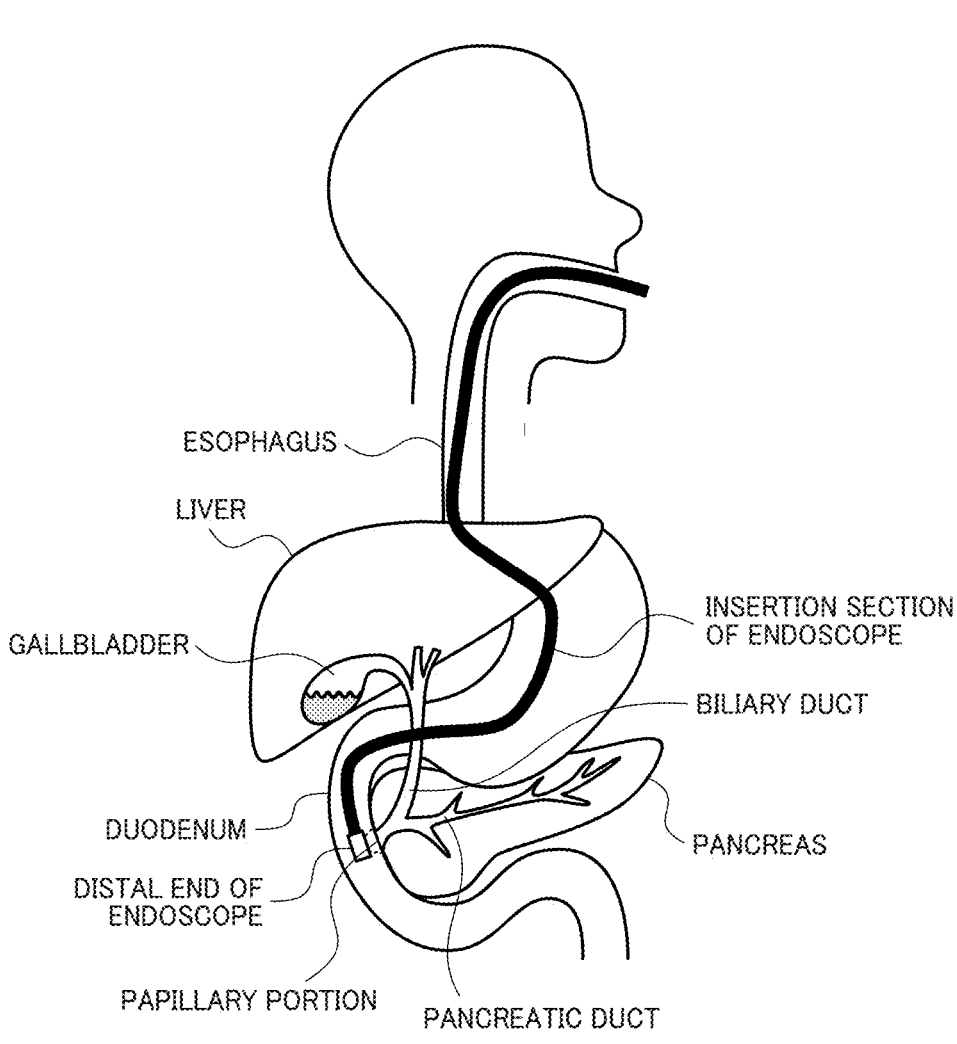
FIG. 27 shows organs and tissues involved in the ERCP procedure.

FIG. 27 shows organs and tissues involved in the ERCP procedure. The organs include a multiple types of tissues, forming a unique structure with a specific function. In FIG. 27, the liver, gallbladder, pancreas, esophagus, stomach, and duodenum are shown as organs. Tissues are formed by related cells combined, and examples include blood vessels, muscles, skin, and the like. In FIG. 27, a biliary duct and a pancreatic duct are shown as tissues.

The biliary duct is the target of the ERCP procedure. The biliary duct is a pipeline for allowing the bile produced in the liver to flow into the duodenum. When approaching the biliary duct using an endoscope, a treatment tool inserted into the channel of the endoscope is inserted to the biliary duct from the papillary portion of the duodenum while holding the endoscope at the position of the duodenum. Hereinafter, the papillary portion of the duodenum is simply referred to as a papillary portion. The papillary portion is a region including an opening of the luminal tissue with respect to the duodenum. Not only the opening but also the structure around the opening is referred to as a papillary portion. The opening of the luminal tissue is the opening of a common duct with respect to the duodenum. The common duct is formed as the confluence of the biliary duct and pancreatic duct. However, the papillary portion largely varies between individuals. For example, in some cases, the biliary duct opens directly to the duodenum without being merged with the pancreatic duct. In this case, the opening of the luminal tissue is the opening of the biliary duct.

Figure 28:
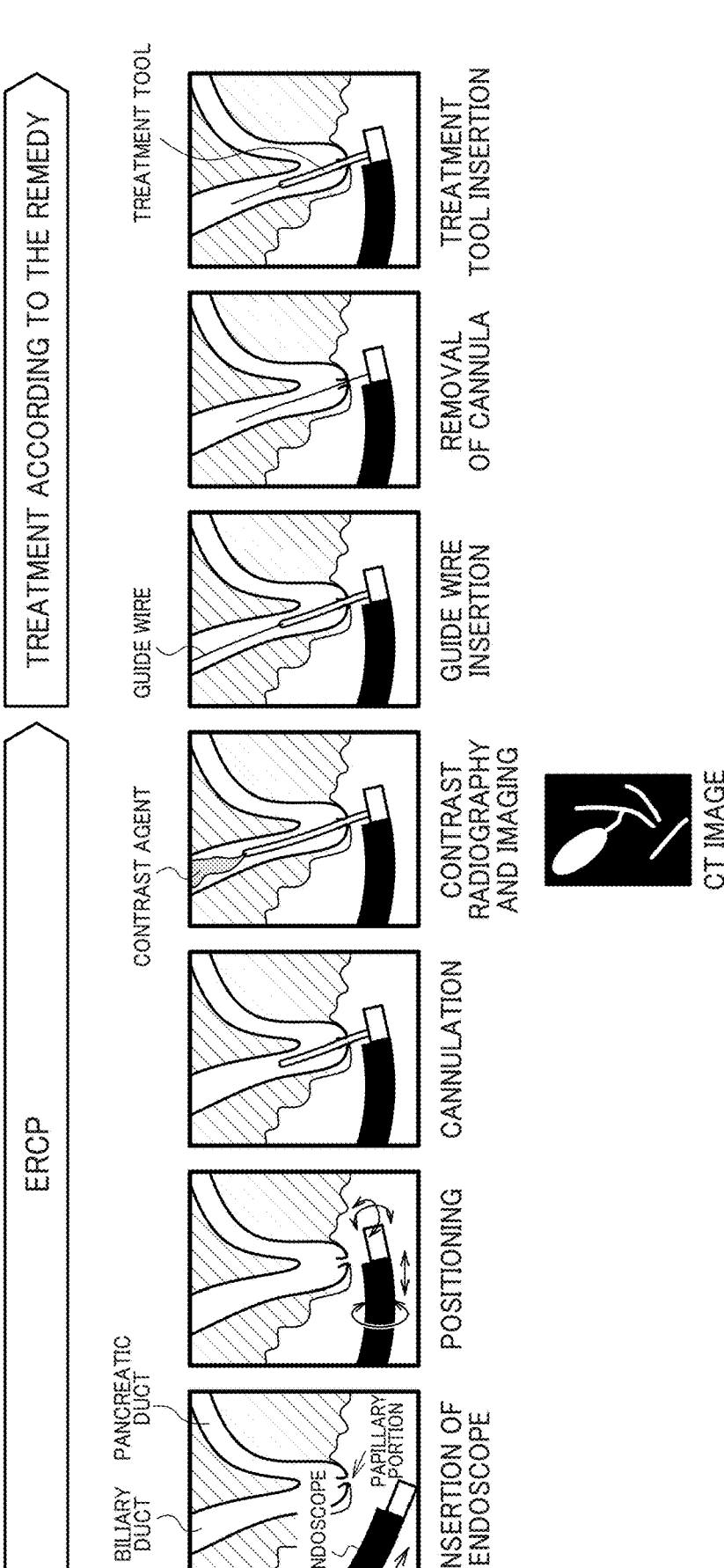
FIG. 28 shows a flow of the ERCP procedure.

FIG. 28 shows a flow of the ERCP procedure. In ERCP, a side-viewing type endoscope in which a camera, an illumination lens, and an opening of a treatment tool channel are provided on a side surface of a distal end section of the endoscope is used. The camera is also referred to as an imaging device.

In the endoscope insertion step, the insertion section of the endoscope is inserted from the mouth to the duodenum through the esophagus and stomach. At this time, the insertion section is inserted until the papillary portion becomes roughly visible in the field of view of the endoscope. Next, in the positioning step, the position of the endoscope is adjusted relative to the papillary portion. Specifically, the position of the distal end section of the endoscope is adjusted so that the papillary portion is within the imaging range of the camera of the endoscope. Alternatively, the position of the distal end section of the endoscope is adjusted so that the camera of the endoscope is facing directly front of the papillary portion and the papillary portion appears in the center of the field of view.

Then, in the cannulation step, a cannula is inserted from the papillary portion into the biliary duct. Specifically, the cannula is inserted into the treatment tool channel of the endoscope so that the cannula protrudes from the channel opening of the distal end section of the endoscope. The distal end of the cannula is inserted into the common duct from the opening of the common duct, and the cannula is further inserted through the confluence of the biliary duct and the pancreatic duct toward the direction of the biliary duct.

Cannulation refers to insertion of a cannula into a body. A cannula is a medical tube that is inserted into a body for medical purposes.

Next, in the contrast radiography and imaging step, a contrast agent is injected into the cannula and poured into the biliary duct through the distal end of the cannula. By performing X-ray or CT imaging in this state, an X-ray image or a CT (Computed Tomography) image showing the biliary duct, gallbladder, and pancreatic duct can be obtained. The procedure of ERCP has been described. After the procedure, various treatments are performed according to the results of diagnosis based on the X-ray image or CT image. An example of the treatment is described below.

In a guide wire insertion step, a guide wire is inserted into a cannula so that the guide wire is protruded from the distal end of the cannula, and the guide wire is inserted into the biliary duct. In a cannula removing step, the cannula is removed while leaving the guide wire inside the biliary duct. As a result, only the guide wire protrudes from the distal end section of the endoscope, indwelling in the biliary duct. Next, in a treatment tool insertion step, the treatment tool is inserted into the biliary duct along the guide wire. An example of a treatment tool is a basket or stent. The basket is used with a catheter. While allowing the guide wire to pass through the catheter, the catheter is inserted into the biliary duct along the guide wire. A basket made of a plurality of metal wires is inserted into the biliary duct from the distal end of the catheter, an object to be removed, such as a gallstone, is placed in the basket and held, and the object to be removed is taken out from the biliary duct by removing the basket and catheter in this state from the biliary duct. A stent is also used in a similar manner with a catheter and inserted into the biliary duct from the distal end of the catheter. The narrow portion of the biliary duct can be widened by inserting a stent; further, by keeping the stent therein, the narrow portion is held in a widened state by the indwelling stent.

The ERCP procedure is performed as described above. However, the endoscope position determined in the positioning step may be disrupted in some cases by subsequent operations such as cannulation. The following describes this issue with reference to FIGS. 29 to 32.

Figure 29:
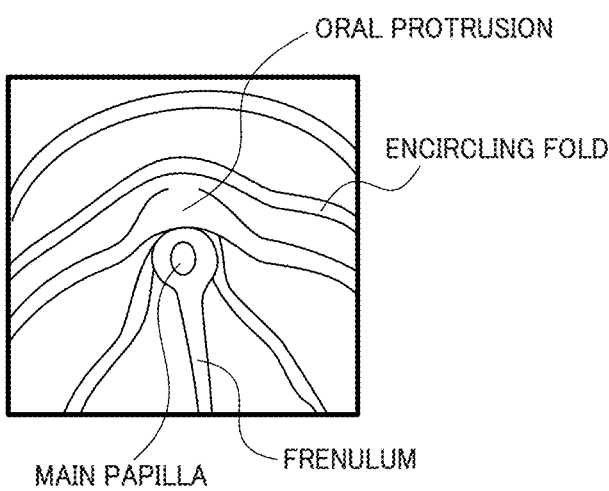
FIG. 29 shows a schematic diagram of the form of papillary portion viewed directly from the front.

FIG. 29 is a diagram schematically showing the form of the papillary portion as viewed directly from the front thereof. As shown in FIG. 29, structures peculiar to the papillary portion are present around the main papilla, which is the opening of the luminal tissue. Specifically, structures called frenulum, encircling fold, and oral protrusion are present around the main papilla. Note that the schematic diagram shows a typical papillary portion form, and the form of the papillary portion may differ from patient to patient due to individual differences.

Figure 30:
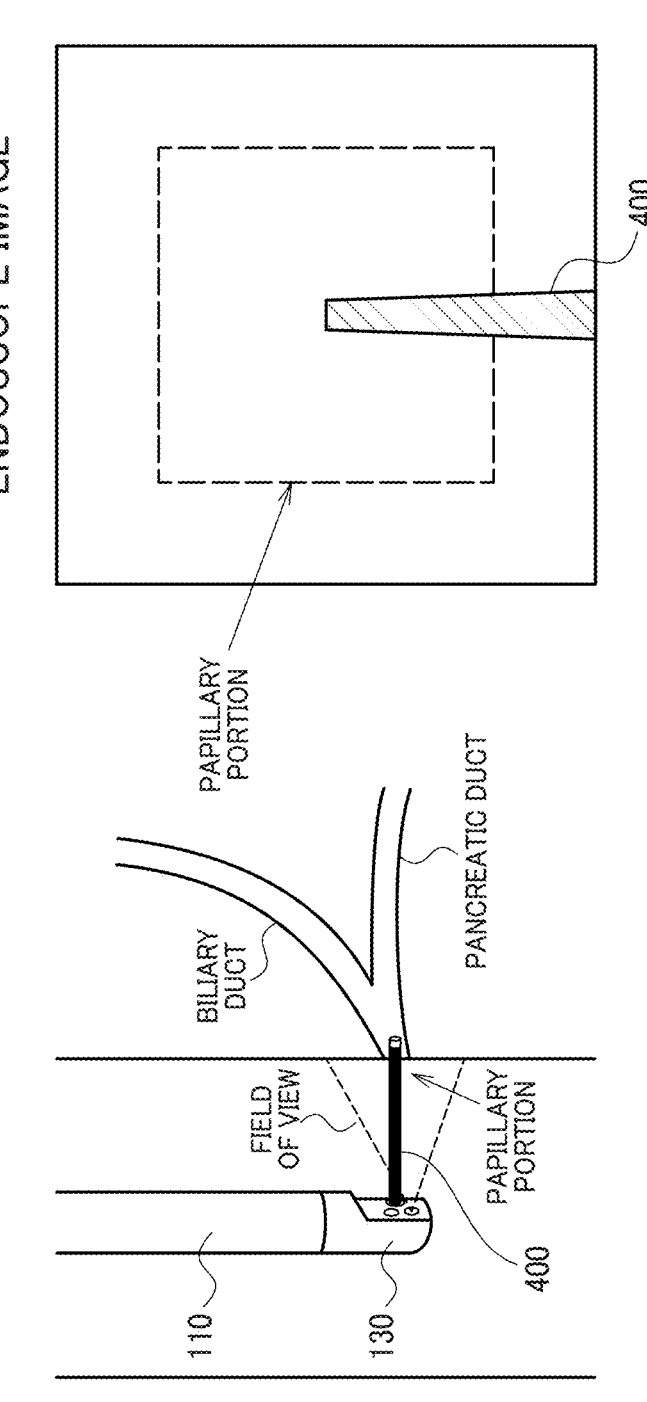
FIG. 30 is an example of an endoscope position determined in a positioning step, and an example of an endoscope image obtained at the position.
Figure 31:
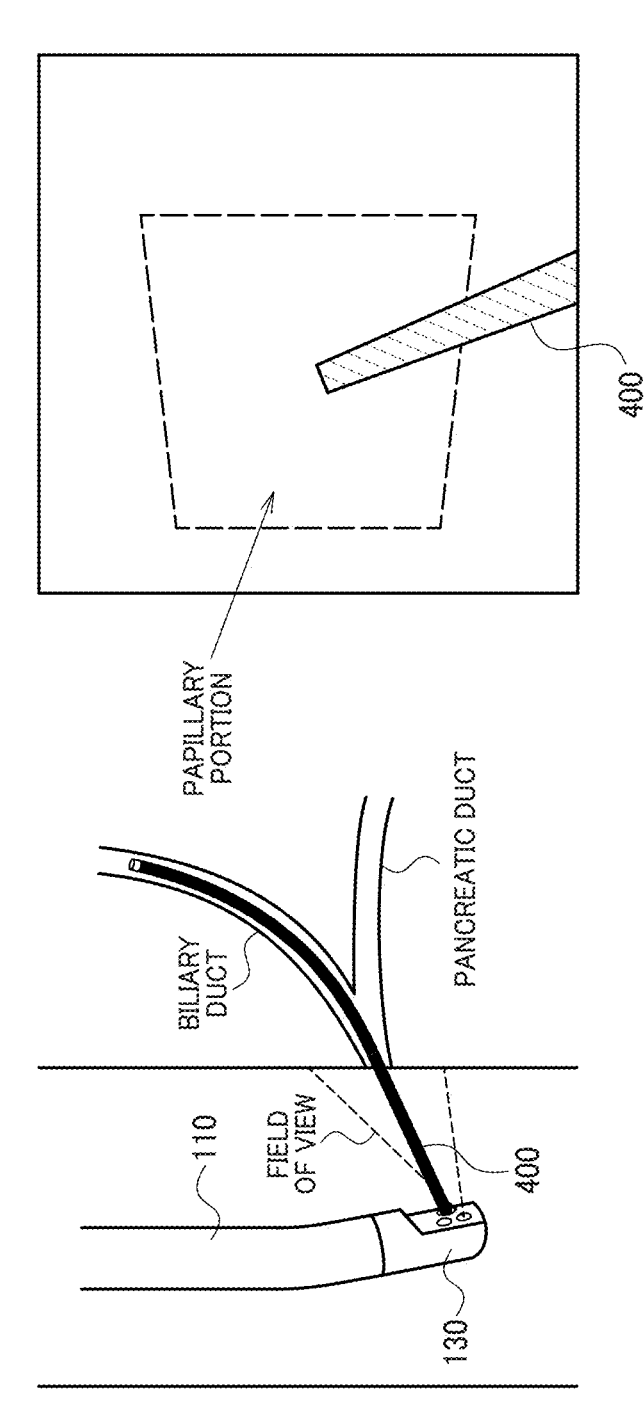
FIG. 31 is an example of an endoscope position upon insertion of a treatment tool into a biliary duct, and an example of an endoscope image obtained at the position.
Figure 32:
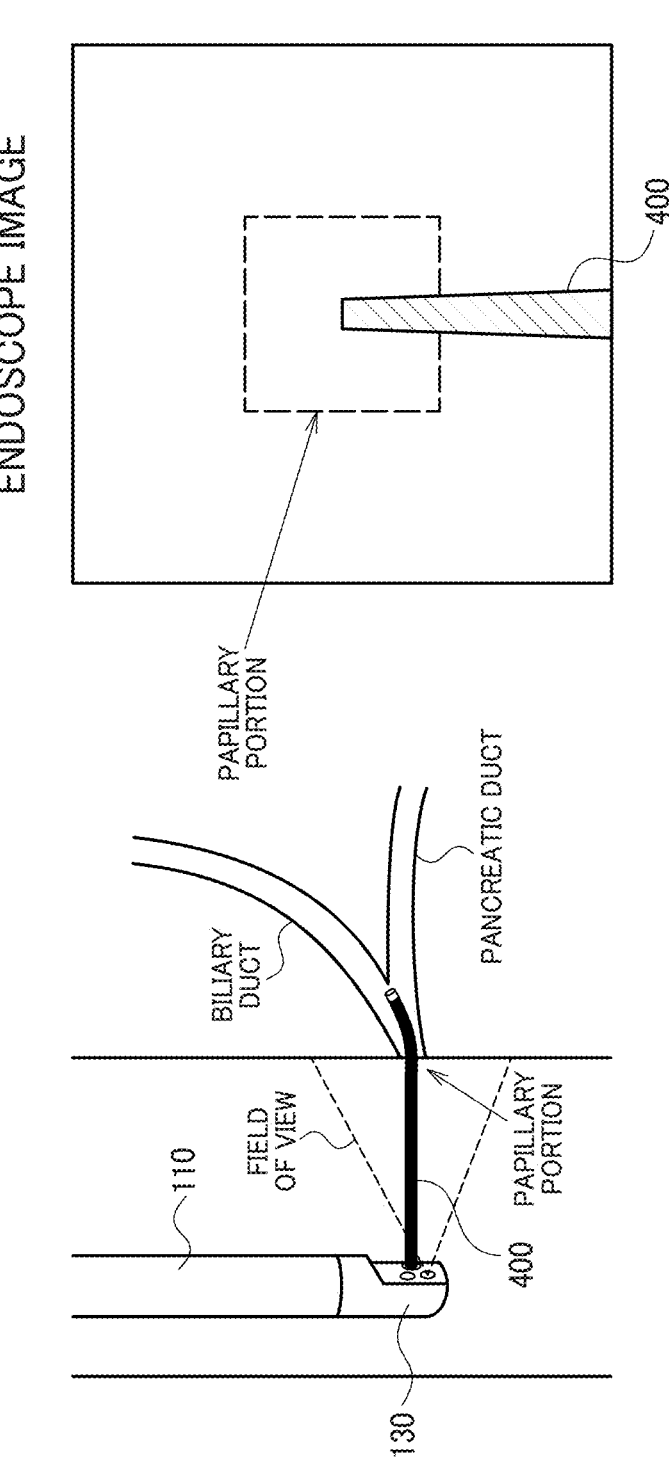
FIG. 32 is an example of an endoscope position upon insertion of a treatment tool in the biliary duct direction from a confluence, and an example of an endoscope image obtained at the position.

The left figure of FIG. 30 shows an example of an endoscope position determined in a positioning step, and the right figure of FIG. 30 shows an example of an endoscope image obtained at the position. In FIGS. 30 to 32, the region of the papillary portion is shown as a quadrangle for ease of explanation; however, the region of the papillary portion is not limited to a quadrangle insofar as the region includes a form specific to the papillary portion.

As shown in the left and right figures of FIG. 30, in the positioning step, the distal end section 130 is positioned so that the camera provided at the distal end section 130 of the insertion section 110 of the endoscope directly faces the papillary portion and the papillary portion is positioned in the center of the endoscope image. The "directly facing the papillary portion" means that the line-of-sight direction of the camera is substantially perpendicular to the intestinal wall, where the papillary portion is present. The "papillary portion is positioned in the center of the endoscope image" means that the region of the papillary portion described in FIG. 29 is located substantially in the center of the endoscope image. For example, it is sufficient that the center of the region including the encircling fold, the oral protrusion, the frenulum and the main papilla is positioned substantially the center of the endoscope image. Alternatively, the opening of the luminal tissue, i.e., the main papilla, may be positioned substantially in the center of the endoscope image.

The endoscope image shown in the right figure of FIG. 30 is a typical view of the endoscope image when performing ERCP the procedure, and this endoscope image is hereinafter referred to as the reference endoscope image. Although an example after the positioning step is referred to in the above, the reference endoscope image is not limited to the endoscope image obtained immediately after the positioning step. It is sufficient that the reference endoscope image is an endoscope image with the papillary portion captured in the predetermined reference position, more specifically, it is sufficient that the camera of the distal end section 130 directly faces the papillary portion and the papillary portion is positioned in the center of the endoscope image. The reference endoscope image may also be an endoscope image in which the region of the papillary portion has a predetermined size. The size of the region of the papillary portion is the size relative to the size of the endoscope image as a whole, and may be, for example, a ratio of area, width, length, or the like.

The operator always observes the papillary portion with the same view by maintaining the view of the reference endoscope image in the procedure, such as cannulation after the positioning step. By always observing the papillary portion with the same view, the operator can easily grasp the progress, condition, or abnormality of the procedure based on past cases or experiences, etc. For example, by viewing the reference endoscope image, the operator can easily determine the status of the luminal tissue with the treatment tool 400 such as a cannula inserted therein, whether the treatment tool 400 is inserted correctly, or whether the insertion of the treatment tool 400 is obstructed due to narrowing of the pipeline or the like. However, as described in FIG. 31 or FIG. 32 below, the view of the endoscope image may be changed depending on the endoscopic operation in the procedure; in this case, the operator needs to perform an operation of returning it to an endoscope position in which the reference endoscope image can be obtained.

The left figure of FIG. 31 shows an example of an endoscope position upon insertion of a treatment tool 400 into a biliary duct, and the right figure of FIG. 31 shows an example of an endoscope image obtained at the position.

The biliary duct is usually not perpendicular to the intestinal wall but extends obliquely with respect to the intestinal wall. When the insertion of the treatment tool 400 is obstructed by an obstacle such as a gallstone, a narrowing of the biliary duct or the like, it is necessary to make the treatment tool 400 face toward the traveling direction of the biliary duct and push the treatment tool 400 into the direction. Therefore, by adjusting the forward/backward movement of the insertion section 110, the bending, the rolling rotation, the raising angle of the treatment tool 400, or the like, the direction of the treatment tool 400 is adjusted. The left figure of FIG. 31 shows an example in which the bending of the insertion section 110 and the raising angle of the treatment tool 400 are adjusted. When such an operation is performed, for example, the camera is no longer facing directly toward the papillary portion and the papillary portion is displaced from the center of the field of view. Therefore, as shown in the right figure of FIG. 31, the endoscope image changes from the reference endoscope image, and therefore, for example, the papillary portion is shown from an oblique direction and the region of the papillary portion is displaced from the center of the endoscope image.

The left figure of FIG. 32 shows an example of an endoscope position upon insertion of the treatment tool 400 toward the biliary duct direction from the confluence, and the right figure of FIG. 32 shows an example of the endoscope image obtained at the position.

The biliary duct and the pancreatic duct merge into a common duct at the confluence thereof, and open to the papillary portion. As shown in the left figure of FIG. 32, when the treatment tool 400 is inserted into the common duct, the distal end of the treatment tool 400 may hit the confluence, a narrowed portion, or the like, and the distal end section 130 of the endoscope 100 may be pushed back to be away from the papillary portion. As shown in the right figure of FIG. 32, the distance between the camera and the papillary portion becomes large, and therefore the size of the region of the papillary portion on the endoscope image becomes smaller than that in the reference endoscope image.

After the operator becomes capable of smoothly inserting the treatment tool 400 by overcoming the obstruction or the narrowed portion such as those shown in FIG. 31 or FIG. 32, the endoscopic position is returned to the original position so that the reference endoscope image is obtained. However, there are difficulties in slightly adjusting the position of the distal end section 130 from the base end side of the insertion section 110. For example, inexperienced operators may need more time for such return operations. In addition, when the operations of changing the endoscope position from the reference position are performed many times, it is troublesome to perform the return operation each time.
Medical System According to the Present Embodiment and Flow of ERCP Procedure Using the Medical System Therefore, in the present embodiment, the above-described return operation to the reference position is automated by an electrically-driven medical system to assist the ERCP procedure. The details of this structure are described below.

Figure 33:
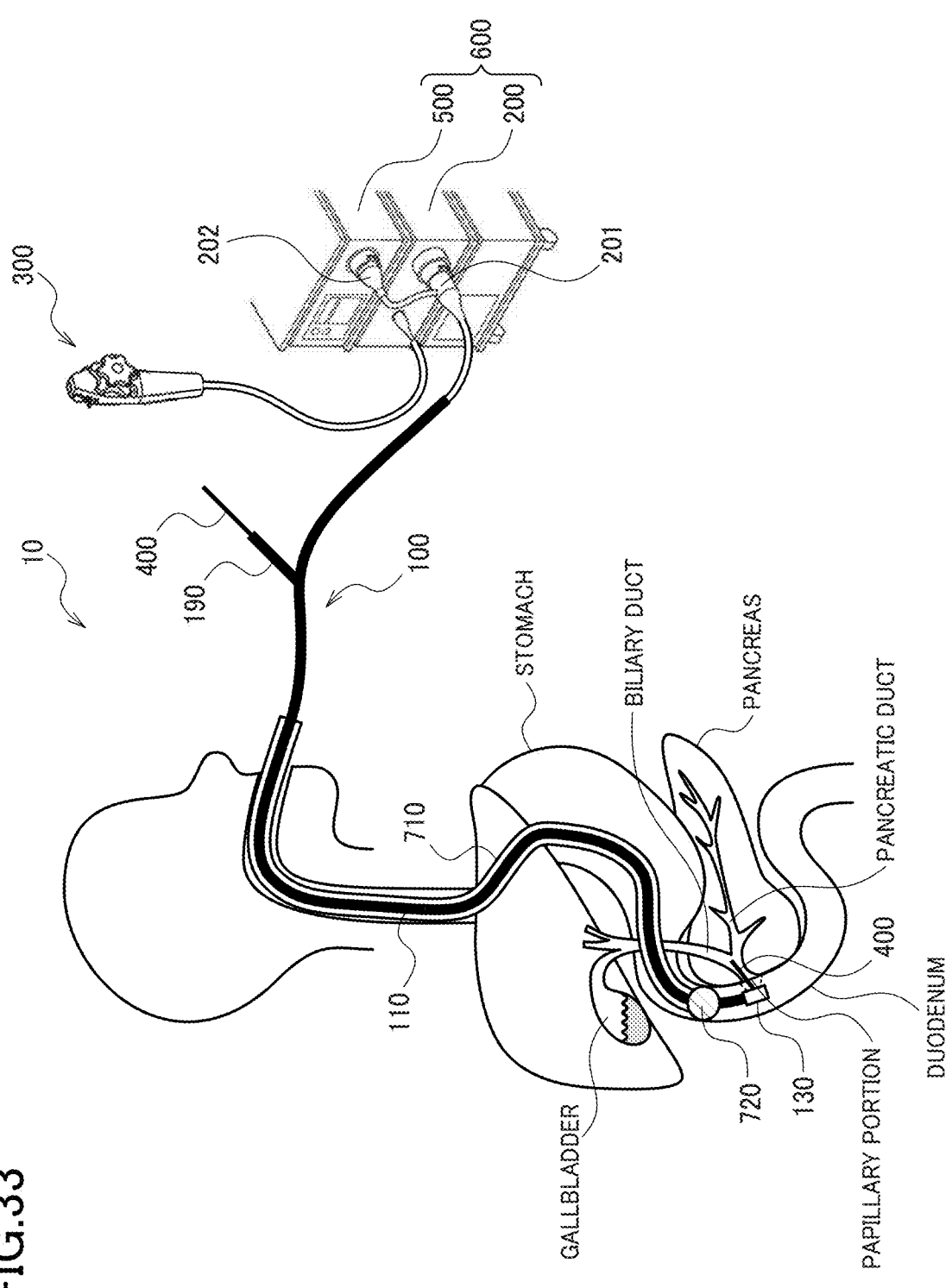
FIG. 33 shows a basic configuration example of a medical system.

FIG. 33 shows a basic configuration example of a medical system 10 according to the present embodiment. The medical system 10 includes an endoscope 100, an operation device 300, an overtube 710, a balloon 720, a treatment tool 400, and a control device 600. The medical system 10 is also referred to as an endoscope system or an electric endoscope system.

The overtube 710 is a tube with a variable hardness that covers the insertion section 110 of the endoscope 100. The balloon 720 is provided near the distal end on the outer side of the overtube 710. The operator inserts the endoscope 100 and the overtube 710, which is in a soft state, to the duodenum, inflates the balloon 720 to fix a portion around the distal end of the overtube 710 to the duodenum, and hardens the overtube 710. When the endoscope 100 and the overtube 710 are inserted into the body, at least the bending section of the insertion section 110 is exposed from the distal end of the overtube 710. The bending section refers to a section structured to be bent at an angle corresponding to the bending operation in the vicinity of the distal end of the insertion section 110. The base end of the overtube 710 is present outside the body. The base end side of the insertion section 110 is exposed from the base end of the overtube 710. Note that the example shown here uses the overtube 710 and the balloon 720, but these may be omitted.

An insertion opening 190 of the treatment tool is provided at the base end side of the insertion section 110, and a treatment tool channel for allowing the treatment tool 400 to pass through from the insertion opening 190 to the opening of the distal end section 130 is provided inside the insertion section 110. The insertion opening 190 of the treatment tool is also called a forceps opening; however, the treatment tool to be used is not limited to forceps.

The endoscope 100 is detachably connected to a control device 600 using connectors 201 and 202. The control device 600 includes a drive control device 200 to which the connector 201 is connected, and a video control device 500 to which the connector 202 is connected. The drive control device 200 controls the electrical driving of the endoscope 100 via the connector 201. The treatment tool channel in the insertion section 110 also serves as an air supply suction channel and is connected to the air supply suction pump in the drive control device 200 via the connector 201. The drive control device 200 is connected to the operation device 300 for enabling manual operation of the electrical driving. The video control device 500 receives an image signal from a camera provided at the distal end section 130 of the endoscope 100 via the connector 202, generates a display image from the image signal, and displays it on a display device (not shown). In FIG. 33, the drive control device 200 and the video control device 500 are shown as separate devices, but they may be structured as a single device. In this case, the connectors 201 and 202 may be integrated into a single connector.

Before describing the return processing of the present embodiment, the flow of ERCP procedure using the medical system 10 is described with reference to FIG. 34. Here, an electric endoscope is assumed in which the forward and backward movement of the insertion section 110 of the endoscope 100, the bending of the bending section of the insertion section 110, and the rolling rotation of the insertion section 110 are electrically driven. However, it is sufficient that at least one of these functions is electrically driven. The term "electrical driving" means that the endoscope is driven by a motor or the like based on an electrical signal for controlling the endoscopic operation. For example, when the electrical driving is manually operated, an operation input to the operation device is converted into an electrical signal, and the endoscope is driven based on the electrical signal. In the following, the forward and backward movement may be simply referred to as "forward/backward movement".

In step S1, the operator inserts the insertion section 110 of the endoscope 100 and the overtube 710 into the duodenum. More specifically, in a state where the insertion section 110 is inserted into the overtube, the insertion section 110 and the overtube 710 are inserted into the duodenum together. The overtube 710, which is changeable in hardness, is soft in step S1. For example, the operator can move the insertion section 110 and the overtube 710 forward by a non-electrically-driven manual operation so that they are inserted into the body. The non-electrical driving means that the endoscope 100 is not electrically driven by a motor or the like, instead, the force applied to the operation section is directly transmitted to the endoscope by a wire or the like, thereby operating the endoscope. For example, in the present embodiment, steps S1 to S4 are not electrically driven. In this case, it is sufficient that at least the forward/backward movement is not electrically driven, and the bending, the rolling rotation, or both may be manually operated by electrical driving.

In step S2, the operator inserts the insertion section 110 until the distal end section 130 reaches the vicinity of the papillary portion. For example, when the operator manually inserts the insertion section 110 by non-electrical driving, the operator inserts the insertion section 110 until the papillary portion becomes visible in the endoscope image. At this point, the distal end of the endoscope 100 does not need to accurately reach the papillary portion; the distal end of the endoscope 100 may reach a position before the papillary portion or past the papillary portion.

In step S3, the operator fixes the distal end of the overtube 710 to the duodenum. As an example, the operator performs an operation to inflate the balloon 720 provided near the distal end of the overtube 710, and fixes the distal end of the overtube 710 to the duodenum by the balloon 720. In step S4, the operator performs an operation to harden the overtube 710. At this time, the overtube 710 is hardened while maintaining its shape in a state immediately before hardening, that is, the shape when it is inserted from the mouth to the duodenum. As a result, the insertion section 110 is held by the hardened overtube 710 and the balloon 720, thereby fixing the insertion route of the insertion section 110. These steps S3 and S4 are referred to as first positioning.

Figure 41:
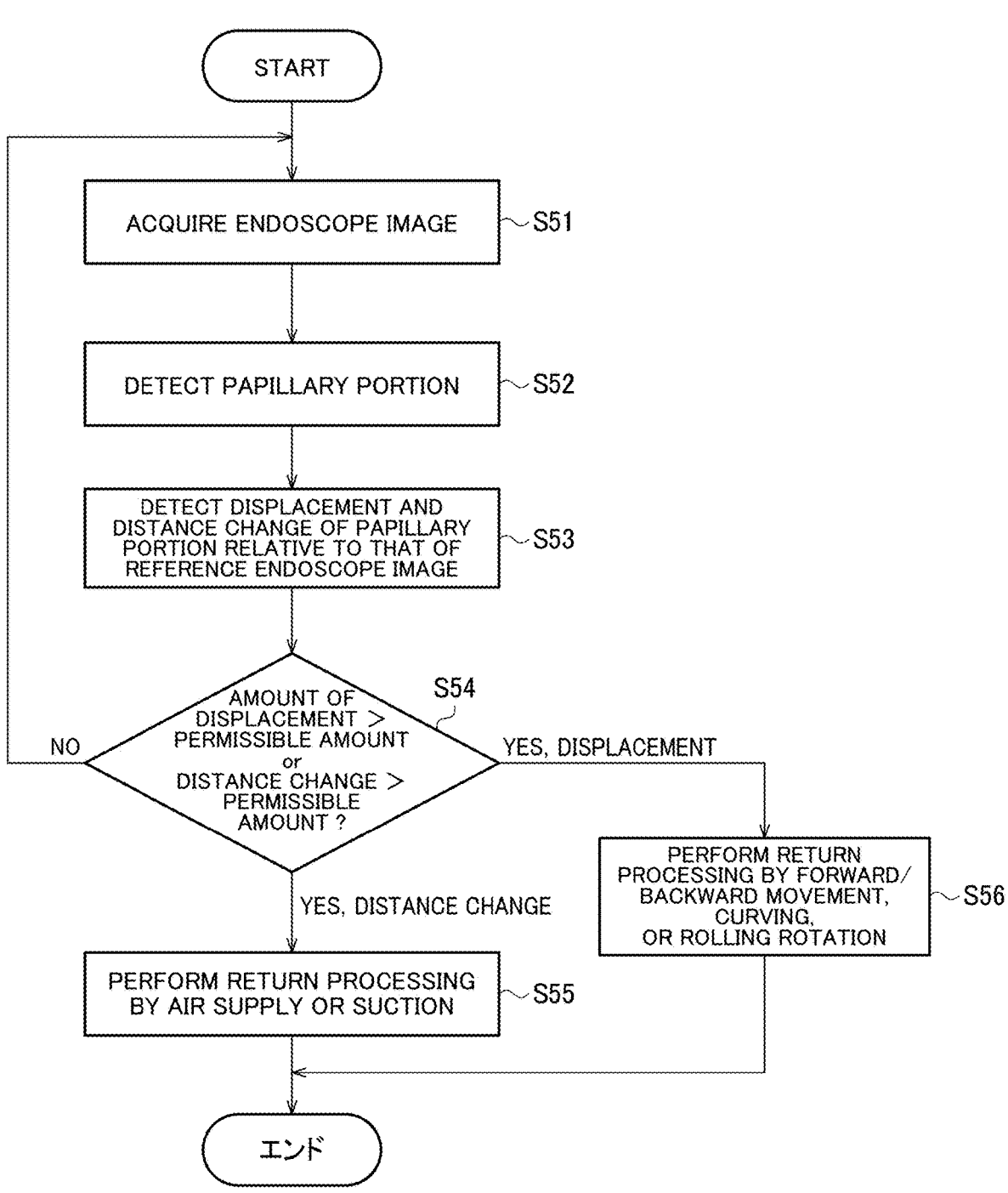
FIG. 41 shows a third detailed flow of return processing.

In step S5, the endoscope 100 is connected to the motor unit, and the non-electrical driving is switched to the electrical driving. The method of switching between the non-electrical driving and the electrical driving varies depending on the configuration of the drive mechanism. For example, when the medical system 10, which is described later with reference to FIG. 41, is used, in steps S1 to S4, the forward/backward movement is non-electrically driven and the bending and the rolling rotation are electrically driven. In this case, the forward/backward movement may be switched from the non-electrical driving to the electrical driving by connecting the endoscope 100 to the forward/backward drive device 800. Further, when the bending operation by non-electrical driving is enabled by providing a bending operation dial or the like capable of non-electrically performing the bending operation, the bending movement may be switched from the non-electrical driving to the electrical driving, for example, by connecting the connector 201 to the drive control device 200. Alternatively, even if the motor unit is kept connected, the motor may be structured to be detachable by a clutch mechanism or the like, and the non-electrical driving may be switched to the electrical driving by the clutch mechanism. Step S5 may be performed before step S1. For example, when the forward/backward movement is manually operated by electrical driving, the endoscope 100 may be connected to the motor unit before step S1.

In step S6, the drive control device 200 automatically positions the distal end section 130 at the papillary portion, and the operator confirms that the position of the distal end section 130 has been adjusted so that the papillary portion is captured at a predetermined position on the endoscope image. The drive control device 200 acquires an endoscope image from the video control device 500 and performs positioning of the distal end section 130 of the endoscope 100 based on the endoscope image. More specifically, the drive control device 200 controls the forward/backward movement, bending, or rolling rotation by electrical driving so that the papillary portion is captured at a position registered in advance on the endoscope image. The position registered in advance is, for example, the center of the image. The positioning may be performed so that the opening of the luminal tissue is captured at a position registered in advance. Further, the drive control device 200 may perform electrical driving control based on the endoscope image so that the camera faces directly the front of the papillary portion or so that the papillary portion is captured at an appropriate angle of view. This step S6 is referred to as second positioning.

In step S7, the operator inserts a cannula into the treatment tool channel through the insertion opening 190 to start cannulation into the biliary duct.

Figure 35:
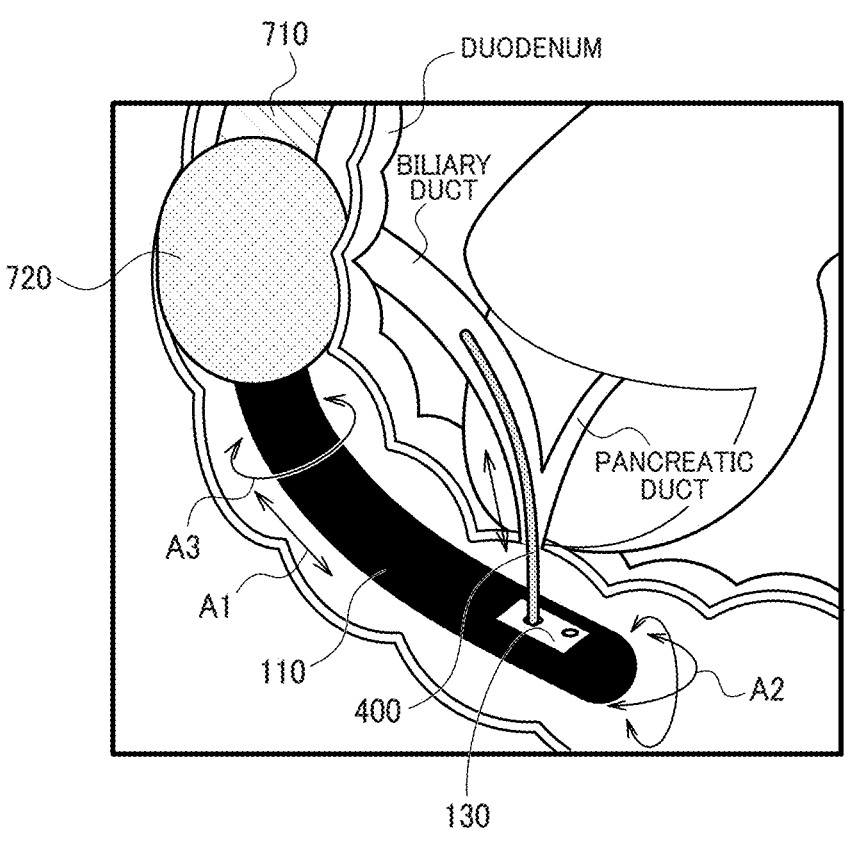
FIG. 35 shows the vicinity of the distal end of an endoscope positioned by an overtube and a balloon.

FIG. 35 shows the vicinity of the distal end of an endoscope positioned by the overtube 710 and the balloon 720. As shown in FIG. 35, the balloon 720 is fixed at a position slightly apart from the papillary portion to the pyloric side of the stomach. More specifically, the balloon 720 is positioned closer to the base end of the insertion section 110 than the base end of the bending section of the insertion section 110. By combining such a balloon 720 with the overtube 710 having a variable hardness, the bending section exposed to the papillary portion side from the balloon 720 and the distal end section 130 can be freely operated without being fixed, and the electrical driving from the base end side can be efficiently transmitted to the distal end section 130 of the endoscope.

The endoscopic operation by the electrical driving is the forward and backward movement shown in A1, a bending movement shown in A2, or a rolling rotation shown in A3. The forward movement is a shift toward the distal end side along the axial direction of the insertion section 110, and the backward movement is a shift toward the base end side along the axial direction of the insertion section 110. In the following, the forward and backward movement is also referred to as the forward/backward movement. The bending movement is a movement by which the angle of the distal end section 130 is changed due to the bending of the bending section. The bending movement includes bending movements in two orthogonal directions, which can be controlled independently. One of the two orthogonal directions is referred to as the vertical direction and the other is referred to as the horizontal direction. The rolling rotation is a rotation about an axis of the insertion section 110.

Return Processing

Figure 36:
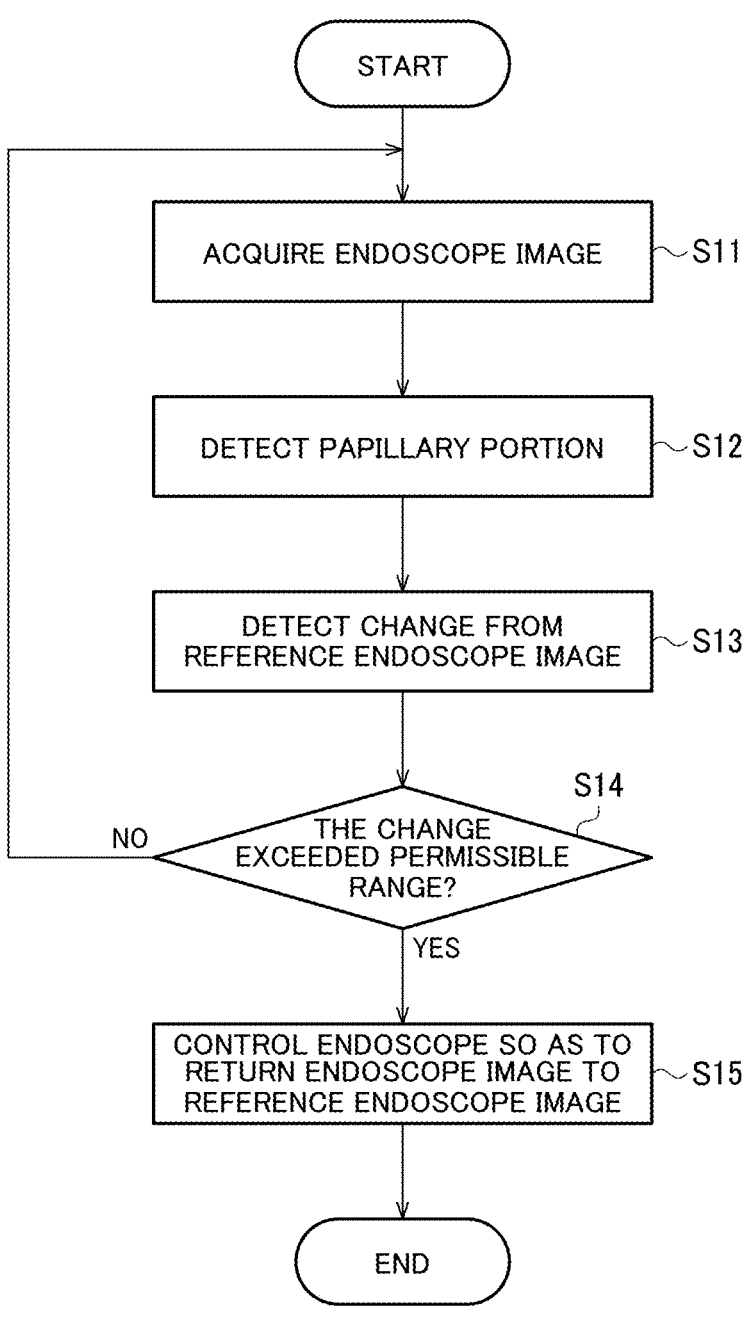
FIG. 36 shows a basic flow of return processing.

FIG. 36 shows a basic flow of return processing. This return processing is performed, for example, in the procedure step after the second positioning described in step S6 of FIG. 34. For example, in the ERCP procedure in FIG. 28, the return processing may be performed in any of the procedure steps in or after the cannulation step.

Figure 34:
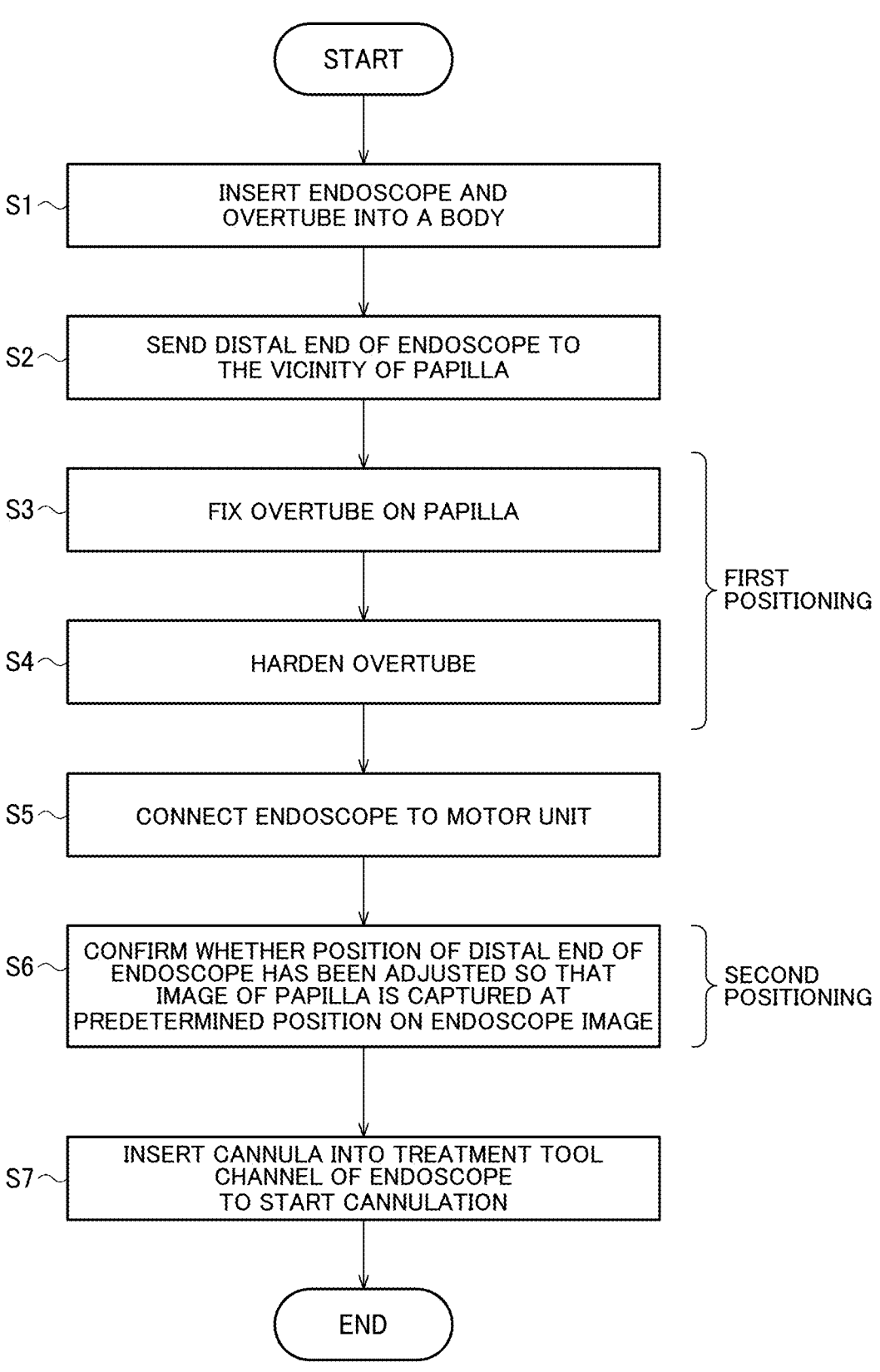
FIG. 34 shows the flow of ERCP procedure using a medical system.

The drive control device 200 stores the endoscope image after the second positioning in FIG. 34 as the reference endoscope image in the storage section in the drive control device 200. It is also possible to store reference endoscope images having been previously captured in various examinees in the storage section.

In step S11, the drive control device 200 acquires an endoscope image from the video control device 500. In step S12, the drive control device 200 detects the papillary portion from the endoscope image. In step S13, the drive control device 200 detects changes between the endoscope image taken in real time and the reference endoscope image. Specifically, the drive control device 200 detects changes between the detection target, which is at least one of the position, the imaging direction, or the size of the papillary portion in the endoscope image, and the detection target in the reference endoscope image. In step S14, it is determined whether the change exceeds the permissible (predetermined)

range. If the change does not exceed the permissible range, the sequence returns to step S11. If the change exceeds the permissible range, in step S15, the drive control device 200 controls the electrically-driven endoscopic operation so that the endoscope image is returned to the reference endoscope image.

According to this flow, even if the endoscope is moved from the basic position during the procedure such as cannulation, the drive control device 200 automatically returns the endoscope to the basic position so as to obtain the reference endoscope image. This enables the operator to easily grasp the progress, condition, or abnormality of the procedure. This also eliminates the need for manual operation to return the endoscope position; therefore, it is possible to assist, for example, inexperienced operators and the like. In addition, even in the case of performing the operations of changing the endoscope position from the reference position many times, such an automatic return eliminates the trouble of performing the manual return operation many times.

Figure 37:
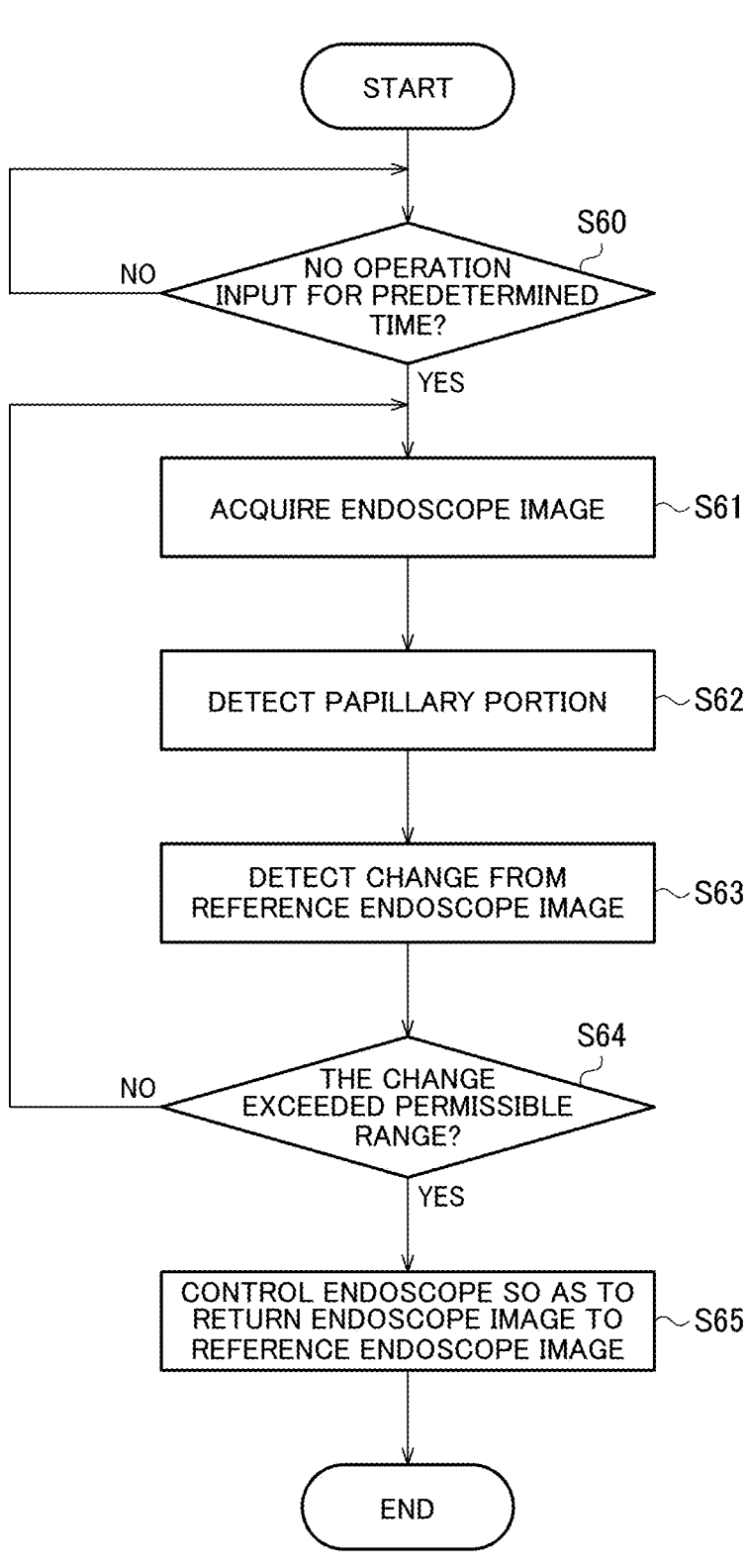
FIG. 37 shows an example flow of a return processing when a predetermined condition is satisfied.

Note that in the procedure such as cannulation, the operator basically manually operates an electric endoscope; therefore, this flow is executed when the predetermined condition is satisfied. FIG. 37 shows an example of this case. In step S60, the drive control device 200 monitors operation input to the operation device 300 and determines whether or not the absence of operation input has been continued for a predetermined time. If the absence of operation input is not continued for a predetermined time, the sequence returns to step S60. If the absence of operation input is continued for a predetermined time, steps S61 to S65 similar to steps S11 to S15 in FIG. 36 are performed.

The trigger for performing steps S61 to S65 is not limited to the above, and may be, for example, a button operation in the operation device 300. Further, when an operation input to the operation device 300 is made during steps S61 to S65, the drive control device 200 may cancel steps S61 to S65 by an interruption processing and switch to the manual operation in which the endoscope is electrically driven according to the operation input.

Figure 38:
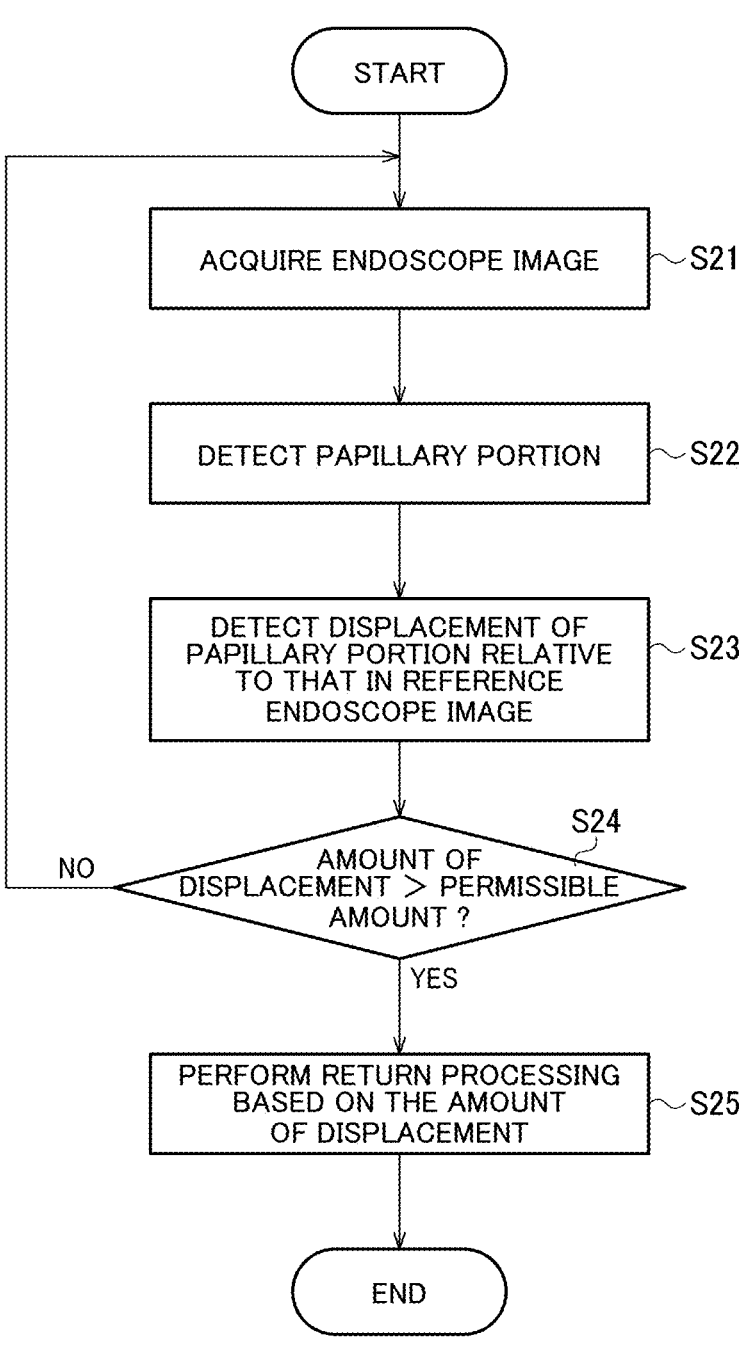
FIG. 38 shows a first detailed flow of return processing.

FIG. 38 shows a first detailed flow of return processing. In step S21, the drive control device 200 acquires an endoscope image from the video control device 500. In step S22, the drive control device 200 detects the papillary portion from the endoscope image. For example, the drive control device 200 extracts the image feature amount of the papillary portion from the endoscope image, extracts the image feature amount of the papillary portion from the reference endoscope image stored in the storage section, and detects the papillary portion based on the result of comparison of the image feature amount. Alternatively, the drive control device 200 may detect the papillary portion from the endoscope image by performing pattern matching processing on the endoscope image using the reference endoscope image stored in the storage section as a template image of the papillary portion. The detection of the papillary portion may also be included in the process using machine learning, as described later.

In step S23, the drive control device 200 detects displacement between the position of the papillary portion on the endoscope image and the position of the papillary portion on the reference endoscope image. The detection of the displacement is detection of a parallel movement in the image; however, it may also include detection of the rotation, detection of changes in imaging direction, or detection of the distance. For example, the drive control device 200 extracts the image feature amount of the papillary portion from the endoscope image, extracts the image feature amount of the papillary portion from the reference endoscope image stored in the storage section, and detects displacement of the position of the papillary portion and the amount of the displacement based on the result of comparison of the image feature amount. Alternatively, the drive control device 200 may detect the displacement of the position of the papillary portion and the amount of the displacement by performing pattern matching processing on the endoscope image using the reference endoscope image stored in the storage section as a template image of the papillary portion. The detection of the displacement in position may also be included in the process using machine learning, as described later.

Steps S22 and S23 may be performed as an integrated process by comparison of the image feature amount or template matching. The detection of the rotation, the detection of the imaging direction, or the detection of the distance may be performed, for example, by preparing the reference endoscope images with various rotation angles, various imaging directions or various distances, and then performing the comparison of the image feature amount or template matching using those reference endoscope images. The method described later with reference to FIG. 39 may also be used for detecting a distance change.

In step S24, the drive control device 200 determines whether the amount of displacement in position detected in step S23 is greater than the permissible amount. If the amount of displacement in position is not greater than the permissible amount, the sequence returns to step S21. If the amount of displacement in position is greater than the permissible amount, in step S25, the drive control device 200 controls the electrically-driven endoscopic operation based on the amount of displacement in position so that the endoscope image is returned to the reference endoscope image. Specifically, the drive control device 200 controls the endoscopic operation so that the amount of displacement in position is equal to or below a predetermined amount. The "predetermined amount" herein may be different from the permissible amount in step S24, e.g., it may be smaller than the permissible amount in step S24.

The relationship between the displacement in position on the image, the forward/backward movement, the bending, and the rolling rotation of the endoscope can be expressed by associating them in a table, a conversion formula or the like. The drive control device 200 controls the forward/backward movement, the bending, and the rolling rotation of the endoscope based on such association and the amount of displacement in position so as to return the endoscope to the reference position. Alternatively, as described below, it may be done by machine learning that also enables the association.

All or part of steps S22 to S25 may be performed by a process using machine learning. More specifically, the storage section of the drive control device 200 stores a trained model, and the drive controller 200 performs all or a part of steps S22 to S25 by performing a process based on the trained model. For example, when all of steps S22 to S25 are performed by machine learning, the trained model receives input of an endoscope image and is trained to output information such as an endoscopic operation to bring the position of the papillary portion in the endoscope image to be closer to the position of the papillary portion in the reference endoscope image. The drive control device 200 presumes information of an endoscopic operation from an endoscope image by a process based on the trained model, and controls the endoscopic operation based on the information. In this example, it is not necessary to store the reference endoscope image in the storage section of the drive control device 200, and information such as the position of the papillary portion included in the reference endoscope image is reflected to the trained model by the learning.

Figure 39:
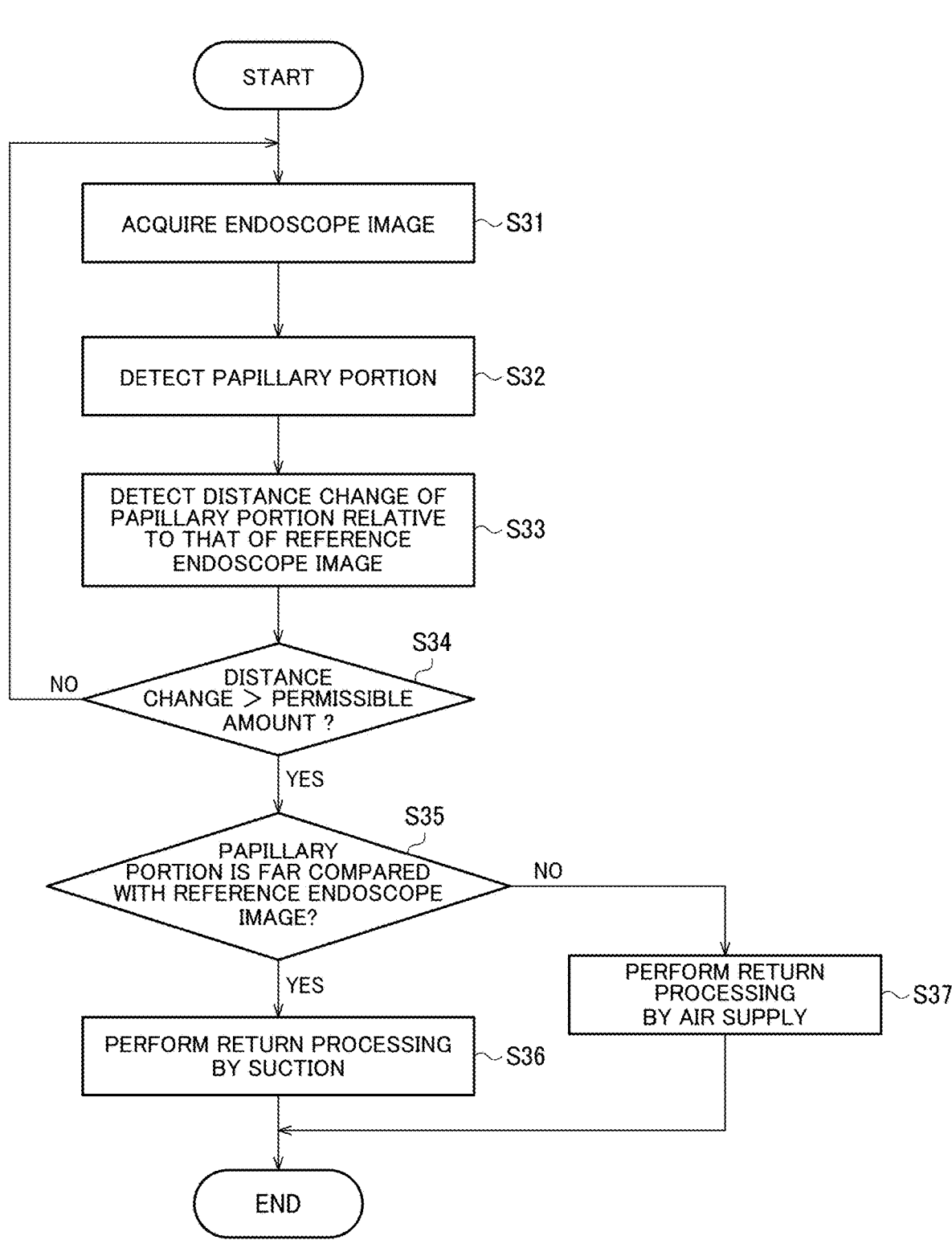
FIG. 39 shows a second detailed flow of return processing.

FIG. 39 shows a second detailed flow of return processing. Steps S31 and S32 are similar to steps S21 and S22 in FIG. 38.

In step S33, the drive control device 200 detects a distance change between the distance between the distal end section of the endoscope and the papillary portion in the endoscope image and the distance between the distal end section of the endoscope and the papillary portion in the reference endoscope image. For example, the drive control device 200 prepares, as template images, the reference endoscope images with various distances by enlarging/reducing the reference endoscope image at various magnifications, and performs template matching of the endoscope image using these template images. The drive control device 200 presumes the distance change from the magnification of a template image with the highest correlation, from among the template images at various magnifications. Alternatively, the drive control device 200 may presume the distance change by comparing the area of the region of the papillary portion in the endoscope image with the area of the region of the papillary portion in the reference endoscope image. For example, the drive control device 200 may detect the region of the papillary portion from the endoscope image using the trained model that has been trained to segment the region from the input image to the region of the papillary portion, and calculate the area of the region. The area of the region of the papillary portion in the reference endoscope image may be, for example, stored in the storage section of the drive control device 200 in advance.

When the template matching is used in step S33, steps S32 and S33 may be executed as an integrated process by template matching.

In step S34, the drive control device 200 determines whether or not the distance change detected in step S33 is greater than the permissible amount. The permissible amount herein is different from the permissible amount of the amount of displacement in position in FIG. 38. If the distance change is not greater than the permissible amount, the sequence returns to step S31. If the distance change is greater than the permissible amount, in step S35, the drive control device 200 determines whether the distance between the distal end section of the endoscope and the papillary portion in the endoscope image is larger than the distance between the distal end section of the endoscope and the papillary portion in the reference endoscope image. Specifically, the drive control device 200 determines that the distance is large when the size of the papillary portion shown in the endoscope image is smaller than that in the reference endoscope image.

If it is determined that the distance to the papillary portion becomes larger, in step S36, the drive control device 200 performs suction, thereby returning the endoscope image to the reference endoscope image. Specifically, the drive control device 200 drives the air supply suction pump to perform suction from the distal end section 130 of the endoscope 100 via the air supply suction channel. For example, the treatment tool channel also serves as the air supply suction channel, and the gas in the duodenum is suctioned through the opening for the treatment tool in the distal end section 130 of the endoscope 100. As a result, the duodenum is contracted, thereby bringing the distal end section 130 and the papillary portion closer.

If it is determined that the papillary portion becomes closer, in Step S37, the drive control device 200 performs air supply, thereby returning the endoscope image to the reference endoscope image. Specifically, the drive control device 200 drives the air supply suction pump to perform air supply from the distal end section 130 of the endoscope 100 via the air supply suction channel. In the air supply, for example, carbon dioxide, oxygen, or like gases are used. As a result, the duodenum is inflated, thereby increasing the distance between the distal end section 130 and the papillary portion.

By performing the air supply suction, it is possible to adjust the distance between the distal end section 130 and the papillary portion with almost no change in the line-of-sight direction of the camera. If only the distance is changed with the camera substantially directly facing the papillary portion, it is more appropriate to perform the adjustment by the air supply suction rather than by bending that changes the line-of-sight direction of the camera. When the distance between the distal end section 130 and the papillary portion is changed by an amount greater than the first permissible amount and smaller than the second permissible amount, the distance may be adjusted by bending; further, when the distance is changed by an amount greater than the second permissible amount, the distance may be adjusted by the air supply suction. The second permissible amount is larger than the first permissible amount. When the distance change is small, the change in the line-of-sight direction due to the bending is small; therefore, the bending that enables rapid control is used for adjustment. When the distance change is large, the air supply suction that causes no change in the line-of-sight direction is used.

The relationship between the amount of distance change detected from the image and the amount of air suction or air supply can be expressed by associating them in a table, a conversion formula or the like. The drive control device 200 controls the amount of air suction or air supply based on such association and the amount of distance change so as to return the endoscope to the reference position. Alternatively, as described below, it may be done by machine learning that also enables the association.

All or part of steps S32 to S35 may be performed by a process using machine learning. More specifically, the storage section of the drive control device 200 stores a trained model, and the drive controller 200 performs all or a part of steps S32 to S35 by performing a process based on the trained model. For example, if steps S32 and S33 are performed by machine learning, they are performed as described above. Alternatively, when all of steps S32 to S35 are performed by machine learning, the trained model receives input of an endoscope image and is trained to output information of air supply suction to bring the size of the region of the papillary portion in the endoscope image to be closer to the size of the region of the papillary portion in the reference endoscope image. The drive control device 200 presumes information of air supply suction from an endoscope image by a process based on the trained model, and controls the air supply suction based on the information.

The detection of distance change is not limited to detection from images. For example, it may be arranged such that a distance measuring device such as a stereo measuring device is provided in the distal end section 130 of the endoscope 100, and the distance between the distal end section 130 and the papillary portion is measured by the distance measuring device.

Figure 40:
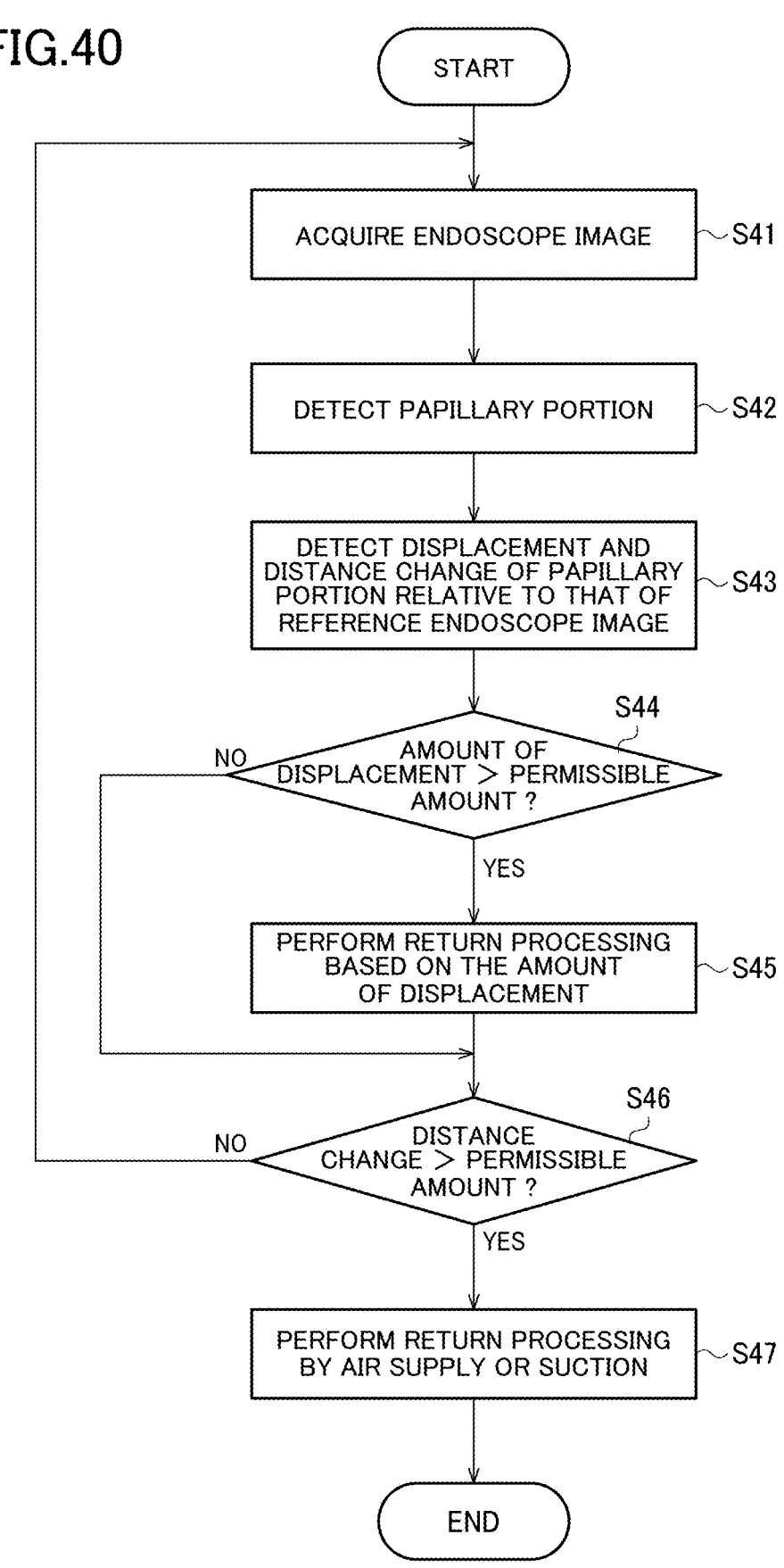
FIG. 40 shows a third detailed flow of return processing.

FIG. 40 shows a third detailed flow of return processing. Steps S41 and S42 are similar to steps S21 and S22 in FIG. 38. In step S43, the drive control device 200 detects the displacement in position and the distance change of the papillary portion in the same manner as in step S23 in FIG. 38 and step S33 in FIG. 39.

In step S44, the drive control device 200 determines whether or not the amount of displacement in position detected in step S43 is greater than the permissible amount. If the amount of displacement in position is not greater than the permissible amount, the sequence goes to step S46. If the amount of displacement in position is greater than the permissible amount, in step S45, the drive control device 200 controls at least one of the forward/backward movement, the bending, and the rolling rotation of the endoscope based on the amount of displacement in position so that the endoscope image is returned to the reference endoscope image.

In step S46, the drive control device 200 determines whether or not the distance change detected in step S43 is greater than the permissible amount. The permissible amount herein is different from the permissible amount of the amount of displacement in position in step S44. If the distance change is not greater than the permissible amount, the sequence returns to step S41. If the distance change is greater than the permissible amount, in step S47, the drive control device 200 performs air supply or suction so that the endoscope image is returned to the reference endoscope image. This control is similar to steps S35 to S37 in FIG. 39.

Although FIG. 40 shows an example in which a return processing based on the amount of displacement in position is performed first, a return processing based on the distance change may be performed first. That is, the order of steps S44 and S45 and steps S46 and S47 may be reversed in the flow shown in FIG. 40.

FIG. 41 shows a third detailed flow of return processing. Steps S51 and S52 are similar to steps S21 and S22 in FIG. 38. Step S53 is similar to step S43 in FIG. 40. In step S54, the drive control device 200 determines whether or not the amount of displacement in position detected in step S53 is greater than the permissible amount and whether or not the distance change detected in step S53 is greater than the permissible amount. The permissible amount of the distance change is different from the permissible amount of the amount of displacement in position.

If the amount of displacement in position is smaller than the permissible amount and the distance change is smaller than the permissible amount, the sequence returns to step S51. If the distance change is greater than the permissible amount, in Step S55, the drive control device 200 performs air supply or suction depending on the amount of the distance change so that the endoscope image is returned to the reference endoscope image. If the amount of displacement in position is greater than the permissible amount, in step S56, the drive control device 200 controls at least one of the forward/backward movement, the bending, and the rolling rotation of the endoscope based on the amount of displacement in position so that the endoscope image is returned to the reference endoscope image.

Detailed Configuration Example of Medical System

Figure 42:
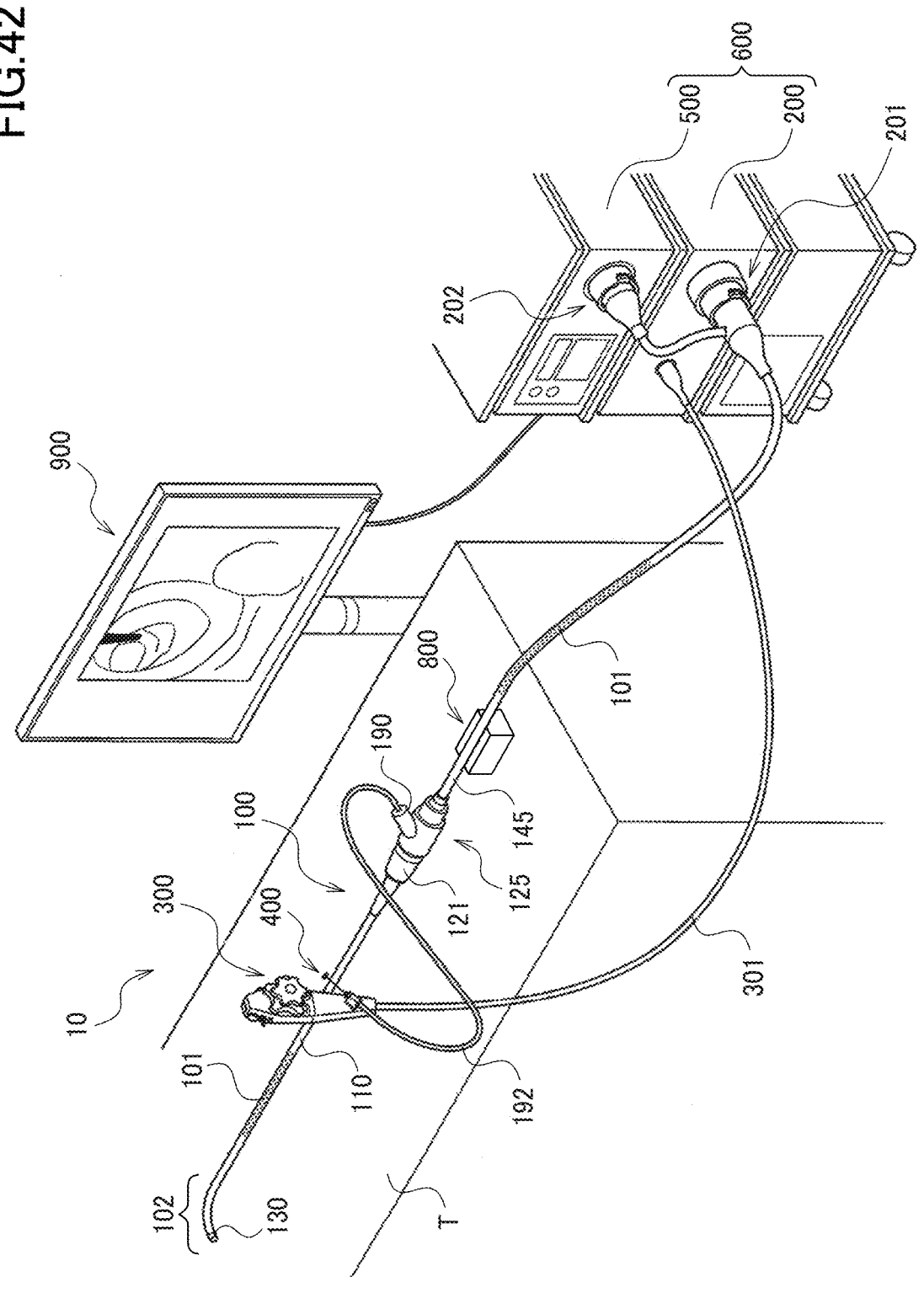
FIG. 42 shows a detailed configuration example of a medical system.

FIG. 42 shows a detailed configuration example of the medical system 10. The medical system 10 is a system for observing or treating the inside of the body of a patient lying on an operating table T. The medical system 10 includes an endoscope 100, a control device 600, an operation device 300, a treatment tool 400, a forward/backward drive device 800, and a display device 900. The control device 600 includes a drive control device 200 and a video control device 500.

The endoscope 100 is a device to be inserted into a lumen of a patient for the observation of an affected part. In this embodiment, the side to be inserted into a lumen of a patient is referred to as "distal end side" and the side to be attached to the control device 600 is referred to as "base end side". The endoscope 100 includes an insertion section 110, a connecting section 125, an extracorporeal soft section 145, and connectors 201 and 202. The insertion section 110, the connecting section 125, the extracorporeal soft section 145, and the connectors 201 and 202 are connected one another in this order from the distal end side.

The insertion section 110 is a portion to be inserted into a lumen of a patient, and is configured in a soft elongated shape. The insertion section 110 includes a bending section 102, an extracorporeal soft section for connecting the base end of the bending section 102 and the connecting section 125, and a distal end section 130 provided at the distal end of the bending section 102. An internal route 101 is provided inside the insertion section 110, the connecting section 125, and the extracorporeal soft section 145, and a bending wire passing through the internal route 101 is connected to the bending section 102. When the drive control device 200 drives the wire via the connector 201, the bending section 102 bends. Further, a raising base wire connected to the raising base provided at the distal end section 130 is connected to the connector 201 through the internal route 101. As the drive control device 200 drives the raising base wire, the raising angle of the treatment tool 400 protruding from the side surface of the distal end section 130 is changed. The side surface of the distal end section 130 is provided with a camera, an illumination lens, and an opening of a treatment tool channel. An image signal line for connecting the camera and the connector 202 is provided in the internal route 101, and an image signal is transmitted from the camera to the video control device 500 via the image signal line. The video control device 500 displays an endoscope image generated from the image signal on the display device 900.

The connecting section 125 is provided with an insertion opening 190 of the treatment tool and a rolling operation section 121. The treatment tool channel is provided in the internal route 101, one end of which is open to the distal end section 130 and the other end of which is open to the insertion opening 190 of the treatment tool. An extension tube 192 extending from the insertion opening 190 to the operation device 300 is connected to the insertion opening 190. The treatment tool 400 is inserted from an opening on the operation device 300 side of the extension tube 192, and protrudes to the opening of the distal end section 130 via the insertion opening 190 and the treatment tool channel. The extension tube 192 may be omitted, and the treatment tool 400 may be inserted through the insertion opening 190. The rolling operation section 121 is attached to the connecting section 125 so as to be rotatable about the axial direction of the insertion section 110. By rotating the rolling operation section 121, the insertion section 110 undergoes rolling rotation. As described later, the rolling operation section 121 can be electrically driven.

The forward/backward drive device 800 is a drive device for moving the insertion section 110 forward and backward by electrical driving. An extracorporeal soft section 140 is detachable from the forward/backward drive device 800, and an insertion section 110 moves forward and backward when the forward/backward drive device 800 causes the extracorporeal soft section 140 to slide in the axial direction in a state in which the extracorporeal soft section 140 is mounted on the forward/backward drive device 800. Although FIG. 42 shows an example in which the extracorporeal soft section 140 and the forward/backward drive device 800 are detachable, there is no such limitation, and it may be arranged such that the connecting section 125 and the forward/backward drive device 800 are detachable.

The operation device 300 is detachably connected to the drive control device 200 via an operation cable 301. The operation device 300 may communicate with the drive control device 200 through wireless communication instead of wired communication. When an operator operates the operation device 300, a signal of the operation input is transmitted to the drive control device 200 via the operation cable 301, and the drive control device 200 electrically drives the endoscope 100 to enable an endoscopic operation corresponding to the operation input based on the signal of the operation input. The operation device 300 has an operation input section having six or more channels corresponding to the forward and backward movement of the endoscope 100, the bending movements in two directions and the rolling rotation, the operation of the raising base, and air supply suction. If one or more of these operations are not electrically driven, the operation input section may be omitted. Each operation input section includes, for example, a dial, a joystick, a D-pad, a button, a switch, a touch panel, and the like.

The drive control device 200 electrically drives the endoscope 100 by driving a built-in motor based on an operation input to the operation device 300. Alternatively, when the motor is present outside the drive control device 200, the drive control device 200 transmits a control signal to the external motor based on an operation input to the operation device 300, thereby controlling the electrical driving. In addition, the drive control device 200 drives a built-in pump or the like based on an operation input to the operation device 300, thereby causing the endoscope 100 to perform air supply suction. The air supply suction is performed through an air supply/suction tube provided in the internal route 101. One end of the air supply/suction tube opens to the distal end section 130 of the endoscope 100, while the other end is connected to the drive control device 200 via the connector 201. In addition, the treatment tool channel may be extended to the connector 201, and the treatment tool channel may also be used as an air supply/suction tube.

Figure 43:
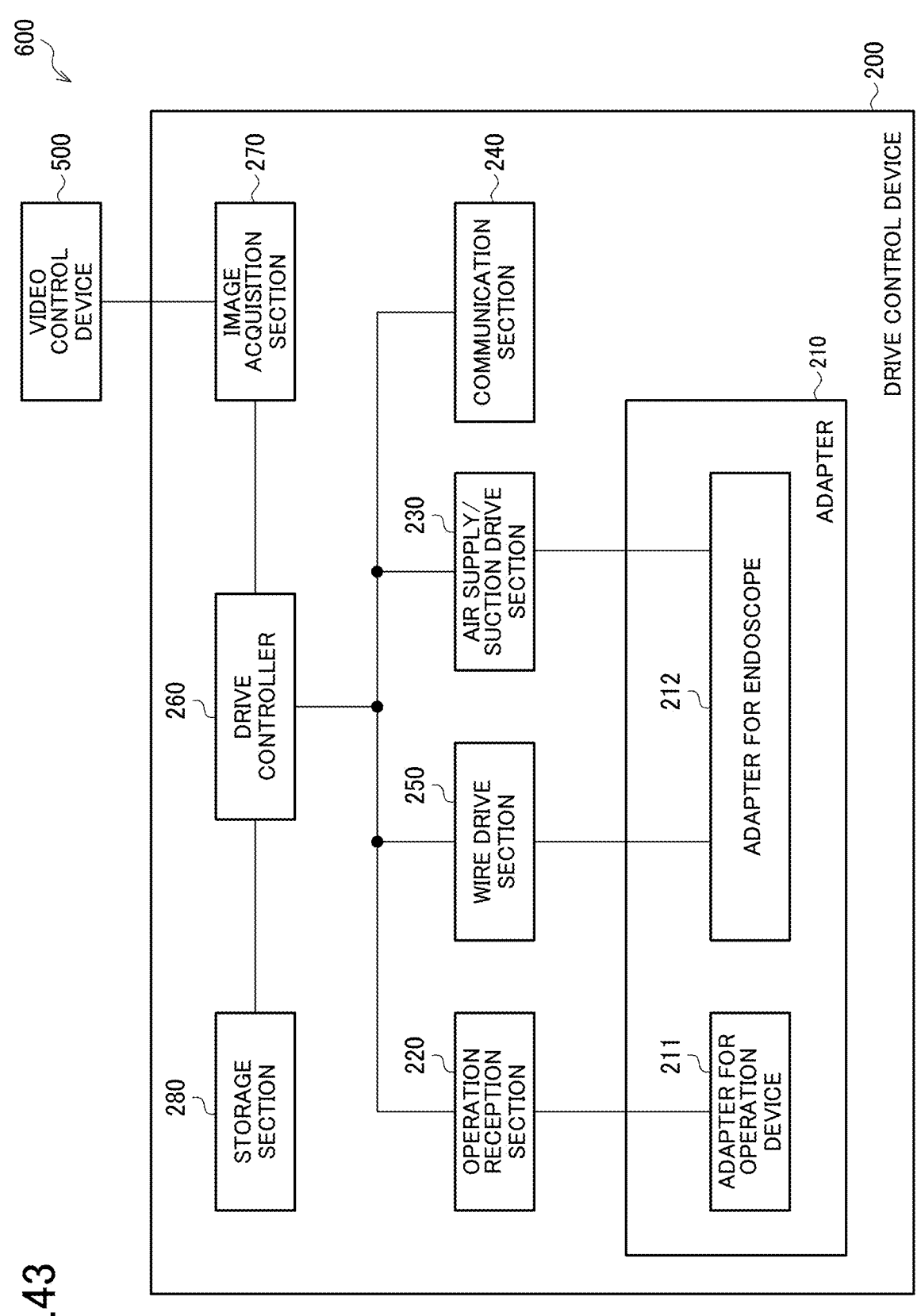
FIG. 43 shows a detailed configuration example of a drive control device.

FIG. 43 shows a detailed configuration example of a drive control device 200. The drive control device 200 includes an image acquisition section 270, a storage section 280, a drive controller 260, an operation reception section 220, a wire drive section 250, an air supply/suction drive section 230, a communication section 240, and an adapter 210.

The adapter 210 includes an operation device adapter 211 to which the operation cable 301 is detachably connected, and an endoscope adapter 212 to which the connector 201 of the endoscope 100 is detachably connected.

The wire drive section 250 drives the bending movement of the bending section 102 of the endoscope 100 or the operation of the raising base of the treatment tool 400 based on the control signal from the drive controller 260. The wire drive section 250 includes a bending movement motor unit for driving the bending section 102 of the endoscope 100 and a raising base motor unit for driving the raising base. The endoscope adapter 212 has a bending movement coupling mechanism for enabling coupling to the bending wire on the endoscope 100 side. When the bending movement motor unit drives the coupling mechanism, the driving force is transmitted to the bending wire on the endoscope 100 side.

Further, the endoscope adapter 212 has a raising base coupling mechanism for enabling coupling to the raising base wire on the endoscope 100 side. When the raising base motor unit drives the coupling mechanism, the driving force is transmitted to the raising base wire on the endoscope 100 side.

The air supply/suction drive section 230 drives air supply suction of the endoscope 100 based on a control signal from the drive controller 260. The air supply/suction drive section 230 is connected to an air supply/suction tube of the endoscope 100 via the endoscope adapter 212. The air supply/suction drive section 230 includes a pump or the like, and supplies air to the air supply/suction tube or sucks air from the air supply/suction tube 172.

The communication section 240 communicates with a drive device provided outside the drive control device 200. The communication may be wireless communication or wired communication. The drive device provided outside is a forward/backward drive device 800 for performing forward and backward movement, or a rolling drive device for performing the rolling rotation.

The drive controller 260 controls the forward and backward movement, the bending movement and the rolling rotation of the endoscope 100, the raising angle of the treatment tool 400 made by the raising base, and the air supply suction by the endoscope 100. The drive controller 260 is, for example, a processor such as a CPU (Central Processing Unit), a GPU (Graphics Processing Unit), a DSP (Digital Signal Processor), or the like. For example, the storage section 280 stores a computer-readable program, and the functions of the drive controller 260 are implemented as processes as the processor executes the program. The storage section 280 is a storage device such as a semiconductor memory or a magnetic storage device. The semiconductor memory may be a volatile memory such as a SRAM or a DRAM, or a nonvolatile memory such as an EEPROM. However, the hardware of the drive controller 260 is not limited to that described above, and may be structured using circuits with various configurations.

The electric control performed by the drive controller 260 includes a manual mode in which the operator manually operates the electrical driving of the endoscope 100 or the like and a return processing mode for automatically restoring the endoscope position described in the flow in FIG. 36 to FIG. 41.

The return processing mode may be regarded a type of the automatic control mode or the semi auto mode. The switching between the manual mode and the return processing modes is as described in FIG. 37.

First, the manual mode is described below. The operation reception section 220 receives an operation input signal from the operation device 300 via the operation cable 301 attached to the operation device adapter 221. When the operation device 300 communicates with the drive control device 200 by wireless communication, the operation reception section 220 may be a wireless communication circuit.

The drive controller 260 controls the electrical driving based on an operation input signal from the operation reception section 220. Specifically, when the bending operation is performed, the drive controller 260 outputs a control signal indicating the bending direction or the bending angle to the wire drive section 250, and the wire drive section 250 drives the bending wire so that the bending section 102 bends in the bending direction or the bending angle. Also, when the forward and backward movement operation is performed, the drive controller 260 transmits a control signal indicating the forward/backward direction or the forward/backward movement amount to the forward/back-ward drive device via the communication section 240, and the forward/backward drive device moves the extracorpo-real soft section 140 forward or backward so that the endoscope 100 moves forward or backward in the forward/backward direction or the forward/backward movement amount. Further, when the rolling rotation operation is performed, the drive controller 260 transmits a control signal indicating the rolling rotation direction or the rolling rotation angle to the rolling drive device via the communi-cation section 240, and the rolling drive device performs rolling rotation of the insertion section 110 so that the endoscope 100 undergoes rolling rotation in the rolling rotation direction or at the rolling rotation angle. When the air supply suction operation is performed, the drive control-ler 260 sends a control signal indicating the amount or speed of the air supply suction to the air supply/suction drive section 230, and the air supply/suction drive section 230 performs the air supply suction with the amount or speed of air supply suction.

The return processing mode is as described in FIG. 36 to FIG. 41. In the return processing mode, the drive controller 260 performs one of the flows described in FIG. 36 to FIG. 41. The storage section 280 stores the reference endoscope image or the trained model described in FIG. 36 to FIG. 41. The drive controller 260 performs the flow described in FIG. 36 to FIG. 41 using the reference endoscope image or the trained model stored in the storage section 280.

Detailed Configuration Example of Each Part of Medical System

Figure 44:
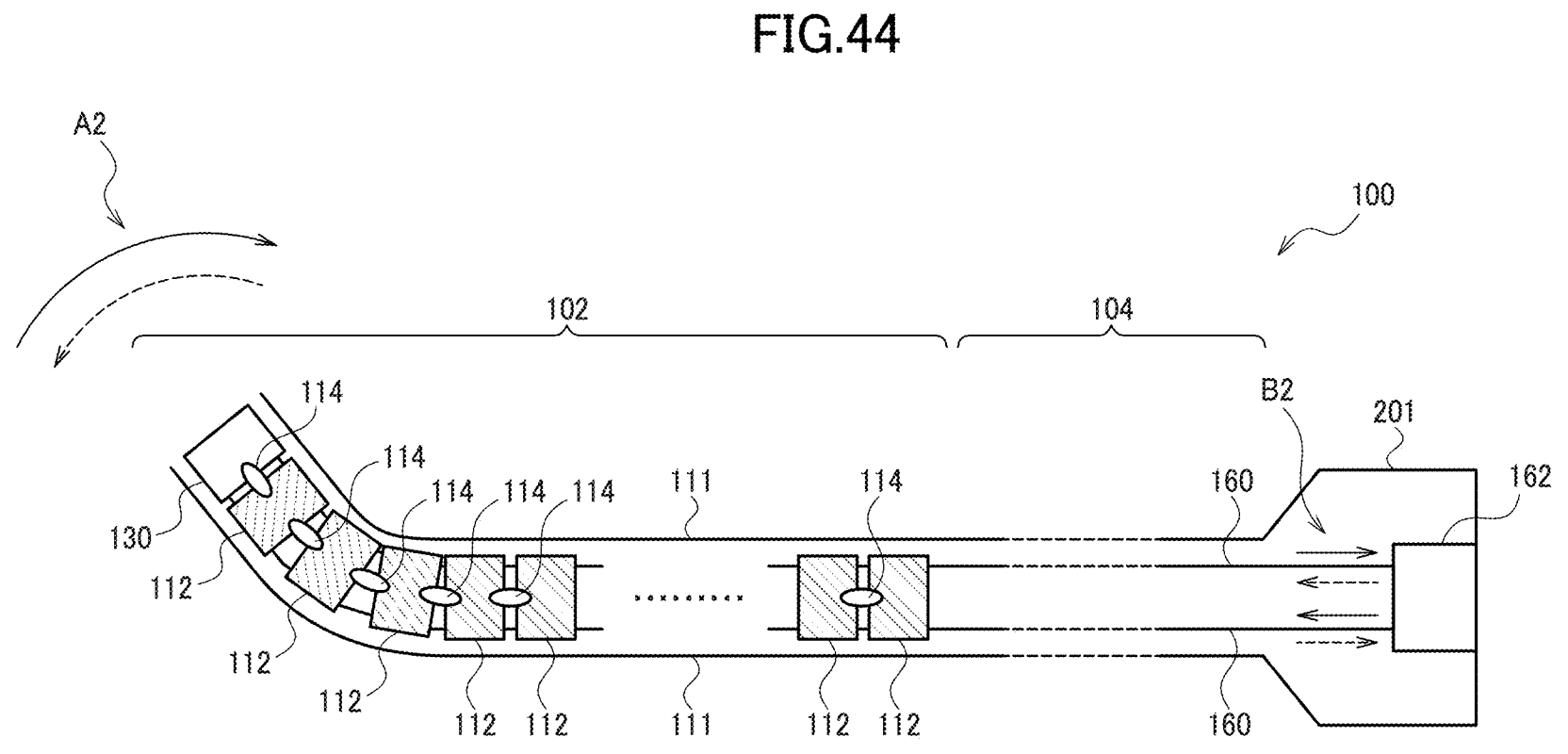

FIG. 44 is a schematic view of an endoscope 100 includ-ing a bending section 102 and a driving mechanism thereof. An endoscope 100 includes a bending section 102, a soft section 104, and a connector 201. The soft section 104 corresponds to the intracorporeal soft section and the extra-corporeal soft section 145 described above with reference to FIG. 42. In FIG. 44, the connecting section 125 is omitted.

The bending section 102 and the soft section 104 are covered with an outer sheath 111. The inside of the tube of the outer sheath 111 corresponds to the internal route 101 in FIG. 42. The bending section 102 includes a plurality of bending pieces 112 and a distal end section 130 connected to the distal end of the bending pieces 112. Each of the plurality of bending pieces 112 and the distal end section 130 is connected in series from the base end side to the distal end side by a rotatable connecting section 114, thereby forming a multi joint structure. The connector 201 is provided with a coupling mechanism 162 on the endoscope side connected to a coupling mechanism on the drive control device 200 side. By attaching the connector 201 to the drive control device 200, it is possible to electrically drive the bending movement. A bending wire 160 is provided in the outer sheath 111. One end of the bending wire 160 is connected to the distal end section 130. The bending wire 160 passes through the soft section 104 by penetrating through a plurality of bending pieces 112, turns back in a coupling mechanism 162, passes through the soft section 104 again, penetrates through the plurality of bending pieces 112. The other end of the bending wire 160 is connected to the distal end section 130. The driving force from the wire drive section 250 is transmitted to the bending wire 160 via the coupling mechanism 162 as the pulling force of the bending wire 160.

As shown by the solid line arrow B2, when the upper wire in the figure is pulled, the lower wire is pushed, whereby the multiple joints of the bending pieces 112 are bent upward in the figure. As a result, as indicated by the solid line arrow A2, the bending section 102 is bent upward in the figure. When the lower wire in the figure is pulled as indicated by the dotted arrow B2, similarly, the bending section 102 is bent downward in the figure as indicated by the dotted arrow A2. As described with reference to FIG. 35, the bending section 102 can be bent independently in two orthogonal directions. Although FIG. 44 shows a bending mechanism for one direction, two sets of bending wires are actually provided, and each bending wire can be bent independently in two directions by being pulled independently by the coupling mechanism 162.

Note that the mechanism for the electrically-driven bend-ing is not limited to that described above. For example, a motor unit may be provided instead of the coupling mecha-nism 162. Specifically, it may be arranged such that the drive control device 200 transmits a control signal to the motor unit via the connector 201, and the motor unit drives the bending movement by pulling or relaxing the bending wire 160 based on the control signal.

Figure 45:
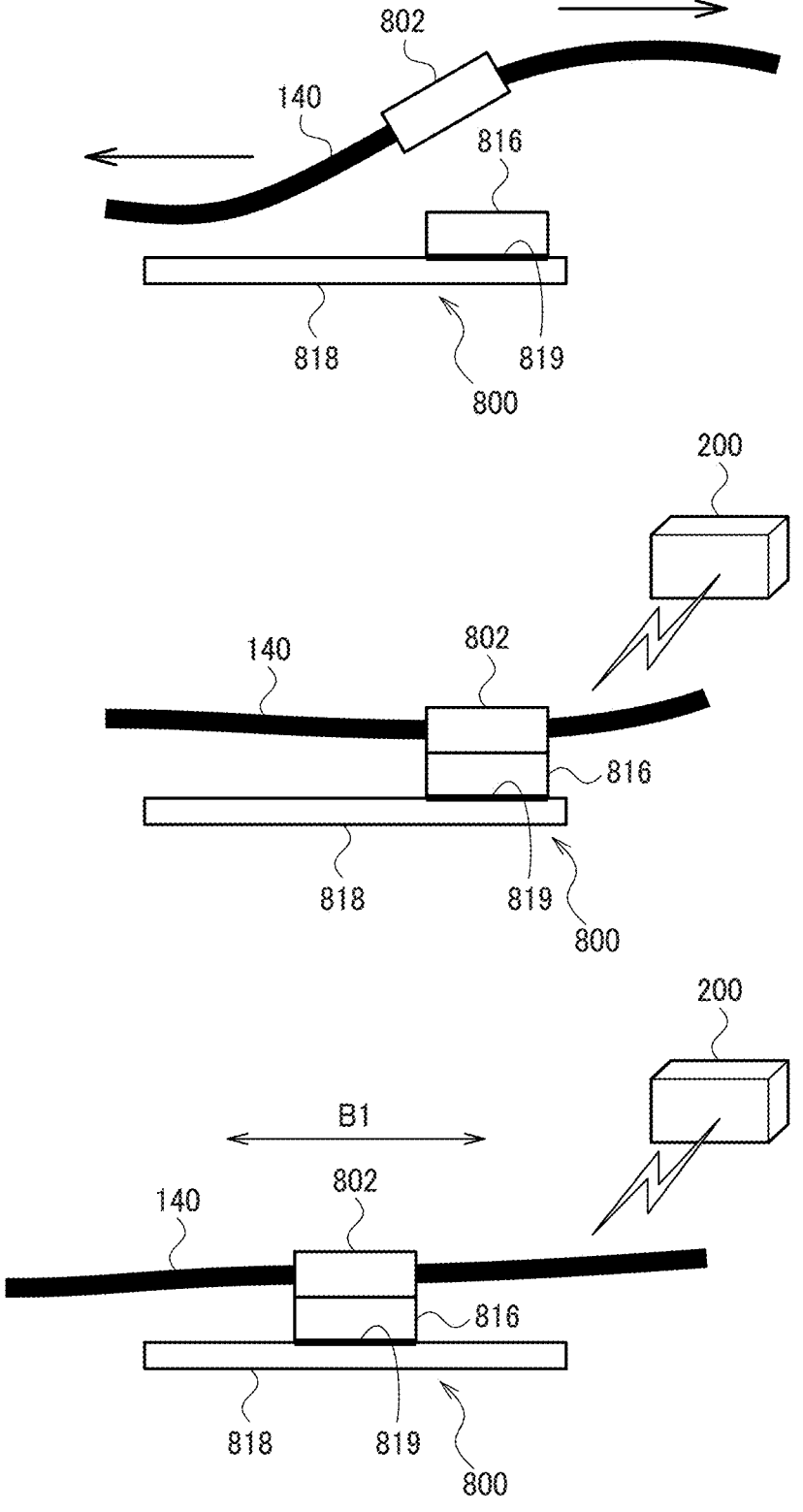
FIG. 45 shows a detailed configuration example of a forward/backward drive device.

FIG. 45 shows a detailed configuration example of a forward/backward drive device 800. The forward/backward drive device 800 includes a motor unit 816, a base 818, and a slider 819.

As shown in the upper and middle figures, the extracor-poreal soft section 140 of the endoscope 100 is provided with an attachment 802 detachable from the motor unit 816. As shown in the middle figure, the attachment of the attachment 802 to the motor unit 816 enables electrical driving of forward/backward movement. As shown in the lower figure, the slider 819 supports the motor unit 816 while enabling the motor unit 816 to move linearly with respect to the base 818. The slider 819 is fixed to the operating table T shown in FIG. 42. As shown in B1, the drive control device 200 transmits a forward or backward control signal to the motor unit 816 by wireless communi-cation, and the motor unit 816 and the attachment 802 move linearly on the slider 819 based on the control signal. As a result, the forward and backward movement of the endo-scope 100 shown in A1 in FIG. 35 is achieved. Note that the drive control device 200 and the motor unit 816 may be connected by wired connection.

Figure 46:
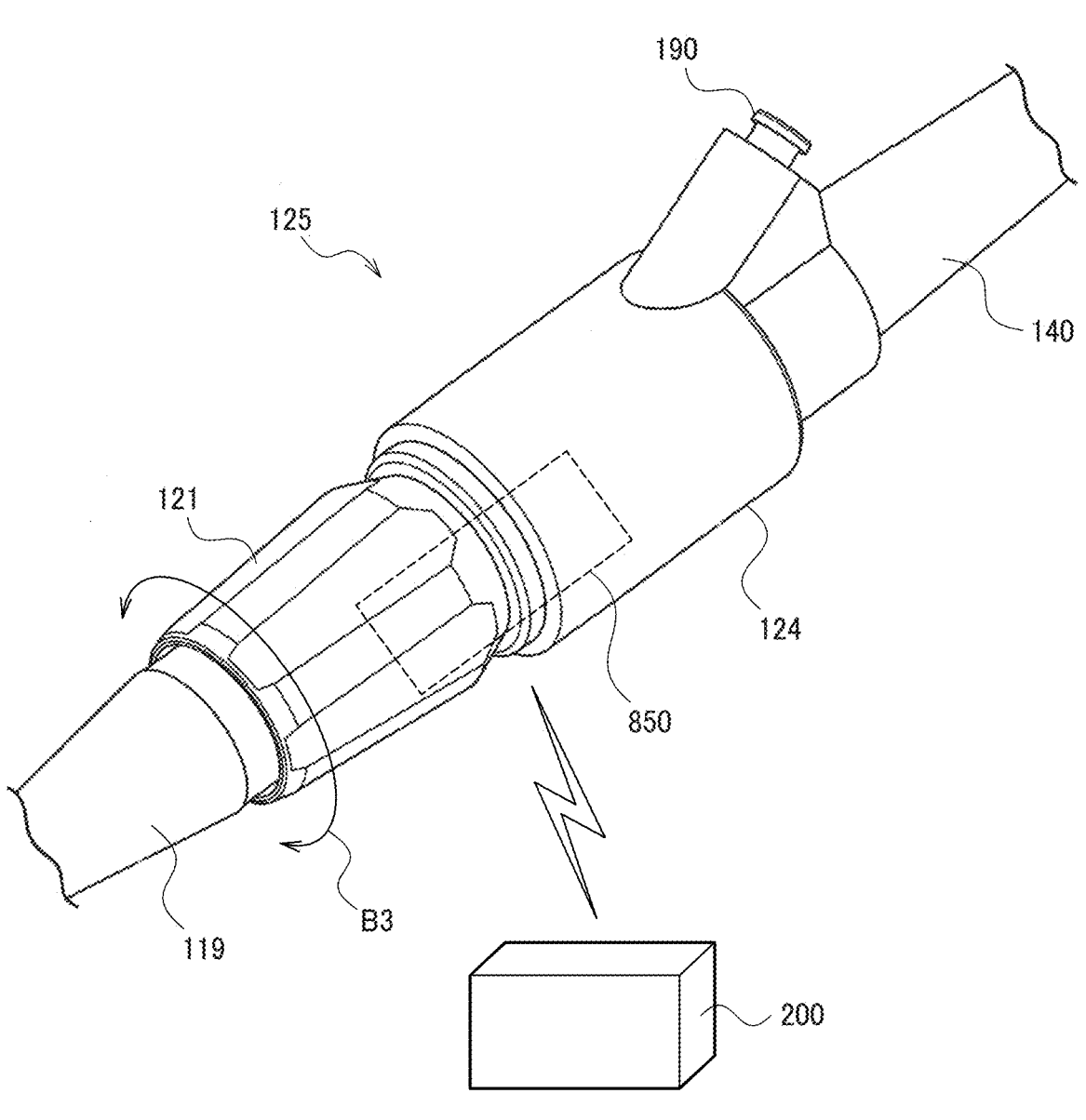
FIG. 46 is a perspective view of a connecting section including a rolling drive device.

FIG. 46 is a perspective view of the connecting section 125 including a rolling drive device 850. The connecting section 125 includes a connecting section main body 124 and a rolling drive device 850.

The insertion opening 190 of the treatment tool is pro-vided in the connecting section main body 124 and is connected to the treatment tool channel inside the connect-ing section main body 124. The connecting section main body 124 has a cylindrical shape, and a cylindrical member coaxial with the cylinder is rotatably provided inside the connecting section main body 124. The base end section of the intracorporeal soft section 119 is fixed to the outside of the cylindrical member, and the base end section serves as a rolling operation section 121. As a result, the intracorpo-real soft section 119 and the cylindrical member can rotate with respect to the connecting section main body 124 about the axial direction of the intracorporeal soft section 119. The rolling drive device 850 is a motor unit provided inside the connecting section main body 124. As shown in B3, the drive control device 200 transmits a rolling rotation control signal to the rolling drive device 850 by wireless commu-nication, and the rolling drive device 850 rotates the base end section of the intracorporeal soft section 119 with respect to the connecting section main body 124 based on the control signal, thereby causing rolling rotation of the intracorporeal soft section 119. As a result, the rolling rotation of the endoscope 100 shown in A3 in FIG. 35 is achieved. The rolling drive device 850 may include a clutch mechanism, and the rolling rotation may be switched between non-electrical driving and electrical driving by the clutch mechanism. The drive control device 200 and the rolling drive device 850 may be connected by wired connection via a signal line passing through the internal route 101.

Figure 47:
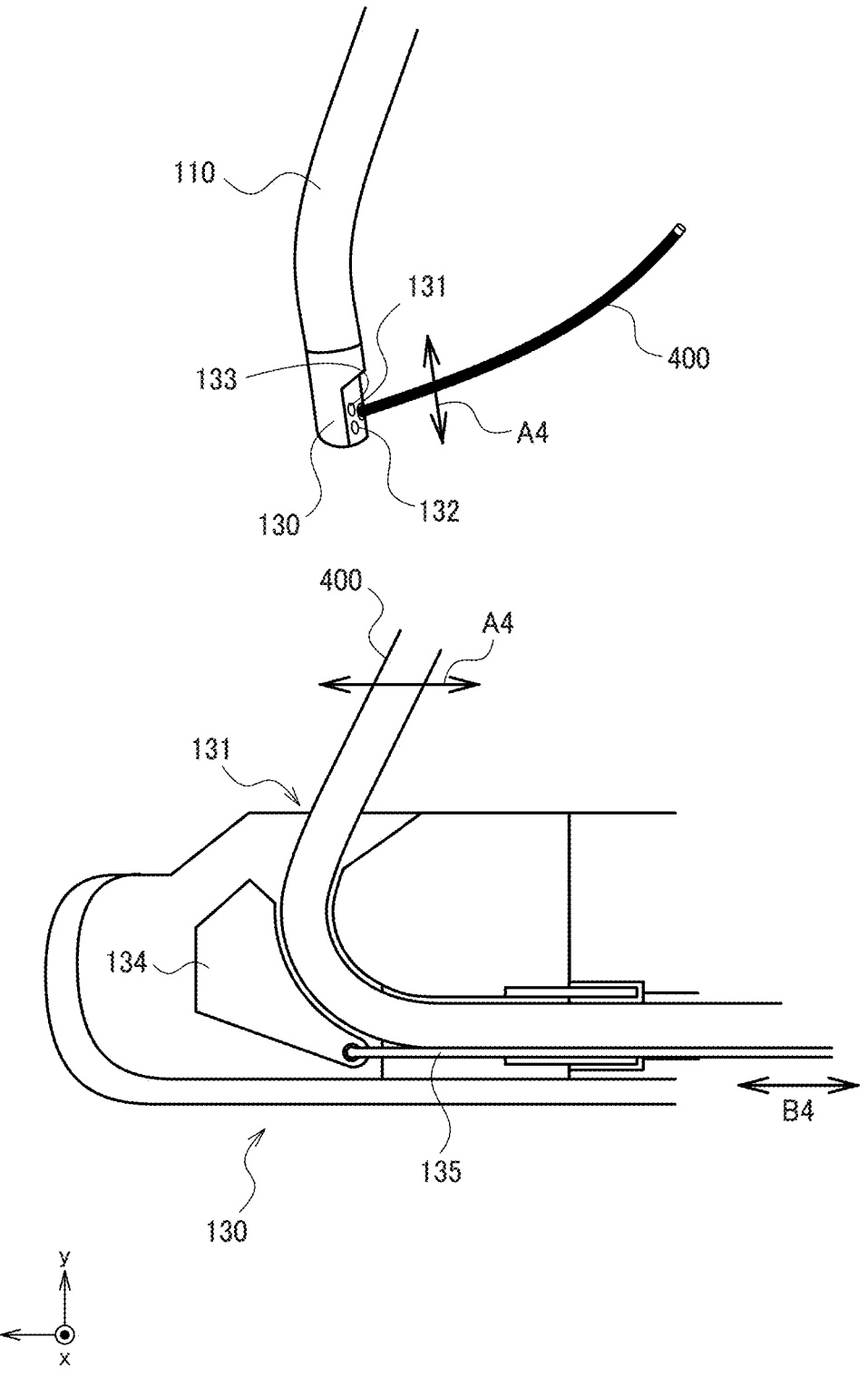
FIG. 47 shows a detailed configuration example of a distal end section of an endoscope including a raising base of a treatment tool.

FIG. 47 shows a detailed configuration example of a distal end section 130 of an endoscope including a raising base of a treatment tool. The upper figure shows an external view of the distal end section 130. An opening 131 of a treatment tool channel, a camera 132, and an illumination lens 133 are provided on the side surface of the distal end section 130. As shown in the lower figure, the direction parallel to the axial direction of the distal end section 130 is defined as z direction, the direction parallel to the line-of-sight direction of the camera 132 is defined as y direction, and the direction orthogonal to the z direction and the y direction is defined as x direction. The lower figure shows a cross-sectional view of the distal end section 130 in a plane that is parallel to the yz plane of the treatment tool channel and that passes through the opening 131 of the treatment tool channel.

The distal end section 130 includes a raising base 134 and a raising base wire 135. The raising base 134 is swingable about an axis parallel to the x direction. One end of the raising base wire 135 is connected to the raising base 134, while the other end is connected to the drive control device 200 via the connector 201. As shown in B4, the wire drive section 250 of the drive control device 200 pushes and pulls the raising base wire 135 to swing the raising base 134, thereby, as shown in A4, changing the raising angle of the treatment tool 400. The raising angle is an angle of the treatment tool 400 protruding from the opening 131. The raising angle can be defined, for example, by an angle formed by the treatment tool 400 protruding from the opening 131 and the z direction.

Figure 48:
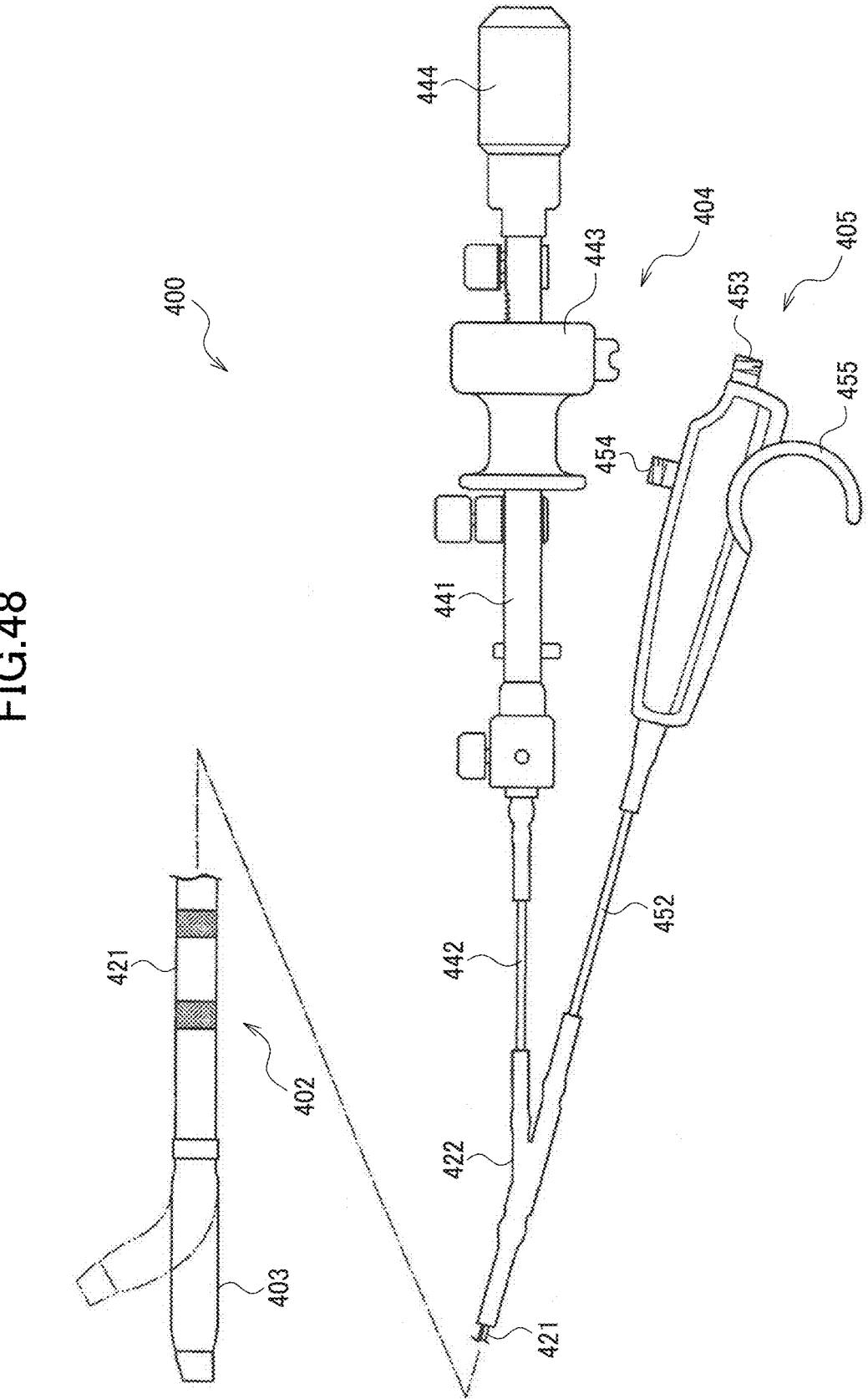
FIG. 48 shows a detailed configuration example of a treatment tool.

FIG. 48 shows a detailed configuration example of the treatment tool 400. Herein, as an example of the treatment tool 400, a cannula capable of operating bending of the distal end is shown. The treatment tool 400 includes a long-length insertion section 402 extending in the axial direction, a bending movement section 403 capable of bending movement, a first operation section 404 for operating the bending movement section 403, and a second operation section 405 for inserting a contrast agent or a guide wire.

The insertion section 402 has a tube 421, and the bending movement section 403 is connected to the distal end of the tube 421. In FIG. 48, the distal end side of the tube 421 is enlarged. The tube 421 is also referred to as a sheath. The operator holds the tube 421 of the treatment tool 400 inserted into the treatment tool channel of the endoscope 100, and pushes and pulls the tube 421 to move the treatment tool 400 forward and backward.

A connector 422 is connected to the base end of the tube 421. The first operation section 404 and the second operation section 405 are connected to the connector 422. The first operation section 404 includes a connecting tube 442, one end of which is connected to the connector 422, a first operation main body 441 connected to the other end of the connecting tube 442, a grip 444 fixed to the base end of the first operation main body 441, and a slider 443 provided movable forward and backward in the axial direction of the first operation main body 441. Inside the tube 421, the connector 422, the connecting tube 442, and the first operation main body 441, a wire for connecting the bending movement section 403 and the slider 443 is provided. When the operator pulls the slider 443 while holding the grip 444, the wire is pulled and the bending movement section 403 is bent.

The second operation section 405 includes a connecting tube 452, one end of which is connected to the connector 422, a second operation main body 451 connected to the other end of the connecting tube 452, a first opening 453 opened in the axial direction of the connecting tube 452 on the base end side of the second operation main body, a second opening 454 opened to the outer surface of the second operation main body 451, and a hook 455 provided on the second operation main body 451. The hook 455 has elasticity and is formed in a substantially C-shape, and is used for locking the treatment tool 400 to the endoscope 100 or the like. The first opening 453 and the second opening 454 are connected to the tube 421 via the second operation main body 451, the connecting tube 452, and the connector 422. By inserting a contrast agent or a guide wire from the first opening 453 or the second opening 454, the contrast agent can be injected into the body or the guide wire can be inserted into the body from the distal end of the treatment tool 400.

Although an example in which the treatment tool 400 is manually operated by non-electrical driving has been described herein, the operation of the treatment tool 400 may be operated by electrical driving. For example, using a method similar to the electrical driving of the endoscope 100, it is possible to perform the forward/backward movement of the treatment tool 400, the bending of the distal end, or the rolling rotation by electrical driving.

As explained above, by maintaining the view of the reference endoscope image in cannulation or other procedures after the positioning step during the ERCP procedure, it becomes easier to grasp the progress, condition, or abnormality of the procedure based on past cases or experiences, etc. However, the endoscope position determined in the positioning step may be disrupted in some cases by subsequent operations such as cannulation. At this time, to obtain the reference endoscope image, it is desirable to restore the endoscope position; however, for example, for inexperienced operators, it is difficult to slightly adjust the endoscope position, and it is also troublesome to repeatedly perform the return operation. The U.S. Patent Application Publication No. 2017/0086929 described above discloses an example in which a robotic catheter system is applied to ERCP, but does not disclose or suggest any of the above-mentioned problems or subject matter for solving them.

Therefore, the medical system 10 of the present embodiment includes the endoscope 100 and the control device 600. In the endoscope 100, the endoscopic operation is electrically driven, thereby capturing an endoscope image. The endoscopic operation is at least one of forward and backward movement of the insertion section 110, the bending angle of the bending section 102 of the insertion section 110, the rolling rotation of the insertion section 110, and air supply suction. The control device 600 controls the electrically-driven endoscopic operation. The control device 600 performs the return processing. A return processing is a process of controlling the electrically-driven endoscopic operation so as to return an endoscope image to the reference endoscope image of the papillary portion of duodenum.

According to the present embodiment, even if the endoscope is moved from the basic position during the procedure such as cannulation, the endoscopic operation is automatically controlled so that the endoscope returns to the position in which the reference endoscope image can be obtained. This enables the operator to easily grasp the progress, condition, or abnormality of the procedure. This also eliminates the need for manual operation to return the endoscope position; therefore, it is possible to assist, for example, inexperienced operators and the like. In addition, even in the case of performing the operations of changing the endoscope position from the reference position many times, such an automatic return eliminates the trouble of performing the manual return operation many times.

The forward and backward movement, the bending, and the rolling rotation are described with reference to FIG. 35 in "Medical System According to the Present Embodiment and Flow of ERCP Procedure Using the Medical System", etc. Further, the mechanism of air supply suction is described with reference to FIG. 33 in "Medical System According to the Present Embodiment and Flow of ERCP Procedure Using the Medical System" or FIGS. 42 and 43 in "Detailed Configuration Example of Medical System". The return processing and the reference endoscope image are described in FIGS. 36 to 41 in "Return Processing", etc. The papillary portion of the duodenum is described with reference to FIG. 27 in "Explanation of ERCP", etc.

Further, in the present embodiment, the control device 600 may perform the return processing when determining that the endoscope image has been changed from the reference endoscope image.

In the present embodiment, the return processing is performed when the view of the papillary portion in the endoscope image changes to a view that is different from that of the papillary portion in the reference endoscope image. This enables the operator to observe the papillary portion always with the same view, thereby easily grasping the progress, condition, or abnormality of the procedure based on past cases or experiences, etc.

Further, in the present embodiment, the control device 600 may perform the return processing when determining that the amount of displacement between the position of the papillary portion on the endoscope image and the position of the papillary portion on the reference endoscope image exceeds a permissible amount.

Further, in the present embodiment, it is determined the endoscope image changes from the reference endoscope image when the amount of displacement between the position of the papillary portion on the endoscope image and the position of the papillary portion on the reference endoscope image exceeds a permissible amount. As a result, when the view of the papillary portion changes more than a certain degree and becomes inappropriate for the observation of the papillary portion, it is possible to automatically restore the view of the papillary portion to that in the reference endoscope image.

The detection of displacement in position and the amount of displacement in position are described in FIG. 38 in "Return Processing", etc.

Further, in the present embodiment, the reference endoscope image may be an image in which the papillary portion is front-viewed and shown in the center of the image. The control device 600 may perform the return processing when the papillary portion is displaced from the center of the endoscope image by an operation of cannulation to a biliary duct.

It is generally desirable that the operator observes the papillary portion front-viewed and shown in the center of the image while keeping the view in the same state. According to the present embodiment, even if the papillary portion is displaced from the center of the endoscope image due to, for example, the operation of cannulation to the biliary duct, the papillary portion can be automatically restored to the state in which papillary portion is shown in the center of the endoscope image.

Further, in the present embodiment, the control device 600 may perform a return processing of controlling the bending angle so as to reduce the amount of displacement between the position of the papillary portion on the endoscope image and the position of the papillary portion on the reference endoscope image. Further, in the present embodiment, the control device 600 may perform a return processing of controlling the bending angle, and at least one of the forward and backward movement and the rolling rotation so as to reduce the amount of displacement in position.

Thus, the return processing may be performed by the bending movement alone, or by the bending movement and at least one of the forward and backward movement and the rolling rotation. As explained in FIG. 44 etc., the bending movement can be electrically driven by simply replacing the wire traction with a motor drive, and is believed to be more easily electrically driven than the forward/backward movement or the rolling rotation. For this reason, the return processing may be conducted only by the bending movement. Alternatively, the forward/backward movement or the rolling rotation may be electrically driven to further increase the flexibility or accuracy of the return operation.

Further, in the present embodiment, the control device 600 may perform the return processing when determining that the difference of the size of the papillary portion on the endoscope image and the size of the papillary portion on the reference endoscope image exceeds a permissible amount.

Further, in the present embodiment, it is determined the endoscope image changes from the reference endoscope image when the difference of a size of the papillary portion on the endoscope image and a size of the papillary portion on the reference endoscope image exceeds a permissible amount. As a result, when the distance between the distal end section of the endoscope and the papillary portion changes more than a certain degree and becomes inappropriate for the observation of the papillary portion, it is possible to automatically restore the distance between the distal end section of the endoscope and the papillary portion to an appropriate distance.

The distance change and the method for the detection thereof are described in FIG. 39 in "Return Processing", etc.

Further, in the present embodiment, the control device 600 may perform the return processing by air supply suction based on the size of the papillary portion on the endoscope image.

In the present embodiment, by performing the air supply suction, it is possible to adjust the distance between the distal end section of the endoscope and the papillary portion with almost no change in the line-of-sight direction of the camera. If only the distance is changed with the camera substantially directly facing the papillary portion, it is more appropriate to perform the adjustment by the air supply suction rather than by bending that changes the line-of-sight direction of the camera.

The return processing by way of air supply suction is described in FIG. 39 in "Return Processing", etc.

Further, in the present embodiment, the control device 600 performs the return processing so as to return the endoscope image to the reference endoscope image in which a predetermined size of the papillary portion is shown.

According to the present embodiment, when the size of the papillary portion on the endoscope image changes from a predetermined size, the image may be automatically returned to the state where a predetermined size of the papillary portion is shown. This enables the operator to always observe the same size of papillary portion, thereby easily grasping the progress, condition, or abnormality of the procedure based on past cases or experiences, etc.

Further, in the present embodiment, the control device 600 may perform the return processing by air supply suction when the size of papillary portion on the endoscope image is different from a predetermined size. The control device 600 may perform the return processing by at least one of the forward and backward movement, the bending angle, and the rolling rotation when the position of the papillary portion on the endoscope image is different from the position of the papillary portion on the reference endoscope image.

According to the present embodiment, an appropriate endoscopic operation is selected depending on whether the position of the papillary portion on the image has been changed or the distance between the distal end section of the endoscope and the papillary portion has been changed. That is, in the case where the position of the papillary portion in the image has been changed, at least one of the forward and backward movement, the bending angle, and the rolling rotation is selected because the correction cannot sufficiently be done only by the air supply suction. In the case where the distance between the distal end section of the endoscope and the papillary portion has been changed, the air supply suction in which the line-of-sight direction is less likely to change is selected.

The selection of the return processing of the endoscopic operation depending on the displacement in position or the distance change is described in FIG. 40 or FIG. 41 in "Return Processing", etc.

Further, in the present embodiment, the control device 600 may monitor an operation input to the operation device 300, and perform the return processing when the operation input is not performed for a predetermined time.

When the operator is manually operating the electric endoscope, it is likely that the operator is performing the necessary operations for the procedure; therefore, intervention of automatic control should be avoided. According to the present embodiment, the return processing is performed when operation input has not been performed for a predetermined time of time. In this way, there will be no intervention of automatic return while the operator is performing a manual operation, and the automatic return is performed when the manual operation by the operator is completed.

The execution of return processing when operation input has not been performed for a predetermined time is described in FIG. 37 in "Return Processing", etc.

Further, in the medical system 10, the electrical driving of the bending movement of the endoscope 100 is not limited to the structure of the present embodiment. For example, it may be structured such that an attachment equipped with an electric motor is detachably attached to a bending operation knob of a non-electrically-driven endoscope. The drive control device 200 and the attachment are structured to communicate with each other, and, upon reception of a bending control signal from the drive control device 200, the attachment is driven to perform the bending. In this case, the manual control and the automatic control can be switched by attaching and detaching the attachment. It may also be arranged such that a handle capable of controlling the driving of the drive control device 200 is detachably attached to a motor unit for bending control corresponding to the drive control device 200. In this case, the manual control and the automatic control can be switched by attaching and detaching the handle.

The present embodiment may also be performed as a method of operating the medical system 10 as follows. That is, the method of operating the medical system 10 includes a step of causing the endoscope 100 that electrically drives an endoscopic operation, which is at least one of forward and backward movement of the insertion section 100, a bending angle of a bending section 102 of the insertion section 110, rolling rotation of the insertion section 110, and air supply suction to capture an endoscope image; and a step of performing a return processing for controlling the electrically-driven endoscopic operation so as to return the endoscope image to the reference endoscope image of the papillary portion of the duodenum. In the method of operating the medical system 10, the subject of each step is the medical system 10.

According to some aspects of the present embodiment, the following are provided.

1. A medical system comprising:
an endoscope configured to electrically drive an endoscopic operation, which is at least one of forward and backward movement of an insertion section, a bending angle of a bending section of the insertion section, rolling rotation of the insertion section, air supply suction, and capturing an endoscope image; and
a controller comprising hardware, the controller being configured to control the electrically-driven endoscopic operation,
the controller performing a return processing of controlling the electrically-driven endoscopic operation so as to return the endoscope image to a reference endoscope image of a papillary portion of a duodenum.

2. The medical system as defined in claim 1, wherein the controller performs the return processing when determining that the endoscope image has been changed from the reference endoscope image.

3. The medical system as defined in claim 2, wherein the controller performs the return processing when determining that an amount of displacement between a position of the papillary portion on the endoscope image and a position of the papillary portion on the reference endoscope image exceeds a permissible amount.

4. The medical system as defined in claim 1, wherein the reference endoscope image is an image in which a front view of the papillary portion is shown in a center of the endoscope image.

5. The medical system as defined in claim 4, wherein the controller performs the return processing when the papillary portion is displaced from the center of the endoscope image by an operation of cannulation to a biliary duct.

6. The medical system as defined in claim 1, wherein the controller performs the return processing of controlling the bending angle so as to reduce an amount of displacement between a position of the papillary portion on the endoscope image and a position of the papillary portion on the reference endoscope image.

7. The medical system as defined in claim 6, wherein the controller performs the return processing of controlling the bending angle, and at least one of the forward and backward movement and the rolling rotation so as to reduce the amount of displacement.

8. The medical system as defined in claim 2, wherein the controller performs the return processing when determining that a difference of a size of the papillary portion on the endoscope image and a size of the papillary portion on the reference endoscope image exceeds a predetermined amount.

9. The medical system as defined in claim 8, wherein the controller performs the return processing by the air supply suction based on the size of the papillary portion on the endoscope image.

10. The medical system as defined in claim 1, wherein the controller performs the return processing so as to return the endoscope image to the reference endoscope image in which a predetermined size of the papillary portion is shown.

11. The medical system as defined in claim 10, wherein the controller:

performs the return processing by the air supply suction when the size of the papillary portion on the endoscope image is different from the predetermined size, and performs the return processing by at least one of the forward and backward movement, the bending angle, and the rolling rotation when a position of the papillary portion on the endoscope image is different from a position of the papillary portion on the reference endoscope image.

12. The medical system as defined in claim 1, wherein the controller monitors an operation input to the operation device, and performs the return processing when the operation input is not performed for a predetermined time.

13. A method for operating a medical system, comprising:

causing an endoscope that electrically drives an endoscopic operation, which is at least one of forward and backward movement of an insertion section, a bending angle of a bending section of the insertion section, rolling rotation of the insertion section, and air supply suction, to capture an endoscope image; and performing a return processing of controlling the electrically-driven endoscopic operation so as to return the endoscope image to a reference endoscope image of a papillary portion of a duodenum.

An embodiment of the present disclosure relates to a medical system including:

a medical instrument whose instrument motion is electrically driven, the instrument motion being at least one of forward and backward movement of an insertion section, a bending angle of a bending section of the insertion section, and rolling rotation of the insertion section;

an operation device configured to perform an operation input of the instrument motion; and a controller comprising hardware, the controller being configured to control the electrically-driven instrument motion based on the operation input.

When determining that the operation input is abnormal operation input different from normal operation input, the controller performs control to restrict the electrically-driven instrument motion.

Another embodiment of the present disclosure relates to:

a method of operating a medical system, including based on an operation input of an instrument motion of a medical instrument whose instrument motion is electrically driven, controlling the electrically-driven instrument motion, the instrument motion being at least one of forward and backward movement of an insertion section, a bending angle of a bending section of the insertion section, and rolling rotation of the insertion section; and when determining that the operation input is abnormal operation input different from normal operation input, performing control to restrict the electrically-driven instrument motion.

Explanation of ERCP

The present embodiment relates to prevention of erroneous operation when performing ERCP using an electric medical system. ERCP stands for Endoscopic Retrograde Cholangiopancreatography. First, before describing the present embodiment, the details of procedure of ERCP is described below. However, the medical system of the present embodiment is applicable to the procedures other than ERCP.

Figure 49:
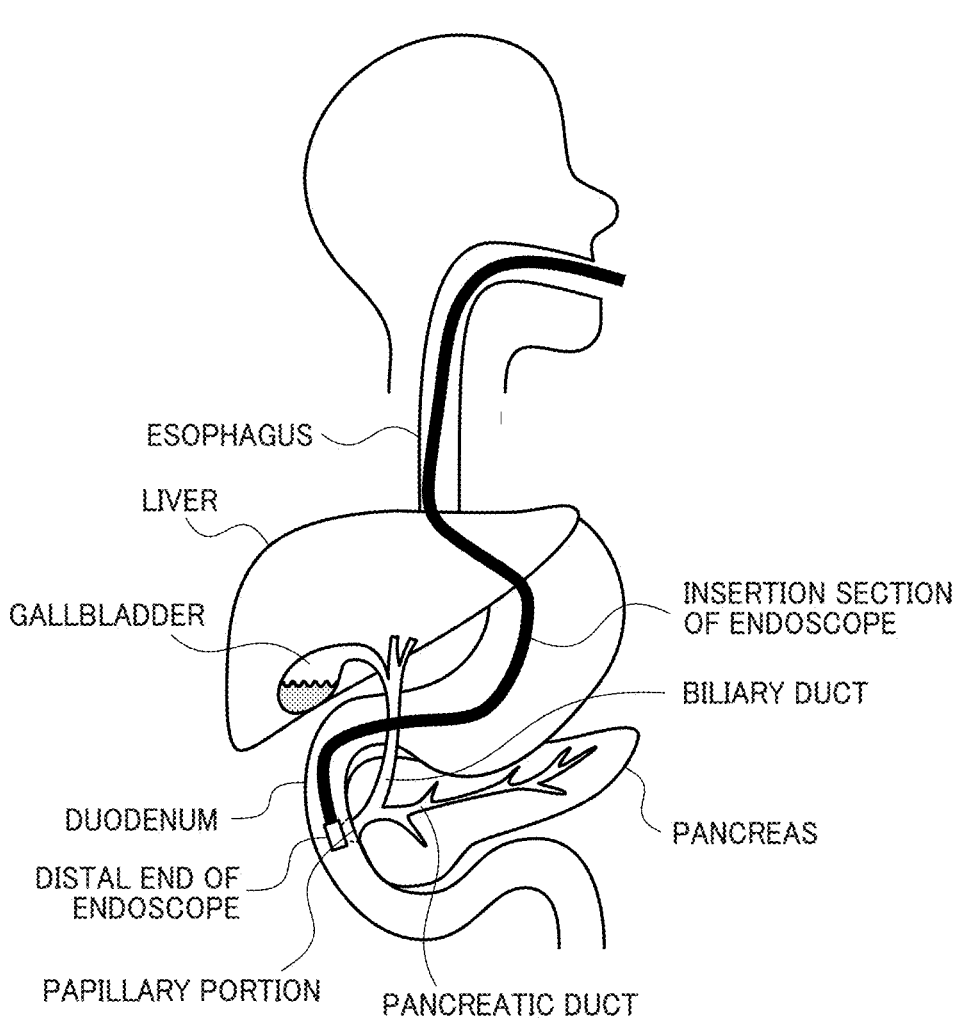
FIG. 49 shows organs and tissues involved in the ERCP procedure.

FIG. 49 shows organs and tissues involved in the ERCP procedure. The organs include a multiple types of tissues, forming a unique structure with a specific function. In FIG. 49, the liver, gallbladder, pancreas, esophagus, stomach, and duodenum are shown as organs. Tissues are formed by related cells combined, and examples include blood vessels, muscles, skin, and the like. In FIG. 49, a biliary duct and a pancreatic duct are shown as tissues.

The biliary duct is the target of the ERCP procedure. The biliary duct is a pipeline for allowing the bile produced in the liver to flow into the duodenum. When approaching the biliary duct using an endoscope, a treatment tool inserted into the channel of the endoscope is inserted to the biliary duct from the papillary portion of the duodenum while holding the endoscope at the position of the duodenum. Hereinafter, the papillary portion of the duodenum is simply referred to as a papillary portion. The papillary portion is a region including an opening of the luminal tissue with respect to the duodenum. Not only the opening but also the structure around the opening is referred to as a papillary portion. The opening of the luminal tissue is the opening of a common duct with respect to the duodenum. The common duct is formed as the confluence of the biliary duct and pancreatic duct. However, the papillary portion largely varies between individuals. For example, in some cases, the biliary duct opens directly to the duodenum without being merged with the pancreatic duct. In this case, the opening of the luminal tissue is the opening of the biliary duct.

Figure 50:
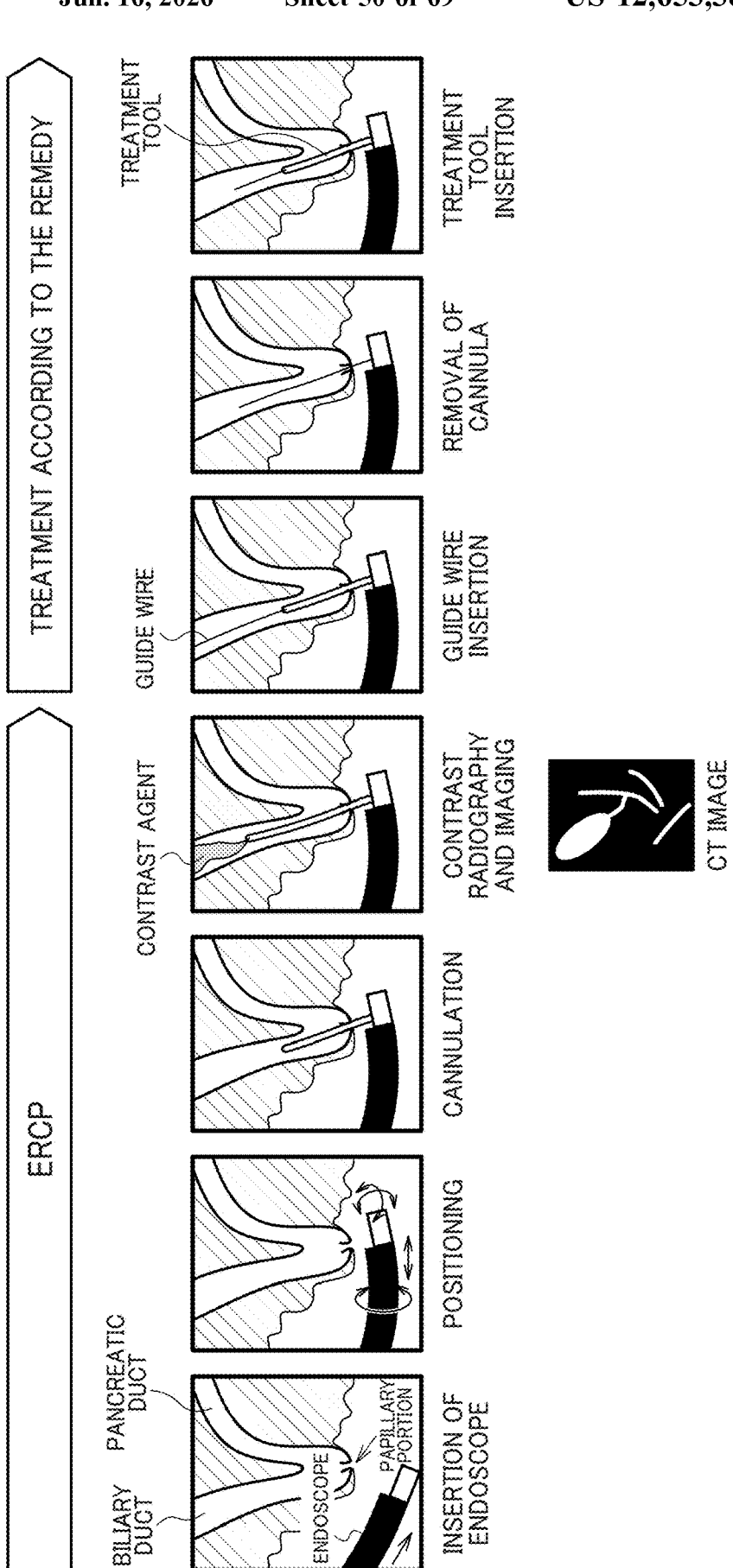
FIG. 50 shows a flow of the ERCP procedure.

FIG. 50 shows a flow of the ERCP procedure. In ERCP, a side-viewing type endoscope in which a camera, an illumination lens, and an opening of a treatment tool channel are provided on a side surface of a distal end section of the endoscope is used. The camera is also referred to as an imaging device.

In the endoscope insertion step, the insertion section of the endoscope is inserted from the mouth to the duodenum through the esophagus and stomach. At this time, the insertion section is inserted until the papillary portion becomes roughly visible in the field of view of the endoscope. Next, in the positioning step, the position of the endoscope is adjusted relative to the papillary portion. Specifically, the position of the distal end section of the endoscope is adjusted so that the papillary portion is within the imaging range of the camera of the endoscope. Alternatively, the position of the distal end section of the endoscope is adjusted so that the camera of the endoscope is facing directly front of the papillary portion and the papillary portion appears in the center of the field of view.

Then, in the cannulation step, a cannula is inserted from the papillary portion into the biliary duct. Specifically, the cannula is inserted into the treatment tool channel of the endoscope so that the cannula protrudes from the channel opening of the distal end section of the endoscope. The distal end of the cannula is inserted into the common duct from the opening of the common duct, and the cannula is further inserted through the confluence of the biliary duct and the pancreatic duct toward the direction of the biliary duct. Cannulation refers to insertion of a cannula into a body. A cannula is a medical tube that is inserted into a body for medical purposes.

Next, in the contrast radiography and imaging step, a contrast agent is injected into the cannula and poured into the biliary duct through the distal end of the cannula. By performing X-ray or CT imaging in this state, an X-ray image or a CT (Computed Tomography) image showing the biliary duct, gallbladder, and pancreatic duct can be obtained. The procedure of ERCP has been described. After the procedure, various treatments are performed according to the results of diagnosis based on the X-ray image or CT image. An example of the treatment is described below.

In a guide wire insertion step, a guide wire is inserted into a cannula so that the guide wire is protruded from the distal end of the cannula, and the guide wire is inserted into the biliary duct. In a cannula removing step, the cannula is removed while leaving the guide wire inside the biliary duct. As a result, only the guide wire protrudes from the distal end section of the endoscope, indwelling in the biliary duct. Next, in a treatment tool insertion step, the treatment tool is inserted into the biliary duct along the guide wire. An example of a treatment tool is a basket or stent. The basket is used with a catheter. While allowing the guide wire to pass through the catheter, the catheter is inserted into the biliary duct along the guide wire. A basket made of a plurality of metal wires is inserted into the biliary duct from the distal end of the catheter, an object to be removed, such as a gallstone, is placed in the basket and held, and the object to be removed is taken out from the biliary duct by removing the basket and catheter in this state from the biliary duct. A stent is also used in a similar manner with a catheter and inserted into the biliary duct from the distal end of the catheter. The narrow portion of the biliary duct can be widened by inserting a stent; further, by keeping the stent therein, the narrow portion is held in a widened state by the indwelling stent.

When using a medical system that is electrically driven, the operator operates the electric driving of the medical instrument by operating the controller, thereby performing the procedure of ERCP. The medical instrument is, for example, an endoscope or a treatment tool. At this time, there is a possibility of accidental operation input not intended by the operator due to an erroneous operation or falling of the controller. When such an operation input occurs, movement of the medical instrument unintended by the operator occurs, and consequently causes influences such as contact of the medical instrument with an organ, removal of the medical instrument from an organ or tissue, or disruption of the position of the medical instrument. For example, in ERCP, it is important to maintain the endoscope at a predetermined position determined by the positioning step, and therefore it is not desirable if the position of the endoscope is disrupted by an operation input unintended by the operator. Also, if the distal end section of the endoscope moves significantly while the treatment tool is inserted into the biliary duct, the treatment tool inserted in the biliary duct may also move significantly, causing influences such as removal of the treatment tool from the biliary duct, or the like.

The above-mentioned U.S. Patent Application Publication No. 2018/0040126 uses a non-electric endoscope. Thus, even if the endoscope speed is detected and an alert is generated, it is the operator who recognizes the alert and adjusts the endoscope speed. That is, the U.S. Patent Application Publication No. 2018/0040126 nowhere discloses or suggests that the operator controls an electric endoscope, for example, to prevent the endoscope from contacting an organ due to operation input unintended by the operator.

Medical System and Processing Flow

Therefore, in the present embodiment, while the operator is performing an electrically-driven manual operation in an electric medical system, the medical system detects whether or not an operation input unintended by the operator has occurred. The medical system restricts electric driving of the medical instrument when an operation input unintended by the operator is detected, thereby assisting the procedure in the ERCP. The details of this structure are described below.

Figure 51:
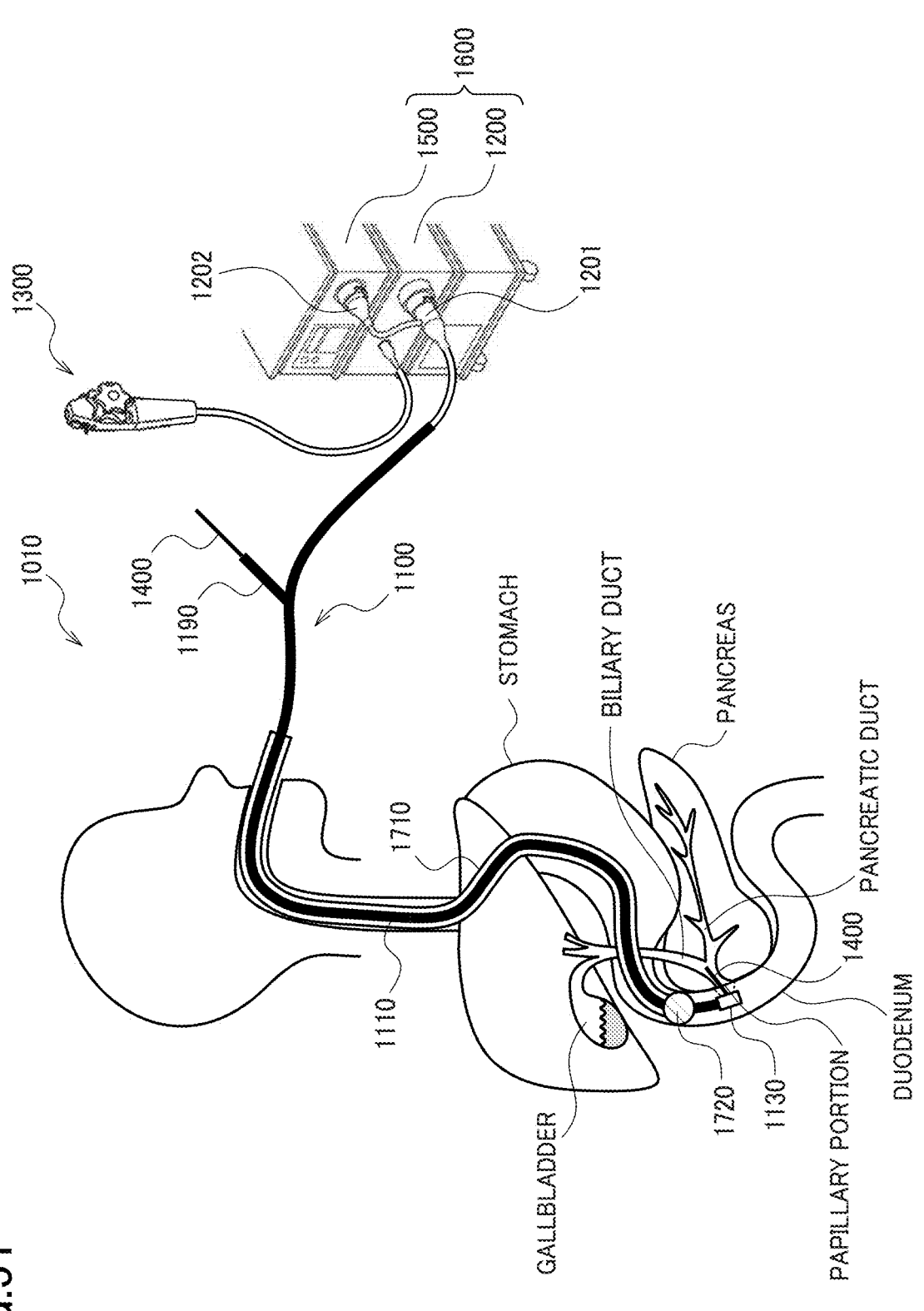
FIG. 51 shows a basic configuration example of a medical system.

FIG. 51 shows a basic configuration example of a medical system 1010 according to the present embodiment. The medical system 1010 includes an endoscope 1100, an operation device 1300, an overtube 1710, a balloon 1720, a treatment tool 1400, and a control device 1600. The medical system 1010 is also referred to as an endoscope system or an electric endoscope system. Herein, an example in which, among the endoscope 1100 and the treatment tool 1400, only the endoscope 1100 is electrically driven is described. It is also possible to use an electrically-driven treatment tool 1400. The details of the medical system 1010 using an electrically-driven treatment tool 1400 are described later.

The overtube 1710 is a tube with a variable hardness that covers the insertion section 1110 of the endoscope 1100. The balloon 1720 is provided near the distal end on the outer side of the overtube 1710. The operator inserts the endoscope 1100 and the overtube 1710, which is in a soft state, to the duodenum, inflates the balloon 1720 to fix a portion around the distal end of the overtube 1710 to the duodenum, and hardens the overtube 1710. When the endoscope 1100 and the overtube 1710 are inserted into the body, at least the bending section of the insertion section 1110 is exposed from the distal end of the overtube 1710. The bending section refers to a section structured to be bent at an angle corresponding to the bending operation in the vicinity of the distal end of the insertion section 1110. The base end of the overtube 1710 is present outside the body. The base end side of the insertion section 1110 is exposed from the base end of the overtube 1710. Although the example herein uses the overtube 1710 and the balloon 1720, they may be omitted.

An insertion opening 1190 of the treatment tool is provided at the base end side of the insertion section 1110, and a treatment tool channel for allowing the treatment tool 1400 to pass through from the insertion opening 1190 to the opening of the distal end section 1130 is provided inside the insertion section 1110. The insertion opening 1190 of the treatment tool is also called a forceps opening; however, the treatment tool to be used is not limited to forceps.

The endoscope 1100 is detachably connected to a control device 1600 using connectors 1201 and 1202. The control device 1600 includes a drive control device 1200 to which the connector 1201 is connected, and a video control device 1500 to which the connector 1202 is connected. The drive control device 1200 controls the electrical driving of the endoscope 1100 via the connector 1201. The operation device 1300 for manually operating the electrical driving is connected to the drive control device 1200. The video control device 1500 receives an image signal from a camera provided at the distal end section 1130 of the endoscope 1100 via the connector 1202, generates a display image from the image signal, and displays it on a display device (not shown). In FIG. 51, the drive control device 1200 and the video control device 1500 are shown as separate devices, but they may be structured as a single device. In this case, the connectors 1201 and 1202 may be integrated into a single connector.

The term "electrical driving" means that the drive control device 1200 drives an endoscope by a motor or the like based on an electrical signal for controlling the endoscopic operation. The electrically-driven manual operation means that the operation device 1300 converts the operation input made by the operator from the operation device 1300 into an electrical signal, thereby driving the endoscope by a motor or the like based on the electrical signal. However, the medical system 1010 may be switchable between electrical driving and non-electrical driving by attaching or detaching the connector 1201. In this case, the non-electrical driving means that the endoscope 1100 is not electrically driven by a motor or the like, instead, the force applied to the non-electrical operation device is directly transmitted to the endoscope by a wire or the like, thereby operating the endoscope. For example, in the ERCP in FIG. 50, the endoscope insertion step may be non-electrically driven, and the positioning step and onward may be electrically driven.

Figure 52:
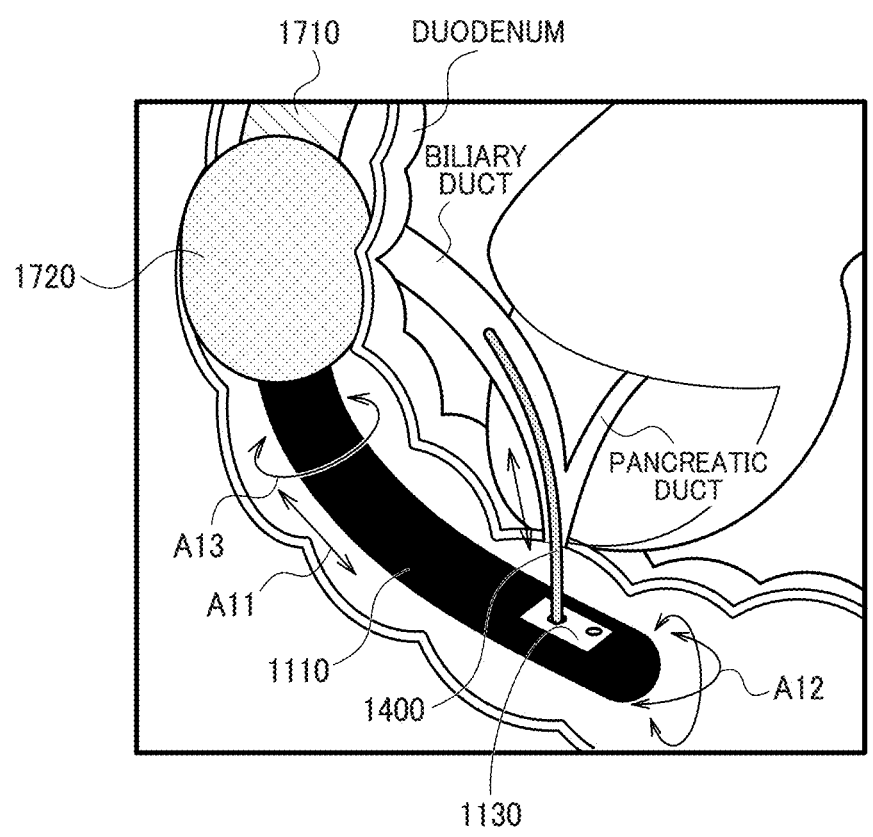
FIG. 52 shows the vicinity of the distal end of an endoscope positioned by an overtube and a balloon.

FIG. 52 shows the vicinity of the distal end of an endoscope positioned by the overtube 1710 and the balloon 1720. As shown in FIG. 52, the balloon 1720 is fixed at a position slightly apart from the papillary portion to the pyloric side of the stomach. More specifically, the balloon 1720 is positioned closer to the base end of the insertion section 1110 than the base end of the bending section of the insertion section 1110. By combining such a balloon 1720 with the overtube 1710 having a variable hardness, the bending section exposed to the papillary portion side from the balloon 1720 and the distal end section 1130 can be freely operated without being fixed, and the electrical driving from the base end side can be efficiently transmitted to the distal end section 1130 of the endoscope.

The endoscopic operation by the electrical driving is the forward and backward movement shown in A11, a bending movement shown in A12, or a rolling rotation shown in A13. The forward movement is a shift toward the distal end side along the axial direction of the insertion section 1110, and the backward movement is a shift toward the base end side along the axial direction of the insertion section 1110. In the following, the forward and backward movement may also be referred to as forward/backward movement. The bending movement is a movement by which the angle of the distal end section 1130 is changed due to the bending of the bending section. The bending movement includes bending movements in two orthogonal directions, which can be controlled independently. One of the two orthogonal directions is referred to as the vertical direction and the other is referred to as the horizontal direction. The rolling rotation is a rotation about an axis of the insertion section 1110.

If the treatment tool 1400 is electrically driven in addition to the endoscope 1100, the electrically-driven treatment tool motion is the forward and backward movement, the bending movement or the rolling rotation. The meanings of these motions are the same as those in the case of the endoscopic operation described above. The adjustment of the raising angle of the treatment tool 1400, which protrudes from an opening on the side surface of the distal end section 1130, may be electrically driven.

Figure 53:
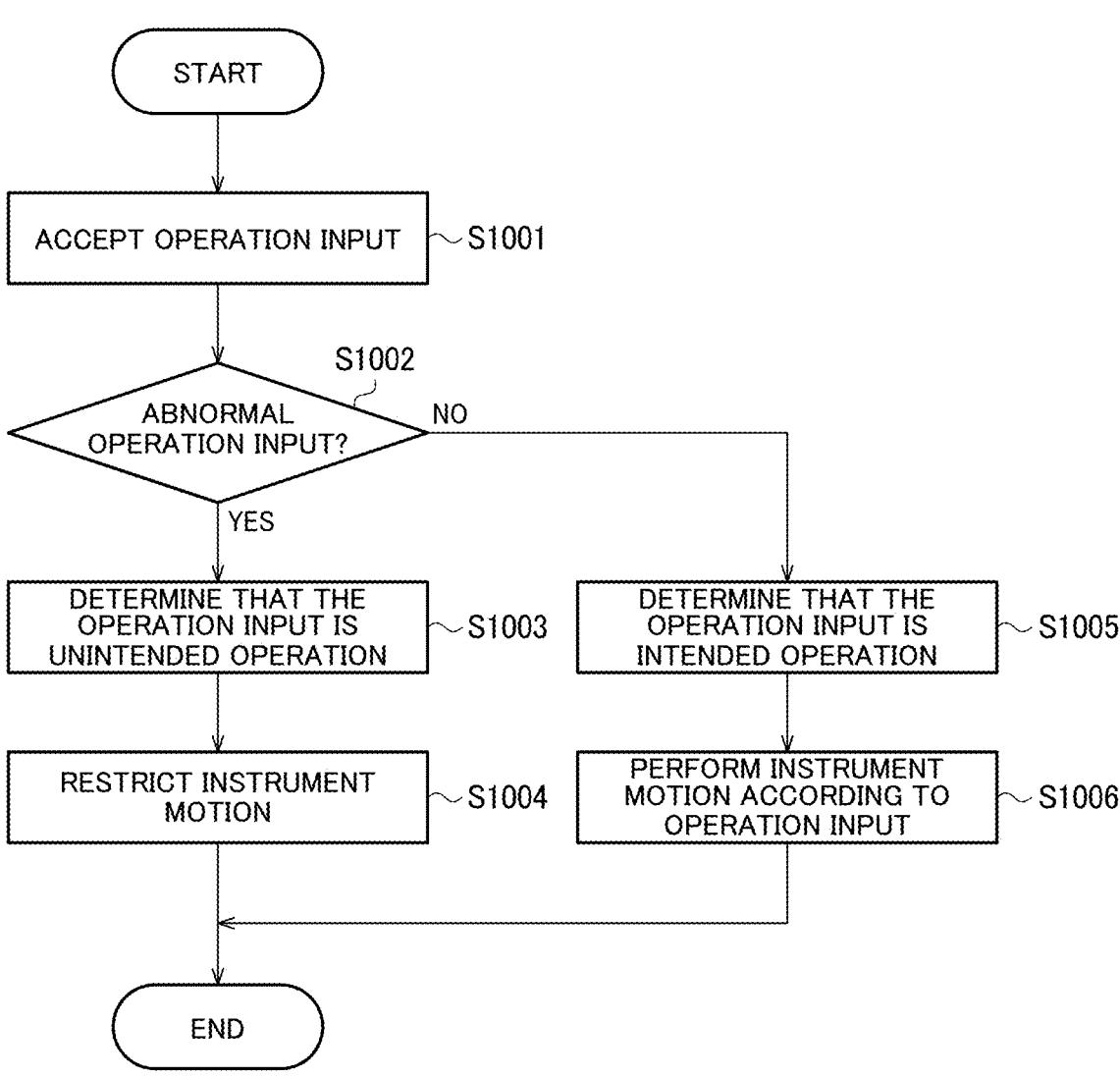
FIG. 53 is a basic flowchart of the processing performed by a medical system.

FIG. 53 is a basic flowchart of the processing performed by the medical system 1010. In step S1001, the drive control device 1200 accepts an operation input signal from the operation device 1300. This operation input may have been entered into the operation device 1300 by the operator, or it may have been input to the operation device 1300 due to factors other than operation by the operator, such as falling of the operation device 1300.

In step S1002, the drive control device 1200 determines whether or not the operation input is an abnormal operation input that is different from the normal operation input. The normal operation input is an operation input of an operation intended by the operator, which is within the range of operation inputs that the operator is expected to normally perform. Specifically, the normal operation input is an operation input having an operation speed or input pattern, etc., normally assumed in each step of the procedure. The abnormal operation input is an operation input of an operation unintended by the operator, which is within the range of operation inputs that the operator is not expected to normally perform. Specifically, the abnormal operation input is an operation input having an operation speed or input pattern that is not normally assumed in each step of the procedure. The type of the operation speed or input pattern etc. to be considered as the normal operation input or the abnormal operation input may be different in each step of the procedure. The parameters used in the determination are not limited to the operation speed or the input pattern.

If the operation input is determined to be an abnormal operation input in step S1002, in step S1003, the drive control device 1200 determines that an operation input unintended by the operator has been input to the operation device 1300. In Step S1004, the drive control device 1200 restricts the instrument motion of the medical instrument. Note that "restrict the instrument motion" means that the amount or speed of the movement of the instrument motion is reduced compared to the case where the instrument motion is performed according to the operation input. The medical instrument is the endoscope 1100 and the instrument motion is the endoscopic operation. The endoscopic operation is at least one of forward and backward movement of an insertion section, a bending angle of a bending section, and rolling rotation of the insertion section in the endoscope 1100. Alternatively, when the treatment tool 1400 is electrically driven, the medical instrument may be the treatment tool 1400, and the instrument motion may be the treatment tool motion. The treatment tool motion is at least one of forward and backward movement of an insertion section, a bending angle of a bending section, and rolling rotation of the insertion section in the treatment tool 1400. The treatment tool motion may also include an adjustment of the raising angle.

In step S1004, the instrument motion corresponding to the operation input that was determined to be an abnormal operation input in step S1002 is restricted. For example, if an abnormal operation input is entered to the operation channel that operates the bending angle of the endoscope, the bending movement of the endoscope is restricted. However, other instrument motions may further be restricted. For example, if the operation input of one of the forward/backward movement, the bending angle and the rolling rotation of the endoscope is an abnormal operation input, all of the endoscopic operations may be restricted. Alternatively, if the operation input of the forward/backward movement, the bending angle, or the rolling rotation of the treatment tool is an abnormal operation input, all of the treatment tool motions may be restricted, or all of the treatment tool motions and the endoscopic operations may be restricted.

When it is determined in step S1002 that the operation input is not an abnormal operation input, in step S1005, the drive control device 1200 determines that the operation performed was intended by the operator. In step S1006, the drive control device 1200 electrically drives the medical instrument based on the operation input entered to the operation device 1300, thereby causing the medical instrument to perform an instrument motion according to the operation input.

According to the present embodiment, even if there was an operation input unintended by the operator due to an erroneous operation or falling of the controller, the operation of the medical instrument is restricted so that the medical instrument is prevented from moving by a large amount or at a high speed. This prevents influences such as contact of the medical instrument with an organ, removal of the medical instrument from an organ or tissue, disruption of the position of the medical instrument, and the like.

Figure 54:
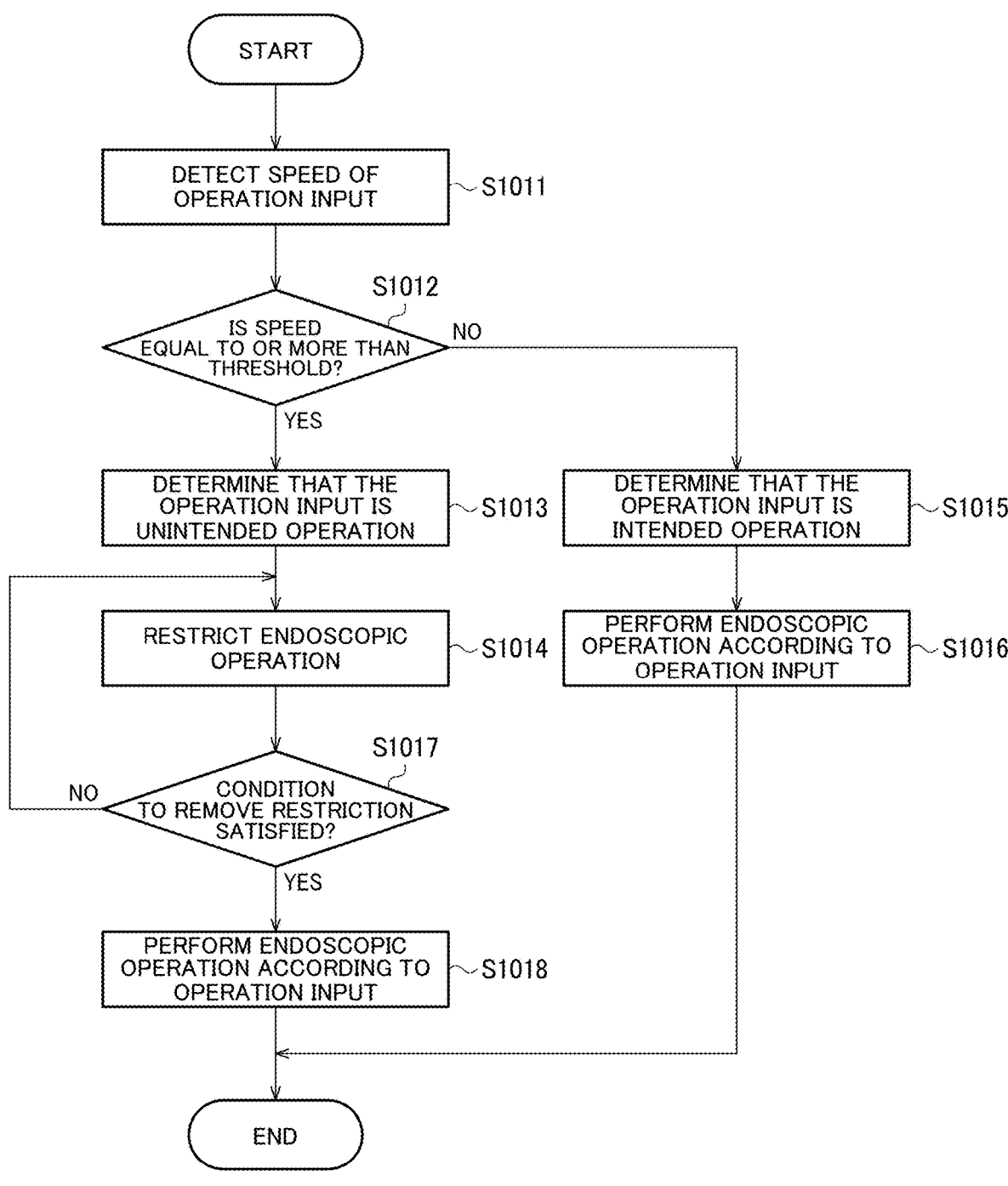
FIG. 54 is a first detailed flowchart of the processing performed by a medical system.

FIG. 54 is a first detailed flowchart of the processing performed by the medical system 1010. In the following, an example where only the endoscope is electrically driven is mainly described; however, if the treatment tool is electrically driven, the treatment tool motion may be restricted in a similar method.

In step S1011, the drive control device 1200 accepts signals of operation inputs of the forward/backward movement, the bending, and the rolling rotation of the endoscope, and detects the speed of each operation input. The speed of an operation input is the change in the operation amount with respect to the operation device, i.e., the time derivative of the operation amount, and is not the speed of the endoscopic operation caused by the operation input.

In step S1012, the drive control device 1200 determines whether or not the speed of each operation input is equal to or greater than the threshold. A different threshold may be set for each of the forward/backward movement, the bending, and the rolling rotation. The parameter used to determine the abnormal operation input is not limited to the speed of the operation input, but may be, for example, the change in the speed of the operation input, i.e., the acceleration of the operation input.

In step S1012, when it is determined that the speed of any of the operation inputs of the forward/backward movement, the bending, and the rolling rotation is equal to or greater than the threshold, in step S1013, the drive control device 1200 determines that an operation input unintended by the operator is input to the operation device 1300. In step S1014, the drive control device 1200 restricts the endoscopic operation. For example, when the speed of the operation input of the forward/backward movement is equal to or greater than the threshold, the drive control device 1200 restricts the forward/backward movement of the endoscope 1100, or also restricts the bending and/or the rolling rotation of the endoscope 1100 in addition to the forward/backward movement of the endoscope 1100.

In step S1017, the drive control device 1200 determines whether or not the condition to remove the restriction has been satisfied. If it is determined that the condition to remove the restriction is not satisfied, the drive control device 1200 returns to step S1014 and maintains the restriction in the endoscopic operation. If it is determined that the condition to remove the restriction is satisfied, the drive control device 1200 electrically drives the endoscope 1100 based on the operation input entered into the operation device 1300 in step S1018, thereby causing the endoscope 1100 to perform the endoscopic operation according to the operation input. Steps S1017 and S1018 may be omitted.

If it is determined in step S1012 that none of the speeds of the operation inputs of the forward/backward movement, the bending, and the rolling rotation are equal to or greater than the threshold, in step S1015, the drive control device

1200 determines that the operation performed was intended by the operator. In step S1016, the drive control device 1200 electrically drives the endoscope 1100 based on the operation input entered to the operation device 1300, thereby causing the endoscope 1100 to perform the endoscopic operation according to the operation input.

Figure 55:
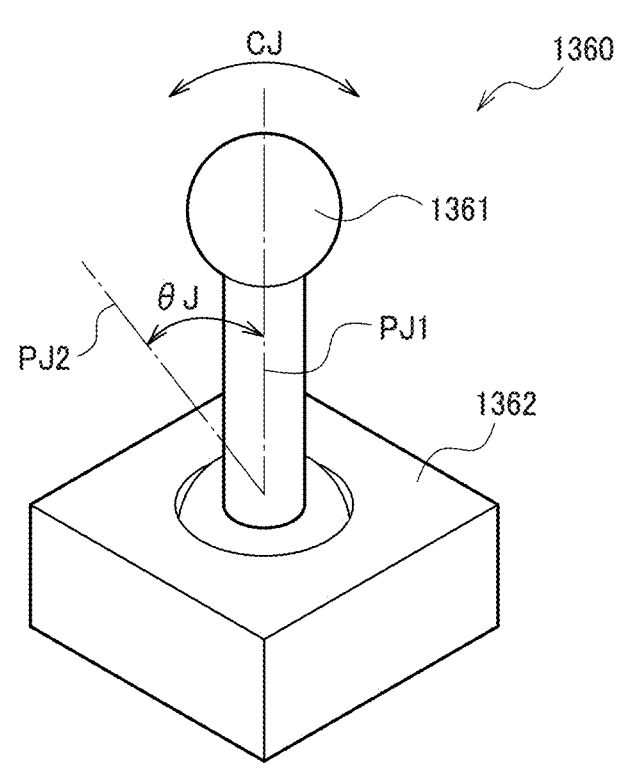
FIG. 55 shows a first detailed example of an operation device and operation input.
Figure 56:
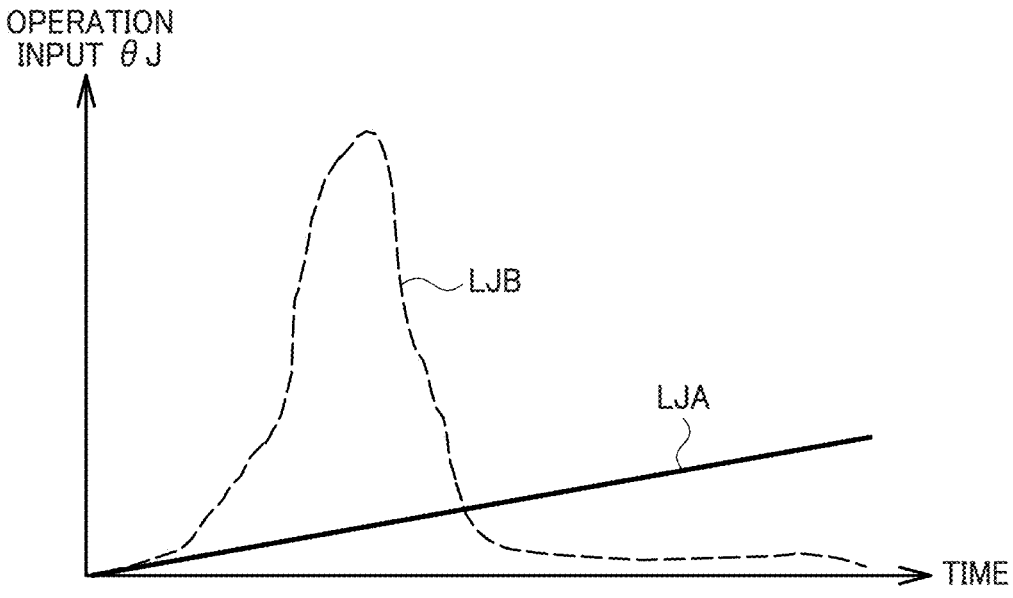
FIG. 56 shows a first detailed example of an operation device and operation input.

FIG. 55 and FIG. 56 show a first detailed example of an operation device and operation input. FIG. 55 shows a joystick-type controller 1360 as an example of the operation device 1300. Although an example where the bending operation is performed by the joystick-type controller 1360 is described herein, the same applies to the cases where the forward/backward movement or the rolling rotation is performed.

The joystick-type controller 1360 includes a base section 1362, and a stick section 1361 movable with respect to the base section 1362. As shown in CJ, the stick section 1361 can be operated so that the stick section 1361 is tilted by being rotated about the root thereof on the base section 1362. PJ1 is the axis line when the stick section 1361 is in the reference position. θJ is the angle formed by the axis line PJ1 and the axis line PJ2, which is an axis line when the stick section 1361 is tilted. This angle θJ corresponds to an operation input. The angle θJ is detected by, for example, an optical position sensor, a potentiometer, or the like, and the drive control device 1200 detects the operation speed from the time change of the angle θJ thus detected. The correspondence between the angle θJ and the bending movement can be assumed in various ways. For example, the angle θJ may correspond to the bending angle. In this case, a change of θJ changes the bending angle and the bending angle is maintained when θJ is maintained. Further, angle θJ may correspond to the bending speed. In this case, a change of θJ changes the bending speed, and when θJ is maintained, the bending movement occurs at a speed corresponding to θJ.

FIG. 56 shows an example of waveform of the angle θJ as an operation input. LJA is an example of waveform in the normal operation input. In the normal operation input, it is assumed that the stick section 1361 is gradually tilted and the angle θJ gradually increases. The inclination of the waveform corresponds to the operation speed; the operation speed is small in the normal operation input. The time derivative of the inclination in the waveform corresponds to the acceleration of the operation, and the acceleration of the operation is small in the normal operation input.

LJB is an example of waveform in an abnormal operation input. In an abnormal operation input, the angle θJ of the stick section 1361 changes abruptly. In the example in FIG. 56, the stick section 1361 is tilted abruptly and then returns to the reference position abruptly. In an abnormal operation input, the operation speed or the operation acceleration is greater than those in the normal operation input. In the present embodiment, by judging the operation speed or the operation acceleration based on the threshold, the bending movement can be restricted upon the abnormal operation input.

Figure 57:
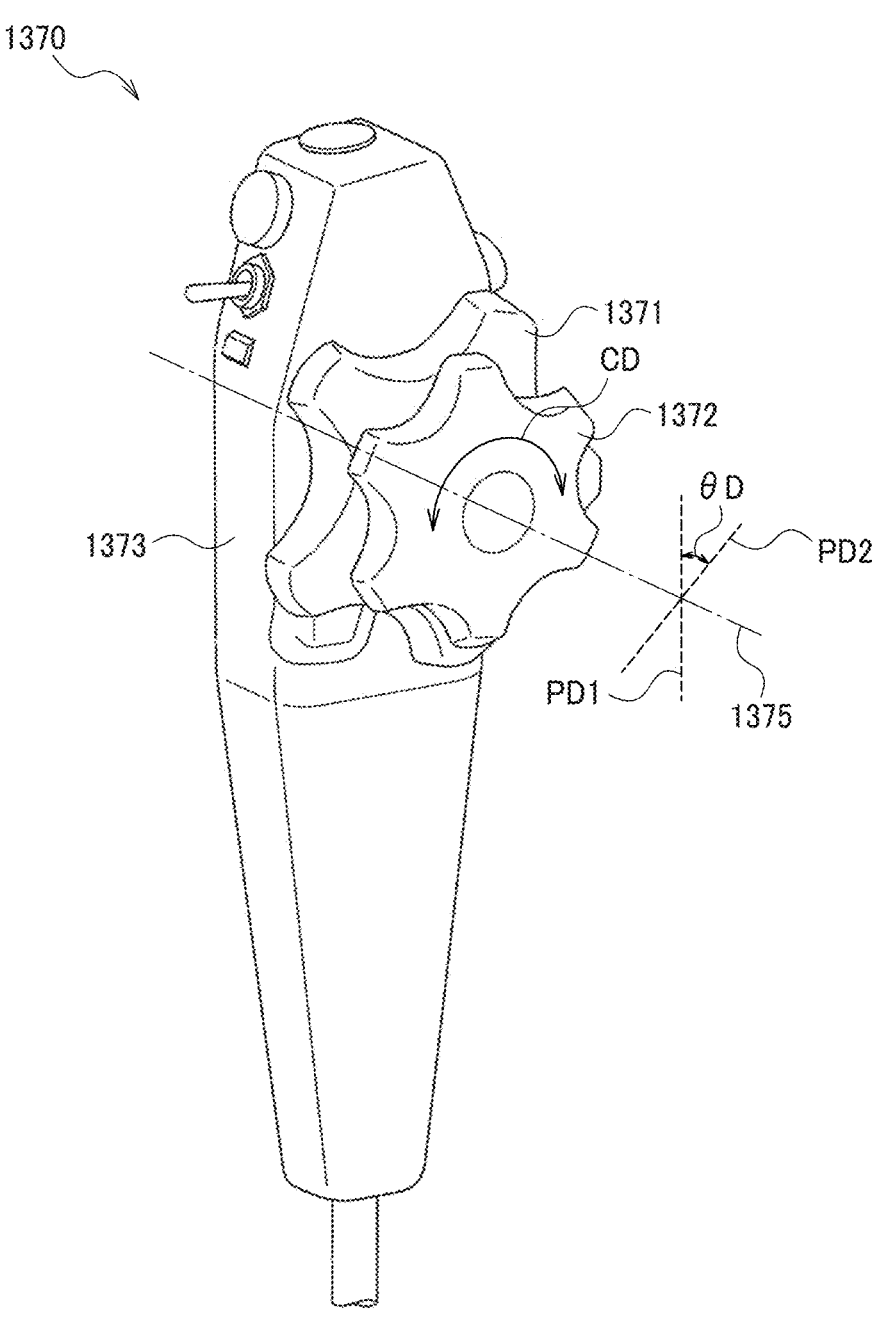
FIG. 57 shows a second detailed example of an operation device and operation input.
Figure 58:
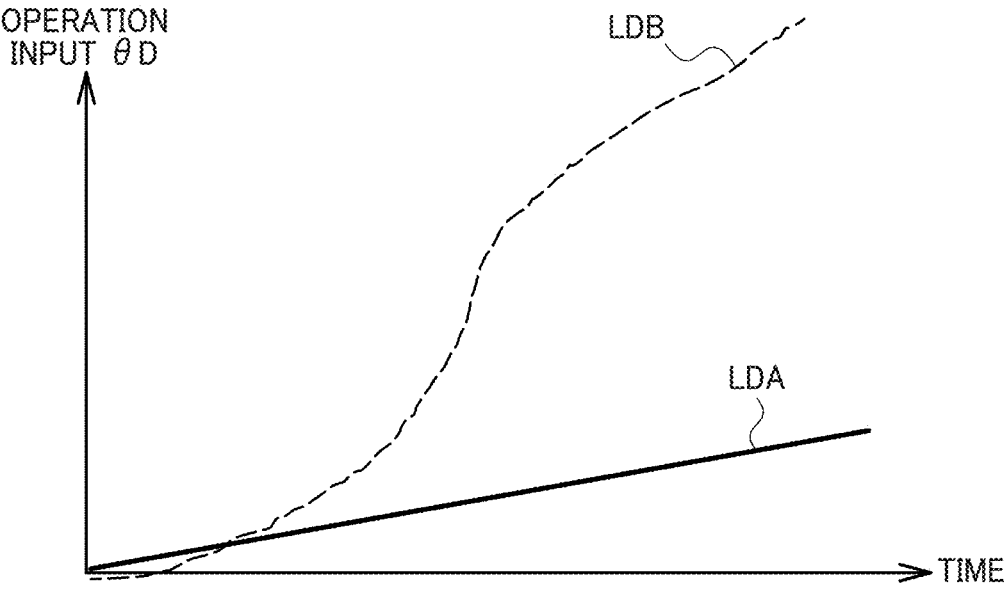
FIG. 58 shows a second detailed example of an operation device and operation input.

FIG. 57 and FIG. 58 show a second detailed example of an operation device and operation input. FIG. 57 shows a dial-type controller 1370 as an example of the operation device 1300. Although an example where the bending operation is performed by the dial-type controller 1370 is described herein, the same applies to the cases where the forward/backward movement or the rolling rotation is performed.

The dial-type controller 1370 includes a base section 1373 and a first dial 1371 and a second dial 1372 movable with respect to the base section 1373. As shown in CD, the first dial 1371 and the second dial 1372 are independently rotatable about the rotation axis 1375. For example, the bending operation in the vertical (up and down) direction is assigned to the first dial 1371 and the bending operation in the horizontal (left and right) direction is assigned to the second dial 1372. The following describes the first dial 1371 as an example. PD1 is the reference position of the first dial 1371, and the angle θD is the angle formed by the reference position PD1 and the position PD2, which is the position when the first dial 1371 is turned. This rotation angle θD corresponds to the operation input. The rotation angle θD is detected by, for example, an optical position sensor, a potentiometer, or the like, and the drive control device 1200 detects the operation speed from the time change of the rotation angle θD thus detected. In a controller simulating non-electric dial operation, the rotation angle θD corresponds to the bending angle. That is, a change of θD changes the bending angle and the bending angle is maintained when θD is maintained. However, the correspondence between the rotation angle θD and the bending movement is not limited to this.

FIG. 58 shows an example of waveform of the rotation angle θD as an operation input. LDA is an example of waveform in the normal operation input. In the normal operation input, it is assumed that the first dial 1371 is turned gradually and the rotation angle θD increases gradually. The inclination of the waveform corresponds to the operation speed; the operation speed is small in the normal operation input. The time derivative of the inclination in the waveform corresponds to the acceleration of the operation, and the acceleration of the operation is small in the normal operation input.

LDB is an example of waveform in an abnormal operation input. In an abnormal operation input, the rotation angle θD of the first dial 1371 changes abruptly. The example in FIG. 58 shows the waveform when the first dial 1371 is turned abruptly in a given direction. In an abnormal operation input, the operation speed or the operation acceleration is greater than those in the normal operation input. In the present embodiment, by judging the operation speed or the operation acceleration based on the threshold, the bending movement can be restricted upon the abnormal operation input.

In addition to the above examples, various types of operation device may be used. For example, the operation device may be a touch pad or a touch panel. In such cases, the swipe distance, etc. in the swipe operation is regarded as an operation input. In addition to the operation speed and the operation acceleration, various other parameters may be used for the judgment based on the threshold. For example, the input time of the operation input may be used for the judgment based on the threshold. For example, in a joystick-type controller 1360, if the bending speed changes according to the angle θJ, it is difficult to assume that the stick section 1361 is kept tilted for a long time in the normal operation input. On the other hand, if the stick section 1361 is tilted due to falling of the operation device or the like, the operation input may continue for a long time. In this case, the drive control device 1200 may restrict the bending movement when the input time is equal to or greater than the threshold.

For example, the following first and second examples may be used as the method for restricting the endoscopic operation in step S1014 in FIG. 54. If the treatment tool 1400 is electrically driven, the treatment tool motion may be restricted in a similar method.

In the first example, the drive control device 1200 restricts the endoscopic operation so that the operation speed of the endoscopic operation does not exceed a predetermined value. That is, even when an operation input to set an operation speed higher than the predetermined value is entered, the drive control device 1200 restricts the operation speed of the endoscopic operation to a value at or below the predetermined value. More specifically, the drive control device 1200 restricts the speed of the target movement, which is the forward/backward movement, the bending, and/or the rolling rotation, so that the speed of the target movement is equal to or below the predetermined value. A different predetermined value may be set for each of the forward/backward movement speed, the bending speed, and the rolling rotation speed.

In the second example, the drive control device 1200 restricts the endoscopic operation so that the operation amount of the endoscopic operation does not exceed a predetermined value. That is, even when an operation input to set an operation amount greater than the predetermined value is entered, the drive control device 1200 restricts the operation amount of the endoscopic operation to a value at or below the predetermined value. More specifically, the drive control device 1200 restricts the amount of the target movement, which is the forward/backward movement, the bending, and/or the rolling rotation, so that the amount of the target movement is at or below the predetermined value. A different predetermined value may be set for each of the forward/backward movement amount, the bending angle, and the rolling rotation angle. For example, the endoscope 1100 can be prevented from being overly pulled by restricting the amount of the forward/backward movement by the drive control device 1200. If the endoscope 1100 is overly pulled when the distal end section of the endoscope 1100 is in the duodenum, the distal end section may return to the stomach and fall into the stomach; however, in the present embodiment, such an accident due to over-pulling can be prevented by automatic control.

For example, the following first to third examples may be used as the condition to remove the restriction in step S1017 of FIG. 54. If the treatment tool 1400 is electrically driven, the restriction of the treatment tool motion may be removed in a similar method.

In the first example, the drive control device 1200 removes the restriction when a predetermined time has elapsed after the restriction of the endoscopic operation was started, and allow the endoscope 1100 to perform the endoscopic operation according to the operation input. A different predetermined time may be set for each of the forward/backward movement, the bending, and the rolling rotation.

In the second example, the drive control device 1200 removes the restriction when an operation to remove the restriction is received from the operator during the restriction of the endoscopic operation. For example, a button for removing the restriction is provided in the operation device 1300, and the drive control device 1200 removes the restriction of the endoscopic operation when a signal indicating button pushing is input.

In the third example, the drive control device 1200 may acquire an endoscope image from the video control device 1500 and may determine the removal of the restriction based on the endoscope image. Specifically, the drive control device 1200 may remove the restriction of the endoscopic operation when it recognizes from the endoscope image that the distal end section of the endoscope 1100 has reached the predetermined position. For example, if the endoscope insertion step in FIG. 50 is performed by electrically-driven manual operation, the drive control device 1200 may remove the restriction of the endoscopic operation when the papillary portion of the duodenum is detected from the endoscope image.

Figure 59:
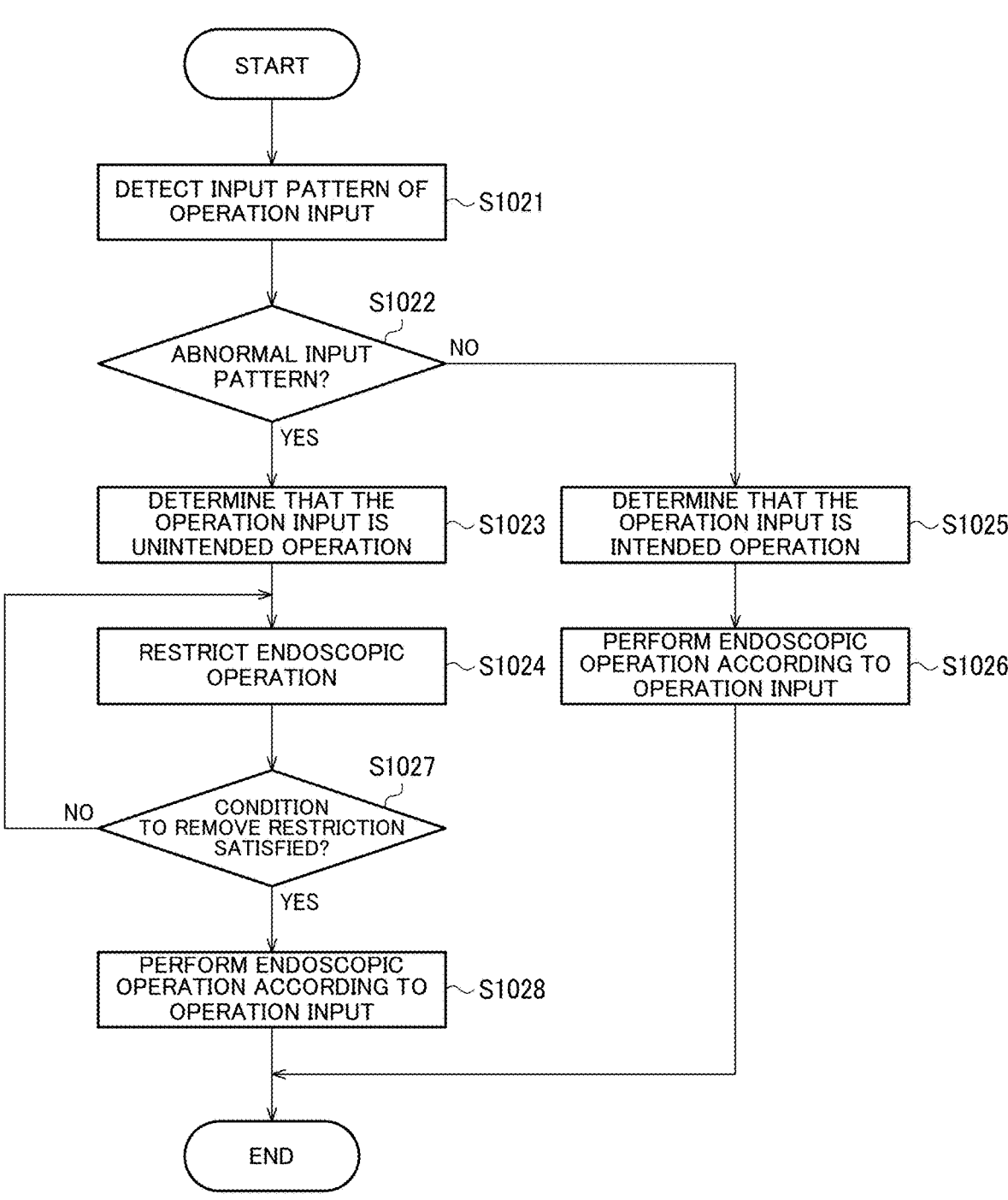
FIG. 59 is a second detailed flowchart of the processing performed by a medical system.

FIG. 59 is a second detailed flowchart of the processing performed by the medical system 1010. In the following, an example where only the endoscope is electrically driven is mainly described; however, if the treatment tool is electrically driven, the treatment tool motion may be restricted in a similar method.

In step S1021, the drive control device 1200 accepts signals of operation inputs of the forward/backward movement, the bending, and the rolling rotation of the endoscope, and detects the input pattern of each operation input. The input pattern of the operation input is the shape of the input waveform in the operation input, or the pattern indicating the type and the order of the operations performed. The operation device 1300 converts the operation input into an electrical signal. The waveform of the electrical signal corresponds to the input waveform. The shape of the input waveform can also be regarded a change in the operation amount over time, e.g., the shapes of the waveforms LJA, LJB at angle θJ or the change of angle θJ over time in FIGS. 55 and 56. The pattern indicating the type and the order of the performed operations designates the sequence of operations; e.g., first, the bending is stopped, then the bending operation in a predetermined direction is performed, and then the bending is stopped.

In step S1022, the drive control device 1200 determines whether or not the input pattern for each operation input is an abnormal input pattern. A different determination condition may be set for each of the forward/backward movement, the bending, and the rolling rotation. An abnormal input pattern is an input pattern different from those of normally performed operations in the procedure, or an input pattern of an operation that is not expected to be normally performed in the procedure. For example, in the example in FIG. 56, the waveform LJA of the normal operation input and the waveform LJB of the abnormal operation input have different waveform shapes or different operation sequences. The drive control device 1200 may determine whether or not the input pattern of the operation input is an abnormal input pattern by using a trained model that has learned various input patterns of operation input by machine learning.

In step S1022, when it is determined that an input pattern of any of the operation inputs of the forward/backward movement, the bending, and the rolling rotation is an abnormal input pattern, in step S1023, the drive control device 1200 determines that an operation input unintended by the operator is input to the operation device 1300. In step S1024, the drive control device 1200 restricts the endoscopic operation. The method of restriction is the same as that in FIG. 54. Steps S1027 and S1028 are similar to steps S1017 and S1018 in FIG. 54. Steps S1027 and S1028 may be omitted.

If it is determined in step S1022 that none of the input patterns of the operation inputs of the forward/backward movement, the bending, and the rolling rotation are abnormal input patterns, in step S1025, the drive control device 1200 determines that the operation performed was intended by the operator. In step S1026, the drive control device 1200 electrically drives the endoscope 1100 based on the operation input entered to the operation device 1300, thereby causing the endoscope 1100 to perform the endoscopic operation according to the operation input.

Figure 60:
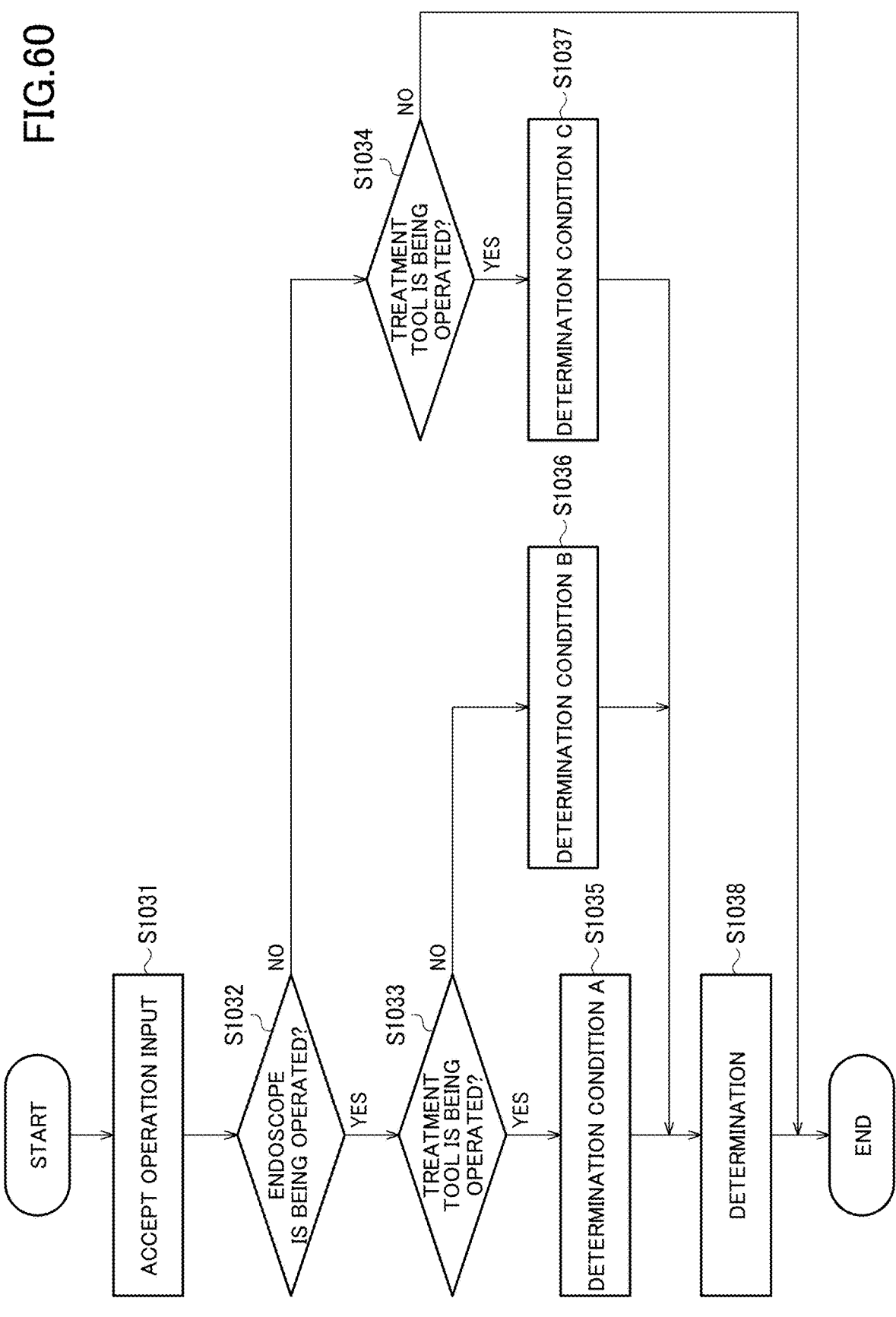
FIG. 60 is a third detailed flowchart of the processing performed by a medical system.

FIG. 60 is a third detailed flowchart of the processing performed by a medical system 1010. In this processing, both the endoscope and the treatment tool are electrically driven.

In step S1031, the drive control device 1200 accepts an operation input signal from the operation device 1300. In steps S1032 to S1034, the drive control device 1200 determines whether or not the endoscope 1100 is being operated and whether or not the treatment tool 1400 is being operated based on the operation input signals.

If it is determined in steps S1032 to S1034 that the endoscope 1100 and the treatment tool 1400 are being operated, in step S1035, the drive control device 1200 sets the determination condition, which is a condition to determine whether or not the instrument motion is to be restricted, to determination condition A. The determination condition is used to determine whether or not the operation input is an abnormal operation input. Examples of the determination condition include the threshold of the operation speed in FIG. 54, the abnormal input pattern in FIG. 59, and the like.

If it is determined in steps S1032 to S1034 that the endoscope 1100 is being operated and the treatment tool 1400 is not being operated, in step S1036, the drive control device 1200 sets the determination condition, which is a condition to determine whether or not the instrument motion is to be restricted, to determination condition B. The determination condition B is different from determination condition A.

If it is determined in steps S1032 to S1034 that the endoscope 1100 is not being operated and the treatment tool 1400 is being operated, in step S1037, the drive control device 1200 sets the determination condition, which is a condition to determine whether or not the instrument motion is to be restricted, to determination condition C. The determination condition C is different from determination conditions A and B.

After the determination condition is set in steps S1035 to S1037, in step S1038, the drive control device 1200 determines whether or not to restrict the instrument motion according to the set determination condition. In step S1038, the processing flow shown in FIG. 54 or FIG. 59 is performed.

As an example of the application of this processing flow, it is assumed that the determination condition is changed in each step of the ERCP procedure in FIG. 50. For example, only the endoscope is electrically driven in the positioning step, while only the treatment tool or both the endoscope and the treatment tool are electrically driven in the cannulation step. By changing the determination condition according to such operation states, a different determination condition may be set for the positioning step and the cannulation step. The operation amount and the operation pattern are different in each step of the procedure, and a determination condition according to the operation amount and the operation pattern may be set in each step.

Figure 61:
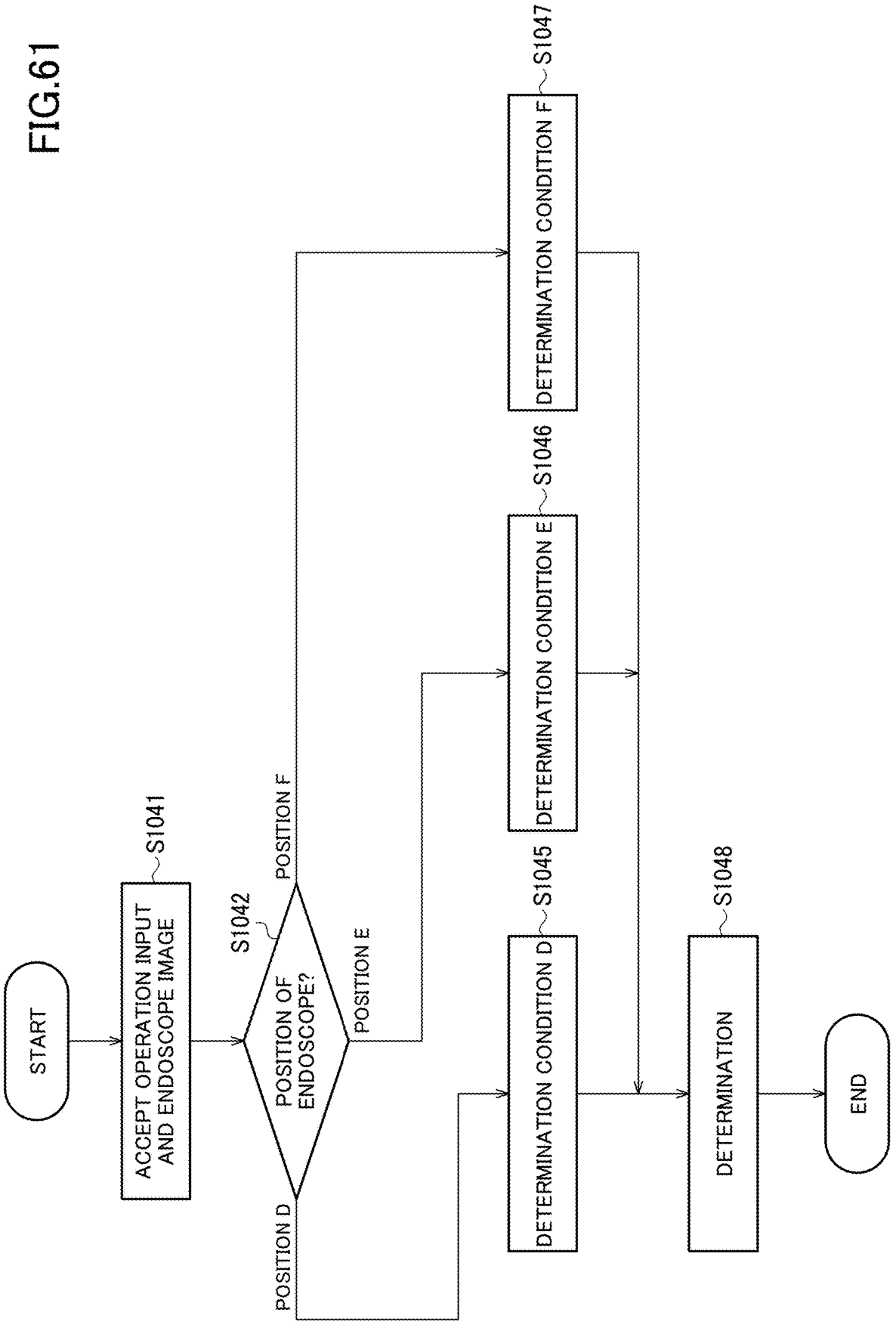
FIG. 61 is a fourth detailed flowchart of the processing performed by a medical system.

FIG. 61 is a fourth detailed flowchart of the processing performed by the medical system 1010. In the following, an example where only the endoscope is electrically driven is mainly described; however, if the treatment tool is electrically driven, the treatment tool motion may be restricted in a similar method.

In step S1041, the drive control device 1200 accepts an operation input signal from the operation device 1300 and an endoscope image from the video control device 1500. In step S1042, the drive control device 1200 determines the position of the distal end section 1130 of the endoscope 1100 in the body based on the endoscope image. The drive control device 1200 may identify the position, for example, by an image recognition process using the image feature amount, or by an image recognition process using machine learning. Each of the positions D to F is an organ, a further-divided site in an organ, a tissue, or the like. For example, in the ERCP, the position D may be the stomach, the position E may be the duodenum, and the position F may be the papillary portion of the duodenum.

If it is determined in step S1042 that the distal end section 1130 is in the position D, in step S1045, the drive control device 1200 sets the determination condition, which is a condition to determine whether or not the instrument motion is to be restricted, to condition D. If it is determined in step S1042 that the distal end section 1130 is in the position E, in step S1046, the drive control device 1200 sets the determination condition, which is a condition to determine whether or not the instrument motion is to be restricted, to condition E. If it is determined in step S1042 that the distal end section 1130 is in the position F, in step S1047, the drive control device 1200 sets the determination condition, which is a condition to determine whether or not the instrument motion is to be restricted, to condition F. The determination conditions D, E, and F are different from each other.

After the determination conditions are set in steps S1045 to S1047, in step S1048, the drive control device 1200 determines whether or not to restrict the instrument motion using the set determination condition. In step S1048, the processing flow shown in FIG. 54 or FIG. 59 is performed.

For example, it may be arranged such that the drive control device 1200 increases the threshold of the operation speed when the distal end section of the endoscope 1100 is in the stomach and decreases the threshold of the operation speed when the distal end section of the endoscope 1100 reaches the papillary portion of the duodenum.

First Detailed Configuration Example of Medical System

Figure 62:
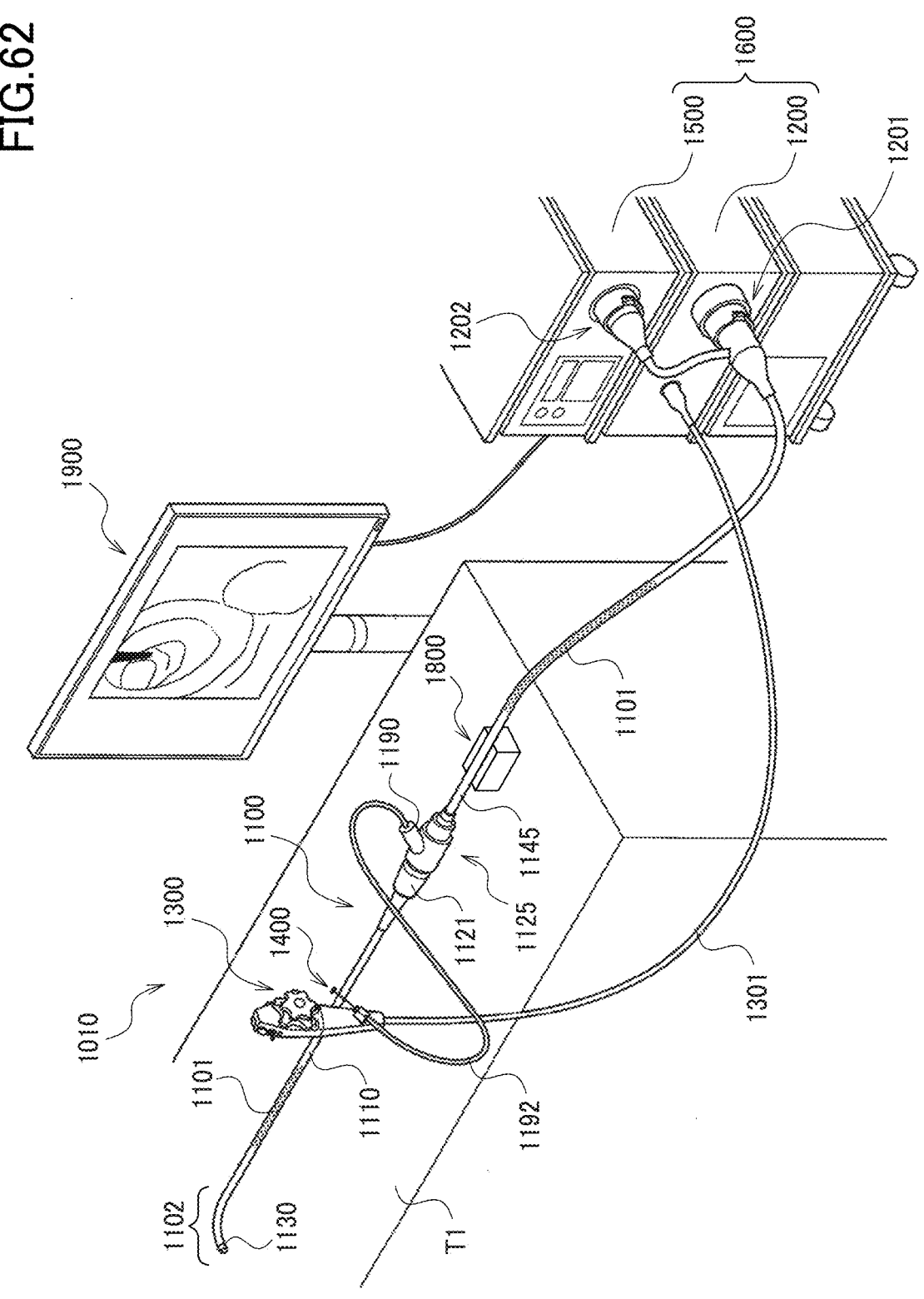
FIG. 62 shows a first detailed configuration example of a medical system.

FIG. 62 shows a first detailed configuration example of the medical system 1010. In this configuration example, among the endoscope and the treatment tool, the endoscope is electrically driven. The medical system 1010 is a system for observing or treating the inside of the body of a patient lying on an operating table T1. The medical system 1010 includes an endoscope 1100, a control device 1600, an operation device 1300, a treatment tool 1400, a forward/backward drive device 1800, and a display device 1900. The control device 1600 includes a drive control device 1200 and a video control device 1500.

The endoscope 1100 is a device to be inserted into a lumen of a patient for the observation of an affected part. In this embodiment, the side to be inserted into a lumen of a patient is referred to as "distal end side" and the side to be attached to the control device 1600 is referred to as "base end side". The endoscope 1100 includes an insertion section 1110, a connecting section 1125, an extracorporeal soft section 1145, and connectors 1201 and 1202. The insertion section 1110, the connecting section 1125, the extracorporeal soft section 1145, and the connectors 1201 and 1202 are connected one another in this order from the distal end side.

The insertion section 1110 is a portion to be inserted into a lumen of a patient, and is configured in a soft elongated shape. The insertion section 1110 includes a bending section 1102, an extracorporeal soft section for connecting the base end of the bending section 1102 and the connecting section 1125, and a distal end section 1130 provided at the distal end of the bending section 1102. An internal route 1101 is provided inside the insertion section 1110, the connecting section 1125, and the extracorporeal soft section 1145, and a bending wire passing through the internal route 1101 is connected to the bending section 1102. When the drive control device 1200 drives the wire via the connector 1201, the bending section 1102 bends. Further, a raising base wire connected to the raising base provided at the distal end section 1130 is connected to the connector 1201 through the internal route 1101. As the drive control device 1200 drives the raising base wire, the raising angle of the treatment tool 1400 protruding from the side surface of the distal end section 1130 is changed. The side surface of the distal end section 1130 is provided with a camera, an illumination lens, and an opening of a treatment tool channel. An image signal line for connecting the camera and the connector 1202 is provided in the internal route 1101, and an image signal is transmitted from the camera to the video control device 1500 via the image signal line. The video control device 1500 displays an endoscope image generated from the image signal on the display device 1900.

The connecting section 1125 is provided with an insertion opening 1190 of the treatment tool and a rolling operation section 1121. The treatment tool channel is provided in the internal route 1101, one end of which is open to the distal end section 1130 and the other end of which is open to the insertion opening 1190 of the treatment tool. An extension tube 1192 extending from the insertion opening 1190 to the operation device 1300 is connected to the insertion opening 1190. The treatment tool 1400 is inserted from an opening on the operation device 1300 side of the extension tube 1192, and protrudes to the opening of the distal end section 1130 via the insertion opening 1190 and the treatment tool channel. The extension tube 1192 may be omitted, and the treatment tool 1400 may be inserted through the insertion opening 1190. The rolling operation section 1121 is attached to the connecting section 1125 so as to be rotatable about the axial direction of the insertion section 1110. By rotating the rolling operation section 1121, the insertion section 1110 undergoes rolling rotation. As described later, the rolling operation section 1121 can be electrically driven.

The forward/backward drive device 1800 is a drive device for moving the insertion section 1110 forward and backward by electrical driving. An extracorporeal soft section 1140 is detachable from the forward/backward drive device 1800, and an insertion section 1110 moves forward and backward when the forward/backward drive device 1800 causes the extracorporeal soft section 1140 to slide in the axial direction in a state in which the extracorporeal soft section 1140 is mounted on the forward/backward drive device 1800. Although FIG. 62 shows an example in which the extracorporeal soft section 1140 and the forward/backward drive device 1800 are detachable, there is no such limitation, and it may be arranged such that the connecting section 1125 and the forward/backward drive device 1800 are detachable.

The operation device 1300 is detachably connected to the drive control device 1200 via an operation cable 1301. The operation device 1300 may communicate with the drive control device 1200 through wireless communication instead of wired communication. When an operator operates the operation device 1300, a signal of the operation input is transmitted to the drive control device 1200 via the operation cable 1301, and the drive control device 1200 electrically drives the endoscope 1100 to enable an endoscopic operation corresponding to the operation input based on the signal of the operation input. The operation device 1300 has an operation input section having five or more channels corresponding to the forward and backward movement of the endoscope 1100, the bending movements in two directions and the rolling rotation, and the operation of the raising base. If one or more of these operations are not electrically driven, the operation input section may be omitted. Each operation input section includes, for example, a dial, a joystick, a D-pad, a button, a switch, a touch panel, and the like.

The drive control device 1200 electrically drives the endoscope 1100 by driving a built-in motor based on an operation input to the operation device 1300. Alternatively, when the motor is present outside the drive control device 1200, the drive control device 1200 transmits a control signal to the external motor based on an operation input to the operation device 1300, thereby controlling the electrical driving. In addition, the drive control device 1200 may drive a built-in pump or the like based on an operation input to the operation device 1300, thereby causing the endoscope 1100 to perform air supply suction. The air supply suction is performed through an air supply/suction tube provided in the internal route 1101. One end of the air supply/suction tube opens to the distal end section 1130 of the endoscope 1100, while the other end is connected to the drive control device 1200 via the connector 1201. In addition, the treatment tool channel may be extended to the connector 1201, and the treatment tool channel may also be used as an air supply/suction tube.

Figure 63:
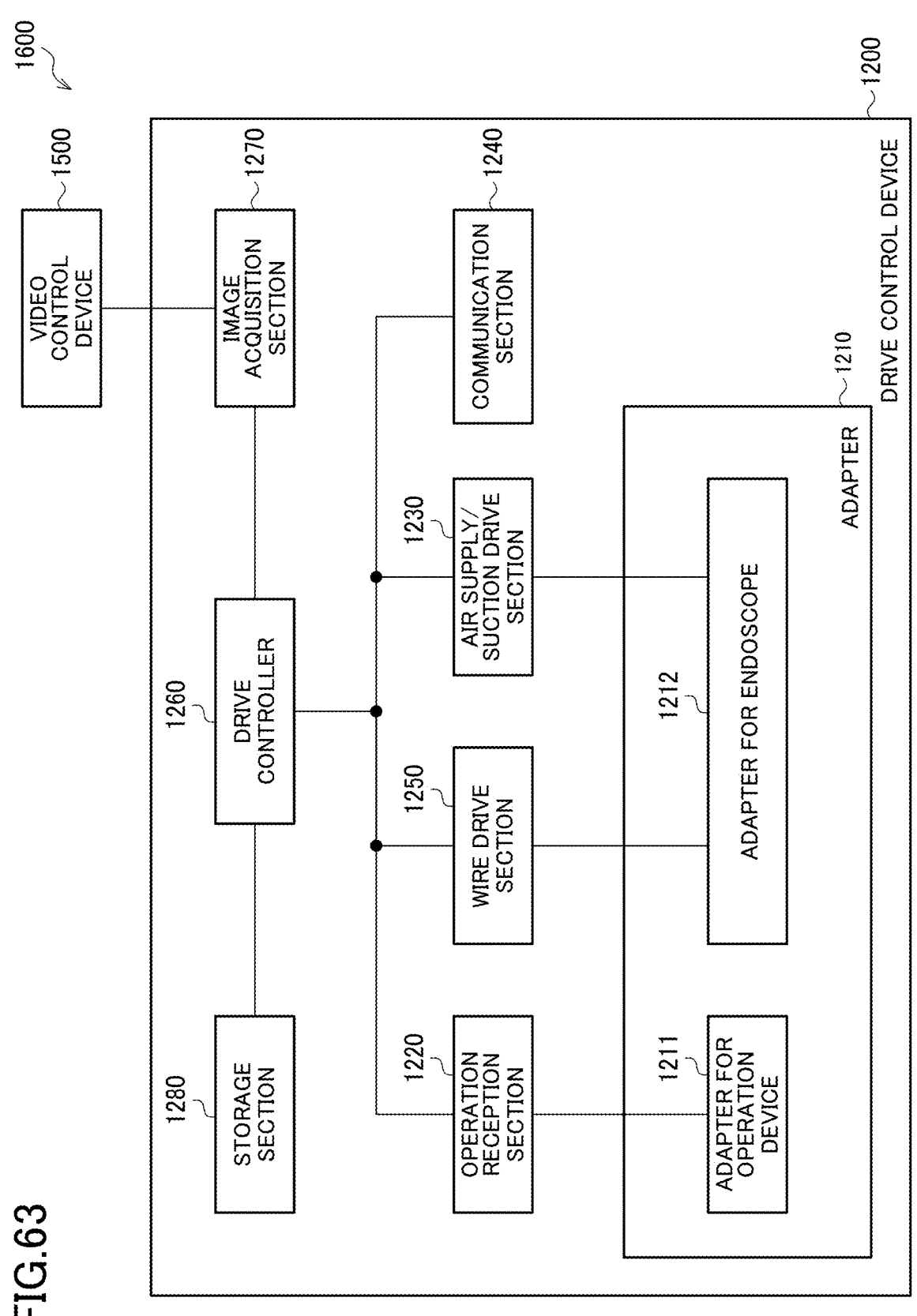
FIG. 63 shows a detailed configuration example of a drive control device.

FIG. 63 shows a detailed configuration example of a drive control device 1200. The drive control device 1200 includes a storage section 1280, a drive controller 1260, an operation reception section 1220, a wire drive section 1250, an air supply/suction drive section 1230, a communication section 1240, and an adapter 1210. Further, the drive control device 1200 may include the image acquisition section 1270.

The adapter 1210 includes an operation device adapter 1211 to which the operation cable 1301 is detachably connected, and an endoscope adapter 1212 to which connector 1201 of the endoscope 1100 is detachably connected.

The wire drive section 1250 drives the bending movement of the bending section 1102 of the endoscope 1100 or the operation of the raising base of the treatment tool 1400 based on the control signal from the drive controller 1260. The wire drive section 1250 includes a bending movement motor unit for driving the bending section 1102 of the endoscope 1100 and a raising base motor unit for driving the raising base. The endoscope adapter 1212 has a bending movement coupling mechanism for enabling coupling to the bending wire on the endoscope 1100 side. When the bending movement motor unit drives the coupling mechanism, the driving force is transmitted to the bending wire on the endoscope 1100 side. Further, the endoscope adapter 1212 has a raising base coupling mechanism for enabling coupling to the raising base wire on the endoscope 1100 side. When the raising base motor unit drives the coupling mechanism, the driving force is transmitted to the raising base wire on the endoscope 1100 side.

The air supply/suction drive section 1230 drives air supply suction of the endoscope 1100 based on a control signal from the drive controller 1260. The air supply/suction drive section 1230 is connected to an air supply/suction tube of the endoscope 1100 via the endoscope adapter 1212. The air supply/suction drive section 1230 includes a pump or the like, and supplies air to the air supply/suction tube or sucks air from the air supply/suction tube 1172.

The communication section 1240 communicates with a drive device provided outside the drive control device 1200.

The communication may be wireless communication or wired communication. The drive device provided outside is a forward/backward drive device 1800 for performing forward and backward movement, a rolling drive device for performing the rolling rotation or the like.

The drive controller 1260 controls the forward and backward movement, the bending movement and the rolling rotation of the endoscope 1100, the raising angle of the treatment tool 1400 made by the raising base, and the air supply suction by the endoscope 1100. The drive controller 1260 is, for example, a processor such as a CPU (Central Processing Unit), a GPU (Graphics Processing Unit), a DSP (Digital Signal Processor), or the like. For example, the storage section 1280 stores a computer-readable program, and the functions of the drive controller 1260 are implemented as processes as the processor executes the program. However, the hardware of the drive controller 1260 is not limited to that described above, and may be structured using circuits with various configurations.

First, the control in which the endoscopic operation is not restricted is described below. The operation reception section 1220 receives an operation input signal from the operation device 1300 via the operation cable 1301 attached to the operation device adapter 1221. When the operation device 1300 communicates with the drive control device 1200 by wireless communication, the operation reception section 1220 may be a wireless communication circuit.

The drive controller 1260 controls the electrical driving based on an operation input signal from the operation reception section 1220. Specifically, when the bending operation is performed, the drive controller 1260 outputs a control signal indicating the bending direction or the bending angle to the wire drive section 1250, and the wire drive section 1250 drives the bending wire so that the bending section 1102 bends in the bending direction or the bending angle. Also, when the forward and backward movement operation is performed, the drive controller 1260 transmits a control signal indicating the forward/backward direction or the forward/backward movement amount to the forward/backward drive device via the communication section 1240, and the forward/backward drive device moves the extracorporeal soft section 1140 forward or backward so that the endoscope 1100 moves forward or backward in the forward/backward direction or the forward/backward movement amount. Further, when the rolling rotation operation is performed, the drive controller 1260 transmits a control signal indicating the rolling rotation direction or the rolling rotation angle to the rolling drive device via the communication section 1240, and the rolling drive device performs rolling rotation of the insertion section 1110 so that the endoscope 1100 undergoes rolling rotation in the rolling rotation direction or at the rolling rotation angle. Similar controls are performed for other electrical driving.

Next, the restriction of the endoscopic operation is described below. The operation reception section 1220 receives an operation input signal from the operation device 1300. The drive controller 1260 determines whether or not the operation input is an abnormal operation input based on the operation input signal from the operation reception section 1220. The details of the determination are as described in FIG. 53, FIG. 54 or FIG. 59. The drive controller 1260 restricts the endoscopic operation when it is determined that the operation input is an abnormal operation input. Specifically, the drive controller 1260 outputs a control signal for restricting the endoscopic operation to the wire drive section 1250, or transmits the control signal to an external drive device via the communication section 1240.

For example, in the restriction of the bending movement, the drive controller 1260 generates a control signal indicating the bending direction or the bending angle based on the operation input signal; at this time, the drive controller 1260 generates the control signal so that the bending speed is restricted to no higher than a predetermined value or that the bending angle is restricted to no higher than a predetermined value. The same applies to the restriction of the forward/backward movement or the restriction of the rolling rotation.

The storage section 1280 stores the threshold or the input pattern for determining whether or not the operation input is an abnormal operation input, as well as a predetermined value used for the restriction of the endoscopic operation to no higher than the predetermined value. The storage section 1280 is a storage device such as a semiconductor memory or a magnetic storage device. The semiconductor memory may be a volatile memory such as a SRAM or a DRAM, or a nonvolatile memory such as an EEPROM.

The drive controller 1260 may determine whether or not the operation input is an abnormal operation input based on the result of signal processing using machine learning. More specifically, the storage section 1280 stores a trained model, and the drive controller 1260 performs the determination described above by performing a processing based on the trained model. The trained model is trained to, in response to input of an operation input signal, output a determination result indicating whether the operation input is a normal operation input or an abnormal operation input. For example, the trained model is trained to determine, based on input patterns of a plurality of operation inputs and a correct answer label attached to each input pattern, whether each input pattern is a normal input pattern or an abnormal input pattern. The correct answer label indicates whether or not each input pattern is a normal input pattern or an abnormal input pattern.

As described in FIG. 61, the drive controller 1260 may vary the determination condition based on the endoscope image. In this case, the drive control device 1200 may include the image acquisition section 1270 that outputs image data of the received endoscope image to the drive controller 1260. The image acquisition section 1270 is a communication interface for receiving image data of an endoscope image from the video control device 1500 by wired communication or wireless communication. In embodiments where the drive controller 1260 does not use endoscope images, such as FIG. 60, etc., the drive control device 1200 may not include the image acquisition section 1270.

Detailed Configuration Example of Each Part of Medical System

Figure 64:
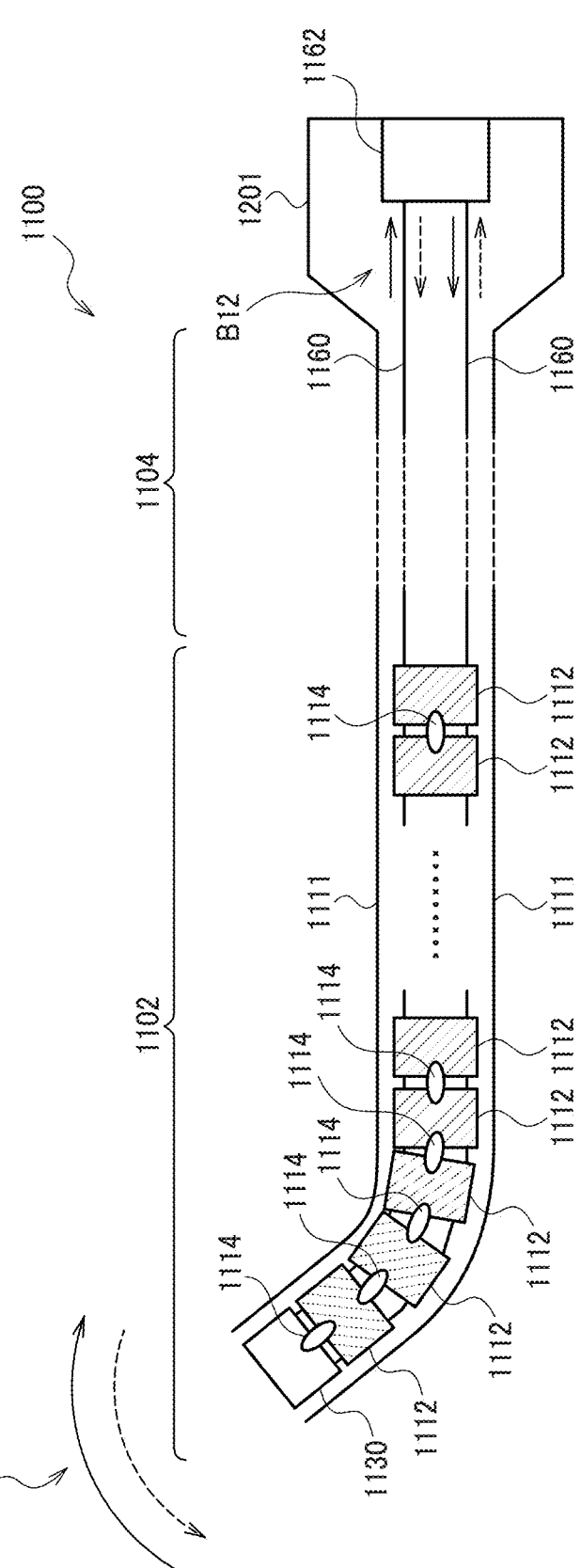
FIG. 64 is a schematic view of an endoscope including a bending section and a driving mechanism thereof.

FIG. 64 is a schematic view of an endoscope 1100 including a bending section 1102 and a driving mechanism thereof. An endoscope 1100 includes a bending section 1102, a soft section 1104, and a connector 1201. The soft section 1104 corresponds to the intracorporeal soft section and the extracorporeal soft section 1145 described above with reference to FIG. 62. In FIG. 64, the connecting section 1125 is omitted.

The bending section 1102 and the soft section 1104 are covered with an outer sheath 1111. The inside of the tube of the outer sheath 1111 corresponds to the internal route 1101 in FIG. 62. The bending section 1102 includes a plurality of bending pieces 1112 and a distal end section 1130 connected to the distal end of the bending pieces 1112. Each of the plurality of bending pieces 1112 and the distal end section 1130 is connected in series from the base end side to the distal end side by a rotatable connecting section 1114, thereby forming a multi-joint structure. The connector 1201 is provided with a coupling mechanism 1162 on the endoscope side connected to a coupling mechanism on the drive control device 1200 side. By attaching the connector 1201 to the drive control device 1200, it is possible to electrically drive the bending movement. A bending wire 1160 is provided in the outer sheath 1111. One end of the bending wire 1160 is connected to the distal end section 1130. The bending wire 1160 passes through the soft section 1104 by penetrating through a plurality of bending pieces 1112, turns back in a coupling mechanism 1162, passes through the soft section 1104 again, penetrates through the plurality of bending pieces 1112. The other end of the bending wire 1160 is connected to the distal end section 1130. The driving force from the wire drive section 1250 is transmitted to the bending wire 1160 via the coupling mechanism 1162 as the pulling force of the bending wire 1160.

As shown by the solid line arrow B12, when the upper wire in the figure is pulled, the lower wire is pushed, whereby the multiple joints of the bending pieces 1112 are bent upward in the figure. As a result, as indicated by the solid line arrow A12, the bending section 1102 is bent upward in the figure. When the lower wire in the figure is pulled as indicated by the dotted arrow B12, similarly, the bending section 1102 is bent downward in the figure as indicated by the dotted arrow A12. As described with reference to FIG. 52, the bending section 1102 can be bent independently in two orthogonal directions. Although FIG. 64 shows a bending mechanism for one direction, two sets of bending wires are actually provided, and each bending wire can be bent independently in two directions by being pulled independently by the coupling mechanism 1162.

Note that the mechanism for the electrically-driven bending is not limited to that described above. For example, a motor unit may be provided instead of the coupling mechanism 1162. Specifically, it may be arranged such that the drive control device 1200 transmits a control signal to the motor unit via the connector 1201, and the motor unit drives the bending movement by pulling or relaxing the bending wire 1160 based on the control signal.

Figure 65:
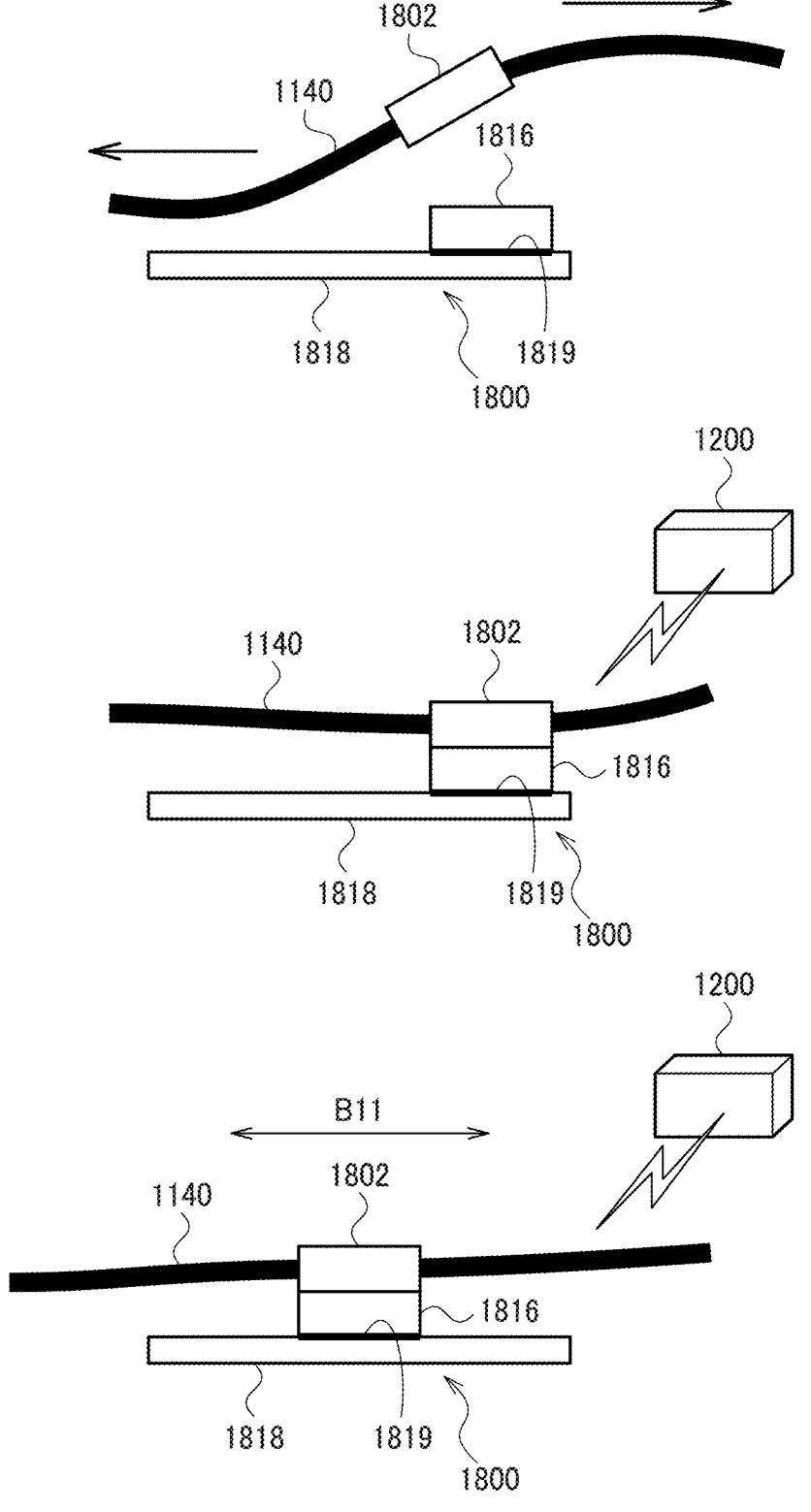
FIG. 65 shows a detailed configuration example of a forward/backward drive device.

FIG. 65 shows a detailed configuration example of a forward/backward drive device 1800. The forward/backward drive device 1800 includes a motor unit 1816, a base 1818, and a slider 1819.

As shown in the upper and middle figures, the extracorporeal soft section 1140 of the endoscope 1100 is provided with an attachment 1802 detachable from the motor unit 1816. As shown in the middle figure, the attachment of the attachment 1802 to the motor unit 1816 enables electrical driving of forward/backward movement. As shown in the lower figure, the slider 1819 supports the motor unit 1816 while enabling the motor unit 1816 to move linearly with respect to the base 1818. The slider 1819 is fixed to the operating table T1 shown in FIG. 62. As shown in B11, the drive control device 1200 transmits a forward or backward control signal to the motor unit 1816 by wireless communication, and the motor unit 1816 and the attachment 1802 move linearly on the slider 1819 based on the control signal. As a result, the forward and backward movement of the endoscope 1100 shown in A11 in FIG. 52 is achieved. Note that the drive control device 1200 and the motor unit 1816 may be connected by wired connection.

Figure 66:
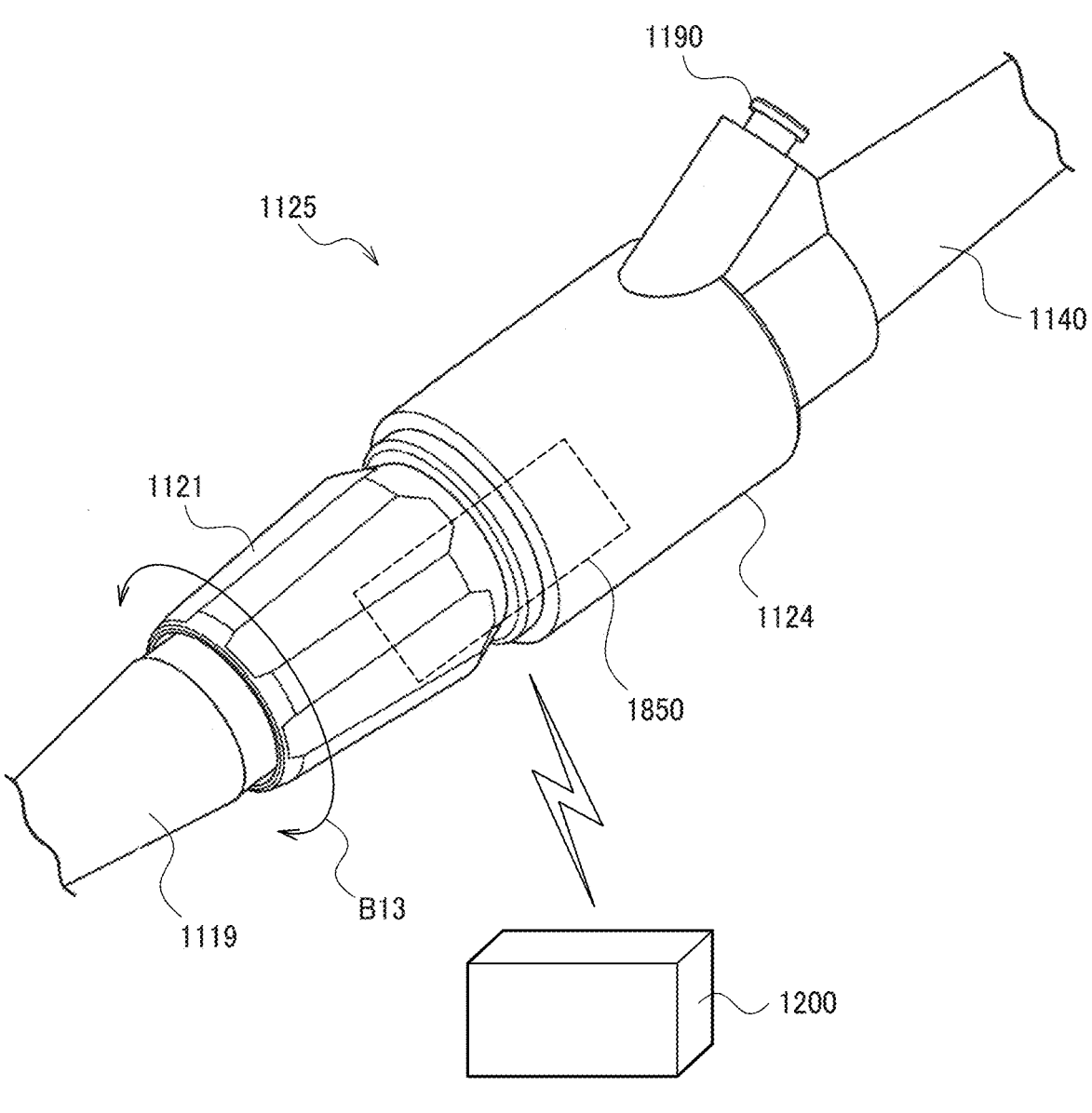
FIG. 66 is a perspective view of a connecting section including a rolling drive device.

FIG. 66 is a perspective view of the connecting section 1125 including a rolling drive device 1850. The connecting section 1125 includes a connecting section main body 1124 and a rolling drive device 1850.

The insertion opening 1190 of the treatment tool is provided in the connecting section main body 1124 and is connected to the treatment tool channel inside the connecting section main body 1124. The connecting section main body 1124 has a cylindrical shape, and a cylindrical member coaxial with the cylinder is rotatably provided inside the connecting section main body 1124. The base end section of the intracorporeal soft section 1119 is fixed to the outside of the cylindrical member, and the base end section serves as a rolling operation section 1121. As a result, the intracorporeal soft section 1119 and the cylindrical member can rotate with respect to the connecting section main body 1124 about the axial direction of the intracorporeal soft section 1119. The rolling drive device 1850 is a motor unit provided inside the connecting section main body 1124. As shown in B13, the drive control device 1200 transmits a rolling rotation control signal to the rolling drive device 1850 by wireless communication, and the rolling drive device 1850 rotates the base end section of the intracorporeal soft section 1119 with respect to the connecting section main body 1124 based on the control signal, thereby causing rolling rotation of the intracorporeal soft section 1119. As a result, the rolling rotation of the endoscope 1100 shown in A13 in FIG. 52 is achieved. The rolling drive device 1850 may include a clutch mechanism, and the rolling rotation may be switched between non-electrical driving and electrical driving by the clutch mechanism. The drive control device 1200 and the rolling drive device 1850 may be connected by wired connection via a signal line passing through the internal route 1101.

Figure 67:
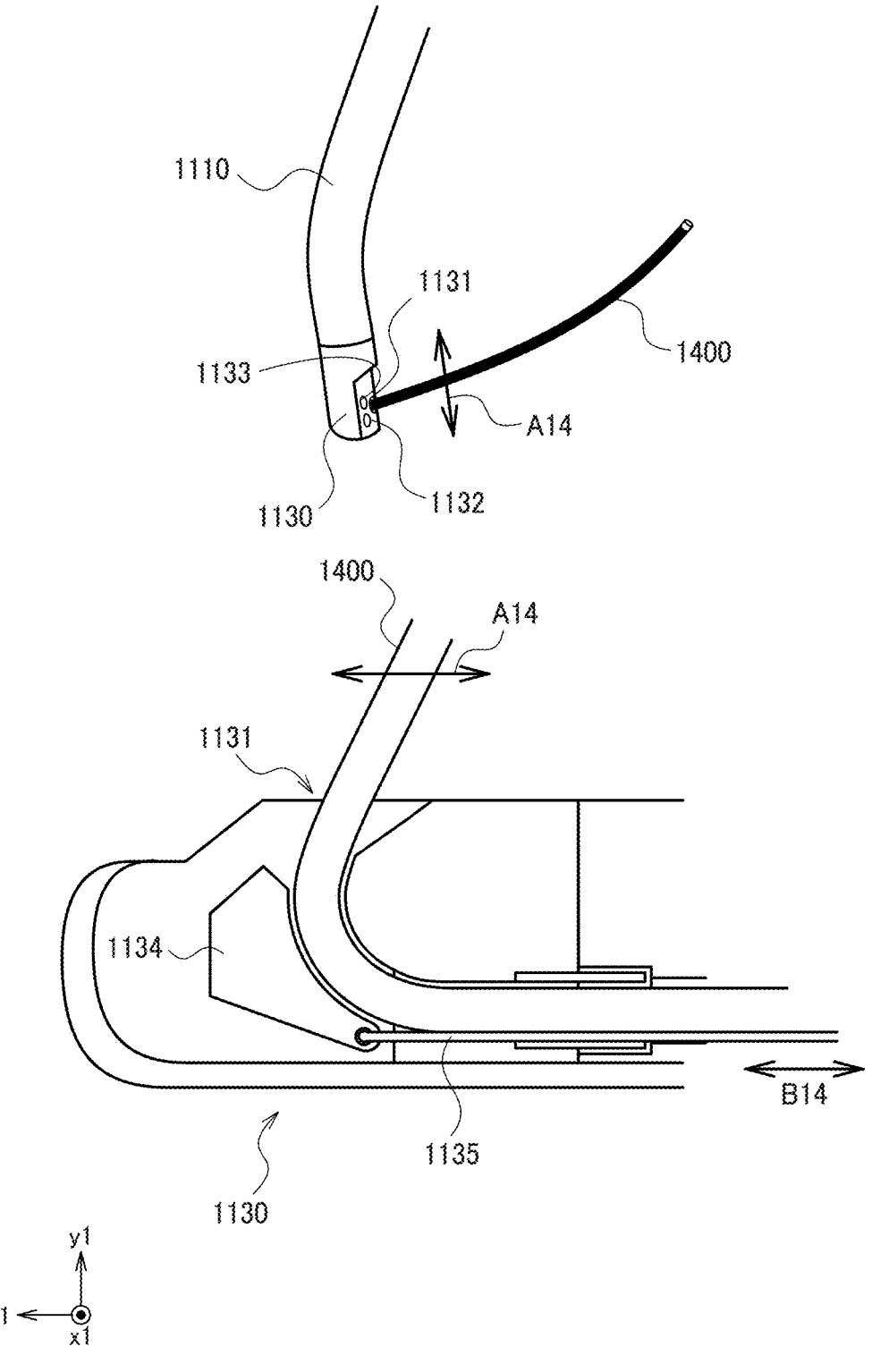
FIG. 67 shows a detailed configuration example of a distal end section of an endoscope including a raising base of a treatment tool.

FIG. 67 shows a detailed configuration example of a distal end section 1130 of an endoscope including a raising base of a treatment tool. The upper figure shows an external view of the distal end section 1130. An opening 1131 of a treatment tool channel, a camera 1132, and an illumination lens 1133 are provided on the side surface of the distal end section 1130. As shown in the lower figure, the direction parallel to the axial direction of the distal end section 1130 is defined as z1 direction, the direction parallel to the line-of-sight direction of the camera 1132 is defined as y1 direction, and the direction orthogonal to the z1 direction and the y1 direction is defined as x1 direction. The lower figure shows a cross-sectional view of the distal end section 1130 in a plane that is parallel to the y1z1 plane of the treatment tool channel and that passes through the opening 1131 of the treatment tool channel.

The distal end section 1130 includes a raising base 1134 and a raising base wire 1135. The raising base 1134 is swingable about an axis parallel to the x1 direction. One end of the raising base wire 1135 is connected to the raising base 1134, while the other end is connected to the drive control device 1200 via the connector 1201. As shown in B14, the wire drive section 1250 of the drive control device 1200 pushes and pulls the raising base wire 1135 to swing the raising base 1134, thereby, as shown in A14, changing the raising angle of the treatment tool 1400. The raising angle is an angle of the treatment tool 1400 protruding from the opening 1131. The raising angle can be defined, for example, by an angle formed by the treatment tool 1400 protruding from the opening 1131 and the z1 direction.

Figure 68:
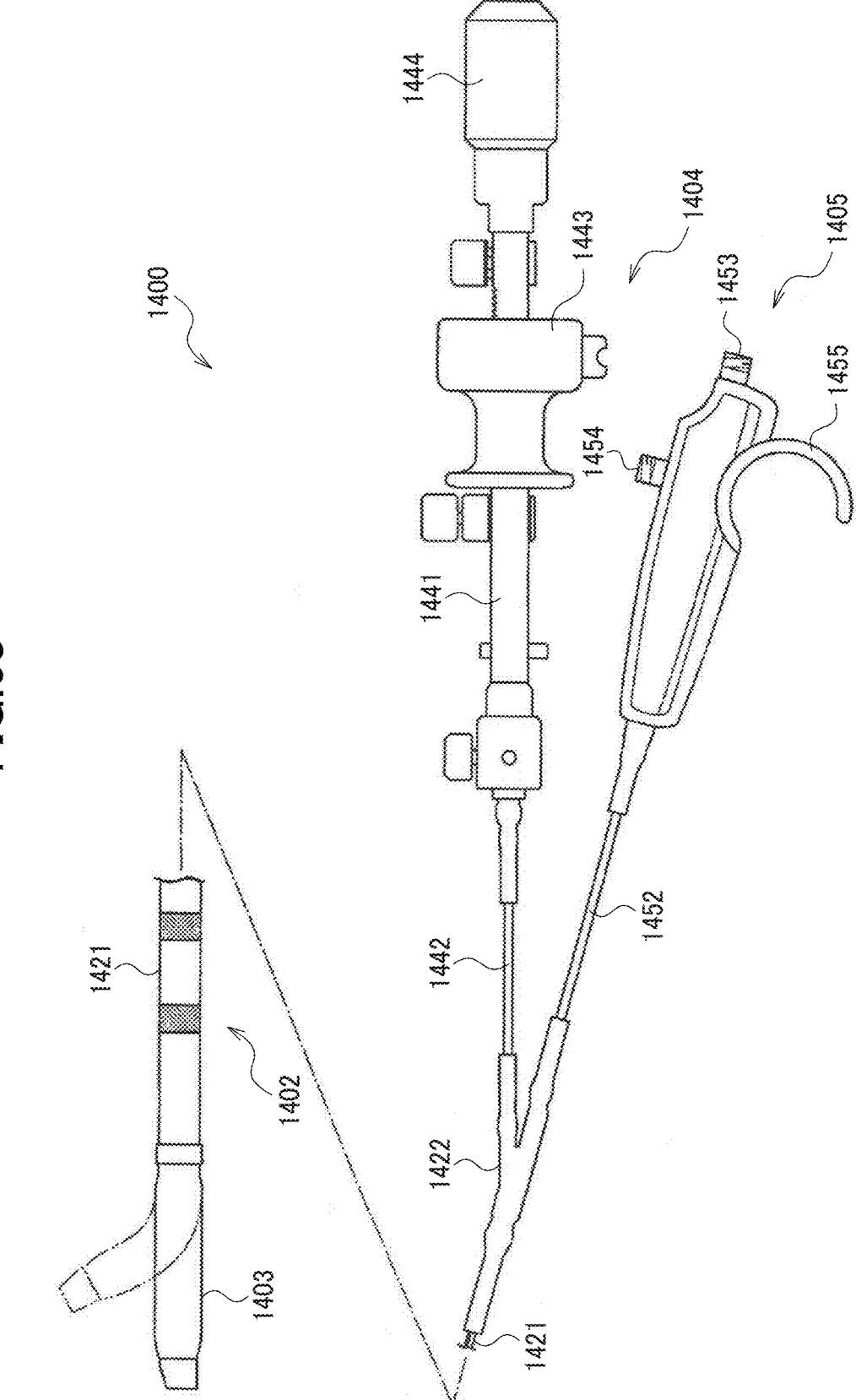
FIG. 68 shows a detailed configuration example of a non-electric treatment tool.

FIG. 68 shows a detailed configuration example of the non-electric treatment tool 1400. Herein, as an example of the treatment tool 1400, a cannula capable of operating bending of the distal end is shown. The treatment tool 1400 includes a long-length insertion section 1402 extending in the axial direction, a bending movement section 1403 capable of bending movement, a first operation section 1404 for operating the bending movement section 1403, and a second operation section 1405 for inserting a contrast agent or a guide wire.

The insertion section 1402 has a tube 1421, and the bending movement section 1403 is connected to the distal end of the tube 1421. In FIG. 68, the distal end side of the tube 1421 is enlarged. The tube 1421 is also referred to as a sheath. The operator holds the tube 1421 of the treatment tool 1400 inserted into the treatment tool channel of the endoscope 1100, and pushes and pulls the tube 1421 to move the treatment tool 1400 forward and backward.

A connector 1422 is connected to the base end of the tube 1421. The first operation section 1404 and the second operation section 1405 are connected to the connector 1422. The first operation section 1404 includes a connecting tube 1442, one end of which is connected to the connector 1422, a first operation main body 1441 connected to the other end of the connecting tube 1442, a grip 1444 fixed to the base end of the first operation main body 1441, and a slider 1443 provided movable forward and backward in the axial direction of the first operation main body 1441. Inside the tube 1421, the connector 1422, the connecting tube 1442, and the first operation main body 1441, a wire for connecting the bending movement section 1423 and the slider 1443 is provided. When the operator pulls the slider 1443 while holding the grip 1444, the wire is pulled and the bending movement section 1423 is bent.

The second operation section 1405 includes a connecting tube 1452, one end of which is connected to the connector 1422, a second operation main body 1451 connected to the other end of the connecting tube 1452, a first opening 1453 opened in the axial direction of the connecting tube 1452 on the base end side of the second operation main body, a second opening 1454 opened to the outer surface of the second operation main body 1451, and a hook 1455 provided on the second operation main body 1451. The hook 1455 has elasticity and is formed in a substantially C-shape, and is used for locking the treatment tool 1400 to the endoscope 1100 or the like. The first opening 1453 and the second opening 1454 are connected to the tube 1421 via the second operation main body 1451, the connecting tube 1452, and the connector 1422. By inserting a contrast agent or a guide wire from the first opening 1453 or the second opening 1454, the contrast agent can be injected into the body or the guide wire can be inserted into the body from the distal end of the treatment tool 1400.

Second Detailed Configuration Example of Medical System

Figure 69:
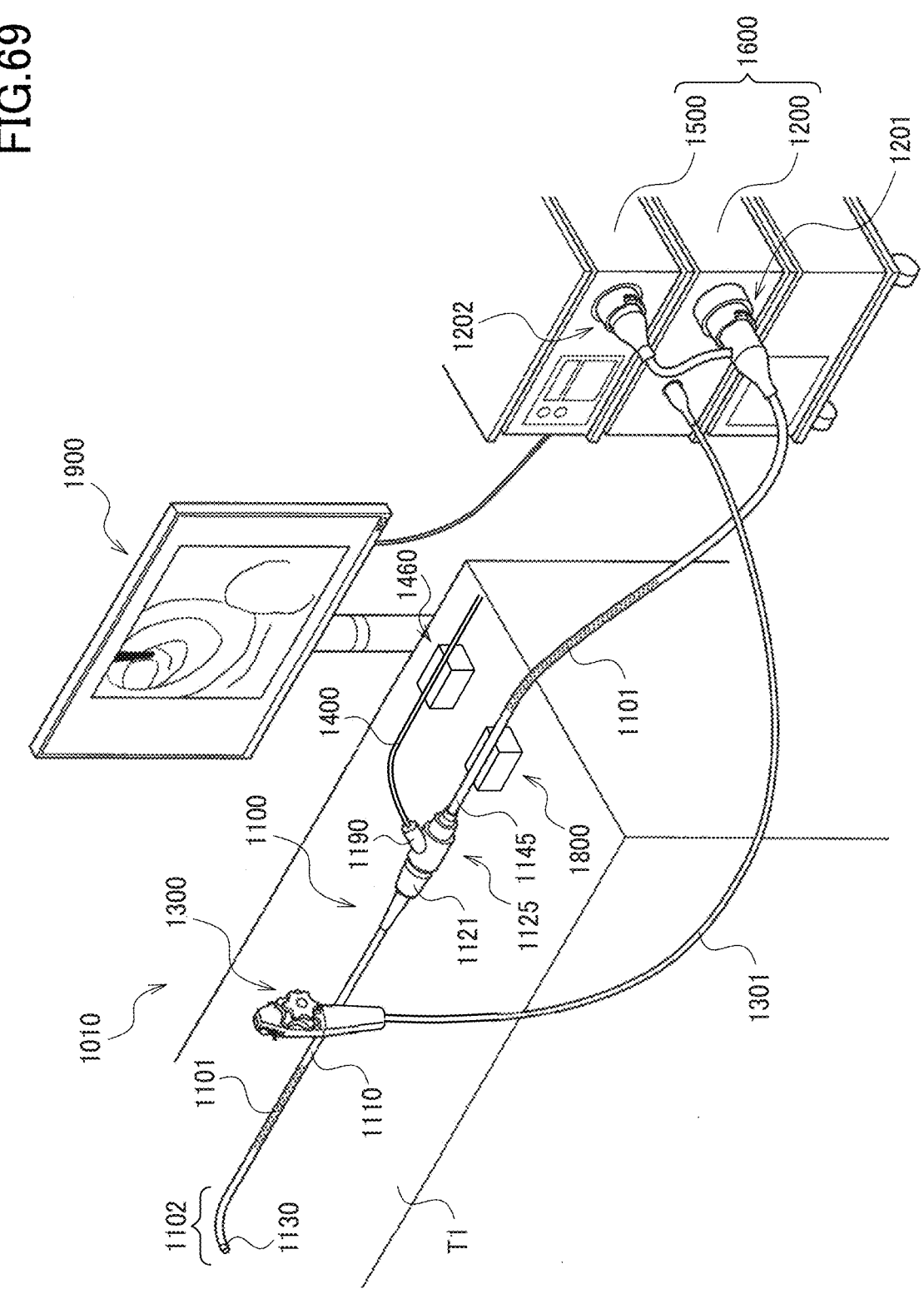
FIG. 69 shows a second detailed configuration example of a medical system.

FIG. 69 shows a second detailed configuration example of the medical system 1010. In this configuration example, the endoscope and the treatment tool are electrically driven. The following mainly describes structures different from the first detailed configuration example. The medical system 1010 includes a forward/backward drive device 1460 for a treatment tool.

The treatment tool 1400 is inserted from an insertion opening 1190 of the connecting section 1125, and protrudes to the opening of the distal end section 1130 via the treatment tool channel. In this configuration example, the extension tube 1192 of the first detailed configuration example is omitted. The forward/backward drive device 1460 is a drive device for moving the treatment tool 1400 forward and backward by electrical driving. The tube 1421 of the insertion section 1402 is detachable from the forward/backward drive device 1800, and the insertion section 1402 moves forward and backward when the forward/backward drive device 1460 slides the tube 1421 in the axial direction in a state in which the tube 1421 is mounted on the forward/backward drive device 1460. The operation device 1300 includes an operation input section having eight or more channels corresponding to the forward and backward movement of the endoscope, the bending movements in two directions and the rolling rotation of the endoscope, the movement of the raising base, the forward and backward movement of the treatment tool, and the bending movements in one direction and the rolling rotation of the treatment tool. If one or more of these operations are not electrically driven, the operation input section thereof may be omitted.

Figure 70:
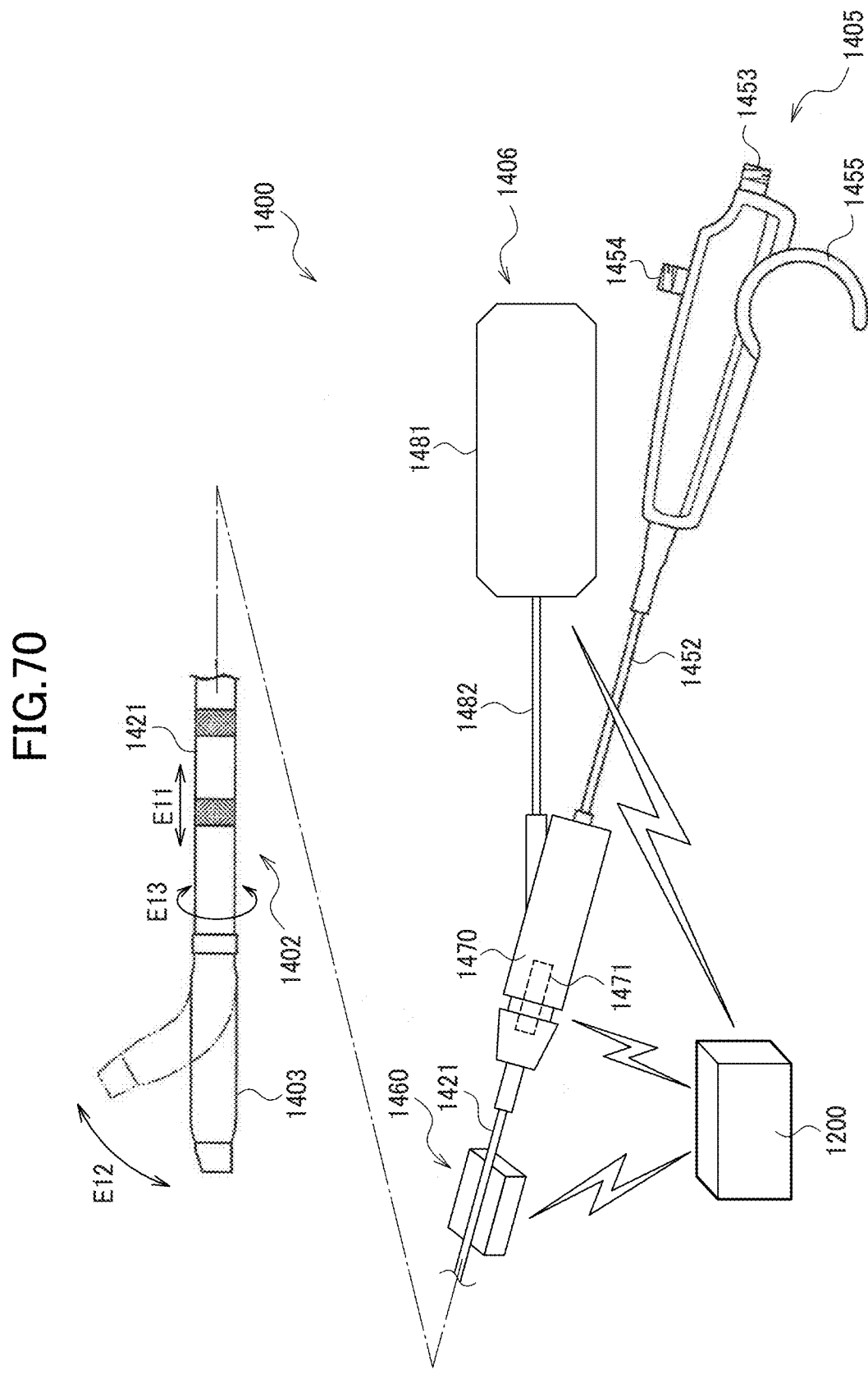
FIG. 70 shows a detailed configuration example of an electric treatment tool.

FIG. 70 shows a detailed configuration example of an electric treatment tool 1400. The treatment tool 1400 includes an insertion section 1402, a bending movement section 1403, a bending driving section 1406 for electrically driving the bending movement section 1403, and an operation section 1405. Although the reference number 1405 is referred to as the second operation section in FIG. 68, 1405 is herein referred to as an operation section. The following mainly describes structures different from FIG. 68.

The tube 1421 of the insertion section 1402 is detachable from the forward/backward drive device 1460, and has a structure similar to, for example, the forward/backward drive device 1800 for use in endoscopes, which has been described with reference to FIG. 65. That is, the tube 1421 has an attachment detachable from the forward/backward drive device 1460, and the attachment is attached to the motor unit of the forward/backward drive device 1460, thereby enabling the forward/backward movement to be electrically driven. The drive control device 1200 transmits a forward or backward control signal to the motor unit by wireless communication, and the motor unit and the attachment move linearly in the axial direction of the tube 1421 based on the control signal, thereby moving the insertion section 1402 forward or backward. The drive control device 1200 and the forward/backward drive device 1460 may be connected by wired connection.

A connector 1470 is connected to the base end of the tube 1421. The bending driving section 1406 and the operation section 1405 are connected to the connector 1470. The connector 1470 includes a connecting tube 1482, one end of which is connected to the connector 1470, and a motor unit 1481 connected to the other end of the connecting tube 1482. Inside the tube 1421, the connector 1470, and the connecting tube 1482, a wire for connecting the bending movement section 1403 and the motor unit 1481 is provided. The drive control device 1200 transmits a bending movement control signal to the motor unit 1481 by wireless communication, and the motor unit 1481 drives the wire based on the control signal, thereby bending the bending movement section 1403. For example, the electrical driving of the bending movement section 1403 can be realized by a structure similar to the structure having a plurality of bending pieces described in FIG. 64. However, although the bending movement of the endoscope in FIG. 64 is capable of bending in four directions (up, down, left, right), the treatment tool in FIG. 70 is capable of, for example, bending in one direction. Note that the drive control device 1200 and the motor unit 1481 may be connected by wired connection.

Inside the connector 1470, a motor unit 1471 is provided to electrically drive the rolling rotation of the insertion section 1402. The structures of the connector 1470 and the motor unit 1471 are similar to, for example, those of the connecting section 1125 and the motor unit of the rolling drive device 1850 in FIG. 66. Specifically, the connector main body of the connector 1470 has a cylindrical shape, and a cylindrical member coaxial with the cylinder is rotatably provided inside the connector main body. The base end section of the tube 1421 of the insertion section 1402 is fixed to the outside of the cylindrical member. As a result, the tube 1421 and the cylindrical member are rotatable with respect to the connector main body about the axial direction of the tube 1421. The drive control device 1200 transmits a rolling rotation control signal to the motor unit 1471 by wireless communication, and the motor unit 1471 rotates the base end section of the tube 1421 with respect to the connector main body based on the control signal, thereby allowing the insertion section 1402 to undergo rolling rotation. Note that the drive control device 1200 and the motor unit 1471 may be connected by wired connection.

As described above, in the electrically-driven medical system, there is a possibility of accidental operation input not intended by the operator due to an erroneous operation or falling of the controller. When such an operation input occurs, there may be influences such as contact of the medical instrument with an organ, removal of the medical instrument from an organ or tissue, or disruption of the position of the medical instrument. The above-mentioned U.S. Patent Application Publication No. 2018/0040126 uses a non-electric endoscope. Therefore, even if an alert is generated by detecting the speed of the endoscope, the automatic control to avoid, for example, the contact of the endoscope with an organ, cannot be performed.

Therefore, the medical system 1010 of the present embodiment includes the medical instrument whose instrument motion is electrically driven, the operation device 1300 that performs an operation input of the instrument motion, and the control device 1600 that controls the electrically-driven instrument motion based on the operation input. The instrument motion is at least one of forward and backward movement of an insertion section of the medical instrument, a bending angle of a bending section of the insertion section, and rolling rotation of the insertion section. When the control device 1600 determines that the operation input is abnormal operation input different from normal operation input, the control device 1600 performs control to restrict the electrically-driven instrument motion.

According to the present embodiment, if there was an operation input unintended by the operator due to an erroneous operation, falling of the controller, etc., the control device 1600 determines that the operation input is an abnormal operation input, and restricts the instrument motion so that the medical instrument is prevented from moving by a large amount or at a high speed by the operation input. This prevents influences such as contact of the medical instrument with an organ, removal of the medical instrument from an organ or tissue, disruption of the position of the medical instrument, and the like.

The medical instrument, instrument motion, electrical driving, normal operation input, abnormal operation input, and restriction of instrument motion are described in FIG. 52 and FIG. 53 in "Medical System and Processing Flow", etc.

Further, in the present embodiment, the control device 1600 may determine whether or not the operation input is an abnormal operation input by determining whether or not the operation input is more abrupt than the normal operation input.

When the operator is operating the medical instrument as intended, it is unlikely that the operator makes an abrupt move in the forward/backward movement, the bending, or the rolling rotation. On the other hand, when an erroneous operation, falling of the controller or the like occurs, the operation input is likely to be abrupt. According to the present embodiment, when an operation input more abrupt than the normal operation input occurs, the control device 1600 determines that the operation input is an abnormal operation input.

The abrupt operation input is described and exemplified in FIG. 56 and FIG. 58 in "Medical System and Processing Flow", etc.

Further, in the present embodiment, the control device 1600 may also determine whether or not the operation input is an abnormal operation input based on the operation speed of the operation input. More specifically, the control device 1600 may determine whether or not the operation input is an abnormal operation input by comparing the operation speed or a change of the operation speed with a threshold.

When the operator is operating the medical instrument as intended, the operation speed or changes in the operation speed are likely to be relatively small. On the other hand, when an erroneous operation, falling of the controller or the like occurs, the operation speed or changes in the operation speed are likely to increase. According to the present embodiment, when the operation speed or changes in the operation speed exceed a threshold, the control device 1600 determines that the operation input is an abnormal operation input.

The operation speed and changes in the operation speed are described and exemplified in FIG. 56 and FIG. 58 in "Medical System and Processing Flow", etc.

Further, in the present embodiment, the control device 1600 may determine whether or not the operation input is an abnormal operation input by determining whether or not the operation input has an input pattern different from the input pattern of the normal operation input.

When the operator is operating the medical instrument as intended, it is assumed that the medical instrument is operated with an input pattern of normal operation in the procedure. On the other hand, when an erroneous operation, falling of the controller or the like occurs, it is assumed that an operation input with an input pattern different from the input pattern of the normal operation in the procedure is entered. According to the present embodiment, when an operation input with an input pattern different from the input pattern of the normal operation input occurs, the control device 1600 determines the operation input to be an abnormal operation input.

The input pattern of the operation input is explained in FIG. 59 in "Medical System and Processing Flow", etc.

Further, in the present embodiment, the control device 1600 may also determine whether or not the operation input is an abnormal operation input based on the input waveform of the operation input.

According to the present embodiment, the control device 1600 is capable of detecting the input pattern of the operation input based on the input waveform in the operation input. This allows the control device 1600 to determine whether or not the operation input has an input pattern different from the input pattern of the normal operation input based on the input waveform of the operation input.

The input waveform of the operation input is explained in FIG. 59 in "Medical System and Processing Flow", etc.

Further, in the present embodiment, the control device 1600 may change the determination criteria for determining whether or not the operation input is an abnormal operation input in an operation state in which, among the endoscope

1100 and the treatment tool 1400, the endoscope 1100 is operated and an operation state in which the treatment tool 1400 is operated.

The operation to be performed changes depending on the operation state of the endoscope 1100 and the operation state of the treatment tool 1400. For example, when the treatment tool 1400 is operated, it is assumed that the endoscope 1100 is hardly operated or operated with only small movements. According to the present embodiment, by using a different criteria for determining whether or not the operation input is an abnormal operation input depending on the operation state of the endoscope 1100 and the operation state of the treatment tool 1400, it is possible to perform an appropriate abnormal operation input determination according to the operation state.

The determination criteria according to the operation state are explained in FIG. 60 in "Medical System and Processing Flow", etc. For example, "the operation state in which the endoscope 1100 is operated" corresponds to a branch to determination condition B, and "the operation state in which the treatment tool 1400 is operated" corresponds to a branch to determination condition C or A. In FIG. 60, the endoscope 1100 and the treatment tool 1400 are electrically driven; however, herein, at least the endoscope 1100 is electrically driven. If the treatment tool 1400 is not electrically driven, the operation state of the treatment tool 1400 may be detected, for example, by operation detection using an optical sensor, potentiometer or motion capture, motion detection of the treatment tool on the image by motion detection on the endoscope image, or the like.

Further, in the present embodiment, the medical instrument may be the endoscope 1100 in which the endoscopic operation, which is the instrument motion, is electrically driven. The control device 1600 may change the determination criteria for determining whether or not the operation input of the endoscopic operation is an abnormal operation input in a first operation state in which, among the endoscope 1100 and the treatment tool 1400, the endoscope 1100 is operated and a second operation state in which the endoscope 1100 and the treatment tool 1400 are operated. For example, the first operation state may be an operation state that performs positioning of the distal end section of the insertion section of the endoscope 1100 with respect to the papillary portion of the duodenum. The second operation state may be an operation state that performs cannulation from the papillary portion to a biliary duct.

The operation to be performed changes in each step of the procedure. For example, in the step of positioning the distal end section of the insertion section of the endoscope 1100 with respect to the papillary portion of the duodenum, the treatment tool 1400 is not operated and the forward/backward movement etc. is operated with a relatively large movement so as to insert the endoscope 1100. In the step of cannulation from the papillary portion to the biliary duct, it is assumed that both endoscope 1100 and the treatment tool 1400 are operated, and that the operation amount is relatively small. According to the present embodiment, by using different determination criteria for whether or not the operation input of the endoscopic operation is an abnormal operation input in respective steps of the procedure, it is possible to appropriately determine an abnormal operation input in each step.

In FIG. 60, the first operation state corresponds to a branch to determination condition B, and the second operation state corresponds to a branch to determination condition A. The "operation state that performs positioning of the distal end section of the insertion section of the endoscope 1100 with respect to the papillary portion of the duodenum" is described, for example, in the positioning step in "Explanation of ERCP". The operation state that performs cannulation from the papillary portion to the biliary duct" is described, for example, in the cannulation step in "Explanation of ERCP."

Further, in the present embodiment, the control device 1600 may change the determination criteria for determining whether or not the operation input is an abnormal operation input based on the endoscope image captured by the endoscope 1100.

The scenes showing organs, tissues or the treatment details etc. in the endoscope images presumably vary depending on the step, etc. of the procedure, and the type of the operation to be performed varies depending on the scene. According to the present embodiment, by using a different determination criteria for determining whether or not the operation input is an abnormal operation input based on the endoscope image, it is possible to appropriately determine an abnormal operation input according to the scene shown in the endoscope image.

Using different determination criteria based on the endoscope image is explained, for example, in FIG. 61 in "Medical System and Processing Flow", etc.

Further, in the present embodiment, the medical instrument may be the endoscope 1100 in which the endoscopic operation, which is the instrument motion, is electrically driven. The control device 1600 may determine the position of the insertion section 1110 of the endoscope 1100 in the body based on the endoscope image, and may change the determination criteria for determining whether or not the operation input of the endoscopic operation is an abnormal operation input based on the determined position.

According to the present embodiment, the control device 1600 uses a different determination criteria depending on the position of the insertion section 1110 of the endoscope 1100 judged from the endoscope image, thereby appropriately determining an abnormal operation input according to the scene shown in the endoscope image.

Further, in the present embodiment, the control device 1600 may also perform a restriction control to restrict the bending angle or the bending speed of the bending section of the medical instrument. Further, in the present embodiment, the control device 1600 may also perform a restriction control to restrict the amount or speed of the forward and backward movement of the insertion section of the medical instrument.

Excessive bending angle or bending speed, or excessive amount or speed of the forward and backward movement by an abnormal operation input may cause influences such as contact of the medical instrument with an organ or the like, or removal of the medical instrument from an organ or the like. According to the present embodiment, the control device 1600 restricts the bending angle, the bending speed of the medical instrument, as well as the amount and speed of the forward and backward movement of the medical instrument upon occurrence of an abnormal operation input, thereby preventing such influences.

Further, in the medical system 1010, the electrical driving of the bending movement of the endoscope 1100 is not limited to the structure of the present embodiment. For example, it may be structured such that an attachment equipped with an electric motor is detachably attached to a bending operation knob of a non-electrically-driven endoscope. The drive control device 1200 and the attachment are structured to communicate with each other, and, upon reception of a bending control signal from the drive control device 1200, the attachment is driven to perform the bending. In this case, the manual control and the automatic control can be switched by attaching and detaching the attachment. It may also be arranged such that a handle capable of controlling the driving of the drive control device 1200 is detachably attached to a motor unit for bending control corresponding to the drive control device 1200. In this case, the manual control and the automatic control can be switched by attaching and detaching the handle.

The present embodiment may also be performed as a method of operating the medical system 1010 as follows. That is, the method of operating the medical system 1010 includes a step of controlling the electrically-driven instrument motion based on the operation input of the instrument motion of the medical instrument, and a step of performing control to restrict the electrically-driven instrument motion when determining that the operation input is an abnormal operation input different from a normal operation input. In the method of operating the medical system 1010, the subject of each step is the medical system 1010.

According to some aspects of the present embodiment, the following are provided.

1. A medical system comprising:
   a medical instrument whose instrument motion is electrically driven, the instrument motion being at least one of forward and backward movement of an insertion section, a bending angle of a bending section of the insertion section, and rolling rotation of the insertion section;
   an operation device configured to perform an operation input of the instrument motion; and
   a control device configured to control the electrically-driven instrument motion based on the operation input,
   when determining that the operation input is an abnormal operation input different from normal operation input, the controller performing control to restrict the electrically-driven instrument motion.

2. The medical system as defined in claim 1, wherein the controller determines whether or not the operation input is the abnormal operation input by determining whether or not the operation input is a more abrupt operation input than the normal operation input.

3. The medical system as defined in claim 1, wherein the controller determines whether or not the operation input is the abnormal operation input based on an operation speed of the operation input.

4. The medical system as defined in claim 3, wherein the controller determines whether or not the operation input is the abnormal operation input by comparing the operation speed or a change in the operation speed with a predetermined threshold.

5. The medical system as defined in claim 1, wherein the controller determines whether or not the operation input is the abnormal operation input by determining whether or not the operation input has an input pattern different from an input pattern of the normal operation input.

6. The medical system as defined in claim 1, wherein the controller determines whether or not the operation input is the abnormal operation input based on an input waveform of the operation input.

7. The medical system as defined in claim 1, wherein the medical instrument is an endoscope whose endoscopic operation, which is the instrument motion, is electrically driven, or a treatment tool whose treatment tool motion, which is the instrument motion, is electrically driven.

8. The medical system as defined in claim 1, wherein the controller changes a determination criteria for determining whether or not the operation input is the abnormal operation input in an operation state in which, among the endoscope and the treatment tool, the endoscope is operated, and an operation state in which the treatment tool is operated.

9. The medical system as defined in claim 1, wherein the medical instrument is an endoscope whose endoscopic operation, which is the instrument motion, is electrically driven, and the controller changes a determination criteria for determining whether or not the operation input of the endoscopic operation is the abnormal operation input in a first operation state in which, among the endoscope and the treatment tool, the endoscope is operated, and a second operation state in which the endoscope and treatment tool are operated.

10. The medical system as defined in claim 9, wherein the first operation state is an operation state that performs positioning of a distal end section of the insertion section of the endoscope with respect to a papillary portion of duodenum, and the second operation state is an operation state that performs cannulation from the papillary portion to a biliary duct.

11. The medical system as defined in claim 1, wherein the controller changes a determination criteria for determining whether or not the operation input is the abnormal operation input based on an endoscope image captured by an endoscope.

12. The medical system as defined in claim 11, wherein the medical instrument is an endoscope whose endoscopic operation, which is the instrument motion, is electrically driven, and the controller determines a position of the insertion section of the endoscope in a body based on the endoscope image, and changes the determination criteria for determining whether or not the operation input of the endoscopic operation is the abnormal operation input based on the determined position.

13. The medical system as defined in claim 1, wherein the controller performs control to restrict a bending angle or a bending speed of the bending section as the restriction control.

14. The medical system as defined in claim 1, wherein the controller performs control to restrict an amount of forward and backward movement of the insertion section or a speed of the forward and backward movement of the insertion section as the restriction control.

15. A method of operating a medical system, comprising: based on an operation input of an instrument motion of a medical instrument whose instrument motion is electrically driven, controlling the electrically-driven instrument motion, the instrument motion being at least one of forward and backward movement of an insertion section, a bending angle of a bending section of the insertion section, and rolling rotation of the insertion section; and when determining that the operation input is abnormal operation input different from normal operation input, performing control to restrict the electrically-driven instrument motion.

Although the embodiments to which the present disclosure is applied and the modifications thereof have been described above, the present disclosure is not limited to the embodiments and the modifications thereof, and various modifications and variations in elements may be made in implementation without departing from the spirit and scope of the present disclosure. The plurality of elements disclosed in the embodiments and the modifications described above may be combined as appropriate to form various disclosures. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term (processor) cited with a different term (processing section/control section) having a broader meaning or the same meaning at least once in the specification and the drawings can be replaced by the different term in any place in the specification and the drawings.

What is claimed is:

1. An information processing system comprising:
a processor comprising hardware, the processor being configured to:
acquire an endoscope image from an endoscope, the endoscope image showing a papillary portion;
determine route information of a lumen based on the endoscope image, the lumen being at least one of a biliary duct and a pancreatic duct;
generate a display image based on a result of the determination of the route information of the lumen, the display image having a route guide image showing a route of the lumen leading to the papillary portion superimposed on the endoscope image; and
control a display to display the display image.

2. The information processing system of claim 1, wherein the route guide image comprises a lumen route image indicating a route of the biliary duct and a route of the pancreatic duct.

3. The information processing system of claim 1, wherein the route guide image comprises at least one of:
an image indicating a distance between a distal end of a treatment tool of the endoscope and the papillary portion; and
an image indicating an insertion direction of the treatment tool.

4. The information processing system of claim 1, further comprising a storage for storing a trained model trained to output the route information of the lumen based on the endoscope image,
wherein the processor is configured to determine the route information from the endoscope image by a processing based on the trained model.

5. The information processing system of claim 4, wherein the trained model is trained using training data based on a classification pattern of the papillary portion.

6. The information processing system of claim 5, wherein the classification pattern of the papillary portion is set as a correct answer data among the training data.

7. The information processing system of claim 4, wherein the trained model is trained using training data based on a magnetic resonance cholangio pancreatgraphy (MRCP) image.

8. The information processing system of claim 7, wherein the processor is configured to control another display to display the MRCP image.

9. The information processing system of claim 7, wherein the processor is configured to:
control the display to display the endoscope image in a first display region of the display; and

control the display to display the MRCP image on a second display region of the display.

10. The information processing system of claim 7, wherein the processor is configured to acquire the MRCP image prior to an insertion operation of the endoscope.

11. The information processing system of claim 7, wherein the MRCP image is set as a correct answer data among the training data.

12. The information processing system of claim 4, wherein the trained model is trained using training data based on an ultrasound endoscope image.

13. The information processing system of claim 1, wherein the processor is configured to:

acquire an MRCP image showing a part of the lumen; and determine a route of the lumen between the papillary portion and the part of the lumen shown in the MRCP image based on the endoscope image and the MRCP image.

14. The information processing system of claim 13, further comprising:

a storage configured to store a trained model trained to output the route information of the lumen based on the endoscope image and the MRCP image, wherein the processor is configured to determine the route of the lumen between the papillary portion and the part of the lumen shown in the MRCP image by inputting the endoscope image and the MRCP image into the trained model.

15. The information processing system of claim 1, wherein:

the endoscope is configured to electrically drive an endoscopic operation, the endoscopic operation being at least one of forward movement and backward movement of an insertion section of the endoscope, a bending angle of a bending section of the insertion section, and rolling rotation of the insertion section; and the processor is configured to:

control positioning of a distal end section of the insertion section of the endoscope with respect to the papillary portion by the electrically-driven endoscopic operation; and subsequent to the positioning, acquire the endoscope image.

16. The information processing system of claim 1, wherein:

the endoscope is configured to electrically drive an endoscopic operation, the endoscopic operation being at least one of forward and backward movement of an insertion section, a bending angle of a bending section of the insertion section, or rolling rotation of the insertion section; and the processor is configured to control the electrically-driven endoscopic operation based on the result of the determination of the route information of the lumen.

17. A medical system comprising:

the information processing system of claim 1; and the endoscope.

* * * * *